US011311611B2

(12) United States Patent
Sahin et al.

(10) Patent No.: US 11,311,611 B2
(45) Date of Patent: Apr. 26, 2022

(54) ANTIGEN-SPECIFIC T CELL RECEPTORS AND T CELL EPITOPES

(71) Applicant: BioNTech Cell & Gene Therapies GmbH, Mainz (DE)

(72) Inventors: Ugur Sahin, Mainz (DE); Ozlem Tureci, Mainz (DE); Petra Simon, Mainz (DE); Tana Omokoko, Mainz (DE)

(73) Assignees: BioNTech Cell & Gene Therapies GmbH, Mainz (DE); Translationale Onkologie an der Universitätsmedizin der Johannes Gutenbera-Universität Mainz Gemeinnützine GmbH, Mainz (DE)

(*) Notice: Subject to any disclaimer, the term of this patent is extended or adjusted under 35 U.S.C. 154(b) by 548 days.

(21) Appl. No.: 16/121,414

(22) Filed: Sep. 4, 2018

(65) Prior Publication Data
US 2019/0060430 A1 Feb. 28, 2019

Related U.S. Application Data

(62) Division of application No. 15/392,677, filed on Dec. 28, 2016, now Pat. No. 10,117,918, which is a division of application No. 13/823,079, filed as application No. PCT/EP2011/004674 on Sep. 19, 2011, now Pat. No. 9,586,997.

(30) Foreign Application Priority Data

Sep. 20, 2010 (EP) .................... 10009990
Jan. 5, 2011 (EP) .................... 11000045

(51) Int. Cl.
*C07K 14/725* (2006.01)
*A61K 39/00* (2006.01)
*C07K 14/47* (2006.01)
*A61K 39/12* (2006.01)
*C07K 14/005* (2006.01)
*C07K 14/705* (2006.01)
*C12N 5/0783* (2010.01)
*C12N 15/85* (2006.01)
*C12N 9/16* (2006.01)
*G01N 33/50* (2006.01)

(52) U.S. Cl.
CPC .......... *A61K 39/0011* (2013.01); *A61K 39/12* (2013.01); *C07K 14/005* (2013.01); *C07K 14/4748* (2013.01); *C07K 14/705* (2013.01); *C07K 14/7051* (2013.01); *C07K 14/70503* (2013.01); *C12N 5/0636* (2013.01); *C12N 9/16* (2013.01); *C12N 15/85* (2013.01); *C12Y 301/03048* (2013.01); *G01N 33/5017* (2013.01); *A61K 2039/53* (2013.01); *A61K 2039/57* (2013.01); *C12N 2510/00* (2013.01); *C12N 2710/16134* (2013.01); *G01N 2333/916* (2013.01)

(58) Field of Classification Search
None
See application file for complete search history.

(56) References Cited

U.S. PATENT DOCUMENTS

| 7,259,247 B1 | 8/2007 | Kroczek |
| 2002/0107388 A1 | 8/2002 | Vandenbark |
| 2005/0261489 A1 | 11/2005 | Kroczek |
| 2009/0042798 A1 | 2/2009 | Wang et al. |
| 2009/0208538 A1 | 8/2009 | Darnell |
| 2010/0011199 A1 | 1/2010 | Duan et al. |

FOREIGN PATENT DOCUMENTS

| CN | 101182531 | 5/2008 | |
| JP | A-2008-500014 | 1/2008 | |
| JP | 2008-263950 | 11/2008 | |
| JP | 2009-278927 A | 12/2009 | |
| WO | 99/13095 | 3/1991 | |
| WO | 01/23560 | 4/2001 | |
| WO | 01/55393 | 8/2001 | |
| WO | 2001/090197 | 11/2001 | |
| WO | WO 02/070552 | 9/2002 | |
| WO | 2005/016862 | 2/2005 | |
| WO | 2005/016962 | 2/2005 | |
| WO | 05/026205 | 3/2005 | |
| WO | WO 2005/116075 | 12/2005 | |
| WO | 06/012641 A2 | 2/2006 | |
| WO | 06/026002 | 3/2006 | |
| WO | WO-2006031221 A1 * | 3/2006 | .............. A61P 35/00 |
| WO | WO-2007017201 A1 * | 2/2007 | ........... C12N 5/0639 |
| WO | 08/042814 A2 | 4/2008 | |

(Continued)

OTHER PUBLICATIONS

Garcia et al., Cell, vol. 122, 333-336, Aug. 12, 2005. (Year: 2005).*
Portolano et al., J Immunol. Feb. 1, 1993;150(3):880-7. (Year: 1993).*
Woodsworth et al., Genome Medicine 2013, 5:98. (Year: 2013).*
Robins et al., Blood. 2009;114:4099-4107. (Year: 2009).*
Kloosterboer et al. (Leukemia (2004) 18, 798-808). (Year: 2004).*
Busson et al., "Prediction of CD4+ T cell epitopes restricted to HLA-DP4 molecules," Journal of Immunological Methods, vol. 317, Issues 1-2, Dec. 20, 2006, pp. 144-151.
Schumacher (Nat Rev Immunol. Jul. 2002;2(7):512-9.

(Continued)

*Primary Examiner* — Zachary S Skelding
(74) *Attorney, Agent, or Firm* — McDonnell Boehnen Hulbert & Berghoff LLP

(57) ABSTRACT

The present invention relates to efficient methods for providing antigen-specific lymphoid cells. These lymphoid cells may be used to provide antigen specific T cell receptors having a defined MHC restriction and to identify immunologically relevant T cell epitopes. Furthermore, the present invention relates to antigen-specific T cell receptors and T cell epitopes and their use in immunotherapy.

16 Claims, 22 Drawing Sheets

Figure 1:
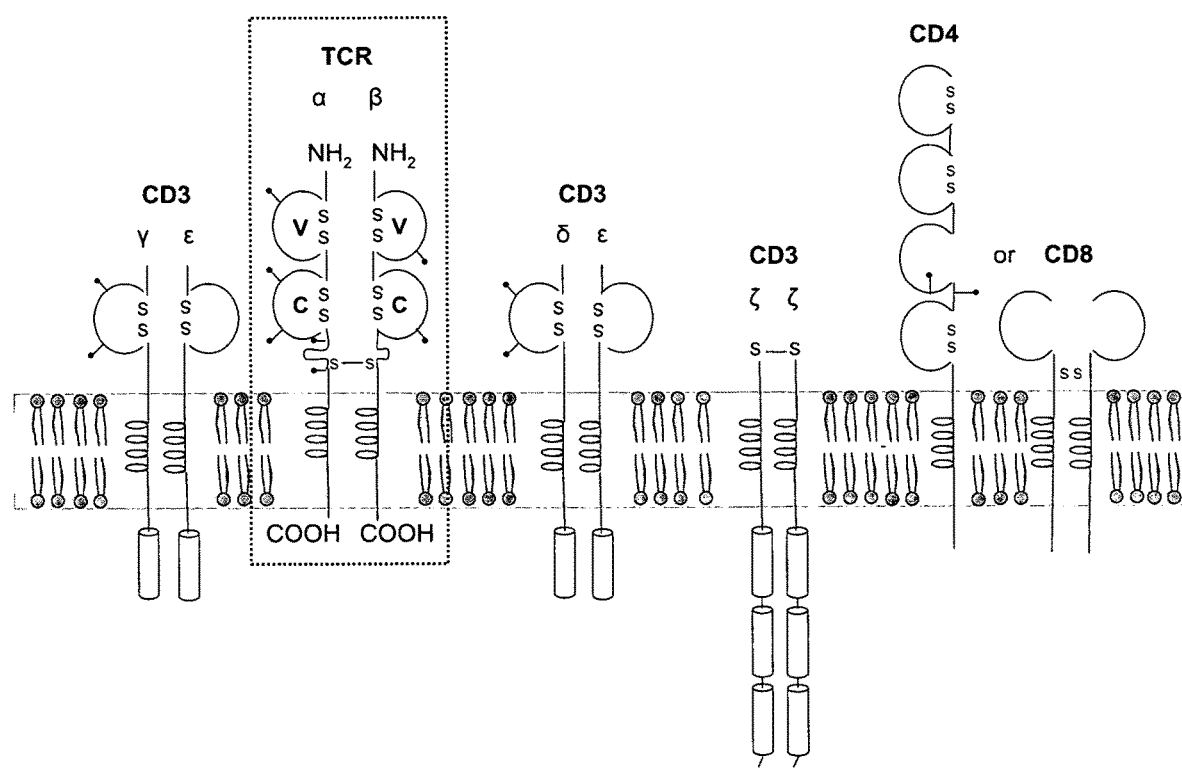

Specification includes a Sequence Listing.

(56) References Cited

FOREIGN PATENT DOCUMENTS

| WO | WO-2008153743 A2 * | 12/2008 | ....... G01N 33/57426 |
|---|---|---|---|
| WO | 2010/008782 | 1/2010 | |
| WO | 2010/105298 | 9/2010 | |

OTHER PUBLICATIONS

Uckert et al. (Cancer Immunol Immunother (2009) 58:809-822.
Boulter et al. (Clinical and Experimental Immunology, 142:454-460).
Janeway et al., Immunobiology, 5th Ed., Garland Science, pp. 106-019, 117-118 and 260-263, (2001).
Goyarts et al., Mol Immunol. Jul. 1998;35(10):593-607.
Kessels et al., Proc Natl Acad Sci U.S.A. Dec. 19, 2000; 97(26):14578-83.
Stanislawski et al., "Circumventing tolerance to a human MDM2-derived tumor antigen by TCR gene transfer", Nature Immunology, 2001, 2(10), 962-970.
Zhao et al., "Primary human lymphocytes transduced with NY-ESO-1 antigen-specific TCR genes recognize and kill diverse human tunior cell lines", Journal of Immunology, 2005, 174(7), 4415-4423.
Morris et al., "Prospects for immunotherapy of malignant disease", Clinical and Experimental Immunology, 2003, 131(1), 1-7.
Kessels et al., "Immunotherapy through TCR gene transfer", Nature Immunology, 2001, 2(10),957-961.
Mandic, et al., One NY-ESO-1 derived epitope that promiscuously binds to multiple HLA-DR and HLA-DP4 molecules and stimulates autologous CD4+ T cells from patients with NY-ESO-1-expressing melanoma, J. Immunol, 174(3), p. 1751-1759 (2005).
Reiser et al (Acta Crystallogr Sect F. Struct Biol Cryst Commun, Nov. 1, 2009:65(Pt 11):1157-61).
Comments of Olivier Kassel posted Nov. 6, 2012 on ResearchGate in response to the question: "Can anybody suggest a method/vector to express peptides (25 mer) in animal cells without using fusion protein or large tags?," one page.
Kurokawa et al., "Paired cloning of the T cell receptor α and ß genes from a single T cell without the establishment of a T cell clone," Clin. Exp. Immunol., vol. 123, (2001) pp. 340-345.
Ozawa et al., "Comprehensive analysis of the functional TCR repertoire at the single-cell level," Biochem. Biophys. Res. Commun., vol. 367, (2008) pp. 820-825.
Tanaka et al., "Single-Cell Analysis of T-Cell Receptor Repertoire of HTLV-1 Tax-Specific Cytotoxic T Cells in Allogeneic Transplant Recipients with Adult T-Cell Leukemia/Lymphoma," Cancer Res., vol. 70, (2010) pp. 6181-6192.
Maryanski et al., "Single-Cell PCR Analysis of TCR Repertoires Selected by Antigen In Vio: A High Magnitude CD8 Response Is Comprised of Very Few Clones," Immunity, vol. 4, (1996) pp. 47-55.
Dong et al., "PLAC1 is a tumor-specific antigen capable of eliciting spontaneous antibody responses in human cancer patients," Int. J. Cancer, vol. 122, (2008) pp. 2038-2043.
Tahara et al., "Reconstitution of CD8 T Cells by Retroviral Transfer of the TCR αß-Chain Genes Isolated from a Clonally Expanded-815-Infiltrating Lymphocyte," J. Immunol. vol. 171, (2003) pp. 2154-2160.
Khong, et al., "Immunization of HLA_A*0201 and/or HLA-DPß*04 Patients with Metastatic Melanoma Using Epitopes from the NY-ESO-1 Antigen," J Immunother vol. 27, pp. 472-477 (2004).
Zeng, et al., "CD4+ T cell recognition of MHO class II-restricted epitopes from NY-ESO-1 presented by a prevalent HLA DP4 allele: Association with NY-ESO-1 antibody production," Proc Natl Acad Sci USA vol. 98, pp. 3964-3969 (2001).
Chen, et al., "A testicular antigen aberrantly expressed in human cancers detected by autologous antibody screening," Proc Natl Acad Sci USA vol. 94, pp. 1914-1918 (1997).
Harris et al., "Toward the Total Chemical Synthesis of the Cancer Protein NY-ESO-1", Biopolymers, 2010, 94(4), 542-550.
Dehghanpisheh et al., "Retrovirally Induced Mouse Anti-TCR Monoclonals Can Synergize the In Vitro Proliferative T Cell Response to Bacterial Superantigens", Scandinavian Journal of Immunology, 1997, 45(6), 645-654.
Dong et al., "Public TCR Use by Herpes Simplex Virus-2-Specific Human CDS CTLs", Journal of Immunology, 2010, 184(6), 3063-3071.
Simon et al. "Functional TOR Retrieval from Single Antigen-Specific Human T Cells Reveals Multiple Novel Epitopes," Cancer Immunol. Res. 2(12): 1230-1244 (2014).

* cited by examiner

Fig. 9

|  | | iDC | | | K562 A*0201 |
|---|---|---|---|---|---|
|  | | NY pool | control | NY RNA | tyr$_{368-376}$ |
| IVSB | TCR$_{CD8}$-NY#2 | ● ● | | | ● ● |
|  | TCR$_{CD8}$-NY#5 | ● ● | | ● ● | ● ● |
|  | TCR control | | | | ● ● |

ANTIGEN-SPECIFIC T CELL RECEPTORS AND T CELL EPITOPES

This application is a divisional of U.S. patent application Ser. No. 15/392,677 filed Dec. 28, 2016 which is a divisional of U.S. patent application Ser. No. 13/823,079 filed Jun. 21, 2013, now U.S. Pat. No. 9,586,997 issued Mar. 7, 2017, which is a 371 application of International Application No. PCT/EP2011/004674 filed Sep. 19, 2011, which claims the benefit of priority of European Application No. 10009990.2 filed Sep. 20, 2010 and European Application No. 11000045.2 filed Jan. 5, 2011, the specifications, claims, abstracts, and drawings of each of which are hereby incorporated by reference in their entirety into the specification of the present application.

TECHNICAL FIELD OF THE INVENTION

The present invention relates to the provision of T cell receptors and T cell epitopes which are useful for immunotherapy.

BACKGROUND OF THE INVENTION

The evolution of the immune system resulted in vertebrates in a highly effective network based on two types of defense: the innate and the adoptive immunity.

In contrast to the evolutionary ancient innate immune system that relies on invariant receptors recognizing common molecular patterns associated with pathogens, the adoptive immunity is based on highly specific antigen receptors on B cells (B lymphocytes) and T cells (T lymphocytes) and clonal selection.

While B cells raise humoral immune responses by secretion of antibodies, T cells mediate cellular immune responses leading to destruction of recognized cells.

T cells play a central role in cell-mediated immunity in humans and animals. The recognition and binding of a particular antigen is mediated by the T cell receptors (TCRs) expressed on the surface of T cells.

The T cell receptor (TCR) of a T cell is able to interact with immunogenic peptides (epitopes) bound to major histocompatibility complex (MHC) molecules and presented on the surface of target cells. Specific binding of the TCR triggers a signal cascade inside the T cell leading to proliferation and differentiation into a maturated effector T cell. To be able to target a vast variety of antigens, the T cell receptors need to have a great diversity.

This diversity is obtained by genetic rearrangement of different discontinuous segments of genes which code for the different structural regions of TCRs. TCRs are composed of one α-chain and one β-chain or of one γ-chain and one δ-chain. The TCR α/β chains are composed of an N-terminal highly polymorphic variable region involved in antigen recognition and an invariant constant region. On the genetic level, these chains are separated into several regions, a variable (V) region, a diversity (D) region (only β- and δ-chain), a joining (J) region and a constant (C) region. The human β-chain genes contain over 60 variable (V), 2 diversity (D), over 10 joining (J) segments, and 2 constant region segments (C). The human α-chain genes contain over 50 V segments, and over 60 J segments but no D segments, as well as one C segment. The murine β-chain genes contain over 30 variable (V), 2 diversity (D), over 10 joining (J) segments, and 2 constant region segments (C). The murine α-chain genes contain almost 100 V segments, 60 J segments, no D segments, but one C segment. During the differentiation of T cells, specific T cell receptor genes are created by rearranging one V, one D (only β- and δ-chain), one J and one C region gene. The diversity of the TCRs is further amplified by imprecise V-(D)-J rearrangement wherein random nucleotides are introduced and/or deleted at the recombination sites. Since the rearrangement of the TCR gene loci occurs in the genome during maturation of T cells, each mature T cell only expresses one specific α/β TCR or γ/δ TCR.

MHC and antigen binding is mediated by the complementary determining regions 1, 2 and 3 (CDR1, CDR2, CDR3) of the TCR. The CDR3 of the β-chain which is most critical for antigen recognition and binding is encoded by the V-D-J junction of the rearranged TCR β-chain gene.

The TCR is a part of a complex signaling machinery, which includes the heterodimeric complex of the TCR α- and β-chains, the co-receptor CD4 or CD8 and the CD3 signal transduction modul (FIG. 1). While the CD3 chains transfer the activation signal inside the cell, the TCR α/β heterodimer is solely responsible for antigen recognition. Thus, the transfer of the TCR α/β chains offers the opportunity to redirect T cells towards any antigen of interest.

Immunotherapy

Antigen-specific immunotherapy aims to enhance or induce specific immune responses in patients to control infectious or malignant diseases. The identification of a growing number of pathogen- and tumor-associated antigens (TAA) led to a broad collection of suitable targets for immunotherapy. Cells presenting immunogenic peptides (epitopes) derived from these antigens can be specifically targeted by either active or passive immunization strategies.

Active immunization tends to induce and expand antigen-specific T cells in the patient, which are able to specifically recognize and kill diseased cells. In contrast passive immunization relies on the adoptive transfer of T cells, which were expanded and optional genetically engineered in vitro (adoptive T cell therapy).

Vaccination

Tumor vaccines aim to induce endogenous tumor-specific immune responses by active immunization. Different antigen formats can be used for tumor vaccination including whole cancer cells, proteins, peptides or immunizing vectors such as RNA, DNA or viral vectors that can be applied either directly in vivo or in vitro by pulsing of DCs following transfer into the patient.

The number of clinical studies where therapy-induced immune responses can be identified is steadily increasing due to improvements of immunization strategies and methods for detection of antigen-specific immune responses (Connerotte, T. et al. (2008). Cancer Res. 68, 3931-3940; Schmitt, M. et al. (2008) Blood 111, 1357-1365; Speiser, D. E. et al. (2008) Proc. Natl. Acad. Sci. U.S.A 105, 3849-3854; Adams, S. et al. (2008) J. Immunol. 181, 776-784).

However, in most cases detected immune responses cannot systemically be correlated with clinical outcomes (Curigliano, G. et al. (2006) Ann. Oncol. 17, 750-762; Rosenberg, S. A. et al. (2004) Nat. Med. 10, 909-915).

The exact definition of peptide epitopes derived from tumor antigens may therefore contribute to improve specificity and efficiency of vaccination strategies as well as methods for immunomonitoring.

Adoptive Cell Transfer (ACT)

ACT based immunotherapy can be broadly defined as a form of passive immunization with previously sensitized T cells that are transferred to non-immune recipients or to the autologous host after ex vivo expansion from low precursor frequencies to clinically relevant cell numbers. Cell types that have been used for ACT experiments are lymphokine-activated killer (LAK) cells (Mule, J. J. et al. (1984) Science 225, 1487-1489; Rosenberg, S. A. et al. (1985) N. Engl. J. Med. 313, 1485-1492), tumor-infiltrating lymphocytes (TILs) (Rosenberg, S. A. et al. (1994) J. Natl. Cancer Inst. 86, 1159-1166), donor lymphocytes after hematopoietic stem cell transplantation (HSCT) as well as tumor-specific T cell lines or clones (Dudley, M. E. et al. (2001) J. Immunother. 24, 363-373; Yee, C. et al. (2002) Proc. Natl. Acad. Sci. U. S. A 99, 16168-16173).

Adoptive T cell transfer was shown to have therapeutic activity against human viral infections such as CMV. While CMV infection and reactivation of endogenous latent viruses is controlled by the immune system in healthy individuals, it results in significant morbidity and mortality in immune compromised individuals such as transplant recipients or AIDS patients. Riddell and co-workers demonstrated the reconstitution of viral immunity by adoptive T cell therapy in immune suppressed patients after transfer of CD8+ CMV-specific T cell clones derived from HLA-matched CMV-seropositive transplant donors (Riddell, S. R. (1992) Science 257, 238-241).

As an alternative approach polyclonal donor-derived CMV- or EBV-specific T cell populations were transferred to transplant recipients resulting in increased persistence of transferred T cells (Rooney, C. M. et al. (1998) Blood 92, 1549-1555; Peggs, K. S. et al. (2003) Lancet 362, 1375-1377).

For adoptive immunotherapy of melanoma Rosenberg and co-workers established an ACT approach relying on the infusion of in vitro expanded autologous tumor-infiltrating lymphocytes (TILs) isolated from excised tumors in combination with a non-myeloablative lymphodepleting chemotherapy and high-dose IL2. A recently published clinical study resulted in an objective response rate of ~50% of treated patients suffering from metastatic melanoma (Dudley, M. E. et al. (2005) J. Clin. Oncol. 23: 2346-2357).

However, patients must fulfill several premises to be eligible for ACT immunotherapy. They must have resectable tumors. The tumors must generate viable TILs under cell culture conditions. The TILs must be reactive against tumor antigens, and must expand in vitro to sufficient numbers. Especially in other cancers than melanoma, it is difficult to obtain such tumor-reactive TILs. Furthermore, repeated in vitro stimulation and clonal expansion of normal human T lymphocytes results in progressive decrease in telomerase activity and shortening of telomeres resulting in replicative senescence and decreased potential for persistence of transferred T cells (Shen, X. et al. (2007) J. Immunother. 30: 123-129).

An approach overcoming the limitations of ACT is the adoptive transfer of autologous T cells reprogrammed to express a tumor-reactive TCR of defined specificity during short-time ex vivo culture followed by reinfusion into the patient. This strategy makes ACT applicable to a variety of common malignancies even if tumor-reactive T cells are absent in the patient. Since the antigenic specificity of T cells is rested entirely on the heterodimeric complex of the TCR α- and β-chain, the transfer of cloned TCR genes into T cells offers the potential to redirect them towards any antigen of interest. Therefore, TCR gene therapy provides an attractive strategy to develop antigen-specific immunotherapy with autologous lymphocytes as treatment option. Major advantages of TCR gene transfer are the creation of therapeutic quantities of antigen-specific T cells within a few days and the possibility to introduce specificities that are not present in the endogenous TCR repertoire of the patient.

Several groups demonstrated, that TCR gene transfer is an attractive strategy to redirect antigen-specificity of primary T cells (Morgan, R. A. et al. (2003) J. Immunol. 171, 3287-3295; Cooper, L. J. et al. (2000) J. Virol. 74, 8207-8212; Fujio, K. et al. (2000) J. Immunol. 165, 528-532; Kessels, H. W. et al. (2001) Nat. Immunol. 2, 957-961; Dembic, Z. et al. (1986) Nature 320, 232-238).

Feasibility of TCR gene therapy in humans was recently demonstrated in clinical trials for the treatment of malignant melanoma by Rosenberg and his group. The adoptive transfer of autologous lymphocytes retrovirally transduced with melanoma/melanocyte antigen-specific TCRs resulted in cancer regression in up to 30% of treated melanoma patients (Morgan, R. A. et al. (2006) Science 314, 126-129; Johnson, L. A. et al. (2009) Blood 114, 535-546).

Target Structures for Antigen-Specific Immunotherapy

The discovery of multiple tumor-associated antigens (TAAs) has provided the basis for antigen-specific immunotherapy concepts (Novellino, L. et al. (2005) Cancer Immunol. Immunother. 54, 187-207). TAAs are unusual proteins expressed on tumor cells due to their genetic instability, which have no or limited expression in normal cells. These TAAs can lead to specific recognition of malignant cells by the immune system.

Molecular cloning of TAAs by screening of tumor-derived cDNA expression libraries using autologous tumor-specific T cells (van der Bruggen, P. et al. (1991) Science 254, 1643-1647) or circulating antibodies (Sahin, U. et al. (1995) Proc. Natl. Acad. Sci. U.S.A 92, 11810-11813), reverse immunology approaches, biochemical methods (Hunt, D. F. et al. (1992) Science 256, 1817-1820), gene expression analyses or in silico cloning strategies (Helftenbein, G. et al. (2008) Gene 414, 76-84) led to a significant number of target candidates for immunotherapeutic strategies. TAAs fall in several categories, including differentiation antigens, overexpressed antigens, tumor-specific splice variants, mutated gene products, viral antigens and the so-called cancer testis antigens (CTAs). The cancer testis family is a very promising category of TAAs as their expression is restricted to the testis and a multitude of different tumor entities (Scanlan, M. J. et al. (2002) Immunol. Rev. 188, 22-32). Until now more than 50 CT genes have been described (Scanlan, M. J. et al. (2004) Cancer Immun. 4, 1) and some of them have been addressed in clinical studies (Adams, S. et al. (2008) J. Immunol. 181, 776-784; Atanackovic, D. et al. (2004) J. Immunol. 172, 3289-3296; Chen, Q. et al. (2004) Proc. Natl. Acad. Sci. U.S.A 101, 9363-9368; Connerotte, T. et al. (2008). Cancer Res. 68, 3931-3940; Davis, I. D. et al. (2004) Proc. Natl. Acad. Sci. U.S.A 101, 10697-10702; Jager, E. (2000) Proc. Natl. Acad. Sci. U.S.A 97, 12198-12203; Marchand, M. et al. (1999) Int. J. Cancer 80, 219-230; Schuler-Thurner, B. et al. (2000) J. Immunol. 165, 3492-3496).

In spite of the growing number of attractive target structures for immunotherapeutic approaches specific T cell clones or lines of defined HLA restriction do only exist for a few of them (Chaux, P. et al. (1999) J. Immunol. 163, 2928-2936; Zhang, Y. et al. (2002) Tissue Antigens 60, 365-371; Zhao, Y. et al. (2005) J. Immunol. 174, 4415-4423). For the majority of CTAs, including TPTE, even evidence for specific T cell responses is missing.

DESCRIPTION OF INVENTION

Summary of the Invention

Immunotherapeutic strategies are promising options for the treatment of infectious diseases and cancer. The identification of a growing number of pathogen- and tumor-associated antigens led to a broad collection of suitable targets for immunotherapy.

By adoptive transfer of T cells engineered to express a defined antigen-specific T cell receptor (TCR) these antigens can be specifically targeted thereby leading to selective destruction of targeted malignant or infected cells. As TCR specificity is restricted by highly polymorphic MHC molecules, broad applicability of adoptive TCR transfer is dependent on the generation of a multitude of TCR reagents for "off the shelf" use, covering a broad range of antigens and MHC restrictions. However, until now only a limited number of suitable TCR candidates have been identified. This is mainly due to the laborious establishment of T cell clones for TCR gene isolation.

The present invention relates to efficient methods for providing antigen-specific lymphoid cells. These lymphoid cells may be used to provide antigen-specific T cell receptors having a defined MHC restriction and to identify immunologically relevant T cell epitopes.

In one aspect the present invention relates to a method for providing antigen-specific lymphoid cells comprising the steps:
(a) providing a single antigen-reactive T cell from a sample comprising T cells, wherein said sample is obtained from a subject previously exposed to said antigen;
(b) providing a nucleic acid encoding a T cell receptor having the specificity of the T cell receptor of said single antigen-reactive T cell; and
(c) introducing said nucleic acid into a lymphoid cell to provide said antigen-specific lymphoid cells.

In one embodiment, the method further comprises the step of determining the epitope specificity of said antigen-specific lymphoid cells and/or the step of determining the MHC restriction of said antigen-specific lymphoid cells.

In a further aspect the present invention relates to a method for providing an antigen-specific T cell receptor having a defined MHC restriction comprising the steps:
(a) providing a single antigen-reactive T cell from a sample comprising T cells, wherein said sample is obtained from a subject previously exposed to said antigen;
(b) providing a nucleic acid encoding a T cell receptor having the specificity of the T cell receptor of said single antigen-reactive T cell;
(c) introducing said nucleic acid into a lymphoid cell to provide antigen-specific lymphoid cells; and
(d) determining the MHC restriction of said antigen-specific lymphoid cells.

In one embodiment, the method further comprises the step of determining the epitope specificity of said antigen-specific lymphoid cells.

In a further aspect the present invention relates to a method for identifying a T cell epitope in an antigen comprising the steps:
(a) providing a single antigen-reactive T cell from a sample comprising T cells, wherein said sample is obtained from a subject previously exposed to said antigen;
(b) providing a nucleic acid encoding a T cell receptor having the specificity of the T cell receptor of said single antigen-reactive T cell;
(c) introducing said nucleic acid into a lymphoid cell to provide antigen-specific lymphoid cells; and
(d) determining the epitope specificity of said antigen-specific lymphoid cells.

In one embodiment, the method further comprises the step of determining the MHC restriction of said antigen-specific lymphoid cells.

In a preferred embodiment, said single antigen-reactive T cell and said nucleic acid encoding a T cell receptor having the specificity of the T cell receptor of said single antigen-reactive T cell are reactive with an antigen administered to a subject. In a preferred embodiment, said single antigen-reactive T cell is provided by isolation.

In one embodiment of the method according to all of the above aspects, said epitope is an MHC presented peptide. In one embodiment of the method according to all of the above aspects, said step of determining the epitope specificity of said antigen-specific lymphoid cells comprises determining the reactivity of said antigen-specific lymphoid cells to MHC molecules exposed to, preferably pulsed, i.e. loaded with, a peptide derived from the antigen. Preferably, said MHC molecules are MHC molecules expressed in the subject. Preferably, said MHC molecules are present on target cells. Said peptide may be part of a peptide library derived from the antigen and the peptide library may comprise a set of overlapping peptides derived from said antigen. Preferably, the set of overlapping peptides covers the entire sequence of said antigen.

In one embodiment of the method according to all of the above aspects, said step of determining the MHC restriction of said antigen-specific lymphoid cells comprises determining the reactivity of said antigen-specific lymphoid cells to selected MHC molecules. Preferably, said selected MHC molecules are present on target cells. Preferably, said selected MHC molecules are MHC molecules expressed in the subject. Preferably, said selected MHC molecules are present on target cells expressing the antigen or a portion thereof. Preferably, said said antigen-specific lymphoid cells or T cell receptor thereof are restricted to MHC molecules expressed in the subject.

Preferably, determining the reactivity of antigen-specific lymphoid cells comprises determining cytokine secretion by the lymphoid cells, wherein said cytokine may be interferon-γ (IFNγ). Other activation markers that can be used are e.g. CD154 and/or CD137.

In one particularly preferred embodiment of the method according to all of the above aspects, said nucleic acid encoding a T cell receptor having the specificity of the T cell receptor of said single antigen-reactive T cell is RNA, preferably in vitro transcribed RNA. Preferably, said lymphoid cell lacks surface expression of an endogenous TCR or is specific for an unrelated antigen. In one embodiment, said lymphoid cell is a lymphocyte, preferably a T cell.

In one embodiment of the method according to all of the above aspects, said step of providing a nucleic acid encoding a T cell receptor having the specificity of the T cell receptor of said single antigen-reactive T cell comprises providing a nucleic acid encoding a T cell receptor comprising at least the CDR sequences, preferably at least the variable region of the T cell receptor of said single antigen-reactive T cell.

In one embodiment of the method according to all of the above aspects, said step of providing a nucleic acid encoding a T cell receptor having the specificity of the T cell receptor of said single antigen-reactive T cell comprises isolating RNA, preferably poly-A+-RNA, from said single antigen-reactive T cell or a clonal population thereof and preferably further comprises obtaining cDNA from said RNA. In one embodiment, said step of providing a nucleic acid encoding a T cell receptor having the specificity of the T cell receptor of said single antigen-reactive T cell further comprises amplifying at least a portion of the cDNA comprising a nucleic acid sequence encoding at least the CDR sequences, preferably at least the variable region of the T cell receptor of said single antigen-reactive T cell.

In one embodiment of the method according to all of the above aspects, said subject is seropositive for said antigen or an agent comprising said antigen. Seropositivity of the subject may be determined by determining an immune response to the antigen or agent or a component thereof.

In one embodiment of the method according to all of the above aspects, said T cells prior to providing a single antigen-reactive T cell are subjected to an antigen-specific expansion and rechallenge, wherein the antigen-specific expansion and rechallenge may be effected by exposing the T cells to preferably autologous antigen presenting cells presenting an antigen. In one embodiment of the method according to all of the above aspects, said single antigen-reactive T cell is positive for an activation marker such as IFNγ or CD137 and CD8 or CD4.

In one embodiment of the method according to all of the above aspects, said single antigen-reactive T cell is isolated from the sample comprising T cells using flow cytometry. Sorting is preferably effected on the basis of positivity for an activation marker, in particular IFNγ or CD137, and CD8 or CD4.

In one embodiment of the method according to all of the above aspects, said T cell receptor comprises T cell receptor α- and β-chains.

In one embodiment of the method according to all of the above aspects, said nucleic acid encoding a T cell receptor having the specificity of the T cell receptor of said single antigen-reactive T cell comprises a nucleic acid sequence encoding at least the CDR sequences, preferably at least the variable region of the T cell receptor of said single antigen-reactive T cell.

In one embodiment of the method according to all of the above aspects, said subject is a mammal, preferably a human being. Preferably, said subject has a disease involving cells expressing the antigen, preferably a T cell related disease. Said disease may be selected from the group consisting of immune system disorders, infections, and malignant diseases.

Furthermore, the present invention relates to T cell receptors specific for the viral antigen CMV-pp65 or the tumor-associated antigen NY-ESO-1, TPTE or PLAC1, in particular when presented on the surface of a cell such as a diseased cell or an antigen-presenting cell, as well as peptides comprising epitopes recognized by these T cell receptors.

In one aspect, the invention relates to a peptide comprising an amino acid sequence selected from the group consisting of SEQ ID NOs: 108 to 139, 172, 173, 175, 178 to 187 and 196 or a variant of said amino acid sequence.

In one embodiment, the peptide is a MHC class I or class II presented peptide, preferably a MHC class I presented peptide, or, if present within cells, can be processed to produce a procession product thereof which is a MHC class I or class II presented peptide, preferably a MHC class I presented peptide. Preferably, said MHC class I or class II presented peptide has a sequence substantially corresponding to the given amino acid sequence, i.e. an amino acid sequence selected from the group consisting of SEQ ID NOs: 108 to 139, 172, 173, 175, 178 to 187 and 196 or a variant of said amino acid sequence. Preferably, a peptide according to the invention is capable of stimulating a cellular response against a disease involving cells characterized by presentation of an antigen from which the peptide is derived, i.e. CMV-pp65, NY-ESO-1, TPTE or PLAC1 with class I MHC.

In further aspects, the invention relates to a nucleic acid encoding the peptide of the invention and a cell comprising the nucleic acid. Such nucleic acid may be present in a plasmid or an expression vector and may be functionally linked to a promoter. Preferably, the cell expresses the peptide. The cell may be a recombinant cell and may secrete the encoded peptide or a procession product thereof, may express it on the surface and preferably may additionally express an MHC molecule which binds to said peptide or a procession product thereof and preferably presents said peptide or a procession product thereof on the cell surface. In one embodiment, the cell expresses the MHC molecule endogenously. In a further embodiment, the cell expresses the MHC molecule and/or the peptide in a recombinant manner. The cell is preferably nonproliferative. In a preferred embodiment, the cell is an antigen-presenting cell, in particular a dendritic cell, a monocyte or a macrophage.

In a further aspect, the invention relates to a cell that presents the peptide of the invention or a procession product thereof, wherein the procession product preferably is a peptide having the given amino acid sequence, i.e. an amino acid sequence selected from the group consisting of SEQ ID NOs: 108 to 139, 172, 173, 175, 178 to 187 and 196 or a variant of said amino acid sequence. The cell may present the peptide or a procession product thereof by MHC molecules on its surface. In one embodiment, the cell endogenously expresses an MHC molecule. In a further embodiment, the cell recombinantly expresses an MHC molecule. In one embodiment, the MHC molecules of the cell are loaded (pulsed) with the peptide by addition of the peptide to the cell. The cell may recombinantly express the peptide and present said peptide or a procession product thereof on the cell surface. The cell is preferably nonproliferative. In a preferred embodiment, the cell is an antigen-presenting cell such as a dendritic cell, a monocyte or a macrophage.

In a further aspect, the invention relates to an immunoreactive cell reactive with a peptide of the invention, in particular when presented on the surface of a cell. The immunoreactive cell may be a cell that has been sensitized in vitro to recognize the peptide. The immunoreactive cell may be a T cell, preferably a cytotoxic T cell. Preferably, the immunoreactive cell binds to a sequence in the peptide substantially corresponding to the given amino acid sequence, i.e. an amino acid sequence selected from the group consisting of SEQ ID NOs: 108 to 139, 172, 173, 175, 178 to 187 and 196 or a variant of said amino acid sequence.

In a further aspect, the invention relates to a T cell receptor reactive with a peptide of the invention, or a polypeptide chain thereof.

In a further aspect, the invention relates to a T cell receptor α-chain comprising at least one, preferably two, more preferably all three of the CDR sequences of a T cell receptor α-chain selected from SEQ ID NOs: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 140, 142, 144, 146, 148, 150, 152, 154, 156, 158, 160, 162, 164, 166, 168, 170, 176, 188, 190, 192, and 194 or a variant thereof, or a T cell receptor comprising said T cell receptor α-chain. The CDR sequences are shown underlined in the sequences of the above mentioned T cell receptor α-chains given herein.

In a further aspect, the invention relates to a T cell receptor α-chain comprising a T cell receptor α-chain sequence selected from SEQ ID NOs: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 140, 142, 144, 146, 148, 150, 152, 154, 156, 158, 160, 162, 164, 166, 168, 170, 176, 188, 190, 192, and 194 or a variant thereof, or a T cell receptor comprising said T cell receptor α-chain.

In a further aspect, the invention relates to a T cell receptor β-chain comprising at least one, preferably two, more preferably all three of the CDR sequences of a T cell receptor β-chain selected from SEQ ID NOs: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 141, 143, 145, 147, 149, 151, 153, 155, 157, 159, 161, 163, 165, 167, 169, 171, 177, 189, 191, 193, and 195 or a variant thereof, or a T cell receptor comprising said T cell receptor β-chain. The CDR sequences are shown underlined in the sequences of the above mentioned T cell receptor β-chains given herein.

In a further aspect, the invention relates to a T cell receptor β-chain comprising a T cell receptor β-chain sequence selected from SEQ ID NOs: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 141, 143, 145, 147, 149, 151, 153, 155, 157, 159, 161, 163, 165, 167, 169, 171, 177, 189, 191, 193, and 195 or a variant thereof, or a T cell receptor comprising said T cell receptor β-chain.

In a further aspect, the invention relates to a T cell receptor comprising:
(i) a T cell receptor α-chain comprising at least one, preferably two, more preferably all three of the CDR sequences of the T cell receptor α-chain of SEQ ID NO: x or a variant thereof, and
(ii) a T cell receptor β-chain comprising at least one, preferably two, more preferably all three of the CDR sequences of a T cell receptor β-chain of SEQ ID NO: x+1 or a variant thereof; wherein x selected from 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 140, 142, 144, 146, 148, 150, 152, 154, 156, 158, 160, 162, 164, 166, 168, 170, 176, 188, 190, 192, and 194.

In a further aspect, the invention relates to a T cell receptor comprising:
(i) a T cell receptor α-chain comprising the T cell receptor α-chain sequence of SEQ ID NO: x or a variant thereof, and
(ii) a T cell receptor β-chain comprising the T cell receptor β-chain sequence of SEQ ID NO: x+1 or a variant thereof; wherein x selected from 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 140, 142, 144, 146, 148, 150, 152, 154, 156, 158, 160, 162, 164, 166, 168, 170, 176, 188, 190, 192, and 194.

The above T cell receptors are preferably specific for the viral antigen CMV-pp65 or the tumor-associated antigen NY-ESO-1, TPTE or PLAC1, in particular when presented on the surface of a cell such as a diseased cell or an antigen-presenting cell.

In a further aspect, the invention relates to a nucleic acid encoding the T cell receptor chain or T cell receptor according to any one of the above aspects.

In a further aspect, the invention relates to a cell comprising the T cell receptor chain or T cell receptor according to any one of the above aspects or the nucleic acid nucleic acid encoding the T cell receptor chain or T cell receptor according to any one of the above aspects. The cell may be an effector or stem cell, preferably an immunoreactive cell.

The immunoreactive cell may be a T cell, preferably a cytotoxic T cell. Preferably, the immunoreactive cell is reactive with the viral antigen CMV-pp65 or the tumor-associated antigen NY-ESO-1, TPTE or PLAC1, in particular when presented on the surface of a cell such as a diseased cell or an antigen-presenting cell, and specifically with a peptide of the invention and preferably binds to a sequence in the peptide substantially corresponding to the given amino acid sequence, i.e. an amino acid sequence selected from the group consisting of SEQ ID NOs: 108 to 139, 172, 173, 175, 178 to 187 and 196 or a variant of said amino acid sequence.

Furthermore, the present invention generally embraces the treatment of diseases by targeting diseased cells. The methods provide for the selective eradication of cells that present an antigen, i.e. the viral antigen CMV-pp65 or the tumor antigen NY-ESO-1, TPTE or PLAC1, thereby minimizing adverse effects to normal cells not presenting said antigen. Thus, preferred diseases for a therapy are those in which one of the antigens described herein are expressed and presented such as viral infectious diseases or malignant diseases, in particular viral diseases and cancer diseases such as those described herein.

In one aspect, the invention relates to a pharmaceutical composition comprising one or more of:
(i) the peptide described above;
(ii) the nucleic acid encoding a peptide or the nucleic acid encoding a T cell receptor chain or T cell receptor described above;
(iii) the cell comprising a nucleic acid encoding a peptide described above, the cell presenting a peptide or a procession product described above, or the cell comprising a T cell receptor chain or T cell receptor or a nucleic acid described above;
(iv) the T cell receptor described above; or
(v) the immunoreactive cell described above.

A pharmaceutical composition of the invention may comprise a pharmaceutically acceptable carrier and may optionally comprise one or more adjuvants, stabilizers etc. The pharmaceutical composition may in the form of a therapeutic or prophylactic vaccine. In one embodiment, the pharmaceutical composition is for use in treating or preventing a viral disease such as hCMV infection or a malignant disease such as those described herein.

Administration of a pharmaceutical composition as described above may provide MHC class II-presented epitopes that are capable of eliciting a CD4+ helper T cell response and/or a CD8+ T cell response against antigens described herein. Alternatively or additionally, administration of a pharmaceutical composition as described above may provide MHC class I-presented epitopes that are capable of eliciting a CD8+ T cell response against tumor antigens described herein.

In one embodiment, the antigen concerned is hCMV-pp65 and the pharmaceutical composition of the present invention is useful in the treatment and/or prevention of hCMV infection.

In one embodiment, the antigen concerned is NY-ESO-1, TPTE or PLAC1 and the pharmaceutical composition of the present invention is is useful in the treatment and/or prevention of a malignant disease.

Another aspect relates to a method for inducing an immune response in a subject, comprising administering to the subject a pharmaceutical composition of the invention.

Another aspect relates to a method for stimulating, priming and/or expanding T cells, comprising contacting T cells with one or more of:

(i) the peptide described above;
(ii) the nucleic acid encoding a peptide described above; and
(iii) the cell comprising a nucleic acid encoding a peptide described above or the cell presenting a peptide or a procession product described above.

In this aspect, the invention may relate to a method for preparing antigen-specific T cells. The T cells may be stimulated, primed and/or expanded in vitro or in vivo. Preferably, the T cells are present in a sample obtained from a subject. The stimulated, primed and/or expanded T cells may be administered to a subject and may be autologous, allogeneic, syngeneic to the subject.

The invention in the above aspects of a method for inducing an immune response in a subject or of a method for stimulating, priming and/or expanding T cells may relate to a method for treating hCMV infections or malignant diseases in a subject.

In one embodiment, the antigen concerned is hCMV-pp65 and the treatment is a therapeutic or prophylactic treatment of hCMV infection.

In one embodiment, the antigen concerned is NY-ESO-1, TPTE or PLAC1 and the treatment is a therapeutic or prophylactic treatment of a malignant disease. In case of the treatment of a malignant disease, the agents and compositions described herein are preferably administered in a way such that the therapeutically active substance is not delivered or not substantially delivered to a tissue or organ wherein the cells when the tissue or organ is free of a malignant disease express a tumor-associated antigen described herein, in particular testicular tissue. To this end, the agents and compositions described herein can be administered locally.

The compositions and agents described herein are preferably capable of inducing or promoting a cellular response, preferably cytotoxic T cell activity, against a disease characterized by presentation of a antigen described herein with class I MHC, e.g. a viral disease or a malignant disease.

In one aspect, the invention provides the agents and compositions described herein for use in the methods of treatment described herein.

The treatments of malignant diseases described herein can be combined with surgical resection and/or radiation and/or traditional chemotherapy.

In another aspect, the invention relates to a method for determining an immune response in a subject, comprising determining T cells reactive with a peptide described above or a cell presenting a peptide or a procession product described above in a biological sample isolated from the subject. The method may comprise the steps of:
(a) incubating a sample comprising T cells isolated from a subject with one or more of:
(i) the peptide described above;
(ii) the nucleic acid encoding a peptide as described above; and
(iii) the cell comprising a nucleic acid encoding a peptide described above or the cell presenting a peptide or a procession product described above;
and
(b) detecting the specific activation of the T cells, therefrom determining the presence or absence of an immune response in said subject.

The invention in the above aspects of a method for determining an immune response in a subject may relate to a method for diagnosing hCMV infections or malignant diseases in a subject.

In one embodiment, the antigen concerned is hCMV-pp65 and diagnosis is a diagnosis of hCMV infection.

In one embodiment, the antigen concerned is NY-ESO-1, TPTE or PLAC1 and diagnosis is a diagnosis of a malignant disease.

In one embodiment of the methods for diagnosis, the biological sample is from a tissue or organ wherein the cells when the tissue or organ is disease free do not substantially express the antigen concerned.

Typically, the level of T cells in a biological sample is compared to a reference level, wherein a deviation from said reference level is indicative of the presence and/or stage of a disease in a subject. The reference level may be a level as determined in a control sample (e.g., from a healthy tissue or subject) or a median level from healthy subjects. A "deviation" from said reference level designates any significant change, such as an increase by at least 10%, 20%, or 30%, preferably by at least 40% or 50%, or even more. Preferably, the presence of the T cells in said biological sample or a quantity of the T cells in the biological sample which is increased compared to a reference level indicates the presence of a disease.

T cells may be isolated from patient peripheral blood, lymph nodes, tissue samples such as derived from biopsy and resection, or other source. Reactivity assays may be performed on primary T cells or other appropriate derivatives. For example, T cells may be fused to generate hybridomas. Assays for measuring T cell responsiveness are known in the art, and include proliferation assays and cytokine release assays.

Assays and indices for detecting reactive T cells include but are not limited to the use of IFNγ ELISPOT and IFNγ intracellular cytokine staining. Other various methods are known in the art for determining whether a T cell clone will respond to a particular peptide. Typically the peptide is added to a suspension of the T cells for a period of from one to three days. The response of the T cells may be measured by proliferation, e.g., uptake of labeled thymidine, or by release of cytokines, e.g., IL-2. Various assays are available for detecting the presence of released cytokines. T cell cytotoxic assays can be used to detect cytotoxic T cells having specificity for antigens. In one embodiment, cytotoxic T cells are tested for their ability to kill target cells presenting an antigen with MHC class I molecules. Target cells presenting an antigen may be labeled and added to a suspension of T cells from a patient sample. The cytotoxicity may be measured by quantifying the release of label from lysed cells. Controls for spontaneous and total release may be included in the assay.

In a further aspect, the invention provides a non-radioactive assay to monitor and quantify target cell killing activity, e.g. mediated by cytotoxic T lymphocytes (CTLs). This assay may provide a measure of cytotoxic effector cell activity and may reliably detect antigen-specific CTL killing of target cells. The assay provides a safer alternative to the standard $^{51}$Cr-release assay most often used to quantify CTL responses. The assay can be used to study CTL-mediated killing of primary host target cells of different cell lineages, and provides a valuable tool for the development of new vaccines and immunotherapies.

The invention relates to a method for determining cytotoxic activity comprising the steps of:
(i) providing a sample comprising target cells producing a reporter enzyme;
(ii) subjecting the target cells to an agent the cytotoxic activity of which is to be determined; and
(iii) subjecting the sample to a detection assay to establish the level of reporter enzyme contained in viable cells in the sample.

Preferably, the cytotoxic activity is cell-mediated cytotoxic activity and the agent the cytotoxic activity of which is to be determined is a cytotoxic effector cell such as a cell selected from the group consisting of a cytotoxic T lymphocyte (CTL), a natural killer (NK) cell, and a macrophage, preferably a cytotoxic T lymphocyte (CTL). In one embodiment, the reporter enzyme is ATP dependent. In one embodiment, the reporter enzyme is a light emitting enzyme such as a luminescence-generating enzyme. Preferably, the reporter enzyme is luciferase. In one embodiment, RNA encoding said reported enzyme has been introduced into said target cells. The method may further comprise the step of adding an ATP degrading enzyme such as ATPase to the sample to substantially degrade any extracellular ATP in the sample. The method may further comprise the step of adding a substrate which is at least partially viable cell permeable. The substrate may be a luminogenic molecule and may be a luciferin derivative. In this embodiment, the method may comprise detecting luminescence in the sample, thereby detecting the number or presence of viable cells in the sample.

Other features and advantages of the instant invention will be apparent from the following detailed description and claims.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., (1995) Helvetica Chimica Acta, CH-4010 Basel, Switzerland.

The practice of the present invention will employ, unless otherwise indicated, conventional methods of biochemistry, cell biology, immunology, and recombinant DNA techniques which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

A reference to SEQ ID NOs: 108 to 139 is to be understood so as to refer individually to each of SEQ ID NOs: 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138 and 139.

Similarly, a reference to SEQ ID NOs: 178 to 187 is to be understood so as to refer individually to each of SEQ ID NOs: 178, 179, 180, 181, 182, 183, 184, 185, 186 and 187.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The term "recombinant" in the context of the present invention means "made through genetic engineering". Preferably, a "recombinant object" such as a recombinant cell in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

The term "immune response" refers to an integrated bodily response to an antigen and preferably refers to a cellular immune response or a cellular as well as a humoral immune response. The immune response may be protective/preventive/prophylactic and/or therapeutic.

"Inducing an immune response" may mean that there was no immune response against a particular antigen before induction, but it may also mean that there was a certain level of immune response against a particular antigen before induction and after induction said immune response is enhanced. Thus, "inducing an immune response" also includes "enhancing an immune response". Preferably, after inducing an immune response in a subject, said subject is protected from developing a disease such as an infectious disease, in particular a viral disease as disclosed herein, or a malignant disease or the disease condition is ameliorated by inducing an immune response. For example, an immune response against a viral antigen such as hCMV-pp65 may be induced in a patient having a viral disease or in a subject being at risk of developing a viral disease. For example, an immune response against a tumor-associated antigen such as NY-ESO-1, TPTE or PLAC1 may be induced in a patient having a malignant disease or in a subject being at risk of developing a malignant disease. Inducing an immune response in this case may mean that the disease condition of the subject is ameliorated, that the subject does not develop metastases, or that the subject being at risk of developing a malignant disease does not develop a malignant disease.

A "cellular immune response", a "cellular response", a "cellular response against an antigen" or a similar term is meant to include a cellular response directed to cells characterized by presentation of an antigen with class I or class II MHC. The cellular response relates to cells called T cells or T-lymphocytes which act as either 'helpers' or 'killers'. The helper T cells (also termed CD4$^+$ T cells) play a central role by regulating the immune response and the killer cells (also termed cytotoxic T cells, cytolytic T cells, CD8$^+$ T cells or CTLs) kill diseased cells such as infected cells or malignant cells, preventing the production of more diseased cells.

The term "antigen" relates to an agent comprising an epitope against which an immune response is to be generated. Preferably, an antigen in the context of the present invention is a molecule which, optionally after processing, induces an immune reaction, which is preferably specific for the antigen. The term "antigen" includes in particular proteins, peptides, polysaccharides, nucleic acids, especially RNA and DNA, and nucleotides.

An antigen is preferably a product which corresponds to or is derived from a naturally occurring antigen. Such naturally occurring antigens may include or may be derived from allergens, viruses, bacteria, fungi, parasites and other infectious agents and pathogens or an antigen may also be a tumor-associated antigen. According to the present invention, an antigen may correspond to a naturally occurring product, for example, a viral protein, or a part thereof.

The term "agent comprising an antigen" relates to an entity comprising an antigen such as a virus comprising a viral antigen. One example is hCMV comprising hCMV-pp65.

In a preferred embodiment, an antigen is a tumor-associated antigen, i.e., a constituent of malignant cells which may be derived from the cytoplasm, the cell surface and the cell nucleus, in particular those antigens which are produced, preferably in large quantity, intracellular or as surface antigens on malignant cells.

In particular, the antigen or peptides thereof should be recognizable by a T cell receptor. Preferably, the antigen or peptide if recognized by a T cell receptor is able to induce in the presence of appropriate co-stimulatory signals, clonal expansion of the T cell carrying the T cell receptor specifically recognizing the antigen or peptide. In the context of the embodiments of the present invention, the antigen is preferably presented by a cell, preferably by an antigen presenting cell and/or a diseased cell, in the context of MHC molecules, which results in an immune reaction against the antigen.

In the context of the present invention, the terms "tumor-associated antigen" or "tumor antigen" relate to proteins that are under normal conditions specifically expressed in a limited number of tissues and/or organs or in specific developmental stages, for example, the tumor-associated antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2. The tumor-associated antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor-associated antigen is preferably associated with the cell surface of a malignant cell and is preferably not or only rarely expressed in normal tissues. Preferably, the tumor-associated antigen or the aberrant expression of the tumor-associated antigen identifies malignant cells. In the context of the present invention, the tumor-associated antigen that is expressed by a malignant cell in a subject, e.g., a patient suffering from a malignant disease, is preferably a self-protein in said subject. In preferred embodiments, the tumor-associated antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system. Preferably, the amino acid sequence of the tumor-associated antigen is identical between the tumor-associated antigen which is expressed in normal tissues and the tumor-associated antigen which is expressed in malignant tissues. Preferably, a tumor-associated antigen is presented by a malignant cell in which it is expressed.

In preferred embodiments, an antigen is a viral antigen such as hCMV-pp65 and the present invention involves the stimulation of a CTL response against infected cells expressing such viral antigen and preferably presenting such viral antigen with class I MHC.

Cytomegalovirus is a herpes viral genus of the herpesviruses group. In humans it is commonly known as hCMV or Human Herpesvirus 5 (HHV-5). All herpesviruses share a characteristic ability to remain latent within the body over long periods.

hCMV infections are frequently associated with salivary glands, though they may be found throughout the body. hCMV infection can also be life threatening for patients who are immunocompromised (e.g. patients with HIV, organ transplant recipients, or neonates). Other CMV viruses are found in several mammal species, but species isolated from animals differ from hCMV in terms of genomic structure, and have not been reported to cause human disease.

hCMV is found throughout all geographic locations and socioeconomic groups, and infects between 50% and 80% of adults in the United States (40% worldwide) as indicated by the presence of antibodies in much of the general population. hCMV is also the virus most frequently transmitted to a developing fetus. hCMV infection is more widespread in developing countries and in communities with lower socioeconomic status and represents the most significant viral cause of birth defects in industrialized countries.

Two CMV proteins, phosphoprotein 65 (pp65; CMV-pp65) and immediate early protein-1 (IE-1), are major targets of the cellular immune response.

The term "hCMV-pp65" preferably relates to a protein comprising the amino acid sequence according to SEQ ID NO: 1 or a variant of said amino acid sequence.

Whenever according to the various aspects of the invention hCMV-pp65, in particular SEQ ID NO: 1, an epitope sequence of hCMV-pp65, in particular SEQ ID NOs: 108-110, or a T cell receptor sequence specific for hCMV-pp65, in particular SEQ ID NOs: 4-29, is involved, the aim is preferably to induce or determine an immune response against hCMV or a target cell infected by hCMV and preferably being characterized by presentation of hCMV-pp65, and to diagnose, treat or prevent hCMV infection. Preferably the immune response involves the stimulation of an anti-hCMV-pp65 CTL response against infected cells expressing hCMV-pp65 and preferably presenting hCMV-pp65 with class I MHC.

In preferred embodiments, an antigen is a tumor-associated antigen such as NY-ESO-1, TPTE or PLAC1 and the present invention involves the stimulation of an anti-tumor CTL response against malignant cells expressing such tumor-associated antigen and preferably presenting such tumor-associated antigen with class I MHC.

NY-ESO-1 is a cancer/testis antigen expressed in normal adult tissues solely in the testicular germ cells of normal adults and in various cancers. It induces specific humoral and cellular immunity in patients with NY-ESO-1-expressing cancer.

The term "NY-ESO-1" preferably relates to human NY-ESO-1, and, in particular, to a protein comprising the amino acid sequence according to SEQ ID NO: 2 of the sequence listing or a variant of said amino acid sequence.

Whenever according to the various aspects of the invention NY-ESO-1, in particular SEQ ID NO: 2, an epitope sequence of NY-ESO-1, in particular SEQ ID NOs: 111-117 and 175 or a T cell receptor sequence specific for NY-ESO-1, in particular SEQ ID NOs: 30-47, 140-151, 176 and 177 is involved, the aim is preferably to induce or determine an immune response against malignant cells expressing NY-ESO-1 and preferably being characterized by presentation of NY-ESO-1, and to diagnose, treat or prevent a malignant disease involving cells expressing NY-ESO-1. Preferably the immune response involves the stimulation of an anti-NY-ESO-1 CTL response against malignant cells expressing NY-ESO-1 and preferably presenting NY-ESO-1 with class I MHC.

The term "TPTE" relates to "transmembrane phosphatase with tensin homology". The term "TPTE" preferably relates to human TPTE, and, in particular, to a protein comprising the amino acid sequence according to SEQ ID NO: 3 of the sequence listing or a variant of said amino acid sequence.

TPTE expression in healthy tissues is confined to testis and transcript amounts are below the detection limit in all other normal tissue specimens. In contrast, TPTE expression is found across different cancer types including malignant melanoma, breast cancer, lung cancer, prostate cancer, mammary cancer, ovarian cancer, renal cell carcinoma and cervical cancer.

TPTE transcription is initiated during the course of malignant transformation by cancer-associated DNA hypomethylation. Furthermore, TPTE promotes cancer progression and metastatic spread of cancer cells. In particular, TPTE is vital for efficient chemotaxis, a process which is involved in multiple aspects of cancer progression including cancer invasion and metastasis with impact on homing and metastatic destination of cancer cells. TPTE expression in primary tumors is associated with a significantly higher rate of metastatic disease.

Whenever according to the various aspects of the invention TPTE, in particular SEQ ID NO: 3, an epitope sequence of TPTE, in particular SEQ ID NOs: 118-139 and 178-187, or a T cell receptor sequence specific for TPTE, in particular SEQ ID NOs: 48-107 and 188-193, is involved, the aim is preferably to induce or determine an immune response against malignant cells expressing TPTE and preferably being characterized by presentation of TPTE, and to diagnose, treat or prevent a malignant disease involving cells expressing TPTE. Preferably the immune response involves the stimulation of an anti-TPTE CTL response against malignant cells expressing TPTE and preferably presenting TPTE with class I MHC.

The term "PLAC1" relates to "placenta-specific protein 1". The term "PLAC1" preferably relates to human PLAC1, and, in particular, to a protein comprising the amino acid sequence according to SEQ ID NO: 174 of the sequence listing or a variant of said amino acid sequence.

PLAC1 is a placenta-specific gene which is frequently aberrantly activated and highly expressed in a variety of tumor types. PLAC1 expression has been found, for example, in breast cancer, lung cancer, ovarian cancer, gastric cancer, prostate cancer, pancreatic cancer, renal cell cancer, hepatic cancer, sarcoma, thyroid cancer, and head and neck cancer. PLAC1 is expressed in 82% of breast cancer patients. Regarding lung cancer and gastric cancer, PLAC1 is expressed in 42 and 58% of the cases, respectively.

RNAi-mediated silencing of PLAC1 in MCF-7 and BT-549 breast cancer cells profoundly impairs motility, migration, and invasion and induces a G1/S cell cycle block with nearly complete abrogation of proliferation. Knock down of PLAC1 is associated with decreased expression of cyclin D1 and reduced phosphorylation of AKT kinase. PLAC1 is involved not only in cell proliferation but also cell motility, migration and invasion.

Whenever according to the various aspects of the invention PLAC1, in particular SEQ ID NO: 174, an epitope sequence of PLAC1, in particular SEQ ID NOs: 172, 173 and 196, or a T cell receptor sequence specific for PLAC1, in particular SEQ ID NOs: 152-171, 194 and 195, is involved, the aim is preferably to induce or determine an immune response against malignant cells expressing PLAC1 and preferably being characterized by presentation of PLAC1, and to diagnose, treat or prevent a malignant disease involving cells expressing PLAC1. Preferably the immune response involves the stimulation of an anti-PLAC1 CTL response against malignant cells expressing PLAC1 and preferably presenting PLAC1 with class I MHC.

The above described antigen sequences include any variants of said sequences, in particular mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The terms "CMV-pp65", "NY-ESO-1", "TPTE" and "PLAC1" shall encompass (i) splice variants, (ii) posttranslationally modified variants, particularly including variants with different glycosylation such as N-glycosylation status, (iii) conformation variants, and (iv) disease related and non-disease related variants. Preferably, "CMV-pp65", "NY-ESO-1", "TPTE" or "PLAC1" is present in its native conformation.

"Target cell" shall mean a cell which is a target for an immune response such as a cellular immune response. Target cells include cells that present an antigen or an antigen epitope, i.e. a peptide fragment derived from an antigen, and include any undesirable cell such as a virus infected cell or malignant cell as described above. In preferred embodiments, the target cell is a cell expressing an antigen as described herein and preferably presenting said antigen with class I MHC.

The term "subject previously exposed to an antigen" means a subject such as a human being previously having contact with an antigen and preferably being seropositive for the antigen and/or an agent comprising the antigen. Such seropositivity may be determined by determining an immune response to the antigen or an agent comprising the antigen or a component of said agent other than the antigen, e.g. another antigen, in the subject. Said determination of an immune response preferably comprises determining an antibody response such as a IgG response.

The term "epitope" refers to an antigenic determinant in a molecule such as an antigen, i.e., to a part in or fragment of the molecule that is recognized by the immune system, for example, that is recognized by a T cell, in particular when presented in the context of MHC molecules. An epitope of a protein such as a tumor-associated antigen or viral antigen preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 9, 10, 11, 12, 13, 14, 15, 16, 17, 18, 19, 20, 21, 22, 23, 24, or 25 amino acids in length. It is particularly preferred that the epitope in the context of the present invention is a T cell epitope.

The terms "epitope", "fragment of an antigen", "antigen peptide" and "peptide" are used interchangeably herein and preferably relate to an incomplete representation of an antigen which is preferably capable of eliciting an immune response against the antigen or a cell expressing or comprising and preferably presenting the antigen. Preferably, the terms relate to an immunogenic portion of an antigen. Preferably, it is a portion of an antigen that is recognized (i.e., specifically bound) by a T cell receptor, in particular if presented in the context of MHC molecules. Certain preferred immunogenic portions bind to an MHC class I or class II molecule. As used herein, an immunogenic portion is said to "bind to" an MHC class I or class II molecule if such binding is detectable using any assay known in the art.

Preferably, the antigen peptides disclosed herein comprising an amino acid sequence selected from the group consisting of SEQ ID NOs: 108 to 139, 172, 173, 175, 178 to 187 and 196 or a variant of said amino acid sequence are capable of stimulating an immune response, preferably a cellular response against the antigen from which they are derived or cells characterized by expression of the antigen and preferably characterized by presentation of the antigen. Preferably, an antigen peptide is capable of stimulating a cellular response against a cell characterized by presentation of the antigen with class I MHC and preferably is capable of stimulating an antigen-responsive CTL. Preferably, the antigen peptides according to the invention are MHC class I and/or class II presented peptides or can be processed to produce MHC class I and/or class II presented peptides.

Preferably, the sequence bound to the MHC molecule is selected from SEQ ID NOs: 108 to 139, 172, 173, 175, 178 to 187 and 196.

If an antigen peptide is to be presented directly, i.e. without processing, in particular without cleavage, it has a length which is suitable for binding to an MHC molecule, in particular a class I MHC molecule, and preferably is 7-20 amino acids in length, more preferably 7-12 amino acids in length, more preferably 8-11 amino acids in length, in particular 9 or 10 amino acids in length. Preferably the sequence of an antigen peptide which is to be presented directly substantially corresponds and is preferably completely identical to a sequence selected from SEQ ID NOs: 108 to 139, 172, 173, 175, 178 to 187 and 196.

If an antigen peptide is to be presented following processing, in particular following cleavage, the peptide produced by processing has a length which is suitable for binding to an MHC molecule, in particular a class I MHC molecule, and preferably is 7-20 amino acids in length, more preferably 7-12 amino acids in length, more preferably 8-11 amino acids in length, in particular 9 or 10 amino acids in length. Preferably, the sequence of the peptide which is to be presented following processing substantially corresponds and is preferably completely identical to a sequence selected from SEQ ID NOs: 108 to 139, 172, 173, 175, 178 to 187 and 196. Thus, an antigen peptide according to the invention in one embodiment comprises a sequence selected from SEQ ID NOs: 108 to 139, 172, 173, 175, 178 to 187 and 196 and following processing of the antigen peptide makes up a sequence selected from SEQ ID NOs: 108 to 139, 172, 173, 175, 178 to 187 and 196.

Peptides having amino acid sequences substantially corresponding to a sequence of a peptide which is presented by MHC molecules may differ at one or more residues that are not essential for TCR recognition of the peptide as presented by the MHC, or for peptide binding to MHC. Such substantially corresponding peptides preferably are also capable of stimulating an antigen-specific cellular response such as antigen-specific CTL. Peptides having amino acid sequences differing from a presented peptide at residues that do not affect TCR recognition but improve the stability of binding to MHC may improve the immunogenicity of the antigen peptide, and may be referred to herein as "optimized peptides". Using existing knowledge about which of these residues may be more likely to affect binding either to the MHC or to the TCR, a rational approach to the design of substantially corresponding peptides may be employed. Resulting peptides that are functional are contemplated as antigen peptides. Sequences as discussed above are encompassed by the term "variant" used herein.

An antigen peptide may bind to MHC molecules such as MHC molecules on the surface of a cell and thus, may be a "MHC binding peptide". The term "MHC binding peptide" relates to a peptide which binds to an MHC class I and/or an MHC class II molecule. In the case of class I MHC/peptide complexes, the binding peptides are typically 8-10 amino acids long although longer or shorter peptides may be effective. In the case of class II MHC/peptide complexes, the binding peptides are typically 10-25 amino acids long and are in particular 13-18 amino acids long, whereas longer and shorter peptides may be effective.

The term "portion" refers to a fraction. With respect to a particular structure such as an amino acid sequence or protein the term "portion" thereof may designate a continuous or a discontinuous fraction of said structure. Preferably, a portion of an amino acid sequence comprises at least 1%, at least 5%, at least 10%, at least 20%, at least 30%, preferably at least 40%, preferably at least 50%, more preferably at least 60%, more preferably at least 70%, even more preferably at least 80%, and most preferably at least 90% of the amino acids of said amino acid sequence. Preferably, if the portion is a discontinuous fraction said discontinuous fraction is composed of 2, 3, 4, 5, 6, 7, 8, or more parts of a structure, each part being a continuous element of the structure. For example, a discontinuous fraction of an amino acid sequence may be composed of 2, 3, 4, 5, 6, 7, 8, or more, preferably not more than 4 parts of said amino acid sequence, wherein each part preferably comprises at least 5 continuous amino acids, at least 10 continuous amino acids, preferably at least 20 continuous amino acids, preferably at least 30 continuous amino acids of the amino acid sequence.

The terms "part" and "fragment" are used interchangeably herein and refer to a continuous element. For example, a part of a structure such as an amino acid sequence or protein refers to a continuous element of said structure. A portion, a part or a fragment of a structure preferably comprises one or more functional properties of said structure. For example, a portion, a part or a fragment of an epitope, peptide or protein is preferably immunologically equivalent to the epitope, peptide or protein it is derived from. In the context of the present invention, a "part" of a structure such as an amino acid sequence preferably comprises, preferably consists of at least 10%, at least 20%, at least 30%, at least 40%, at least 50%, at least 60%, at least 70%, at least 80%, at least 85%, at least 90%, at least 92%, at least 94%, at least 96%, at least 98%, at least 99% of the entire structure or amino acid sequence. Portions, parts or fragments as discussed above are encompassed by the term "variant" used herein.

"Antigen processing" refers to the degradation of an antigen into procession products, which are fragments of said antigen (e.g., the degradation of a protein into peptides) and the association of one or more of these fragments (e.g., via binding) with MHC molecules for presentation by cells, preferably antigen presenting cells to specific T cells.

An antigen-presenting cell (APC) is a cell that displays antigen in the context of major histocompatibility complex (MHC) on its surface. T cells may recognize this complex using their T cell receptor (TCR). Antigen-presenting cells process antigens and present them to T cells.

Professional antigen-presenting cells are very efficient at internalizing antigen, either by phagocytosis or by receptor-mediated endocytosis, and then displaying a fragment of the antigen, bound to a class II MHC molecule, on their membrane. The T cell recognizes and interacts with the antigen-class II MHC molecule complex on the membrane of the antigen-presenting cell. An additional co-stimulatory signal is then produced by the antigen-presenting cell, leading to activation of the T cell. The expression of co-stimulatory molecules is a defining feature of professional antigen-presenting cells.

The main types of professional antigen-presenting cells are dendritic cells, which have the broadest range of antigen presentation, and are probably the most important antigen-presenting cells, macrophages, B-cells, and certain activated epithelial cells.

Non-professional antigen-presenting cells do not constitutively express the MHC class II proteins required for interaction with naive T cells; these are expressed only upon stimulation of the non-professional antigen-presenting cells by certain cytokines such as IFNγ.

Dendritic cells (DCs) are leukocyte populations that present antigens captured in peripheral tissues to T cells via both MHC class II and I antigen presentation pathways. It is well known that dendritic cells are potent inducers of immune responses and the activation of these cells is a critical step for the induction of antitumoral immunity.

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFa to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which can be used as a simple way to discriminate between two well characterized phenotypes. However, this nomenclature should not be construed to exclude all possible intermediate stages of differentiation.

Immature dendritic cells are characterized as antigen presenting cells with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g. CD54 and CD11) and costimulatory molecules (e.g., CD40, CD80, CD86 and 4-1 BB).

Dendritic cell maturation is referred to as the status of dendritic cell activation at which such antigen-presenting dendritic cells lead to T cell priming, while presentation by immature dendritic cells results in tolerance. Dendritic cell maturation is chiefly caused by biomolecules with microbial features detected by innate receptors (bacterial DNA, viral RNA, endotoxin, etc.), pro-inflammatory cytokines (TNF, IL-1, IFNs), ligation of CD40 on the dendritic cell surface by CD40L, and substances released from cells undergoing stressful cell death. The dendritic cells can be derived by culturing bone marrow cells in vitro with cytokines, such as granulocyte-macrophage colony-stimulating factor (GM-CSF) and tumor necrosis factor alpha.

Cells such as antigen presenting cells or target cells can be loaded with MHC class I presented peptides by exposing, i.e. pulsing, the cells with the peptide or transducing the cells with nucleic acid, preferably RNA, encoding a peptide or protein comprising the peptide to be presented, e.g. a nucleic acid encoding the antigen.

In some embodiments, a pharmaceutical composition of the invention comprises an antigen presenting cell loaded with antigen peptide. In this respect, protocols may rely on in vitro culture/differentiation of dendritic cells manipulated in such a way that they artificially present antigen peptide. Production of genetically engineered dendritic cells may involve introduction of nucleic acids encoding antigens or antigen peptides into dendritic cells. Transfection of dendritic cells with mRNA is a promising antigen-loading technique of stimulating strong antitumor immunity. Such transfection may take place ex vivo, and a pharmaceutical composition comprising such transfected cells may then be used for therapeutic purposes. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al, Immunology and cell Biology 75: 456-460, 1997. Antigen loading of dendritic cells may be achieved by incubating dendritic cells or progenitor cells with antigen, DNA (naked or within a plasmid vector) or RNA; or with antigen-expressing recombinant bacteria or viruses (e.g., vaccinia, fowipox, adenovirus or lentivirus vectors).

The term "immunogenicity" relates to the relative efficiency of an antigen to induce an immune reaction.

The term "immunoreactive cell" in the context of the present invention relates to a cell which exerts effector functions during an immune reaction. An "immunoreactive cell" preferably is capable of binding an antigen or a cell characterized by presentation of an antigen or an antigen peptide derived from an antigen and mediating an immune response. For example, such cells secrete cytokines and/or chemokines, kill microbes, secrete antibodies, recognize infected or cancerous cells, and optionally eliminate such cells. For example, immunoreactive cells comprise T cells (cytotoxic T cells, helper T cells, tumor infiltrating T cells), B cells, natural killer cells, neutrophils, macrophages, and dendritic cells. Preferably, in the context of the present invention, "immunoreactive cells" are T cells, preferably $CD4^+$ and/or $CD8^+$ T cells.

Preferably, an "immunoreactive cell" recognizes an antigen or an antigen peptide derived from an antigen with some degree of specificity, in particular if presented in the context of MHC molecules such as on the surface of antigen presenting cells or diseased cells such as malignant cells or virus-infected cells. Preferably, said recognition enables the cell that recognizes an antigen or an antigen peptide derived from said antigen to be responsive or reactive. If the cell is a helper T cell ($CD4^+$ T cell) bearing receptors that recognize an antigen or an antigen peptide derived from an antigen in the context of MHC class II molecules such responsiveness or reactivity may involve the release of cytokines and/or the activation of $CD8^+$ lymphocytes (CTLs) and/or B-cells. If the cell is a CTL such responsiveness or reactivity may involve the elimination of cells presented in the context of MHC class I molecules, i.e., cells characterized by presentation of an antigen with class I MHC, for example, via apoptosis or perforin-mediated cell lysis. According to the invention, CTL responsiveness may include sustained calcium flux, cell division, production of cytokines such as IFN-γ and TNF-α, up-regulation of activation markers such as CD44 and CD69, and specific cytolytic killing of antigen expressing target cells. CTL responsiveness may also be determined using an artificial reporter that accurately indicates CTL responsiveness. Such CTL that recognizes an antigen or an antigen peptide derived from an antigen and are responsive or reactive are also termed "antigen-responsive CTL" herein. If the cell is a B cell such responsiveness may involve the release of immunoglobulins.

According to the invention, the term "immunoreactive cell" also includes a cell which can mature into an immune cell (such as T cell, in particular T helper cell, or cytolytic T cell) with suitable stimulation. Immunoreactive cells comprise $CD34^+$ hematopoietic stem cells, immature and mature T cells and immature and mature B cells. If production of cytolytic or T helper cells recognizing an antigen is desired, the immunoreactive cell is contacted with a cell presenting an antigen or antigen peptide under conditions which favor production, differentiation and/or selection of cytolytic T cells and of T helper cells. The differentiation of T cell precursors into a cytolytic T cell, when exposed to an antigen, is similar to clonal selection of the immune system.

A "lymphoid cell" is a cell which, optionally after suitable modification, e.g. after transfer of a T cell receptor, is capable of producing an immune response such as a cellular immune response, or a precursor cell of such cell, and includes lymphocytes, preferably T lymphocytes, lymphoblasts, and plasma cells. A lymphoid cell may be an immunoreactive cell as described herein. A preferred lymphoid cell is a T cell lacking endogenous expression of a T cell receptor and which can be modified to express such T cell receptor on the cell surface.

The terms "T cell" and "T lymphocyte" are used interchangeably herein and include T helper cells (CD4+ T cells) and cytotoxic T cells (CTLs, CD8+ T cells) which comprise cytolytic T cells.

T cells belong to a group of white blood cells known as lymphocytes, and play a central role in cell-mediated immunity. They can be distinguished from other lymphocyte types, such as B cells and natural killer cells by the presence of a special receptor on their cell surface called T cell receptors (TCR). The thymus is the principal organ responsible for the T cell's maturation of T cells. Several different subsets of T cells have been discovered, each with a distinct function.

T helper cells assist other white blood cells in immunologic processes, including maturation of B cells into plasma cells and activation of cytotoxic T cells and macrophages, among other functions. These cells are also known as CD4+ T cells because they express the CD4 protein on their surface. Helper T cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T cells destroy virally infected cells and tumor cells, and are also implicated in transplant rejection. These cells are also known as CD8+ T cells since they express the CD8 glycoprotein at their surface. These cells recognize their targets by binding to antigen associated with MHC class I, which is present on the surface of nearly every cell of the body.

A majority of T cells have a T cell receptor (TCR) existing as a complex of several proteins. The actual T cell receptor is composed of two separate peptide chains, which are produced from the independent T cell receptor alpha and beta (TCRα and TCRβ) genes and are called α- and β-TCR chains. γδ T cells (gamma delta T cells) represent a small subset of T cells that possess a distinct T cell receptor (TCR) on their surface. However, in γδ T cells, the TCR is made up of one γ-chain and one δ-chain. This group of T cells is much less common (2% of total T cells) than the αβ T cells.

The structure of the T cell receptor is very similar to immunoglobulin Fab fragments, which are regions defined as the combined light and heavy chain of an antibody arm. Each chain of the TCR is a member of the immunoglobulin superfamily and possesses one N-terminal immunoglobulin (Ig)-variable (V) domain, one Ig-constant (C) domain, a transmembrane/cell membrane-spanning region, and a short cytoplasmic tail at the C-terminal end.

According to the invention, the term "variable region of a T cell receptor" relates to the variable domains of the TCR chains.

The variable domain of both the TCR α-chain and β-chain have three hypervariable or complementarity determining regions (CDRs), whereas the variable region of the β-chain has an additional area of hypervariability (HV4) that does not normally contact antigen and therefore is not considered a CDR. CDR3 is the main CDR responsible for recognizing processed antigen, although CDR1 of the α-chain has also been shown to interact with the N-terminal part of the antigenic peptide, whereas CDR1 of the β-chain interacts with the C-terminal part of the peptide. CDR2 is thought to recognize the MHC. CDR4 of the β-chain is not thought to participate in antigen recognition, but has been shown to interact with superantigens.

According to the invention, the term "at least one of the CDR sequences" preferably means at least the CDR3 sequence. The term "CDR sequences of a T cell receptor chain" preferably relates to CDR1, CDR2 and CDR3 of the α-chain or β-chain of a T cell receptor.

The constant domain of the TCR domain consists of short connecting sequences in which a cysteine residue forms disulfide bonds, which forms a link between the two chains.

All T cells originate from hematopoietic stem cells in the bone marrow. Hematopoietic progenitors derived from hematopoietic stem cells populate the thymus and expand by cell division to generate a large population of immature thymocytes. The earliest thymocytes express neither CD4 nor CD8, and are therefore classed as double-negative (CD4-CD8-) cells. As they progress through their development they become double-positive thymocytes (CD4+ CD8+), and finally mature to single-positive (CD4+CD8− or CD4−CD8+) thymocytes that are then released from the thymus to peripheral tissues.

The first signal in activation of T cells is provided by binding of the T cell receptor to a short peptide presented by the major histocompatibility complex (MHC) on another cell. This ensures that only a T cell with a TCR specific to that peptide is activated. The partner cell is usually a professional antigen presenting cell (APC), usually a dendritic cell in the case of naïve responses, although B cells and macrophages can be important APCs. The peptides presented to CD8+ T cells by MHC class I molecules are 8-10 amino acids in length; the peptides presented to CD4+ T cells by MHC class II molecules are longer, as the ends of the binding cleft of the MHC class II molecule are open.

T cells may generally be prepared in vitro or ex vivo, using standard procedures. For example, T cells may be present within (or isolated from) bone marrow, peripheral blood or a fraction of bone marrow or peripheral blood of a mammal, such as a patient, using a commercially available cell separation system. Alternatively, T cells may be derived from related or unrelated humans, non-human animals, cell lines or cultures. A "sample comprising T cells" may, for example, be peripheral blood mononuclear cells (PBMC).

T cells may be stimulated with antigen, peptide, nucleic acid and/or an antigen presenting cells (APCs) that express an antigen. Such stimulation is performed under conditions and for a time sufficient to permit the generation of T cells that are specific for an antigen, a peptide and/or cells presenting an antigen or a peptide.

Specific activation of CD4+ or CD8+ T cells may be detected in a variety of ways. Methods for detecting specific T cell activation include detecting the proliferation of T cells, the production of cytokines (e.g., lymphokines), or the generation of cytolytic activity. For CD4+ T cells, a preferred method for detecting specific T cell activation is the detection of the proliferation of T cells. For CD8+ T cells, a preferred method for detecting specific T cell activation is the detection of the generation of cytolytic activity.

In order to generate CD8+ T cell lines, antigen-presenting cells, preferably autologous antigen-presenting cells, transfected with a nucleic acid which produces the antigen may be used as stimulator cells.

Nucleic acids such as RNA encoding T cell receptor (TCR) chains may be introduced into lymphoid cells such as T cells or other cells with lytic potential. In a suitable embodiment, the TCR α- and β-chains are cloned out from an antigen-specific T cell line and used for adoptive T cell therapy. The present invention provides T cell receptors specific for an antigen or antigen peptide disclosed herein. In general, this aspect of the invention relates to T cell receptors which recognize or bind antigen peptides presented in the context of MHC. The nucleic acids encoding α- and β-chains of a T cell receptor, e.g. a T cell receptor provided according to the present invention, may be contained on separate nucleic acid molecules such as expression vectors or alternatively, on a single nucleic acid molecule. Accordingly, the term "a nucleic acid encoding a T cell receptor" relates to nucleic acid molecules encoding the T cell receptor chains on the same or preferably on different nucleic acid molecules.

The term "immunoreactive cell reactive with a peptide" relates to an immunoreactive cell which when it recognizes the peptide, in particular if presented in the context of MHC molecules such as on the surface of antigen presenting cells or diseased cells such as malignant cells or virus-infected cells, exerts effector functions of immunoreactive cells as described above.

The term "T cell receptor reactive with a peptide" relates to a T cell receptor which when present on an immunoreactive cell recognizes the peptide, in particular if presented in the context of MHC molecules such as on the surface of antigen presenting cells or diseased cells such as malignant cells or virus-infected cells, such that the immunoreactive cell exerts effector functions of immunoreactive cells as described above.

The term "antigen-reactive T cell" relates to a T cell which recognizes an antigen if presented in the context of MHC molecules such as on the surface of antigen presenting cells or diseased cells such as malignant cells or virus-infected cells and exerts effector functions of T cells as described above.

The term "antigen-specific lymphoid cell" relates to a lymphoid cell which, in particular when provided with an antigen-specific T cell receptor, recognizes the antigen if presented in the context of MHC molecules such as on the surface of antigen presenting cells or diseased cells such as malignant cells or virus-infected cells and preferably exerts effector functions of T cells as described above. T cells and other lymphoid cells are considered to be specific for antigen if the cells kill target cells expressing an antigen and/or presenting an antigen peptide. T cell specificity may be evaluated using any of a variety of standard techniques, for example, within a chromium release assay or proliferation assay. Alternatively, synthesis of lymphokines (such as interferon-γ) can be measured The term "major histocompatibility complex" and the abbreviation "MHC" include MHC class I and MHC class II molecules and relate to a complex of genes which occurs in all vertebrates. MHC proteins or molecules are important for signaling between lymphocytes and antigen presenting cells or diseased cells in immune reactions, wherein the MHC proteins or molecules bind peptides and present them for recognition by T cell receptors. The proteins encoded by the MHC are expressed on the surface of cells, and display both self antigens (peptide fragments from the cell itself) and nonself antigens (e.g., fragments of invading microorganisms) to a T cell.

The MHC region is divided into three subgroups, class I, class II, and class III. MHC class I proteins contain an α-chain and β-microglobulin (not part of the MHC encoded by chromosome 15). They present antigen fragments to cytotoxic T cells. On most immune system cells, specifically on antigen-presenting cells, MHC class II proteins contain α- and β-chains and they present antigen fragments to T-helper cells. MHC class III region encodes for other immune components, such as complement components and some that encode cytokines.

In humans, genes in the MHC region that encode antigen-presenting proteins on the cell surface are referred to as human leukocyte antigen (HLA) genes. However the abbreviation MHC is often used to refer to HLA gene products. HLA genes include the nine so-called classical MHC genes: HLA-A, HLA-B, HLA-C, HLA-DPA1, HLA-DPB1, HLA-DQA1, HLA-DQB1, HLA-DRA, and HLA-DRB1.

In one preferred embodiment of all aspects of the invention an MHC molecule is an HLA molecule.

By "cell characterized by presentation of an antigen", "cell presenting an antigen", "antigen presented by a cell", "antigen presented" or similar expressions is meant a cell such as a diseased cell such as a virus-infected cell or a malignant cell, or an antigen presenting cell presenting the antigen it expresses or a fragment derived from said antigen, e.g. by processing of the antigen, in the context of MHC molecules, in particular MHC Class I molecules. Similarly, the terms "disease characterized by presentation of an antigen" denotes a disease involving cells characterized by presentation of an antigen, in particular with class I MHC. Presentation of an antigen by a cell may be effected by transfecting the cell with a nucleic acid such as RNA encoding the antigen.

By "fragment of an antigen which is presented" or similar expressions is meant that the fragment can be presented by MHC class I or class II, preferably MHC class I, e.g. when added directly to antigen presenting cells. In one embodiment, the fragment is a fragment which is naturally presented by cells expressing an antigen.

Some therapeutic methods are based on a reaction of the immune system of a patient, which results in a lysis of diseased cells which present an antigen with class I MHC. In this connection, for example autologous cytotoxic T lymphocytes specific for a complex of an antigen peptide and an MHC molecule may be administered to a patient having a disease. The production of such cytotoxic T lymphocytes in vitro is known. An example of a method of differentiating T cells can be found in WO-A-9633265. Generally, a sample containing cells such as blood cells is taken from the patient and the cells are contacted with a cell which presents the complex and which can cause propagation of cytotoxic T lymphocytes (e.g. dendritic cells). The target cell may be a transfected cell such as a COS cell. These transfected cells present the desired complex on their surface and, when contacted with cytotoxic T lymphocytes, stimulate propagation of the latter. The clonally expanded autologous cytotoxic T lymphocytes are then administered to the patient.

In another method of selecting cytotoxic T lymphocytes, fluorogenic tetramers of MHC class I molecule/peptide complexes are used for obtaining specific clones of cytotoxic T lymphocytes (Altman et al. (1996), Science 274:94-96; Dunbar et al. (1998), Curr. Biol. 8:413-416, 1998).

Furthermore, cells presenting the desired complex (e.g. dendritic cells) may be combined with cytotoxic T lymphocytes of healthy individuals or another species (e.g. mouse) which may result in propagation of specific cytotoxic T lymphocytes with high affinity. The high affinity T cell receptor of these propagated specific T lymphocytes may be cloned and optionally humanized to a different extent, and the T cell receptors thus obtained then transduced via gene transfer, for example using retroviral vectors, into T cells of patients. Adoptive transfer may then be carried out using these genetically altered T lymphocytes (Stanislawski et al. (2001), Nat Immunol. 2:962-70; Kessels et al. (2001), Nat Immunol. 2:957-61.

Cytotoxic T lymphocytes may also be generated in vivo in a manner known per se. One method uses nonproliferative cells expressing an MHC class I/peptide complex. The cells used here will be those which usually express the complex, such as irradiated tumor cells or cells transfected with one or both genes necessary for presentation of the complex (i.e. the antigenic peptide and the presenting MHC molecule). Another preferred form is the introduction of an antigen in the form of recombinant RNA which may be introduced into cells by liposomal transfer or by electroporation, for example. The resulting cells present the complex of interest and are recognized by autologous cytotoxic T lymphocytes which then propagate.

A similar effect can be achieved by combining an antigen or an antigen peptide with an adjuvant in order to make incorporation into antigen-presenting cells in vivo possible. The antigen or antigen peptide may be represented as protein, as DNA (e.g. within a vector) or as RNA. The antigen may be processed to produce a peptide partner for the MHC molecule, while a fragment thereof may be presented without the need for further processing. The latter is the case in particular, if these can bind to MHC molecules. Preference is given to administration forms in which the complete antigen is processed in vivo by a dendritic cell, since this may also produce T helper cell responses which are needed for an effective immune response (Ossendorp et al., Immunol Lett. (2000), 74:75-9; Ossendorp et al. (1998), J. Exp. Med. 187:693-702. In general, it is possible to administer an effective amount of the tumor-associated antigen to a patient by intradermal injection, for example. However, injection may also be carried out intranodally into a lymph node (Maloy et al. (2001), Proc Natl Acad Sci USA 98:3299-303.

According to the invention, a "reference" such as a reference sample or reference organism may be used to correlate and compare the results obtained in the methods of the invention from a test sample or test organism. Typically the reference organism is a healthy organism, in particular an organism which does not suffer from a disease such as a malignant disease or viral disease. A "reference value" or "reference level" can be determined from a reference empirically by measuring a sufficiently large number of references. Preferably the reference value is determined by measuring at least 2, preferably at least 3, preferably at least 5, preferably at least 8, preferably at least 12, preferably at least 20, preferably at least 30, preferably at least 50, or preferably at least 100 references.

The term "immunoglobulin" relates to proteins of the immunoglobulin superfamily, preferably to antigen receptors such as antibodies or the B cell receptor (BCR). The immunoglobulins are characterized by a structural domain, i.e., the immunoglobulin domain, having a characteristic immunoglobulin (Ig) fold. The term encompasses membrane bound immunoglobulins as well as soluble immunoglobulins. Membrane bound immunoglobulins are also termed surface immunoglobulins or membrane immunoglobulins, which are generally part of the BCR. Soluble immunoglobulins are generally termed antibodies. Immunoglobulins generally comprise several chains, typically two identical heavy chains and two identical light chains which are linked via disulfide bonds. These chains are primarily composed of immunoglobulin domains, such as the $V_L$ (variable light chain) domain, $C_L$ (constant light chain) domain, and the $C_H$ (constant heavy chain) domains $C_H1$, $C_H2$, $C_H3$, and $C_H4$. There are five types of mammalian immunoglobulin heavy chains, i.e., α, δ, ε, γ, and μ which account for the different classes of antibodies, i.e., IgA, IgD, IgE, IgG, and IgM. As opposed to the heavy chains of soluble immunoglobulins, the heavy chains of membrane or surface immunoglobulins comprise a transmembrane domain and a short cytoplasmic domain at their carboxy-terminus. In mammals there are two types of light chains, i.e., lambda and kappa. The immunoglobulin chains comprise a variable region and a constant region. The constant region is essentially conserved within the different isotypes of the immunoglobulins, wherein the variable part is highly divers and accounts for antigen recognition.

The term "antibody" refers to a glycoprotein comprising at least two heavy (H) chains and two light (L) chains inter-connected by disulfide bonds, and includes any molecule comprising an antigen binding portion thereof. The term "antibody" includes monoclonal antibodies and fragments or derivatives thereof, including, without limitation, human monoclonal antibodies, humanized monoclonal antibodies, chimeric monoclonal antibodies, single chain antibodies, e.g., scFv's and antigen-binding antibody fragments such as Fab and Fab' fragments and also includes all recombinant forms of antibodies, e.g., antibodies expressed in prokaryotes, unglycosylated antibodies, and any antigen-binding antibody fragments and derivatives. Each heavy chain is comprised of a heavy chain variable region (abbreviated herein as $V_H$) and a heavy chain constant region. Each light chain is comprised of a light chain variable region (abbreviated herein as $V_L$) and a light chain constant region. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

According to the present invention, a T cell receptor or an antibody is capable of binding to a predetermined target if it has a significant affinity for said predetermined target and binds to said predetermined target in standard assays. "Affinity" or "binding affinity" is often measured by equilibrium dissociation constant ($K_D$). A T cell receptor or an antibody is not (substantially) capable of binding to a target if it has no significant affinity for said target and does not bind significantly to said target in standard assays.

A T cell receptor or an antibody is preferably capable of binding specifically to a predetermined target. A T cell receptor or an antibody is specific for a predetermined target if it is capable of binding to said predetermined target while it is not (substantially) capable of binding to other targets, i.e. has no significant affinity for other targets and does not significantly bind to other targets in standard assays.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect such as induction of a humoral and/or cellular immune response, the strength and/or duration of the induced immune reaction, or the specificity of the induced immune reaction. In the context of the present invention, the term "immunologically equivalent" is preferably used with respect to the immunological effects or properties of a peptide or peptide variant used for immunization. For example, an amino acid sequence is immunologically equivalent to a reference amino acid sequence if said amino acid sequence when exposed to the immune system of a subject induces an immune reaction having a specificity of reacting with the reference amino acid sequence.

The term "immune effector functions" in the context of the present invention includes any functions mediated by components of the immune system that result, for example, in the killing of virally infected cells or tumor cells, or in the inhibition of tumor growth and/or inhibition of tumor development, including inhibition of tumor dissemination and metastasis. Preferably, the immune effector functions in the context of the present invention are T cell mediated effector functions. Such functions comprise in the case of a helper T cell (CD4$^+$ T cell) the recognition of an antigen or an antigen peptide derived from an antigen in the context of MHC class II molecules by T cell receptors, the release of cytokines and/or the activation of CD8$^+$ lymphocytes (CTLs) and/or B-cells, and in the case of CTL the recognition of an antigen or an antigen peptide derived from an antigen in the context of MHC class I molecules by T cell receptors, the elimination of cells presented in the context of MHC class I molecules, i.e., cells characterized by presentation of an antigen with class I MHC, for example, via apoptosis or perforin-mediated cell lysis, production of cytokines such as IFN-γ and TNF-α, and specific cytolytic killing of antigen expressing target cells.

The term "T cell receptor having the specificity of another T cell receptor" means that the two T cell receptors, in particular when present on an immunoreactive cell, recognize the same epitope, in particular when presented in the context of MHC molecules such as on the surface of antigen-presenting cells or diseased cells such as virus-infected cells or malignant cells and preferably provide the immunoreactive cell with effector functions as disclosed above. Preferably, binding specificity and/or binding affinity of the T cell receptors are similar or identical. In one preferred embodiment, a "T cell receptor having the specificity of another T cell receptor" relates to a T cell receptor comprising at least the CDR regions, preferably at least the variable region of the other T cell receptor. In one embodiment, the two T cell receptors are essentially identical or identical.

A nucleic acid is according to the invention preferably deoxyribonucleic acid (DNA) or ribonucleic acid (RNA), more preferably RNA, most preferably in vitro transcribed RNA (IVT RNA). Nucleic acids include according to the invention genomic DNA, cDNA, mRNA, recombinantly prepared and chemically synthesized molecules. A nucleic acid may according to the invention be in the form of a molecule which is single stranded or double stranded and linear or closed covalently to form a circle. A nucleic can be employed for introduction into, i.e. transfection of, cells, for example, in the form of RNA which can be prepared by in vitro transcription from a DNA template. The RNA can moreover be modified before application by stabilizing sequences, capping, and polyadenylation.

The nucleic acids described herein may be comprised in a vector. The term "vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

As the vector for expression of a T cell receptor, either of a vector type in which the T cell receptor chains are present in different vectors or a vector type in which the T cell receptor chains are present in the same vector can be used.

In those cases of the invention in which an MHC molecule presents an antigen or an antigen peptide, a nucleic acid may also comprise a nucleic acid sequence coding for said MHC molecule. The nucleic acid sequence coding for the MHC molecule may be present on the same nucleic acid molecule as the nucleic acid sequence coding for the antigen or the antigen peptide, or both nucleic acid sequences may be present on different nucleic acid molecules. In the latter case, the two nucleic acid molecules may be cotransfected into a cell. If a host cell expresses neither the antigen or the antigen peptide nor the MHC molecule, both nucleic acid sequences coding therefore may be transfected into the cell either on the same nucleic acid molecule or on different nucleic acid molecules. If the cell already expresses the MHC molecule, only the nucleic acid sequence coding for the antigen or the antigen peptide can be transfected into the cell.

As used herein, the term "RNA" means a molecule comprising at least one ribonucleotide residue. By "ribonucleotide" is meant a nucleotide with a hydroxyl group at the 2'-position of a beta-D-ribo-furanose moiety. The term includes double stranded RNA, single stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the present invention, the term "RNA" includes and preferably relates to "mRNA" which means "messenger RNA" and relates to a "transcript" which may be produced using DNA as template and encodes a peptide or protein. mRNA typically comprises a 5' non translated region, a protein or peptide coding region and a 3' non translated region. mRNA has a limited halftime in cells and in vitro. Preferably, mRNA is produced by in vitro transcription using a DNA template. In one embodiment of the invention, the RNA that is to be introduced into a cell is obtained by in vitro transcription of an appropriate DNA template.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". According to the present invention, RNA may be obtained by in vitro transcription of an appropriate DNA template. The promoter for controlling transcription can be any promoter for any RNA polymerase. Particular examples of RNA polymerases are the T7, T3, and SP6 RNA polymerases. A DNA template for in vitro transcription may be obtained by cloning of a nucleic acid, in particular cDNA, and introducing it into an appropriate vector for in vitro transcription. The cDNA may be obtained by reverse transcription of RNA. Preferably cloning vectors are used for producing transcripts which generally are designated transcription vectors.

The cDNA containing vector template may comprise vectors carrying different cDNA inserts which following transcription results in a population of different RNA molecules optionally capable of expressing different factors or may comprise vectors carrying only one species of cDNA insert which following transcription only results in a population of one RNA species capable of expressing only one factor. Thus, it is possible to produce RNA capable of expressing a single factor only or to produce compositions of different RNAs.

The nucleic acids described according to the invention have preferably been isolated. The term "isolated nucleic acid" means according to the invention that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid which is available for manipulation by recombinant DNA techniques.

Nucleic acids may, according to the invention, be present alone or in combination with other nucleic acids, which may be homologous or heterologous. In preferred embodiments, a nucleic acid is functionally linked to expression control sequences which may be homologous or heterologous with respect to said nucleic acid. The term "homologous" means that the nucleic acids are also functionally linked naturally and the term "heterologous" means that the nucleic acids are not functionally linked naturally.

A nucleic acid and an expression control sequence are "functionally" linked to one another, if they are covalently linked to one another in such a way that expression or transcription of said nucleic acid is under the control or under the influence of said expression control sequence. If the nucleic acid is to be translated into a functional protein, then, with an expression control sequence functionally linked to a coding sequence, induction of said expression control sequence results in transcription of said nucleic acid, without causing a frame shift in the coding sequence or said coding sequence not being capable of being translated into the desired protein or peptide.

The term "expression control sequence" or "expression control element" comprises according to the invention promoters, ribosome binding sites, enhancers and other control elements which regulate transcription of a gene or translation of a mRNA. In particular embodiments of the invention, the expression control sequences can be regulated. The exact structure of expression control sequences may vary as a function of the species or cell type, but generally comprises 5'-untranscribed and 5'- and 3'-untranslated sequences which are involved in initiation of transcription and translation, respectively, such as TATA box, capping sequence, CAAT sequence, and the like. More specifically, 5'-untranscribed expression control sequences comprise a promoter region which includes a promoter sequence for transcriptional control of the functionally linked nucleic acid. Expression control sequences may also comprise enhancer sequences or upstream activator sequences.

According to the invention the term "promoter" or "promoter region" relates to a nucleic acid sequence which is located upstream (5') to the nucleic acid sequence being expressed and controls expression of the sequence by providing a recognition and binding site for RNA-polymerase. The "promoter region" may include further recognition and binding sites for further factors which are involved in the regulation of transcription of a gene. A promoter may control the transcription of a prokaryotic or eukaryotic gene. Furthermore, a promoter may be "inducible" and may initiate transcription in response to an inducing agent or may be "constitutive" if transcription is not controlled by an inducing agent. A gene which is under the control of an inducible promoter is not expressed or only expressed to a small extent if an inducing agent is absent. In the presence of the inducing agent the gene is switched on or the level of transcription is increased. This is mediated, in general, by binding of a specific transcription factor.

Promoters which are preferred according to the invention include promoters for SP6, T3 and T7 polymerase, human U6 RNA promoter, CMV promoter, and artificial hybrid promoters thereof (e.g. CMV) where a part or parts are fused to a part or parts of promoters of genes of other cellular proteins such as e.g. human GAPDH (glyceraldehyde-3-phosphate dehydrogenase), and including or not including (an) additional intron(s).

The term "expression" is used herein in its broadest meaning and comprises the production of RNA or of RNA and protein or peptide. With respect to RNA, the term "expression" or "translation" relates in particular to the production of peptides or proteins. Expression may be transient or may be stable. According to the invention, the term expression also includes an "aberrant expression" or "abnormal expression".

"Aberrant expression" or "abnormal expression" means according to the invention that expression is altered, preferably increased, compared to a reference, e.g. a state in a subject not having a disease associated with aberrant or abnormal expression of a certain protein, e.g., a tumor-associated antigen. An increase in expression refers to an increase by at least 10%, in particular at least 20%, at least 50% or at least 100%, or more. In one embodiment, expression is only found in a diseased tissue, while expression in a healthy tissue is repressed.

The term "specifically expressed" means that a protein is essentially only expressed in a specific tissue or organ. For example, a tumor-associated antigen specifically expressed in gastric mucosa means that said protein is primarily expressed in gastric mucosa and is not expressed in other tissues or is not expressed to a significant extent in other tissue or organ types. Thus, a protein that is exclusively expressed in cells of the gastric mucosa and to a significantly lesser extent in any other tissue, such as testis, is specifically expressed in cells of the gastric mucosa. In some embodiments, a tumor-associated antigen may also be specifically expressed under normal conditions in more than one tissue type or organ, such as in 2 or 3 tissue types or organs, but preferably in not more than 3 different tissue or organ types. In this case, the tumor-associated antigen is then specifically expressed in these organs. For example, if a tumor-associated antigen is expressed under normal conditions preferably to an approximately equal extent in lung and stomach, said tumor-associated antigen is specifically expressed in lung and stomach.

The term "translation" according to the invention relates to the process in the ribosomes of a cell by which a strand of messenger RNA directs the assembly of a sequence of amino acids to make a protein or peptide.

According to the invention, the term "nucleic acid encoding" means that nucleic acid, if present in the appropriate environment, preferably within a cell, can be expressed to produce a protein or peptide it encodes.

According to the invention, the stability and translation efficiency of the RNA introduced into a cell may be modified as required. For example, RNA may be stabilized and its translation increased by one or more modifications having a stabilizing effects and/or increasing translation efficiency of RNA. Such modifications are described, for example, in PCT/EP2006/009448 incorporated herein by reference.

For example, RNA having an unmasked poly-A sequence is translated more efficiently than RNA having a masked poly-A sequence. The term "poly-A sequence" or "poly-A+" relates to a sequence of adenyl (A) residues which typically is located on the 3'-end of a RNA molecule and "unmasked poly-A sequence" means that the poly-A sequence at the 3'-end of an RNA molecule ends with an A of the poly-A sequence and is not followed by nucleotides other than A located at the 3'-end, i.e. downstream, of the poly-A sequence. Furthermore, a long poly-A sequence of about 120 base pairs results in an optimal transcript stability and translation efficiency of RNA.

Therefore, in order to increase stability and/or expression of the RNA used according to the present invention, it may be modified so as to be present in conjunction with a poly-A sequence, preferably having a length of 10 to 500, more preferably 30 to 300, even more preferably 65 to 200 and especially 100 to 150 adenosine residues. In an especially preferred embodiment the poly-A sequence has a length of approximately 120 adenosine residues. To further increase stability and/or expression of the RNA used according to the invention, the poly-A sequence can be unmasked.

In addition, incorporation of a 3'-non translated region (UTR) into the 3'-non translated region of an RNA molecule can result in an enhancement in translation efficiency. A synergistic effect may be achieved by incorporating two or more of such 3'-non translated regions. The 3'-non translated regions may be autologous or heterologous to the RNA into which they are introduced. In one particular embodiment the 3'-non translated region is derived from the human β-globin gene.

A combination of the above described modifications, i.e. incorporation of a poly-A sequence, unmasking of a poly-A sequence and incorporation of one or more 3'-non translated regions, has a synergistic influence on the stability of RNA and increase in translation efficiency.

In order to increase expression of the RNA used according to the present invention, it may be modified within the coding region, i.e. the sequence encoding the expressed factor, preferably without altering the sequence of the expressed factor, so as to increase the GC-content and thus, enhance translation in cells.

In further embodiments of the invention, the RNA that is to be introduced into a cell has, at its 5'-end, a Cap structure or a regulatory sequence, which promotes the translation in the host cell. Preferably, RNA is capped at its 5'-end by an optionally modified 7-methylguanosine attached by a 5'-5' bridge to the first transcribed nucleotide of the mRNA chain. Preferably, the 5'-end of the RNA includes a Cap structure having the following general formula:

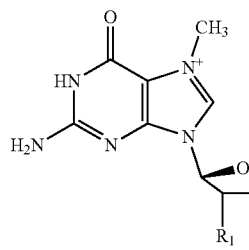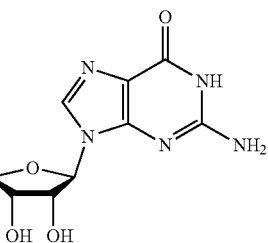

wherein $R_1$ and $R_2$ are independently hydroxy or methoxy and $W^-$, $X^-$ and $Y^-$ are independently oxygen or sulfur. In a preferred embodiment, $R_1$ and $R_2$ are hydroxy and $W^-$, $X^-$ and $Y^-$ are oxygen. In a further preferred embodiment, one of $R_1$ and $R_2$, preferably $R_1$ is hydroxy and the other is methoxy and $W^-$, $X^-$ and $Y^-$ are oxygen. In a further preferred embodiment, $R_1$ and $R_2$ are hydroxy and one of $W^-$, $X^-$ and $Y^-$, preferably $X^-$ is sulfur while the other are oxygen. In a further preferred embodiment, one of $R_1$ and $R_2$, preferably $R_2$ is hydroxy and the other is methoxy and one of $W^-$, $X^-$ and $Y^-$, preferably $X^-$ is sulfur while the other are oxygen. In all of the above described embodiments, in particular in those embodiments where $X^-$ is defined as sulfur, $X^-$ may alternatively be boron or selenium.

In the above formula, the nucleotide on the right hand side is connected to the RNA chain through its 3'-group.

Those Cap structures wherein at least one of $W^-$, $X^-$ and $Y^-$ is sulfur, i.e. which have a phosphorothioate moiety, exist in different diastereoisomeric forms all of which are encompassed herein. Furthermore, the present invention encompasses all tautomers and stereoisomers of the above formula.

Of course, if according to the present invention it is desired to decrease stability and/or translation efficiency of RNA, it is possible to modify RNA so as to interfere with the function of elements as described above increasing the stability and/or translation efficiency of RNA.

According to the present invention, any technique useful for introducing, i.e. transferring or transfecting, nucleic acids into cells may be used. Preferably, RNA is transfected into cells by standard techniques. Such techniques include electroporation, lipofection and microinjection. In one particularly preferred embodiment of the present invention, RNA is introduced into cells by electroporation.

Electroporation or electropermeabilization relates to a significant increase in the electrical conductivity and permeability of the cell plasma membrane caused by an externally applied electrical field. It is usually used in molecular biology as a way of introducing some substance into a cell.

Electroporation is usually done with electroporators, appliances which create an electro-magnetic field in the cell solution. The cell suspension is pipetted into a glass or plastic cuvette which has two aluminum electrodes on its sides. For electroporation, typically a cell suspension of around 50 microliters is used. Prior to electroporation it is mixed with the nucleic acid to be transfected. The mixture is pipetted into the cuvette, the voltage and capacitance is set and the cuvette inserted into the electroporator. Preferably, liquid medium is added immediately after electroporation (in the cuvette or in an eppendorf tube), and the tube is incubated at the cells' optimal temperature for an hour or more to allow recovery of the cells and optionally expression of antibiotic resistance.

According to the invention it is preferred that introduction of nucleic acid encoding a protein or peptide into cells results in expression of said protein or peptide.

The term "peptide" comprises oligo- and polypeptides and refers to substances comprising two or more, preferably 3 or more, preferably 4 or more, preferably 6 or more, preferably 8 or more, preferably 9 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

Preferably, the proteins and peptides described according to the invention have been isolated. The terms "isolated protein" or "isolated peptide" mean that the protein or peptide has been separated from its natural environment. An isolated protein or peptide may be in an essentially purified state. The term "essentially purified" means that the protein or peptide is essentially free of other substances with which it is associated in nature or in vivo.

The teaching given herein with respect to specific amino acid sequences, e.g. those shown in the sequence listing, is to be construed so as to also relate to modifications, i.e. variants, of said specific sequences resulting in sequences which are functionally equivalent to said specific sequences, e.g. amino acid sequences exhibiting properties identical or similar to those of the specific amino acid sequences. One important property is to retain binding of a peptide to an MHC molecule and/or to a T cell receptor or of a T cell receptor to its target or to sustain effector functions of a T cell. Preferably, a sequence modified with respect to a specific sequence, when it replaces the specific sequence in a T cell receptor retains binding of said T cell receptor to the target and preferably functions of said T cell receptor or T cell carrying the T cell receptor as described herein.

It will be appreciated by those skilled in the art that in particular the sequences of the CDR sequences, hypervariable and variable regions can be modified without losing the ability to bind to a target. For example, CDR sequences will be either identical or highly homologous to the CDR sequences specified herein.

A peptide "variant" may retain the immunogenicity of a given peptide (e.g. the ability of the variant to react with T cell lines or clones is not substantially diminished relative to the given peptide). In other words, the ability of a variant to react with T cell lines or clones may be enhanced or unchanged, relative to the given peptide, or may be diminished by less than 50%, and preferably less than 20%, relative to the given peptide.

A variant may be identified by evaluating its ability to bind to a MHC molecule. In one preferred embodiment, a variant peptide has a modification such that the ability of the variant peptide to bind to a MHC molecule is increased relative to the given peptide. The ability of the variant peptide to bind to a MHC molecule may be increased by at least 2-fold, preferably at least 3-fold, 4-fold, or 5-fold relative to that of a given peptide. Accordingly, within certain preferred embodiments, a peptide comprises a variant in which 1 to 3 amino acid resides within an immunogenic portion are substituted such that the ability to react with T cell lines or clones is statistically greater than that for the unmodified peptide. Such substitutions are preferably located within an MHC binding site of the peptide. Preferred substitutions allow increased binding to MHC class I or class II molecules. Certain variants contain conservative substitutions.

By "highly homologous" it is contemplated that from 1 to 5, preferably from 1 to 4, such as 1 to 3 or 1 or 2 substitutions may be made.

The term "variant" according to the invention also includes mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence.

For the purposes of the present invention, "variants" of an amino acid sequence comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids or nucleotides that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

Homologous amino acid sequences exhibit according to the invention at least 40%, in particular at least 50%, at least 60%, at least 70%, at least 80%, at least 90% and preferably at least 95%, at least 98 or at least 99% identity of the amino acid residues.

The amino acid sequence variants described herein may readily be prepared by the skilled person, for example, by recombinant DNA manipulation. The manipulation of DNA sequences for preparing proteins and peptides having substitutions, additions, insertions or deletions, is described in detail in Sambrook et al. (1989), for example. Furthermore, the peptides and amino acid variants described herein may be readily prepared with the aid of known peptide synthesis techniques such as, for example, by solid phase synthesis and similar methods.

The invention includes derivatives of the peptides or proteins described herein which are comprised by the terms "peptide" and "protein". According to the invention, "derivatives" of proteins and peptides are modified forms of proteins and peptides. Such modifications include any chemical modification and comprise single or multiple substitutions, deletions and/or additions of any molecules associated with the protein or peptide, such as carbohydrates, lipids and/or proteins or peptides. In one embodiment, "derivatives" of proteins or peptides include those modified analogs resulting from glycosylation, acetylation, phosphorylation, amidation, palmitoylation, myristoylation, isoprenylation, lipidation, alkylation, derivatization, introduction of protective/blocking groups, proteolytic cleavage or binding to an antibody or to another cellular ligand. The term "derivative" also extends to all functional chemical equivalents of said proteins and peptides. Preferably, a modified peptide has increased stability and/or increased immunogenicity.

Also included are mimetics of peptides. Such mimetics may comprise amino acids linked to one or more amino acid mimetics (i e., one or more amino acids within the peptide may be replaced by an amino acid mimetic) or may be entirely nonpeptide mimetics. An amino acid mimetic is a compound that is conformationally similar to an amino acid, e.g. such that it can be substituted for an amino acid without substantially diminishing the ability to react with T cell lines or clones. A nonpeptide mimetic is a compound that does not contain amino acids, and that has an overall conformation that is similar to a peptide, e.g. such that the ability of the mimetic to react with T cell lines or clones is not substantially diminished relative to the ability of a given peptide.

According to the invention, a variant, derivative, modified form, fragment, part or portion of an amino acid sequence, peptide or protein preferably has a functional property of the amino acid sequence, peptide or protein, respectively, from which it has been derived, i.e. it is functionally equivalent. In one embodiment, a variant, derivative, modified form, fragment, part or portion of an amino acid sequence, peptide or protein is immunologically equivalent to the amino acid sequence, peptide or protein, respectively, from which it has been derived. In one embodiment, the functional property is an immunological property.

A particular property is the ability to form a complex with MHC molecules and, where appropriate, generate an immune response, preferably by stimulating cytotoxic or T helper cells.

The term "derived" means according to the invention that a particular entity, in particular a particular sequence, is present in the object from which it is derived, in particular an organism or molecule. In the case of amino acid sequences, especially particular sequence regions, "derived" in particular means that the relevant amino acid sequence is derived from an amino acid sequence in which it is present.

The term "cell" or "host cell" preferably is an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transformed or transfected with an exogenous nucleic acid. The term "cell" includes according to the invention prokaryotic cells (e.g., *E. coli*) or eukaryotic cells (e.g., dendritic cells, B cells, CHO cells, COS cells, K562 cells, HEK293 cells, HELA cells, yeast cells, and insect cells). The exogenous nucleic acid may be found inside the cell (i) freely dispersed as such, (ii) incorporated in a recombinant vector, or (iii) integrated into the host cell genome or mitochondrial DNA. Mammalian cells are particularly preferred, such as cells from humans, mice, hamsters, pigs, goats, and primates. The cells may be derived from a large number of tissue types and include primary cells and cell lines. Specific examples include keratinocytes, peripheral blood leukocytes, bone marrow stem cells, and embryonic stem cells. In further embodiments, the cell is an antigen-presenting cell, in particular a dendritic cell, a monocyte, or macrophage.

A cell which comprises a nucleic acid molecule preferably express the peptide or protein encoded by the nucleic acid.

The cell may be a recombinant cell and may secrete the encoded peptide or protein, may express it on the surface and preferably may additionally express an MHC molecule which binds to said peptide or protein or a procession product thereof. In one embodiment, the cell expresses the MHC molecule endogenously. In a further embodiment, the cell expresses the MHC molecule and/or the peptide or protein or the procession product thereof in a recombinant manner. The cell is preferably nonproliferative. In a preferred embodiment, the cell is an antigen-presenting cell, in particular a dendritic cell, a monocyte or a macrophage.

The term "clonal expansion" refers to a process wherein a specific entity is multiplied. In the context of the present invention, the term is preferably used in the context of an immunological response in which lymphocytes are stimulated by an antigen, proliferate, and the specific lymphocyte recognizing said antigen is amplified. Preferably, clonal expansion leads to differentiation of the lymphocytes.

A disease associated with antigen expression may be detected based on the presence of T cells that specifically react with a peptide in a biological sample. Within certain methods, a biological sample comprising CD4+ and/or CD8+ T cells isolated from a patient is incubated with a peptide of the invention, a nucleic acid encoding such peptide and/or an antigen-presenting cell that expresses and/or presents at least an immunogenic portion of such a peptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). For CD4+ T cells, activation is preferably detected by evaluating proliferation of the T cells. For CD8+ T cells, activation is preferably detected by evaluating cytolytic activity. A level of proliferation that is at least two fold greater and/or a level of cytolytic activity that is at least 20% greater than in disease-free subjects indicates the presence of a disease associated with antigen expression in the subject.

"Reduce" or "inhibit" as used herein means the ability to cause an overall decrease, preferably of 5% or greater, 10% or greater, 20% or greater, more preferably of 50% or greater, and most preferably of 75% or greater, in the level. The term "inhibit" or similar phrases includes a complete or essentially complete inhibition, i.e. a reduction to zero or essentially to zero.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%.

The agents, compositions and methods described herein can be used to treat a subject with a disease, e.g., a disease characterized by the presence of diseased cells expressing an antigen and presenting an antigen peptide. Examples of diseases which can be treated and/or prevented encompass all diseases expressing one of the antigens described herein. Particularly preferred diseases are viral diseases such as hCMV infection and malignant diseases.

The agents, compositions and methods described herein may also be used for immunization or vaccination to prevent a disease described herein.

According to the invention, the term "disease" refers to any pathological state, including viral infections and malignant diseases, in particular those forms of viral infections and malignant diseases described herein.

The terms "normal tissue" or "normal conditions" refer to healthy tissue or the conditions in a healthy subject, i.e., non-pathological conditions, wherein "healthy" preferably means non-virally infected or non-cancerous.

"Disease involving cells expressing an antigen" means according to the invention that expression of the antigen in cells of a diseased tissue or organ is preferably increased compared to the state in a healthy tissue or organ. An increase refers to an increase by at least 10%, in particular at least 20%, at least 50%, at least 100%, at least 200%, at least 500%, at least 1000%, at least 10000% or even more. In one embodiment, expression is only found in a diseased tissue, while expression in a healthy tissue is repressed. According to the invention, diseases involving or being associated with cells expressing an antigen include viral infections and malignant diseases, in particular those forms of viral infections and malignant diseases described herein.

Malignancy is the tendency of a medical condition, especially tumors, to become progressively worse and to potentially result in death. It is characterized by the properties of anaplasia, invasiveness, and metastasis. Malignant is a corresponding adjectival medical term used to describe a severe and progressively worsening disease. The term "malignant disease" as used herein preferably relates to cancer or a tumor disease. Similarly, the term "malignant cells" as used herein preferably relates to cancer cells or tumor cells. A malignant tumor may be contrasted with a non-cancerous benign tumor in that a malignancy is not self-limited in its growth, is capable of invading into adjacent tissues, and may be capable of spreading to distant tissues (metastasizing), while a benign tumor has none of those properties. Malignant tumor is essentially synonymous with cancer. Malignancy, malignant neoplasm, and malignant tumor are essentially synonymous with cancer.

According to the invention, the term "tumor" or "tumor disease" refers to a swelling or lesion formed by an abnormal growth of cells (called neoplastic cells or tumor cells). By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant.

A benign tumor is a tumor that lacks all three of the malignant properties of a cancer. Thus, by definition, a benign tumor does not grow in an unlimited, aggressive manner, does not invade surrounding tissues, and does not spread to non-adjacent tissues (metastasize). Common examples of benign tumors include moles and uterine fibroids.

The term "benign" implies a mild and nonprogressive disease, and indeed, many kinds of benign tumors are harmless to the health. However, some neoplasms which are defined as "benign tumors" because they lack the invasive properties of a cancer, may still produce negative health effects. Examples of this include tumors which produce a "mass effect" (compression of vital organs such as blood vessels), or "functional" tumors of endocrine tissues, which may overproduce certain hormones (examples include thyroid adenomas, adrenocortical adenomas, and pituitary adenomas).

Benign tumors typically are surrounded by an outer surface that inhibits their ability to behave in a malignant manner. In some cases, certain "benign" tumors may later give rise to malignant cancers, which result from additional genetic changes in a subpopulation of the tumor's neoplastic cells. A prominent example of this phenomenon is the tubular adenoma, a common type of colon polyp which is an important precursor to colon cancer. The cells in tubular adenomas, like most tumors which frequently progress to cancer, show certain abnormalities of cell maturation and appearance collectively known as dysplasia. These cellular abnormalities are not seen in benign tumors that rarely or never turn cancerous, but are seen in other pre-cancerous tissue abnormalities which do not form discrete masses, such as pre-cancerous lesions of the uterine cervix. Some authorities prefer to refer to dysplastic tumors as "pre-malignant", and reserve the term "benign" for tumors which rarely or never give rise to cancer.

Neoplasm is an abnormal mass of tissue as a result of neoplasia. Neoplasia (new growth in Greek) is the abnormal proliferation of cells. The growth of the cells exceeds, and is uncoordinated with that of the normal tissues around it. The growth persists in the same excessive manner even after cessation of the stimuli. It usually causes a lump or tumor. Neoplasms may be benign, pre-malignant or malignant.

"Growth of a tumor" or "tumor growth" according to the invention relates to the tendency of a tumor to increase its size and/or to the tendency of tumor cells to proliferate.

Preferably, a "malignant disease" according to the invention is a cancer disease or tumor disease, and a malignant cell is a cancer cell or tumor cell. Preferably, a "malignant disease" is characterized by cells expressing a tumor-associated antigen such as NY-ESO-1, TPTE or PLAC1.

Cancer (medical term: malignant neoplasm) is a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor but some, like leukemia, do not.

Cancers are classified by the type of cell that resembles the tumor and, therefore, the tissue presumed to be the origin of the tumor. These are the histology and the location, respectively.

The term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the invention also comprises cancer metastases.

The main types of lung cancer are small cell lung carcinoma (SCLC) and non-small cell lung carcinoma (NSCLC). There are three main sub-types of the non-small cell lung carcinomas: squamous cell lung carcinoma, adenocarcinoma, and large cell lung carcinoma. Adenocarcinomas account for approximately 10% of lung cancers. This cancer usually is seen peripherally in the lungs, as opposed to small cell lung cancer and squamous cell lung cancer, which both tend to be more centrally located.

Skin cancer is a malignant growth on the skin. The most common skin cancers are basal cell cancer, squamous cell cancer, and melanoma. Malignant melanoma is a serious type of skin cancer. It is due to uncontrolled growth of pigment cells, called melanocytes.

According to the invention, a "carcinoma" is a malignant tumor derived from epithelial cells. This group represents the most common cancers, including the common forms of breast, prostate, lung and colon cancer.

"Bronchiolar carcinoma" is a carcinoma of the lung, thought to be derived from epithelium of terminal bronchioles, in which the neoplastic tissue extends along the alveolar walls and grows in small masses within the alveoli. Mucin may be demonstrated in some of the cells and in the material in the alveoli, which also includes denuded cells.

"Adenocarcinoma" is a cancer that originates in glandular tissue. This tissue is also part of a larger tissue category known as epithelial tissue. Epithelial tissue includes skin, glands and a variety of other tissue that lines the cavities and organs of the body. Epithelium is derived embryologically from ectoderm, endoderm and mesoderm. To be classified as adenocarcinoma, the cells do not necessarily need to be part of a gland, as long as they have secretory properties. This form of carcinoma can occur in some higher mammals, including humans. Well differentiated adenocarcinomas tend to resemble the glandular tissue that they are derived from, while poorly differentiated may not. By staining the cells from a biopsy, a pathologist will determine whether the tumor is an adenocarcinoma or some other type of cancer. Adenocarcinomas can arise in many tissues of the body due to the ubiquitous nature of glands within the body. While each gland may not be secreting the same substance, as long as there is an exocrine function to the cell, it is considered glandular and its malignant form is therefore named adenocarcinoma. Malignant adenocarcinomas invade other tissues and often metastasize given enough time to do so. Ovarian adenocarcinoma is the most common type of ovarian carcinoma. It includes the serous and mucinous adenocarcinomas, the clear cell adenocarcinoma and the endometrioid adenocarcinoma.

Renal cell carcinoma also known as renal cell cancer or renal cell adenocarcinoma is a kidney cancer that originates in the lining of the proximal convoluted tubule, the very small tubes in the kidney that filter the blood and remove waste products. Renal cell carcinoma is by far the most common type of kidney cancer in adults and the most lethal of all the genitourinary tumors. Distinct subtypes of renal cell carcinoma are clear cell renal cell carcinoma and papillary renal cell carcinoma. Clear cell renal cell carcinoma is the most common form of renal cell carcinoma. When seen under a microscope, the cells that make up clear cell renal cell carcinoma appear very pale or clear. Papillary renal cell carcinoma is the second most common subtype. These cancers form little finger-like projections (called papillae) in some, if not most, of the tumors.

Lymphoma and leukemia are malignancies derived from hematopoietic (blood-forming) cells.

Blastic tumor or blastoma is a tumor (usually malignant) which resembles an immature or embryonic tissue. Many of these tumors are most common in children.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

The cells of a secondary or metastatic tumor are like those in the original tumor. This means, for example, that, if ovarian cancer metastasizes to the liver, the secondary tumor is made up of abnormal ovarian cells, not of abnormal liver cells. The tumor in the liver is then called metastatic ovarian cancer, not liver cancer.

In ovarian cancer, metastasis can occur in the following ways: by direct contact or extension, it can invade nearby tissue or organs located near or around the ovary, such as the fallopian tubes, uterus, bladder, rectum, etc.; by seeding or shedding into the abdominal cavity, which is the most common way ovarian cancer spreads. Cancer cells break off the surface of the ovarian mass and "drop" to other structures in the abdomen such as the liver, stomach, colon or diaphragm; by breaking loose from the ovarian mass, invading the lymphatic vessels and then traveling to other areas of the body or distant organs such as the lung or liver; by breaking loose from the ovarian mass, invading the blood system and traveling to other areas of the body or distant organs.

According to the invention, metastatic ovarian cancer includes cancer in the fallopian tubes, cancer in organs of the abdomen such as cancer in the bowel, cancer in the uterus, cancer in the bladder, cancer in the rectum, cancer in the liver, cancer in the stomach, cancer in the colon, cancer in the diaphragm, cancer in the lungs, cancer in the lining of the abdomen or pelvis (peritoneum), and cancer in the brain. Similarly, metastatic lung cancer refers to cancer that has spread from the lungs to distant and/or several sites in the body and includes cancer in the liver, cancer in the adrenal glands, cancer in the bones, and cancer in the brain.

A relapse or recurrence occurs when a person is affected again by a condition that affected them in the past. For example, if a patient has suffered from a tumor disease, has received a successful treatment of said disease and again develops said disease said newly developed disease may be considered as relapse or recurrence. However, according to the invention, a relapse or recurrence of a tumor disease may but does not necessarily occur at the site of the original tumor disease. Thus, for example, if a patient has suffered from ovarian tumor and has received a successful treatment a relapse or recurrence may be the occurrence of an ovarian tumor or the occurrence of a tumor at a site different to ovary. A relapse or recurrence of a tumor also includes situations wherein a tumor occurs at a site different to the site of the original tumor as well as at the site of the original tumor. Preferably, the original tumor for which the patient has received a treatment is a primary tumor and the tumor at a site different to the site of the original tumor is a secondary or metastatic tumor.

By "treat" is meant to administer a compound or composition as described herein to a subject in order to prevent or eliminate a disease, including reducing the size of a tumor or the number of tumors in a subject; arrest or slow a disease in a subject; inhibit or slow the development of a new disease in a subject; decrease the frequency or severity of symptoms and/or recurrences in a subject who currently has or who previously has had a disease; and/or prolong, i.e. increase the lifespan of the subject.

In particular, the term "treatment of a disease" includes curing, shortening the duration, ameliorating, preventing, slowing down or inhibiting progression or worsening, or preventing or delaying the onset of a disease or the symptoms thereof.

By "being at risk" is meant a subject, i.e. a patient, that is identified as having a higher than normal chance of developing a disease, in particular cancer, compared to the general population. In addition, a subject who has had, or who currently has, a disease, in particular cancer is a subject who has an increased risk for developing a disease, as such a subject may continue to develop a disease. Subjects who currently have, or who have had, a cancer also have an increased risk for cancer metastases.

The term "immunotherapy" relates to a treatment involving a specific immune reaction. In the context of the present invention, terms such as "protect", "prevent", "prophylactic", "preventive", or "protective" relate to the prevention or treatment or both of the occurrence and/or the propagation of a disease in a subject and, in particular, to minimizing the chance that a subject will develop a disease or to delaying the development of a disease. For example, a person at risk for a tumor, as described above, would be a candidate for therapy to prevent a tumor.

A prophylactic administration of an immunotherapy, for example, a prophylactic administration of the composition of the invention, preferably protects the recipient from the development of a disease. A therapeutic administration of an immunotherapy, for example, a therapeutic administration of the composition of the invention, may lead to the inhibition of the progress/growth of the disease. This comprises the deceleration of the progress/growth of the disease, in particular a disruption of the progression of the disease, which preferably leads to elimination of the disease.

Immunotherapy may be performed using any of a variety of techniques, in which agents provided herein function to remove antigen-expressing cells from a patient. Such removal may take place as a result of enhancing or inducing an immune response in a patient specific for an antigen or a cell expressing an antigen.

Within certain embodiments, immunotherapy may be active immunotherapy, in which treatment relies on the in vivo stimulation of the endogenous host immune system to react against diseased cells with the administration of immune response-modifying agents (such as peptides and nucleic acids as provided herein).

Within other embodiments, immunotherapy may be passive immunotherapy, in which treatment involves the delivery of agents with established tumor-immune reactivity (such as effector cells) that can directly or indirectly mediate antitumor effects and does not necessarily depend on an intact host immune system. Examples of effector cells include T lymphocytes (such as CD8+ cytotoxic T lymphocytes and CD4+ T-helper lymphocytes), and antigen-presenting cells (such as dendritic cells and macrophages). T cell receptors specific for the peptides recited herein may be cloned, expressed and transferred into other effector cells for adoptive immunotherapy.

As noted above, immunoreactive peptides as provided herein may be used to rapidly expand antigen-specific T cell cultures in order to generate a sufficient number of cells for immunotherapy. In particular, antigen-presenting cells, such as dendritic cells, macrophages, monocytes, fibroblasts and/or B cells, may be pulsed with immunoreactive peptides or transfected with one or more nucleic acids using standard techniques well known in the art. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al. (1997), Immunological Reviews 157, 177.

Alternatively, a nucleic acid expressing a peptide recited herein may be introduced into antigen-presenting cells taken from a patient and clonally propagated ex vivo for transplant back into the same patient.

Transfected cells may be reintroduced into the patient using any means known in the art, preferably in sterile form by intravenous, intracavitary, intraperitoneal or intratumor administration.

Methods disclosed herein may involve the administration of autologous T cells that have been activated in response to a peptide or peptide-expressing antigen presenting cell. Such T cells may be CD4+ and/or CD8+, and may be proliferated as described above. The T cells may be administered to the subject in an amount effective to inhibit the development of a disease.

The agents and compositions provided herein may be used alone or in combination with conventional therapeutic regimens such as surgery, irradiation, chemotherapy and/or bone marrow transplantation (autologous, syngeneic, allogeneic or unrelated).

The term "immunization" or "vaccination" describes the process of treating a subject with the purpose of inducing an immune response for therapeutic or prophylactic reasons.

The term "in vivo" relates to the situation in a subject.

The terms "subject", "individual", "organism" or "patient" are used interchangeably and relate to vertebrates, preferably mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity such as animals of zoos. The term "animal" as used herein also includes humans. The term "subject" may also include a patient, i.e., an animal, preferably a human having a disease, preferably a disease as described herein.

The term "autologous" is used to describe anything that is derived from the same subject. For example, "autologous transplant" refers to a transplant of tissue or organs derived from the same subject. Such procedures are advantageous because they overcome the immunological barrier which otherwise results in rejection.

The term "heterologous" is used to describe something consisting of multiple different elements. As an example, the transfer of one individual's bone marrow into a different individual constitutes a heterologous transplant. A heterologous gene is a gene derived from a source other than the subject.

As part of the composition for an immunization or a vaccination, preferably one or more agents as described herein are administered together with one or more adjuvants for inducing an immune response or for increasing an immune response. The term "adjuvant" relates to compounds which prolongs or enhances or accelerates an immune response. The composition of the present invention preferably exerts its effect without addition of adjuvants. Still, the composition of the present application may contain any known adjuvant. Adjuvants comprise a heterogeneous group of compounds such as oil emulsions (e.g., Freund's adjuvants), mineral compounds (such as alum), bacterial products (such as *Bordetella pertussis* toxin), liposomes, and immune-stimulating complexes. Examples for adjuvants are monophosphoryl-lipid-A (MPL SmithKline Beecham). Saponins such as QS21 (SmithKline Beecham), DQS21 (SmithKline Beecham; WO 96/33739), QS7, QS17, QS18, and QS-L1 (So et al., 1997, Mol. Cells 7: 178-186), incomplete Freund's adjuvants, complete Freund's adjuvants, vitamin E, montanid, alum, CpG oligonucleotides (Krieg et al., 1995, Nature 374: 546-549), and various water-in-oil emulsions which are prepared from biologically degradable oils such as squalene and/or tocopherol.

According to the invention, a "sample" may be any sample useful according to the present invention, in particular a biological sample such a tissue sample, including body fluids, and/or a cellular sample and may be obtained in the conventional manner such as by tissue biopsy, including punch biopsy, and by taking blood, bronchial aspirate, sputum, urine, feces or other body fluids. According to the invention, the term "sample" also includes processed samples such as fractions or isolates of biological samples, e.g. nucleic acid and peptide/protein isolates.

Other substances which stimulate an immune response of the patient may also be administered. It is possible, for example, to use cytokines in a vaccination, owing to their regulatory properties on lymphocytes. Such cytokines comprise, for example, interleukin-12 (IL-12) which was shown to increase the protective actions of vaccines (cf. *Science* 268:1432-1434, 1995), GM-CSF and IL-18.

There are a number of compounds which enhance an immune response and which therefore may be used in a vaccination. Said compounds comprise co-stimulating molecules provided in the form of proteins or nucleic acids such as B7-1 and B7-2 (CD80 and CD86, respectively).

The therapeutically active agents described herein may be administered via any conventional route, including by injection or infusion. The administration may be carried out, for example, orally, intravenously, intraperitonealy, intramuscularly, subcutaneously or transdermally.

The agents described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

The pharmaceutical compositions of the invention are preferably sterile and contain an effective amount of the therapeutically active substance to generate the desired reaction or the desired effect.

The pharmaceutical compositions of the invention are generally administered in pharmaceutically compatible amounts and in pharmaceutically compatible preparation. The term "pharmaceutically compatible" refers to a nontoxic material which does not interact with the action of the active component of the pharmaceutical composition. Preparations of this kind may usually contain salts, buffer substances, preservatives, carriers, supplementing immunity-enhancing substances such as adjuvants, e.g. CpG oligonucleotides, cytokines, chemokines, saponin, GM-CSF and/or RNA and, where appropriate, other therapeutically active compounds. When used in medicine, the salts should be pharmaceutically compatible. However, salts which are not pharmaceutically compatible may used for preparing pharmaceutically compatible salts and are included in the invention. Pharmacologically and pharmaceutically compatible salts of this kind comprise in a nonlimiting way those prepared from the following acids: hydrochloric, hydrobromic, sulfuric, nitric, phosphoric, maleic, acetic, salicylic, citric, formic, malonic, succinic acids, and the like. Pharmaceutically compatible salts may also be prepared as alkali metal salts or alkaline earth metal salts, such as sodium salts, potassium salts or calcium salts.

A pharmaceutical composition of the invention may comprise a pharmaceutically compatible carrier. The term "carrier" refers to an organic or inorganic component, of a natural or synthetic nature, in which the active component is combined in order to facilitate application. According to the invention, the term "pharmaceutically compatible carrier" includes one or more compatible solid or liquid fillers, diluents or encapsulating substances, which are suitable for administration to a patient. The components of the pharmaceutical composition of the invention are usually such that no interaction occurs which substantially impairs the desired pharmaceutical efficacy.

The pharmaceutical compositions of the invention may contain suitable buffer substances such as acetic acid in a salt, citric acid in a salt, boric acid in a salt and phosphoric acid in a salt.

The pharmaceutical compositions may, where appropriate, also contain suitable preservatives such as benzalkonium chloride, chlorobutanol, paraben and thimerosal.

The pharmaceutical compositions are usually provided in a uniform dosage form and may be prepared in a manner known per se. Pharmaceutical compositions of the invention may be in the form of capsules, tablets, lozenges, solutions, suspensions, syrups, elixirs or in the form of an emulsion, for example.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The present invention is described in detail by the figures and examples below, which are used only for illustration purposes and are not meant to be limiting. Owing to the description and the examples, further embodiments which are likewise included in the invention are accessible to the skilled worker.

FIGURES

FIG. 1: Representation of the TCR-CD3 complex. The intracytoplasmic CD3 immunoreceptor tyrosine-based activation motifs (ITAMs) are indicated as cylinders (adapted from "The T cell receptor facts book", MP Lefranc, G Lefranc, 2001).

Figure 2:
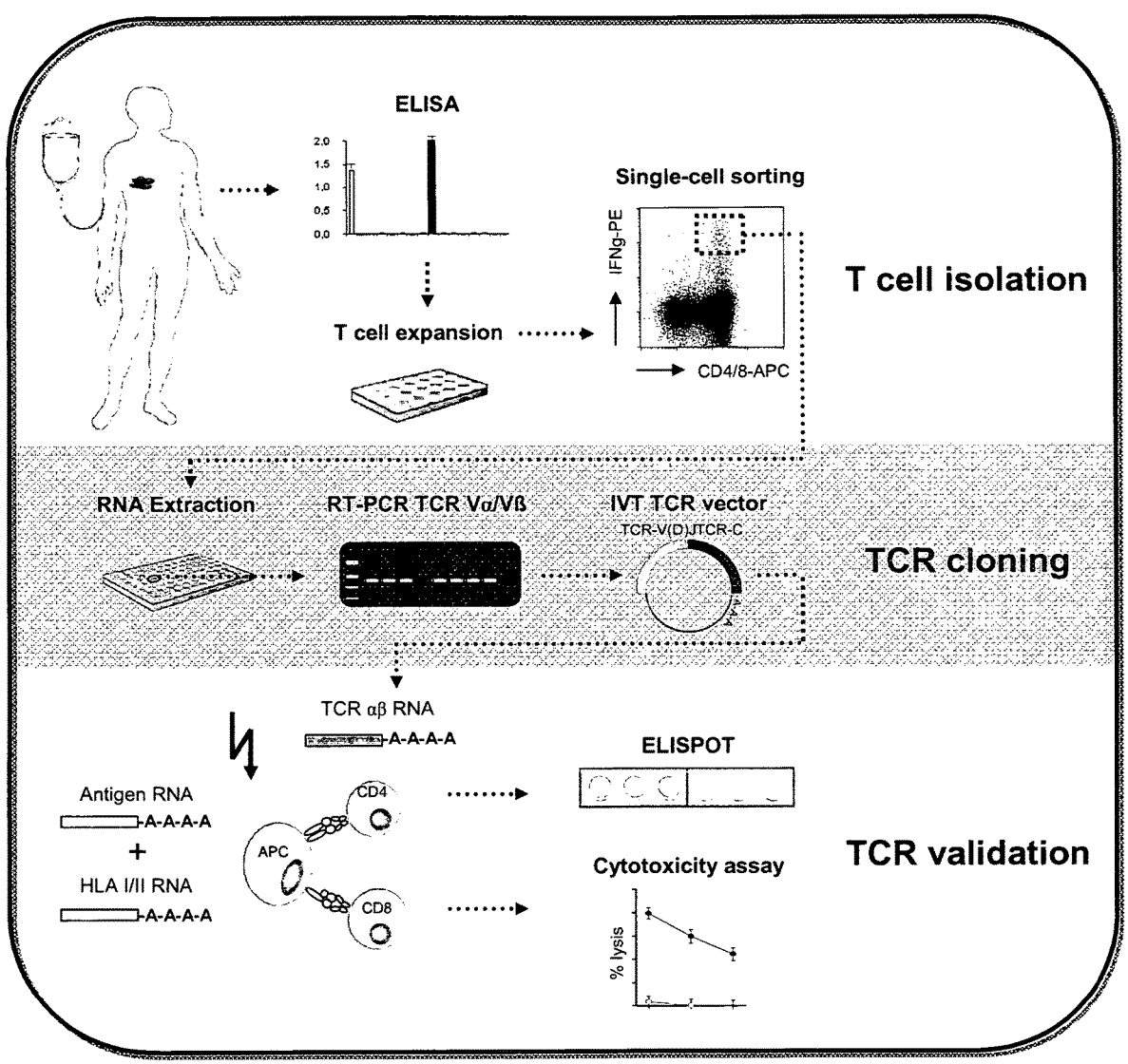

FIG. 2. Technology platform for TCR isolation/validation. The approach integrates all steps from isolation of antigen-specific T cells (top) to TCR cloning (middle) and TCR validation (bottom). Patients are screened for autoantibody responses against the antigen of interest by CrELISA (Crude lysate Enzyme-Linked ImmunoSorbent Assay). Antigen-specific T cells from seropositive donors are stimulated with peptide or RNA loaded autologous DCs and IFNγ secreting CD8+ or CD4+ T cells are isolated by flow cytometry (top). Single cells are harvested in multiwell-plates and subjected to first-strand cDNA synthesis and enrichment by a global PCR amplification step. TCR α/β variable regions are cloned into vectors for in vitro transcription (IVT) containing the constant region cassettes (middle). TCR α/β chain RNAs are transferred into CD4+ or CD8+ T cells, cocultured with APCs expressing the appropriate antigen and HLA molecules and tested for functional reprogramming of engineered T cells (bottom).

Figure 3:
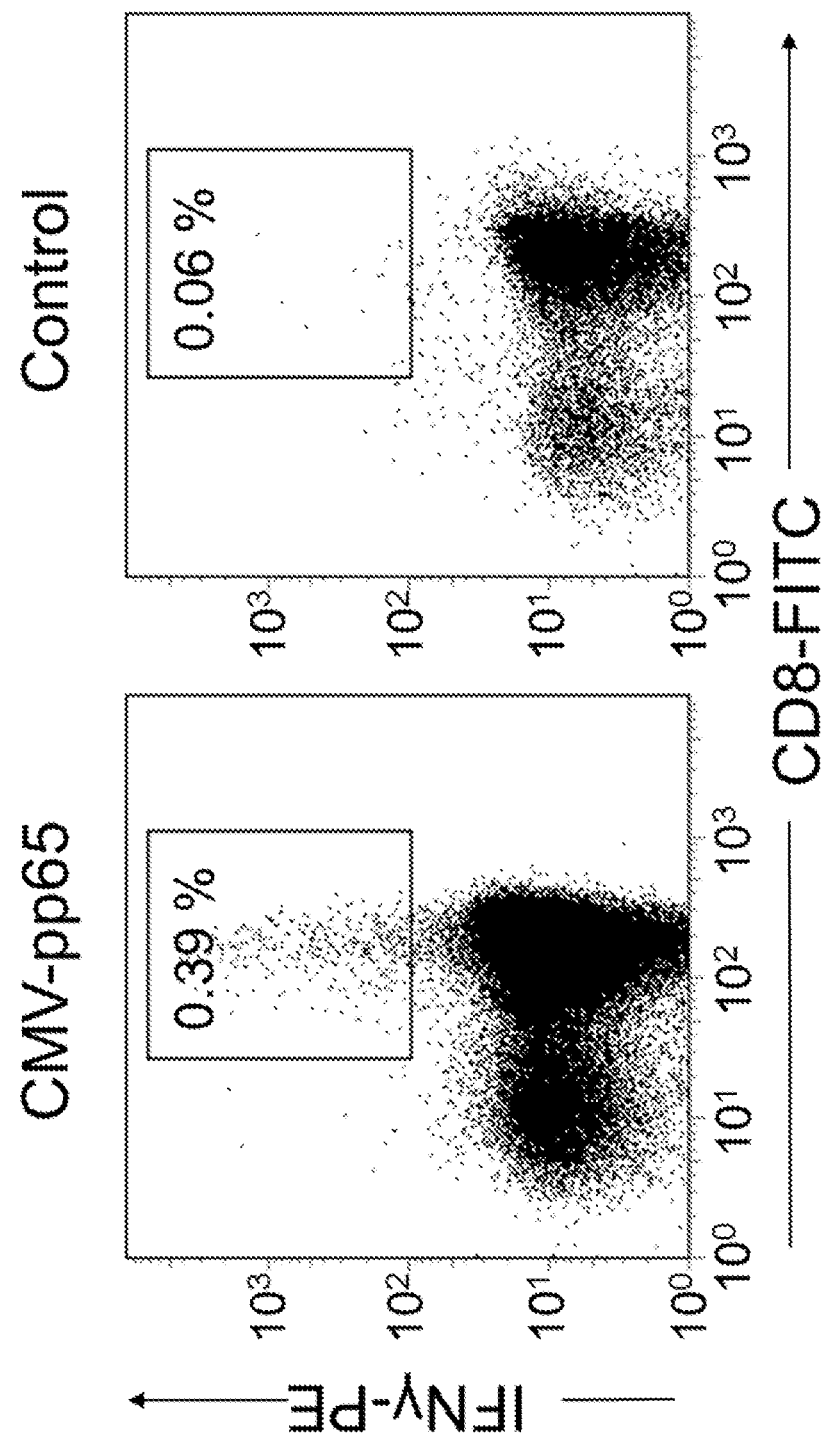

FIG. 3. Flow cytometric sorting of pp65-specific CD8+ T cells from a CMV-seropositive donor after one week of expansion. IFNg secreting CD8+ T cells were isolated after rechallenge with autologous pp65 RNA-transfected iDCs. Control: iDCs transfected with eGFP RNA.

Figure 4:
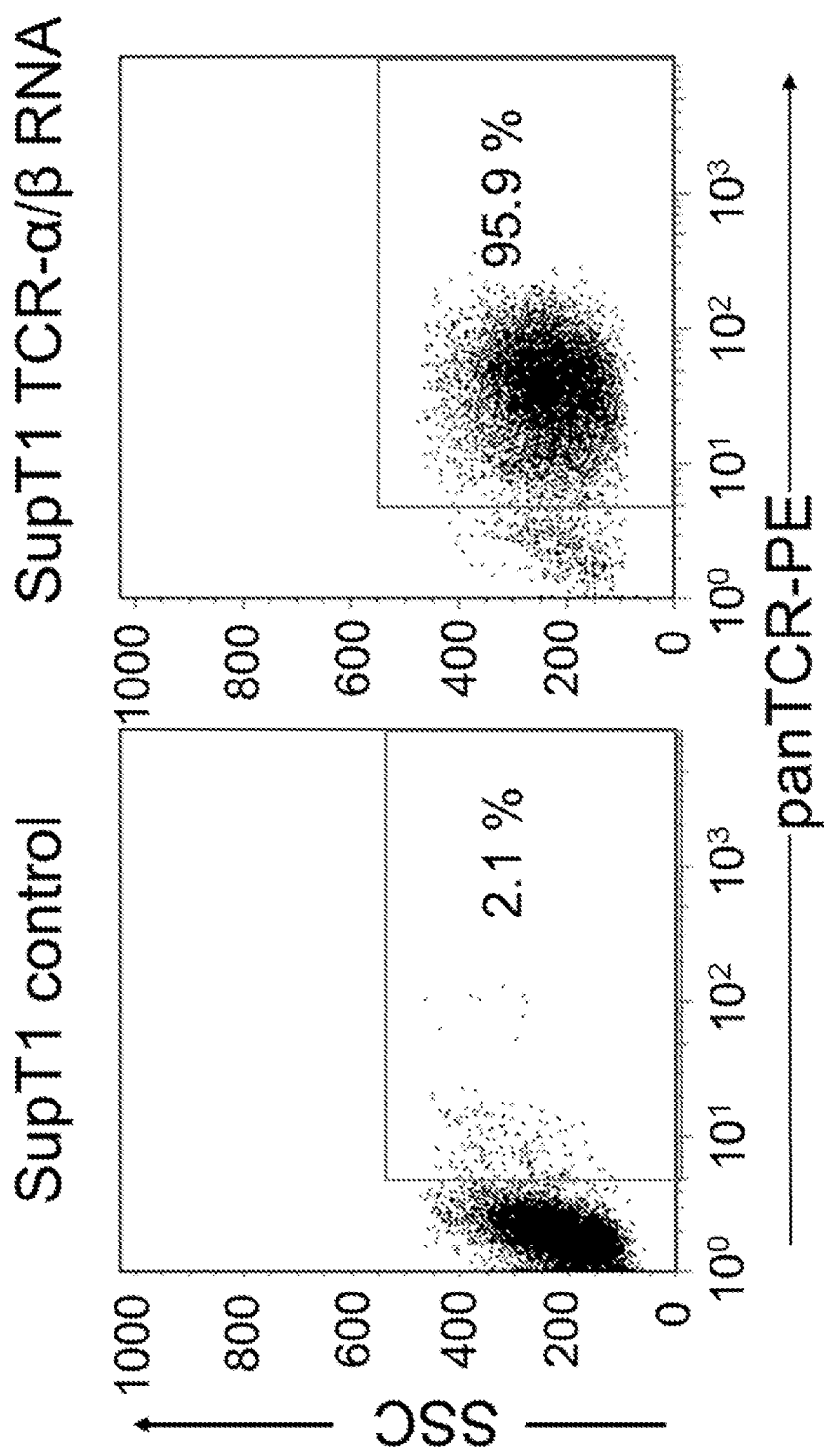

FIG. 4. Verification of TCR surface expression on TCR-transfected SupT1 cells analyzed by flow cytometry. SupT1 cells electroporated with TCR α/β chain RNAs were stained with a pan TCR antibody and analyzed by flow cytometry. SupT1 cells electroporated without RNA served as a negative control.

Figure 5:

FIG. 5. Specificity testing of TCRs obtained from CMV-pp65-specific CD8+ T cells of a CMV seropositive donor after in vitro expansion by IFNγ-ELISPOT. TCR-engineered IVSB cells were tested on antigen-loaded autologous iDCs and K562-A*0201 cells for specific recognition of pp65 peptide pool, $pp65_{495-503}$ or pp65 IVT RNA. Partially overlapping peptides derived from TPTE were used as control peptide pool and $SSX-2_{241-249}$ was used as single peptide control. The tyrosinase derived $Tyr_{368-376}$ epitope was applied as a positive control. Control TCR: TCR cloned from a CMV seronegative donor.

Figure 6:
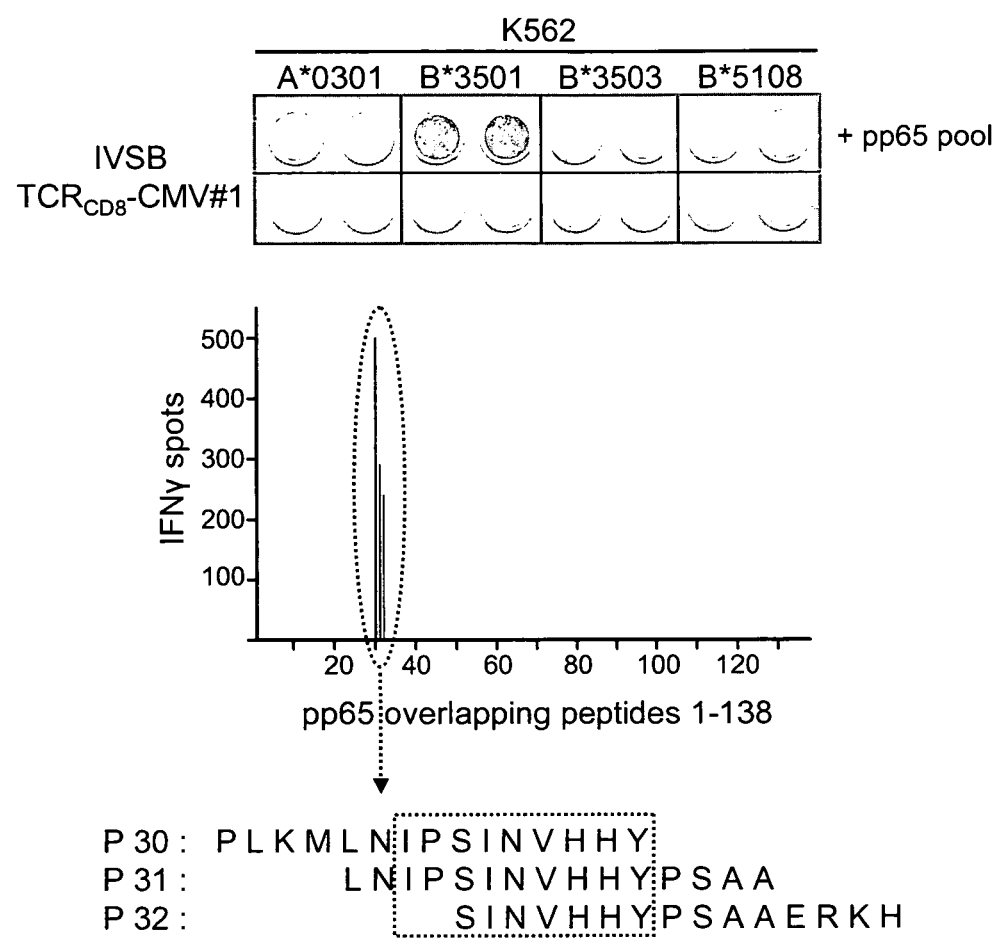

FIG. 6. Determination of HLA restriction and peptide specificity of $TCR_{CD8}$-CMV#1 by IFNγ-ELISPOT. TCR-transgenic IVSB cells were analyzed for recognition of K562 cells expressing selected HLA class I alleles of the donor pulsed with pp65 overlapping peptides or without antigen as a control. K562-B*3501 cells were subsequently used to analyze $TCR_{CD8}$-CMV#1-mediated recognition of individual 15-mer peptides derived from CMV-pp65.

Figure 7:
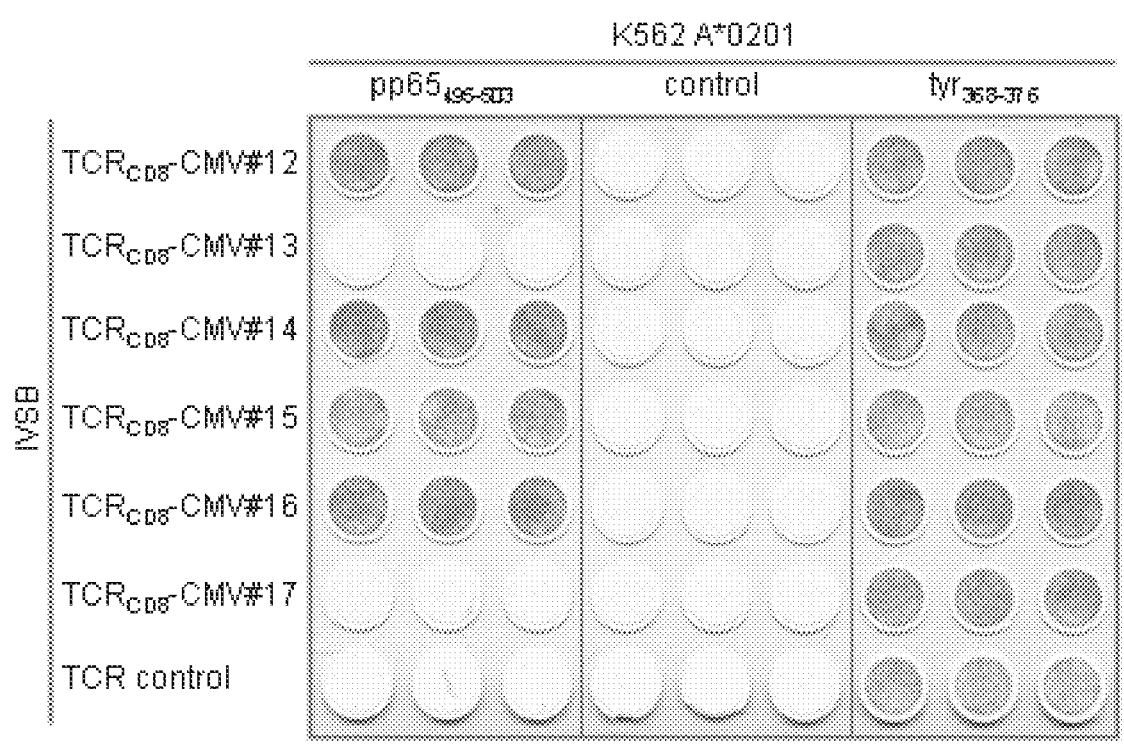

FIG. 7. Specificity testing of TCRs cloned from ex vivo isolated CMV-pp65-specific CD8+ T cells of a CMV seropositive donor by IFNγ-ELISPOT. IVSB cells were transfected with TCR α/β chain RNAs and stimulated with K562-A*0201 pulsed with $pp65_{495-503}$. The unrelated peptide $SSX-2_{241-249}$ and a TCR cloned from a CMV-seronegative donor served as negative, the tyrosinase derived $Tyr_{368-376}$ epitope served as positive control.

Figure 8:
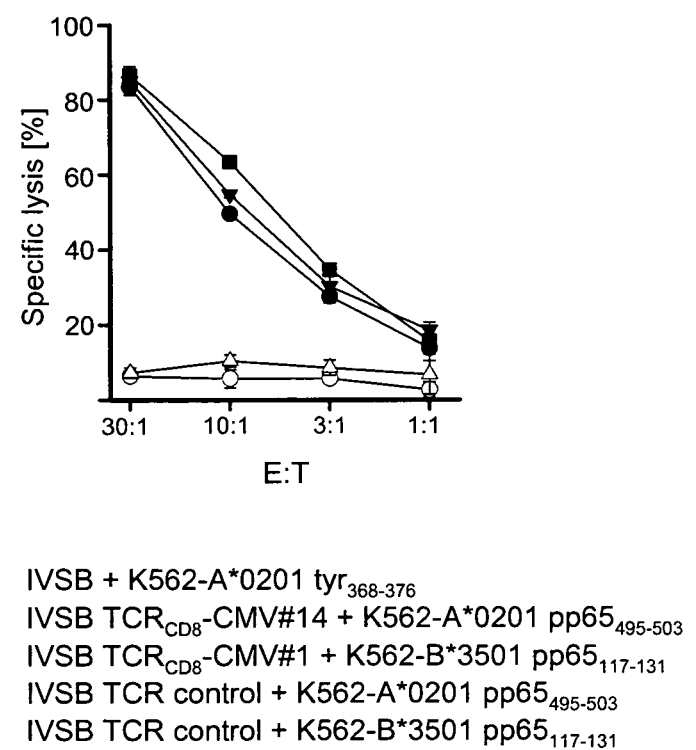

FIG. 8. Specific killing of target cells by TCR-transfected T cells analyzed by luciferase cytotoxicity assay. Peptide-pulsed K562 target cells expressing the appropriate HLA allelotype were used as targets for IVSB cells engineered with CMV-pp65-specific TCRs. As a reference, killing of $Tyr_{368-376}$-pulsed target cells mediated by the endogenous receptor was analyzed. A TCR obtained from a CMV seronegative donor was used as control to exclude unspecific lysis. E:T: effector-to-target ratio.

FIG. 9. Specificity testing of TCRs isolated from NY-ESO-1-specific CD8+ T cells by IFNγ-ELISPOT. $TCR_{CD8}$-NY#2 and -#5 were transferred into IVSB cells and tested for recognition of autologous iDCs loaded with NY-ESO-1 RNA or peptide pool. Negative controls: iDCs pulsed with TPTE peptide pool; a control TCR isolated from a healthy donor. Positive control: $Tyr_{368-376}$-pulsed K562-A*0201.

Figure 10:
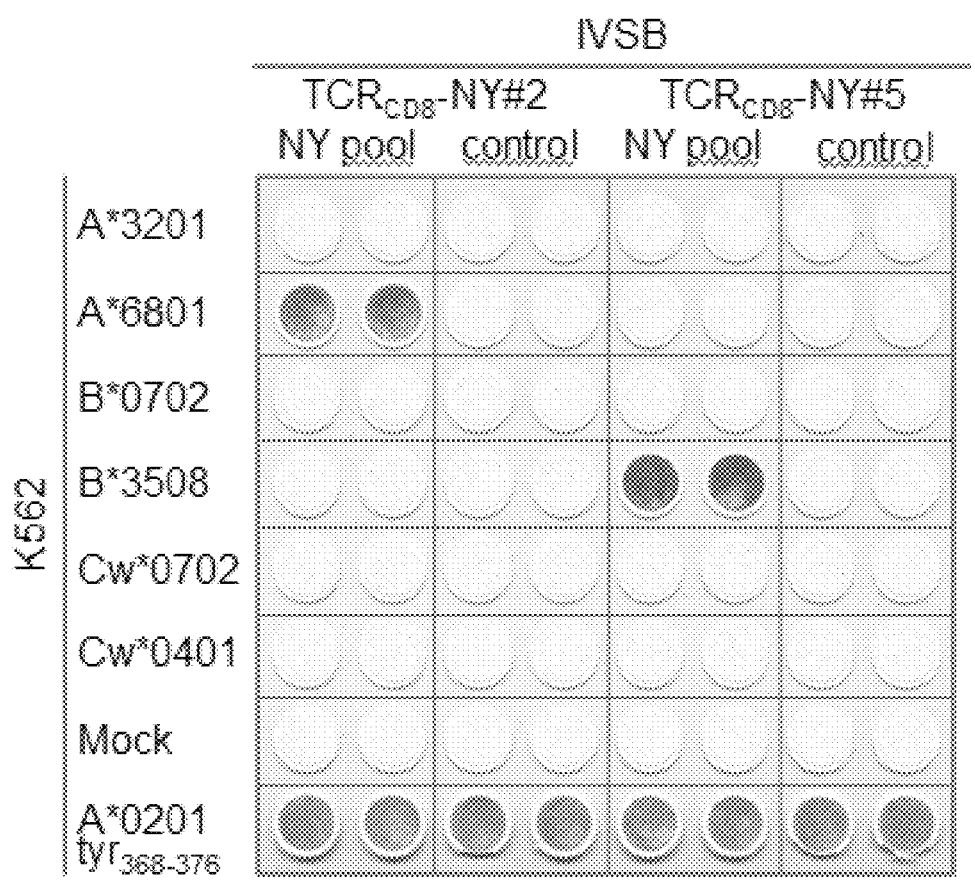

FIG. 10. Identification of HLA restricting elements for NY-ESO-1-specific TCRs by IFNγ-ELISPOT. TCR-engineered IVSB cells were analyzed by IFNg-ELISPOT for recognition of K562 cells transfected with individual HLA class I alleles of the donor and pulsed with NY-ESO-1 peptide pool. Negative controls: HIV-gag peptide pool; K562 electroporated without HLA RNA (mock). Positive control: $TYr_{368-376}$ peptide.

Figure 11:
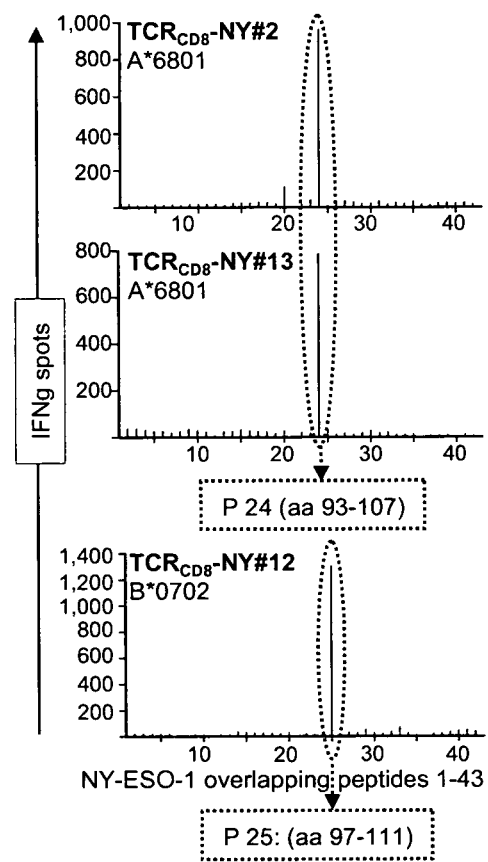

FIG. 11: Identification of 15mer peptides recognized by NY-ESO-1-specific TCRs by IFNγ-ELISPOT. TCR-transfected IVSB T cells were analyzed for recognition of K562 cells expressing the appropriate HLA class I allele and pulsed with individual partially overlapping 15-mers derived from NY-ESO-1.

Figure 12:
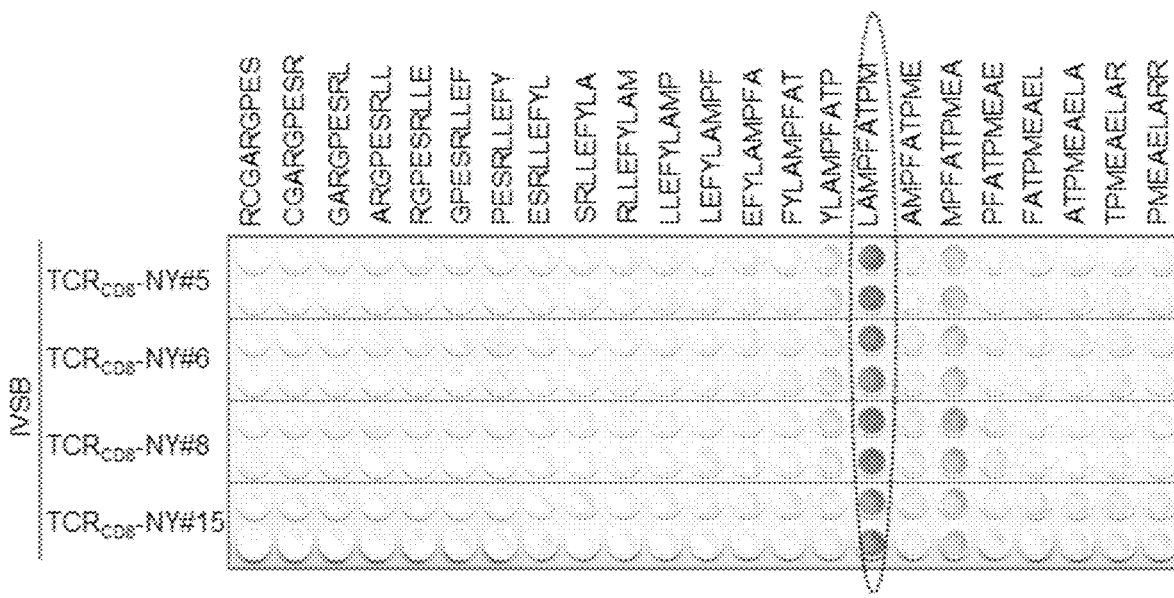

FIG. 12. Epitope mapping for NY-ESO-1-specific TCRs by IFNγ-ELISPOT. IVSB cells transfected with $TCR_{CD8}$-NY#5, #6, #8 or #15 were analyzed for recognition of K562-B*3508 cells pulsed with individual nonamer peptides covering amino acids 77-107 of the NY-ESO-1 protein.

Figure 13:
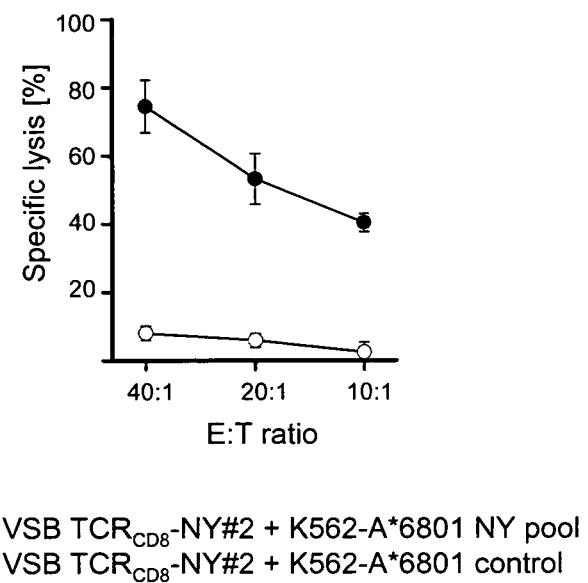

FIG. 13. Specific killing of target cells mediated by $TCR_{CD8}$-NY#2 analyzed by luciferase cytotoxicity assay. Specific lysis of K562-A*6801 cells pulsed with NY-ESO-1 peptide pool by $TCR_{CD8}$-NY#2-transfected IVSB cells was analyzed using different effector-to-target ratios (E:T). Control: target cells pulsed with TPTE peptide pool.

Figure 14:
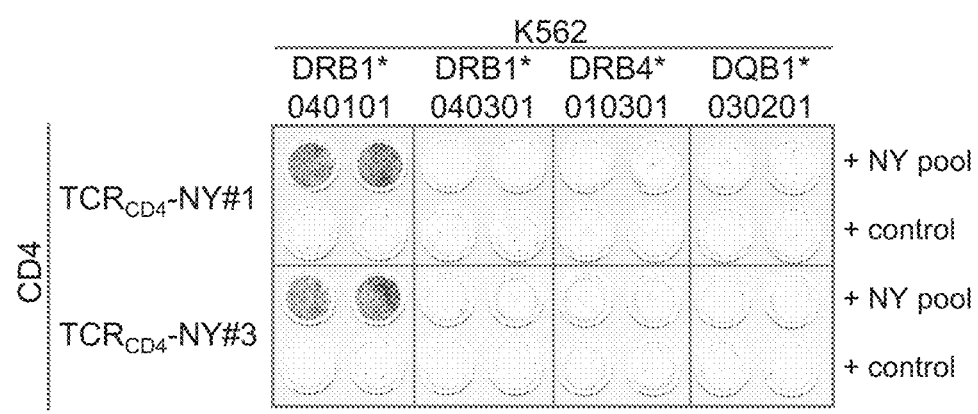

FIG. 14: Determination of HLA restriction elements for NY-ESO-1-specific TCRs obtained from CD4+ T cells by IFNγ-ELISPOT. TCR-transfected CD4+ T cells were analyzed for recognition of K562 expressing individual HLA class II alleles of the patient pulsed with peptide pools of either NY-ESO-1 or HIV-gag as a negative control.

Figure 15:
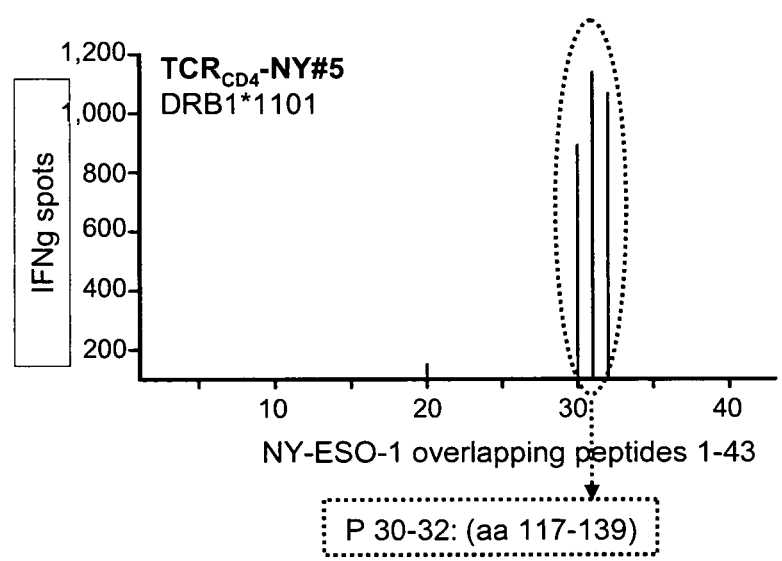

FIG. 15. Epitope mapping for $TCR_{CD4}$-NY#5 by IFNγ-ELISPOT. TCR-engineered CD4+ T cells were tested for recognition of K562 cells expressing the appropriate HLA class II allele and pulsed with partially overlapping 15-mers representing the NY-ESO-1 protein.

Figure 16:
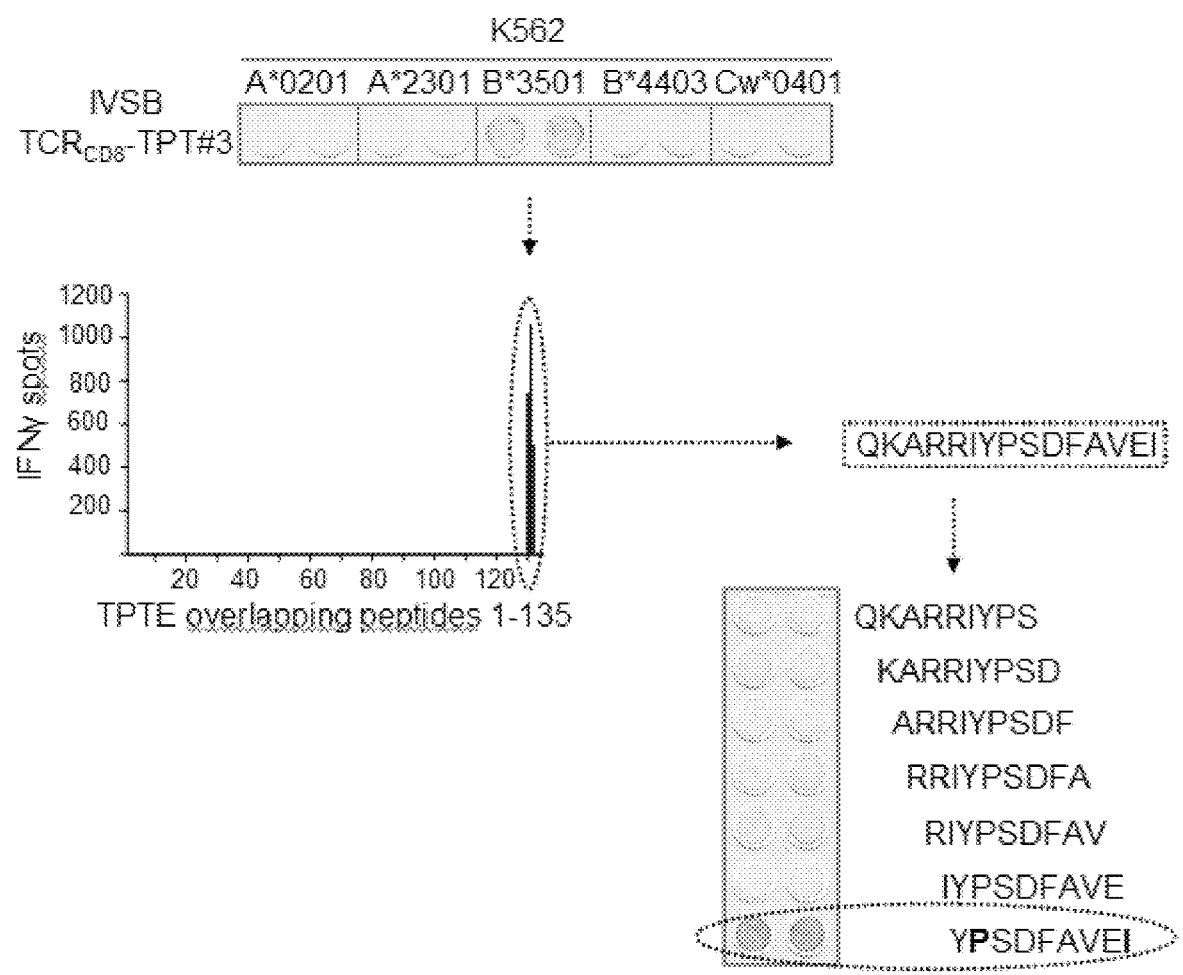

FIG. 16. Determination of HLA restriction and peptide specificity of $TCR_{CD8}$-TPT#3 by IFNγ-ELISPOT. TCR-transfected IVSB cells were analyzed for recognition of K562 cells expressing HLA class I molecules of the patient pulsed with TPTE peptide pool (top). K562-B*3501 cells pulsed with individual 15mer representing the whole antigen (middle) and 9-mer peptides covering amino acids 521-535 of TPTE (bottom) were used to define the epitope recognized by $TCR_{CD8}$-TPT#3. Anchor amino acids of the recognized epitope for binding to HLA B*3501 are shown in bold.

Figure 17:
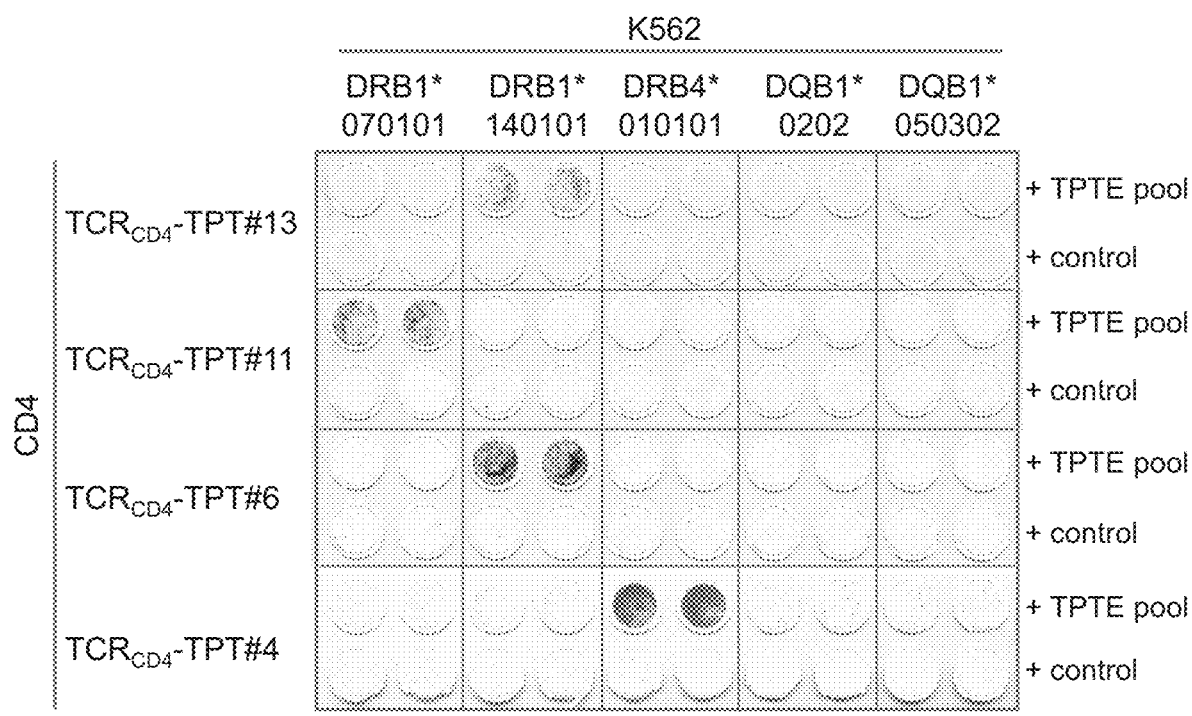

FIG. 17. Determination of HLA restriction elements for TPTE-specific TCRs isolated from CD4+ T cells by IFNγ-ELISPOT. TCR-transfected CD4+ T cells were analyzed for recognition of K562 cells transfected with HLA class II alleles of the patient and pulsed with overlapping peptides corresponding to TPTE or HIV-gag as a control.

Figure 18:
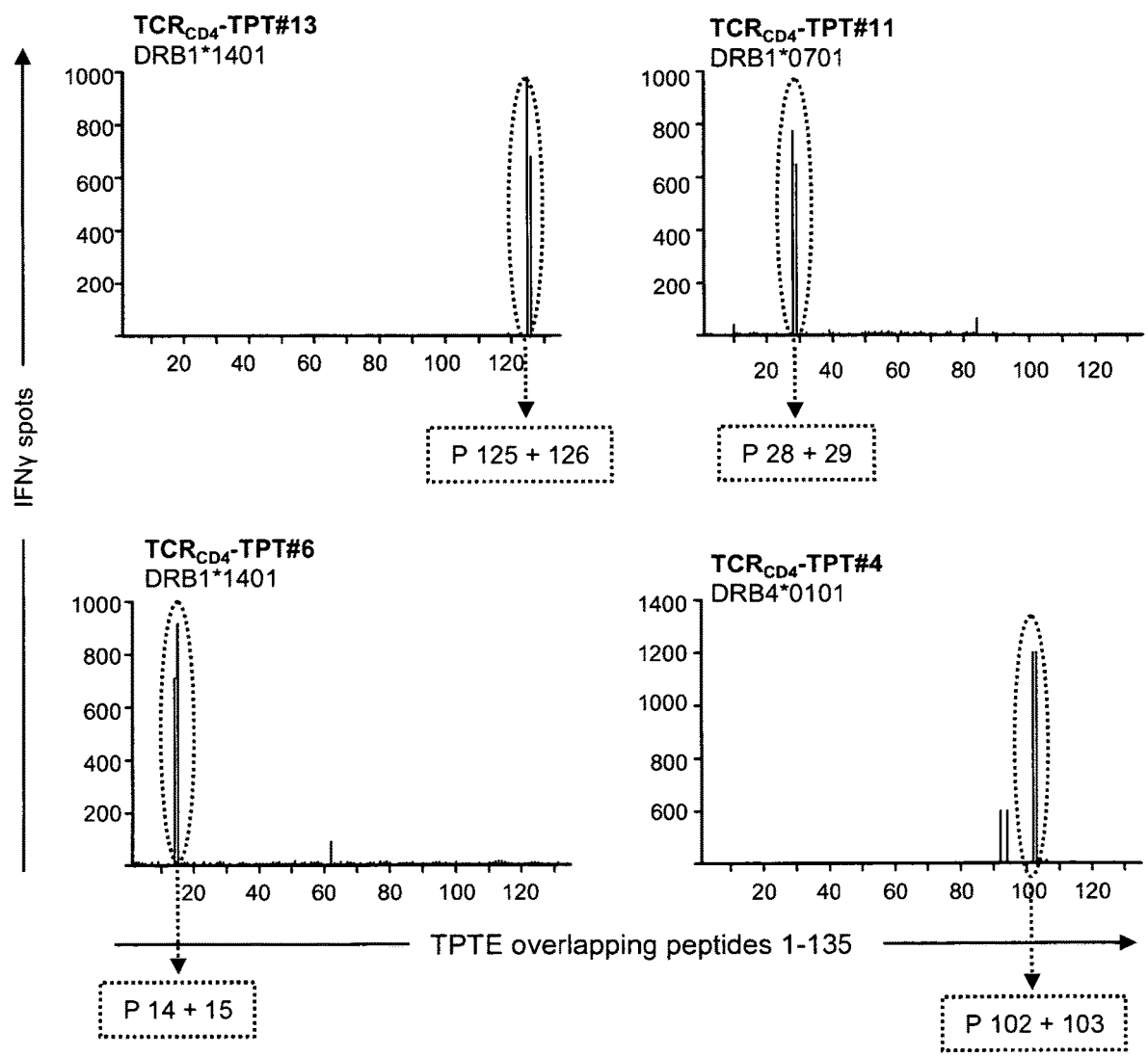

FIG. 18. Epitope mapping for TPTE-specific TCRs isolated from CD4+ T cells by IFNγ-ELISPOT. Epitope locations of TCRs were determined using TCR-transfected CD4+ T cells in combination with K562 cells transfected with the appropriate HLA class II antigen and pulsed with individual partially overlapping 15-mer peptides covering the TPTE protein.

Figure 19:
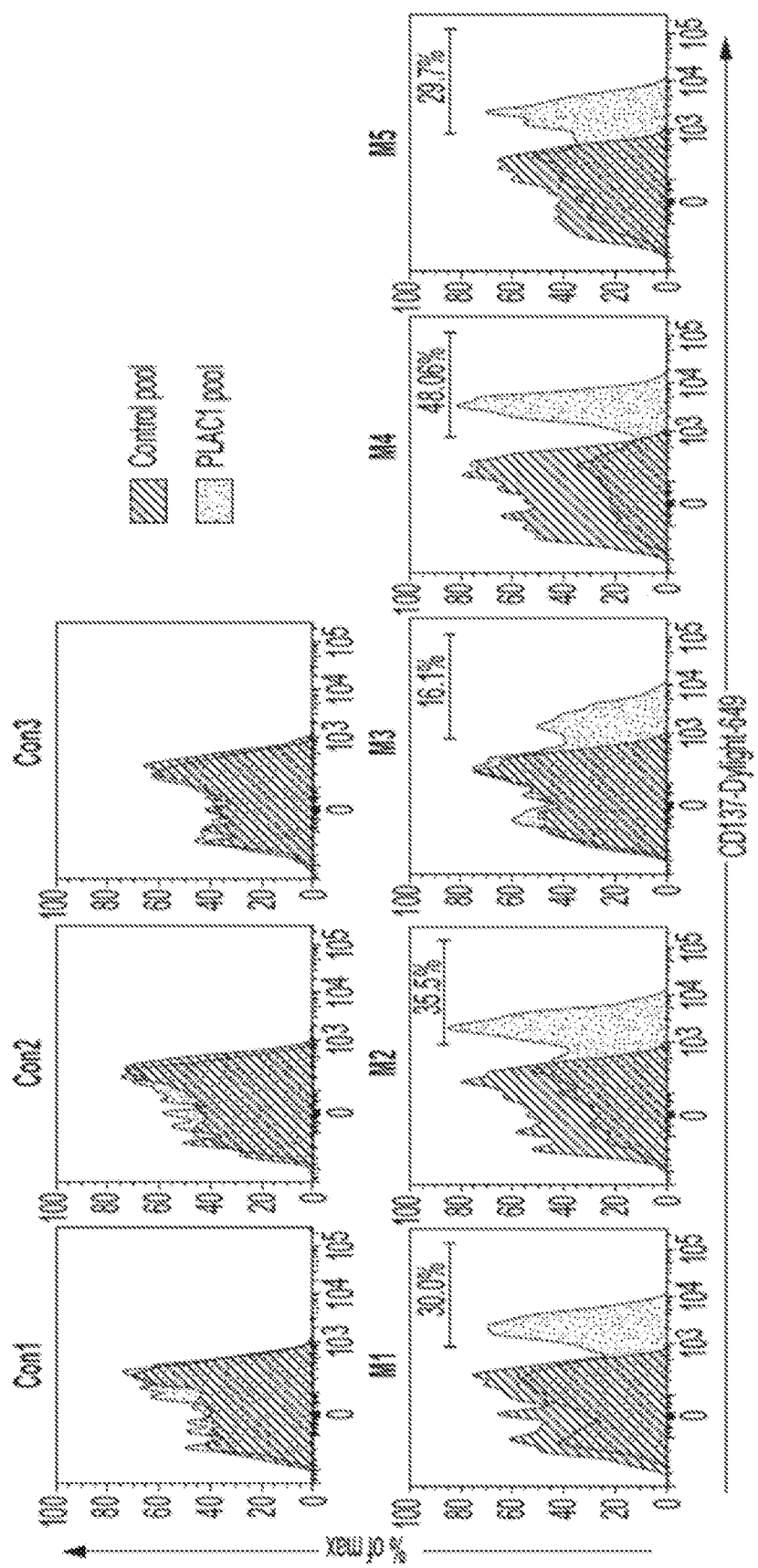

FIG. 19. Flow cytometric sorting of PLAC1-specific CD8+ T cells obtained from immunized mice. Spleen cells of PLAC1-immunized HLA A*0201-transgenic mice (A2.1/DR1 mice) were pulsed with overlapping peptides corresponding to PLAC1 or a control antigen (WT1). 24 h later cells were harvested, stained with fluorochrome-conjugated antibodies and CD3+/CD8+/CD137+ cells were isolated. Histogram plots were gated on CD3+/CD8+ cells. M1-5: PLAC1-immunized mice; Con1-3: control mice.

Figure 20:
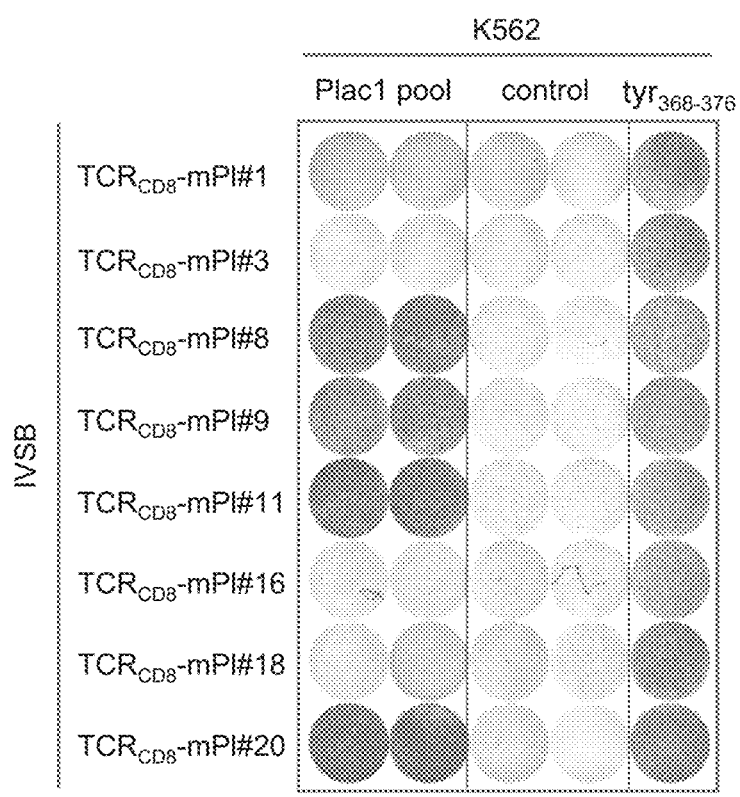

FIG. 20. Specificity testing of TCRs cloned from CD8+ T cells of PLAC1-immunized mice by IFNγ-ELISPOT. TCR-engineered IVSB cells were tested for recognition of K562-A*0201 cells pulsed with overlapping peptides corresponding to PLAC1 or NY-ESO-1 as a control antigen. As a positive control, IFNγ secretion in response to $Tyr_{368-376}$-pulsed target cells was analyzed.

Figure 21:
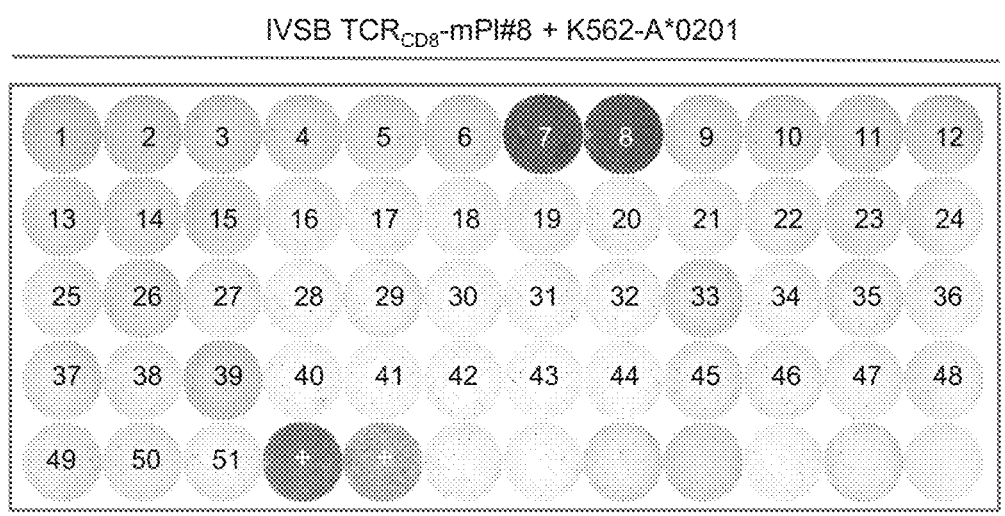

FIG. 21. Determination of peptide specificity of $TCR_{CD8}$-Pl#8 by IFNγ-ELISPOT. TCR-transfected CD8+ T cells were tested for specific recognition of K562-A*0201 cells pulsed with individual partially overlapping 15-mer peptides covering the PLAC1 protein.

Figure 22:
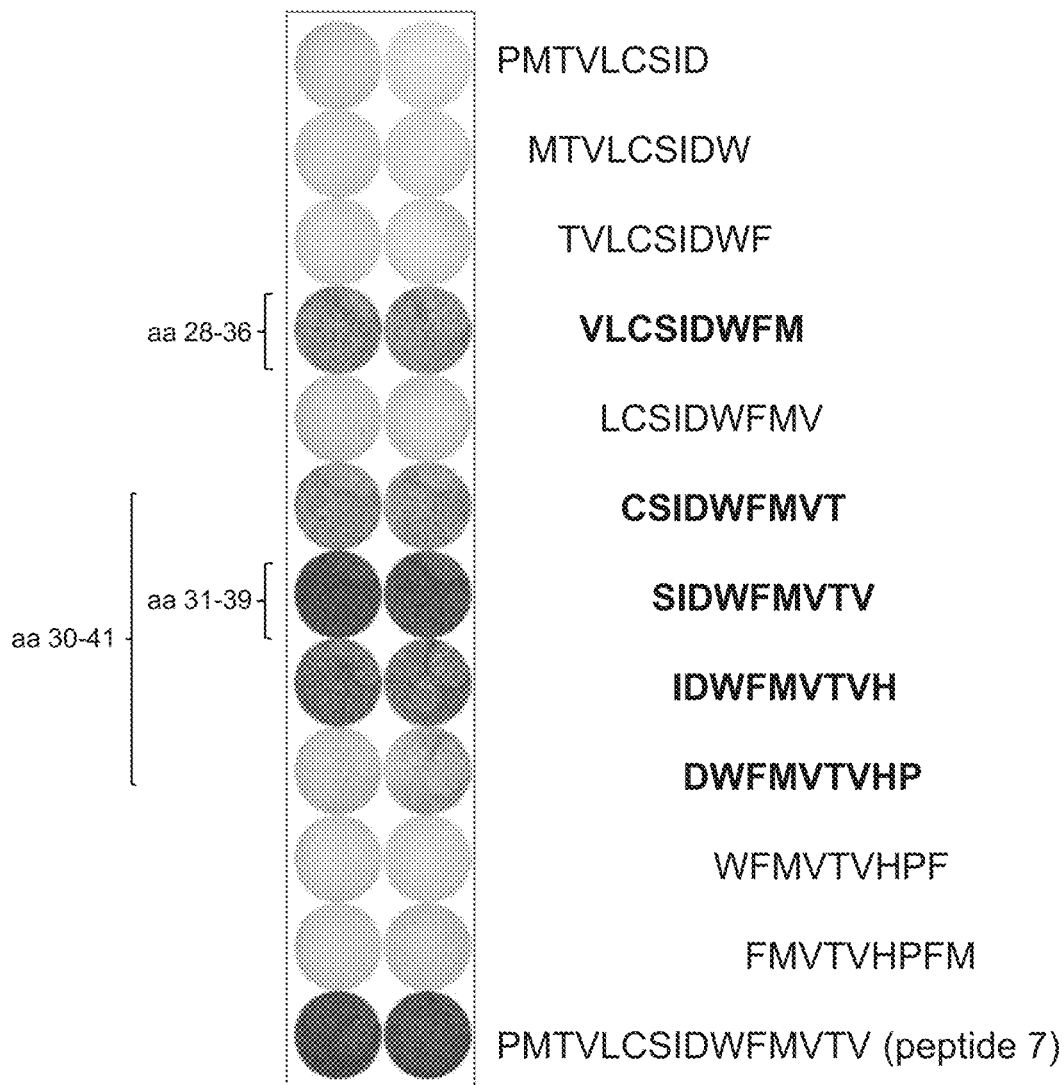

FIG. 22. Definition of A*0201-restricted immunodominant epitopes recognized by PLAC1-specific TCRs by IFNγ-ELISPOT. TCR-transfected IVSB cells were analyzed for recognition of K562-A*0201 cells pulsed with individual 9-mer peptides covering amino acids 25-43 of PLAC1 to define the epitope recognized by $TCR_{CD8}$-Pl#11. Recognized peptides are shown in bold. Positive control: PLAC1 15-mer peptide 7.

EXAMPLES

The techniques and methods used herein are described herein or carried out in a manner known per se and as described, for example, in Sambrook et al., Molecular Cloning: A Laboratory Manual, $2^{nd}$ Edition (1989) Cold Spring Harbor Laboratory Press, Cold Spring Harbor, N.Y. All methods including the use of kits and reagents are carried out according to the manufacturers' information unless specifically indicated.

Example 1: Materials and Methods

Serotyping

An ELISA based on crude lysates of bacteria (CrELISA or Crude Lysate Enzyme-Linked ImmunoSorbent Assay) expressing either full length NY-ESO-1 or the N-terminus of TPTE (amino acids 1-51) was used according to a previously described protocol for determination of IgG autoantibodies (Tureci, O. et al. (2004), J. Immunol. Methods 289, 191-199). CMV-seropositivity was analyzed by a standard ELISA detecting polyclonal CMV-specific IgG responses.

Cell Lines and Reagents

The human lymphoma cell lines SupT1 (ATCC no. CRL-1942) or Jurkat76 (Heemskerk, M. H. et al. (2003), Blood 102, 3530-3540), both lacking surface expression of endogenous TCR, the mouse embryonic fibroblast cell line NIH3T3 (DSMZ no. ACC 59) and the human chronic myeloid leukemia cell line K562 (Lozzio, C. B. & Lozzio, B. B (1975), Blood 45, 321-334) were cultured under standard conditions. K562 cells transiently or stably transfected with HLA allelotypes (Britten, C. M. et al. (2002), J. Immunol. Methods 259, 95-110) (referred to e.g. as K562-A*0201) were used for validation assays. The primary human newborn foreskin fibroblast cell line CCD-1079Sk (ATCC No. CRL-2097) was cultured according to the manufacturers' instructions. The monospecific CTL cell line IVSB specific for the HLA A*0201 restricted tyrosinase-derived epitope $TYr_{368-376}$ (Wolfel, T. et al. (1993), Int. J. Cancer 55, 237-244; Wolfel, T. et al. (1994) Eur. J. Immunol. 24, 759-764) was cultured in AIM-V medium (Invitrogen, Karlsruhe, Germany) with 10% human AB serum (Lonza, Basel, Switzerland), 350 IU/ml IL-2 (Richter-Helm BioLogics, Hamburg, Germany), 5 ng/mL IL-7 (PeproTech, Frankfurt, Germany) and 10 ng/ml IL-15 (R&D Systems, Wiesbaden-Nordenstadt, Germany) and stimulated weekly with irradiated SK29-Mel and AK-EBV cells.

Peripheral Blood Mononuclear Cells (PBMCs), Monocytes and Dendritic Cells (DCs)

PBMCs were isolated by Ficoll-Hypaque (Amersham Biosciences, Uppsala, Sweden) density gradient centrifugation from buffy coats or from blood samples. HLA allelotypes were determined by PCR standard methods. Monocytes were enriched with anti-CD14 microbeads (Miltenyi Biotech, Bergisch-Gladbach, Germany). Immature DCs (iDCs) were obtained by differentiating monocytes for 5 days in cytokine-supplemented culture medium as described in Kreiter et al. (2007), Cancer Immunol. Immunother., CII, 56, 1577-87.

Peptides and Peptide Pulsing of Stimulator Cells

Pools of N- and C-terminally free 15-mer peptides with 11 amino acid overlaps corresponding to sequences of CMV-pp65, HIV-gag, TPTE, NY-ESO-I or PLAC1 (referred to as antigen peptide pool) were synthesized by standard solid phase chemistry (JPT GmbH, Berlin, Germany) and dissolved in DMSO to a final concentration of 0.5 mg/ml. Nonamer peptides were reconstituted in PBS 10% DMSO.

For pulsing stimulator cells were incubated for 1 h at 37° C. in culture medium using different peptide concentrations.

Vectors for In Vitro Transcription (IVT) of RNA

All constructs are variants of the previously described pST1-sec-insert-2βgUTR-A(120)-Sap1 plasmid (Holtkamp, S. et al. (2006), Blood 108, 4009-4017). To obtain plasmids encoding human TCR chains, cDNA coding for TCR-α or TCR-$β_1$ and TCR-$β_2$ constant regions were amplified from human CD8+ T cells and cloned into this backbone. For generation of plasmids encoding murine TCR chains, cDNAs coding for TCR-α, -$β_1$ and -$β_2$ constant regions were ordered from a commercial provider and cloned analogously (GenBank accession numbers M14506, M64239 and X67127, respectively). Specific V(D)J PCR products were introduced into such cassettes to yield full-length TCR chains (referred to as pST1-human/murineTCRαβ-2βgUTR-A(120)).

Analogously, individual HLA class I and II alleles cloned from PBMCs of donors and beta-2-microgobulin (B2M) cDNA from human DCs were inserted into this backbone (referred to as pST1-HLA class I/II-2βgUTR-A(120) and pST1-B2M-2βgUTR-A(120)).

Plasmids coding for pp65 antigen of CMV (pST1-sec-pp65-MITD-2βgUTR-A(120)) and NY-ESO-I (pST1-sec-NY-ESO-1-MITD-2βgUTR-A(120)) linked to a secretion signal (sec) and the MHC class I trafficking signal (MITD) were described previously (Kreiter, S. et al. (2008), J. Immunol. 180, 309-318). PLAC1 encoding plasmid pST1-sec-PLAC1-MITD-2βgUTR-A(120) was generated by cloning a cDNA obtained from a commercial provider (GenBank accession number NM_021796) into the Kreiter et al. backbone. TPTE encoding plasmids pST1-αgUTR-TPTE-2βgUTR-A(120) and pST1-αgUTR-TPTE-MITD-2βgUTR-A(120) were generated by cloning a cDNA obtained from a commercial provider (GenBank accession number AF007118) into a variant of the Holtkamp et al. vector featuring an additional alpha-globin 5'-untranslated region.

Primers were purchased from Operon Biotechnologies, Cologne, Germany.

Generation of In Vitro Transcribed (IVT) RNA and Transfer into Cells

Generation of IVT RNA was performed as described previously (Holtkamp, S. et al. (2006), Blood 108, 4009-4017) and added to cells suspended in X-VIVO 15 medium (Lonza, Basel, Switzerland) in a pre-cooled 4-mm gap sterile electroporation cuvette (Bio-Rad Laboratories GmbH, Munich, Germany). Electroporation was performed with a Gene-Pulser-II apparatus (Bio-Rad Laboratories GmbH, Munich, Germany) (T cells: 450 V/250 µF; IVSB T cells: 350 V/200 µF; SupT1 (ATCC No. CRL-1942): 300 V/200 µF; human DC: 300 V/150 µF; K562: 200 V/300 µF).

In Vitro Expansion of Antigen-Specific T Cells $2.5 \times 10^6$ PBMCs/well were seeded in 24-well plates, pulsed with peptide pool and cultured for 1 week in complete culture medium supplemented with 5% AB serum, 10 U/ml IL-2 and 5 ng/ml IL-7. For some experiments CD8+ or CD4+ T cells were purified from PBMC by positive magnetic cell sorting (Miltenyi Biotech, Bergisch-Gladbach, Germany) and then expanded by coculturing of $2 \times 10^6$ effectors with $3 \times 10^5$ autologous DCs either electroporated with antigen-encoding RNA or pulsed with the overlapping peptide pool for 1 week in complete medium supplemented with 5% AB serum, 10 U/ml IL-2, and 5 ng/ml IL-7.

Single-Cell Sorting of Antigen-Specific CD8+ or CD4+ T Cells after IFNγ Secretion Assay Flow cytometric sorting of single antigen-specific CD8+ or CD4+ T cells was conducted either directly ex vivo from freshly isolated T cells or PBMC or after one week of antigen-specific expansion. $2 \times 10^6$ T cells or PBMC were stimulated with $3 \times 10^5$ autologous DCs loaded with peptide pool or transfected with IVT RNA encoding the respective antigen or a control antigen for 4 to 15 hours depending on the stimulation mode. Cells were harvested, treated with a Phycoerythrin (PE)-conjugated anti-IFNγ antibody, a Fluoresceinisothiocyanat (FITC)-conjugated anti-CD8 and an Allophycocyanin (APC)-conjugated anti-CD4 antibody according to the IFNγ secretion assay kit (Miltenyi Biotech, Bergisch-Gladbach, Germany). Sorting was conducted on a BD FACS Aria flow cytometer (BD Biosciences, Heidelberg, Germany). Cells double-positive for IFNγ and CD8 or CD4 were sorted and one cell per well was harvested in a 96-well V-bottom-plate (Greiner Bio-One GmbH, Solingen, Germany) containing NIH3T3 mouse fibroblasts as feeder cells, centrifuged at 4° C. and stored immediately at −80° C.

In Vivo Priming of T Cells by Intranodal Immunization of HLA A2.1/DR1 Mice with IVT RNA T cells of A2.1/DR1 mice (Pajot A. et al. (2004), Eur. J. Immunol. 34, 3060-69) were primed in vivo against the antigen of interest by repetitive intranodal immunization using antigen-encoding IVT RNA (Kreiter S. et al. (2010), Cancer Research 70, 9031-40). For intranodal immunizations, mice were anesthetized with xylazine/ketamine. The inguinal lymph node was surgically exposed, 10 µL RNA (20 µg) diluted in Ringer's solution and Rnase-free water were injected slowly using a single-use 0.3-ml syringe with an ultrafine needle (31 G, BD Biosciences), and the wound was closed. After six immunization cycles the mice were sacrificed and spleen cells were isolated.

Harvest of Spleen Cells

Following their dissection under sterile conditions, the spleens were transferred to PBS containing falcon tubes. The spleens were mechanically disrupted with forceps and the cell suspensions were obtained with a cell strainer (40 µm). The splenocytes were washed with PBS centrifuged and resuspended in a hypotonic buffer for lysis of the erythrocytes. After 5 min incubation at RT, the reaction was stopped by adding 20-30 ml medium or PBS. The spleen cells were centrifuged and washed twice with PBS.

Single-Cell Sorting of Antigen-Specific CD8+ T Cells after CD137 Staining

For antigen-specific restimulation $2.5 \times 10^{\wedge}6$/well spleen cells from immunized A2.1/DR1 mice were seeded in a 24-well plate and pulsed with a pool of overlapping peptides encoding the antigen of interest or a control antigen. After 24 h incubation cells were harvested, stained with a FITC-conjugated anti-CD3 antibody, a PE-conjugated anti-CD4 antibody, a PerCP-Cy5.5-conjugated anti-CD8 antibody and a Dylight-649-conjugated anti-CD137 antibody. Sorting was conducted on a BD FACS Aria flow cytometer (BD Biosciences). Cells positive for CD137, CD3 and CD8 or CD4 were sorted, one cell per well was harvested in a 96-well V-bottom-plate (Greiner Bio-One) containing human CCD-1079Sk cells as feeder cells, centrifuged at 4° C. and stored immediately at −80° C.

RNA Extraction, SMART-Based cDNA Synthesis and Unspecific Amplification from Sorted Cells RNA from sorted T cells was extracted with the RNeasy Micro Kit (Qiagen, Hilden, Germany) according to the instructions of the supplier. A modified BD SMART protocol was used for cDNA synthesis: BD PowerScript Reverse Transcriptase (BD Clontech, Mountain View, Calif.) was combined with oligo(dT)-T-primer long for priming of the first-strand synthesis reaction and TS-short (Eurogentec S.A., Seraing, Belgium) introducing an oligo(riboG) sequence to allow for creation of an extended template by the terminal transferase activity of the reverse transcriptase and for template switch (Matz, M. et al. (1999) Nucleic Acids Res. 27, 1558-1560). First strand cDNA synthesized according to the manufacturer's instructions was subjected to 21 cycles of amplification with 5 U PfuUltra Hotstart High-Fidelity DNA Polymerase (Stratagene, La Jolla, Calif.) and 0.48 µM primer TS-PCR primer in the presence of 200 µM dNTP (cycling conditions: 2 min at 95° C. for, 30 s at 94° C., 30 s at 65° C., 1 min at 72° C. for, final extension of 6 min at 72° C.). Successful amplification of TCR genes was controlled with either human or murine TCR-β constant region specific primers and consecutive clonotype-specific human or murine Vα-/Vβ-PCRs were only performed if strong bands were detected.

First strand cDNA for the amplification of HLA class I or II sequences was synthesized with SuperScriptII Reverse Transcriptase (Invitrogen) and Oligo(dT) primer with 1-5 jag RNA extracted from patient-derived PBMCs.

Design of PCR Primers for TCR and HLA Amplification

For design of human TCR consensus primers, all 67 TCR-Vβ and 54 TCR-Vα genes (open reading frames and pseudogenes) as listed in the ImMunoGeneTics (IMGT) database (http://www.imgt.org) together with their corresponding leader sequences were aligned with the BioEdit Sequence Alignment Editor (e.g. http://www.bio-soft.net). Forward primers of 24 to 27 bp length with a maximum of 3 degenerated bases, a GC-content between 40-60% and a G or C at the 3' end were designed to anneal to as many leader sequences as possible and equipped with a 15 bp 5' extension featuring a rare restriction enzyme site and Kozak sequence. Reverse primers were designed to anneal to the first exons of the constant region genes, with primer TRACex1_as binding to sequences corresponding to amino acids 7 to 16 of Cα and TRBCex1_as to amino acids (aa) 8 to 16 in Cβ1 and Cβ2. Both oligonucleotides were synthesized with a 5' phosphate. Primers were bundled in pools of 2-5 forward oligos with identical annealing temperature.

This strategy was replicated for the design of murine TCR consensus primers, aligning 129 listed TCR-Vα and 35 listed TCR-Vβ genes. Reverse primers mTRACex1_as and mTRBCex1_as are homologous to sequences corresponding to aa 24 to 31 and 8 to 15, respectively.

HLA consensus primers were designed by aligning all HLA class I and II sequences listed on the Anthony Nolan Research Institute website (www.anthonynolan.com) with the BioEdit Sequence Alignment Editor. Forward primers of 23 to 27 bp length with a maximum of 3 degenerated but code-preserving bases annealing to as many as possible HLA sequences of one locus were equipped with a 5'-phosphate and Kozak sequence extension. Reverse primers were designed analogously but without introduction of wobble bases and equipped with a 14 bp 5'-extension encoding an AsiSI restriction enzyme site.

PCR Amplification and Cloning of V(D)J and HLA Sequences 3-6 µl of preamplified cDNA from isolated T cells was subjected to 40 cycles of PCR in the presence of 0.6 µM Vα-/Vβ-specific oligo pool, 0.6 µM Cα- or Cβ-oligo, 200 µM dNTP and 5 U Pfu polymerase (cycling conditions: 2 min at 95° C., 30 s at 94° C., 30 s annealing temperature, 1 min at 72° C., final extension time of 6 min at 72° C.). PCR products were analyzed using Qiagen's capillary electrophoresis system. Samples with bands at 400-500 bp were size fractioned on agarose gels, the bands excised and purified using a Gel Extraction Kit (Qiagen, Hilden, Germany). Sequence analysis was performed to reveal the sequence of both the V(D)J domain and β constant region, as TRBCex1_as and mTRBCex1_as primer, respectively, match to both TCR constant region genes β1 and β2 in human and mouse, respectively. DNA was digested and cloned into the IVT vectors containing the appropriate backbone for a complete TCR-α/β chain.

HLA sequences were amplified according to the manufacturer's instructions with 2.5 U Pfu polymerase from donor specific cDNA using specific HLA class I or II sense and antisense primers. As transcription of DRB3 genes is at least five fold lower than that of DRB1 genes (Berdoz, J. et al. (1987) J. Immunol. 139, 1336-1341), amplification of DRB3 genes was conducted in two steps using a nested PCR approach. PCR fragments were purified, AsiSI-digested and cloned into the EcoRV- and AsiSI-digested IVT vector. EciI- or SapI-sites within the inserts were mutated using QuikChange Site-Directed Mutagenesis Kits (Stratagene, La Jolla, Calif.).

Flow Cytometric Analyses

Cell surface expression of transfected TCR genes was analyzed by flow cytometry using PE-conjugated anti-TCR antibody against the appropriate variable region family or the constant region of the TCR β chain (Beckman Coulter Inc., Fullerton, USA) and FITC-/APC-labeled anti-CD8/-CD4 antibodies (BD Biosciences). HLA antigens were detected by staining with FITC-labeled HLA class II-specific (Beckman Coulter Inc., Fullerton, USA) and PE-labeled HLA class I-specific antibodies (BD Biosciences). Flow cytometric analysis was performed on a FACS Calibur analytical flow cytometer using Cellquest-Pro software (BD Biosciences).

Luciferase Cytotoxicity Assay

For assessment of cell-mediated cytotoxicity a bioluminescence-based assay was established as an alternative and optimization to $^{51}$Cr release. In contrast to the standard chromium release assay, this assay measures lytic activity of effector cells by calculating the number of viable luciferase expressing target cells following coincubation. The target cells were stably or transiently transfected with the luciferase gene coding for the firefly luciferase from firefly Photinus pyralis (EC 1.13.12.7). Luciferase is an enzyme catalyzing the oxidation of luciferin. The reaction is ATP-dependent and takes place in two steps:

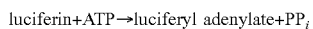

luciferin+ATP→luciferyl adenylate+PP$_i$

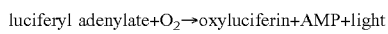

luciferyl adenylate+O$_2$→oxyluciferin+AMP+light

Target cells were plated at a concentration of $10^4$ cells per well in white 96-well plates (Nunc, Wiesbaden, Germany) and were cocultivated with varying numbers of TCR-transfected T cells in a final volume of 100 µl. 3 h later 50 µl of a D-Luciferin (BD Biosciences) containing reaction mix (Luciferin (1 µg/µl), HEPES-buffer (50 mM, pH), Adenosine 5'-triphosphatase (ATPase, 0.4 mU/µl, Sigma-Aldrich, St. Louis, USA) was added to the cells. By addition of ATPase to the reaction mix luminescence resulting from luciferase released from dead cells was diminished.

After a total incubation time of 4 h bioluminescence emitted by viable cells was measured using the Tecan Infinite 200 reader (Tecan, Crailsheim, Germany). Cell-killing activity was calculated in regard to luminescence values obtained after complete cell lysis induced by the addition of 2% Triton-X 100 and in relationship to luminescence emitted by target cells alone. Data output was in counts per second (CPS) and percent specific lysis was calculated as follows:

$$(1-(CPS_{exp}-CPS_{min})/(CPS_{max}-CPS_{min})))*100.$$

Maximum luminescence (maximum counts per second, CPSmax) was assessed after incubating target cells without effectors and minimal luminescences (CPSmin) was assessed after treatment of targets with detergent Triton-X-100 for complete lysis.

ELISPOT (Enzyme-Linked ImmunoSPOT Assay)

Microtiter plates (Millipore, Bedford, Mass., USA) were coated overnight at room temperature with an anti-IFNγ antibody 1-D1k (Mabtech, Stockholm, Sweden) and blocked with 2% human albumin (CSL Behring, Marburg, Germany). $2-5\times10^4$/well antigen presenting stimulator cells were plated in triplicates together with $0.3-3\times10^5$/well TCR-transfected CD4+ or CD8+ effector cells 24 h after electroporation. The plates were incubated overnight (37° C., 5% $CO_2$), washed with PBS 0.05% Tween 20, and incubated for 2 hours with the anti-IFNγ biotinylated mAB 7-B6-1 (Mabtech) at a final concentration of 1 µg/ml at 37° C. Avidin-bound horseradish peroxidase H (Vectastain Elite Kit; Vector Laboratories, Burlingame, USA) was added to the wells, incubated for 1 hour at room temperature and developed with 3-amino-9-ethyl carbazole (Sigma, Deisenhofen, Germany).

Example 2: Isolation of TCRs Specific for the Viral Antigen CMV-pp65

The TCR isolation/validation protocol (FIG. 2) was' established using the human cytomegalovirus (CMV)-phosphoprotein 65 (CMV-pp65, pp65, 65 kDa lower matrix phosphoprotein, UL83) as a model antigen, that is known to induce high frequencies of antigen-specific T cells in the peripheral blood of healthy donors.

CMV is a ubiquitous β-herpesvirus infecting the host via body fluids such as blood or saliva. In healthy individuals primary CMV infection and reactivation of endogenous latent viruses is controlled by the immune system, while in immunocompromised individuals such as transplant recipients or AIDS patients it results in significant morbidity and mortality.

The viral tegument protein pp65 is one of the major targets of CMV-specific cytotoxic T lymphocytes, which are present in high frequencies in the peripheral blood of non-immunocompromised seropositive individuals (Kern, F. et al. (1999), J. Virol. 73, 8179-8184; Wills, M. R. et al. (1996), J. Virol. 70, 7569-7579; Laughlin-Taylor, E. et al. (1994), J. Med. Virol. 43, 103-110).

CMV-pp65-specific IFNγ secreting CD8+ T cells of a seropositive healthy donor were isolated by flow cytometry after one week of antigen-specific expansion and rechallenge with autologous DCs transfected with IVT RNA encoding the whole pp65 antigen (FIG. 2 top, FIG. 3).

TCR α/β variable regions were amplified from single T cells using a set of sequence-specific, partially degenerated oligonucleotides. Amplification products were cloned site-directed into vectors containing the TCR α/β constant regions providing full-length templates for instant in vitro transcription (FIG. 2 middle).

For verification of cell surface expression TCR α/β RNAs were transferred into SupT1 cells otherwise lacking expression of endogenous TCR chains and analyzed by flow cytometry (FIG. 4).

For functional validation of cloned TCRs, the monospecific T cell line IVSB recognizing the tyrosinase-derived epitope $TYr_{368-376}$ (Wölfel T. et al. (1994), Eur. J. Immunol 24, 759-64) was transfected with TCR RNA and analyzed for specific cytokine secretion in response to pp65 antigen by IFNγ-ELISPOT (FIG. 2 bottom, FIG. 5). As the TCRs were generated by stimulation with whole antigen, they were evaluated for mediating specific recognition of autologous DCs either pulsed with pp65 peptide pool or pp65 encoding IVT RNA. An unrelated TPTE peptide pool was used as a control. $TCR_{CD8}$-CMV#1 and $TCR_{CD8}$-CMV#4 both specifically recognized pp65 expressing target cells compared to a control TCR isolated from a CMV seronegative donor.

To determine the HLA restricting element, IVSB cells transfected with $TCR_{CD8}$-CMV#1 were analyzed for specific IFNγ secretion after co-culture with peptide-pulsed K562 cells expressing selected HLA alleles of the patient (FIG. 6 top). HLA B*3501 was identified as restriction element. Analysis of individual 15-mers of the pp65 peptide pool revealed recognition of peptides P30, P31 and P32, with reactivity decreasing gradually (FIG. 6 bottom). This localized the epitope recognized by $TCR_{CD8}$-CMV#1 within the region of amino acids 117-131 of pp65 suggesting its identity with the previously reported and highly immunogenic HLA-B*3501-restricted epitope CMV-pp65$_{123-131}$ (Seq. IPSINVHHY) (Gavin, M. A. et al. (1993), J. Immunol. 151, 3971-3980).

After successful isolation of TCRs from pp65-specific CD8+ T cells expanded in vitro to a high frequency, the TCR isolation protocol was applied to ex vivo sorted T cells present with lower frequencies.

CD8+ T cells magnetically purified from PBMCs of an HLA A*0201 positive donor were stimulated with autologous target cells pulsed with the immunodominant HLA A*0201-restricted epitope pp65$_{495-563}$ and activated IFNγ secreting T cells were sorted by flow cytometry.

Specificity of TCRs obtained ex vivo from the CD8+ T cells after presensitation with pp65$_{495-503}$ was analyzed in an IFNγ-ELISPOT assay. As shown in FIG. 7, four of six TCRs were able to redirect IVSB cells to recognize K562-A*0201 cells pulsed with pp65$_{495-503}$ compared to a control peptide. In contrast, IVSB cells equipped with a control TCR isolated from a CMV-seronegative donor did not secrete IFNγ upon coculture with K562-A*0201 cells pulsed with pp65$_{495-503}$.

In order to show that cloned pp65-specific TCRs are also able to mediate cytolytic effector function a luciferase-based cytotoxicity assay was conducted using IVSB cells transfected with $TCR_{CD8}$-CMV#1 or $TCR_{CD8}$-CMV#14.

Specific killing of appropriate target cells (K562-B*3501 cells pulsed with pp65$_{117-131}$ and K562-A*0201 cells pulsed with peptide pp65$_{495-503}$, respectively) was compared to the killing of $Tyr_{368-376}$-pulsed K562-A*0201 cells mediated by the endogenous TCR of IVSB effectors (FIG. 8).

Titration of the effector-to-target (E:T) ratio confirmed that target cells pulsed with the appropriate pp65 peptide were specifically lysed by TCR-transfected IVSB cells. Up to 85% of target cells were killed by IVSB cells transfected with $TCR_{CD8}$-CMV#1 and $TCR_{CD8}$-CMV#14, respectively. Remarkably, recombinant TCRs mediated equally efficient lysis as the natural TCR at a broad range of E:T ratios.

In summary, 13 hCMV-pp65-specific TCRs were isolated from CD4+ and CD8+ T cells obtained from four different CMV seropositive donors either ex vivo or after antigen-specific expansion as listed in Table 1.

Example 3: Isolation of TCRs Specific for the Tumor Antigen NY-ESO-1

After proof of concept studies using CMV-pp65 as a viral model antigen eliciting high frequencies of antigen-specific T cells, we evaluated the capability of our approach to clone TCRs from tumor antigen-specific T cell populations of low abundance. Frequencies of pre-existing T cells against tumor-associated self proteins are generally much lower than frequencies of T cells elicited by persisting viruses. For application of our method to the tumor setting we resorted to the highly immunogenic tumor antigen NY-ESO-1.

NY-ESO-1 is a cancer/testis antigen expressed in normal adult tissues solely in the testicular germ cells. NY-ESO-1 (synonyms: CTG, CTAG, CTAG1, ESO1, LAGE-2, LAGE2, LAGE2A, LAGE2B, OTTHUMP00000026025, OTTHUMP00000026042) is one of the best characterized cancer testis antigens identified by SEREX (Chen, Y. T. et al. (1997), Proc. Natl. Acad. Sci. U.S.A 94, 1914-1918), which is expressed in a variety of malignant neoplasms, including melanomas, esophageal, breast, prostate, urinary tract, ovarian and lung cancers (Chen, Y. T. et al. (1997) Proc. Natl. Acad. Sci. U.S.A 94, 1914-1918; Jungbluth, A. A. et al. (2001) Int. J. Cancer 92, 856-860; Schultz-Thater, E. et al. (2000) Br. J. Cancer 83, 204-208). Due to its natural immunogenicity it is favored as a model antigen for tumor vaccination strategies. NY-ESO-1 frequently elicits high-titer antibody responses in patients bearing NY-ESO-1 expressing tumors and it was shown that autoantibody responses against NY-ESO-1 are often associated with the presence of antigen-specific CD8+ and CD4+ T cells (Zeng, G. et al. (2001), Proc. Natl. Acad. Sci. U.S.A 98, 3964-3969; Jager, E. et al. (1998), J. Exp. Med. 187, 265-270; Gnjatic, S. et al. (2003), Proc. Natl. Acad. Sci. U.S.A 100, 8862-8867; Valmori, D. et al. (2007), Clin. Immunol. 122, 163-172).

We selected a NSCLC patient based on his autoantibody reactivity against NY-ESO-1, pulsed his bulk PBMCs with NY-ESO-1 peptide pool and expanded for one week. After exposure to autologous NY-ESO-1 RNA transfected DCs IFNγ secreting CD8+ T cells were sorted and TCRs were cloned from single cells. Validation of identified TCRs for specific recognition of NY-ESO-1 expressing target cells by IFNγ ELISPOT assay resulted in seven functional NY-ESO-1-specific TCRs obtained from this patient. As shown in FIG. 9, TCRs recognized DCs either pulsed with NY-ESO-1 peptide pool or transfected with NY-ESO-1 RNA, the latter confirming recognition of a naturally processed epitope.

HLA restrictions of NY-ESO-1-specific TCRs were determined by IFNγ-ELISPOT using TCR-transfected IVSB effectors co-cultured with K562 cells expressing individual HLA class I alleles of the patient and pulsed with NY-ESO-1 peptide pool. A representative result is shown in FIG. 10.

For epitope mapping IVSB T cells were transfected with NY-ESO-1-specific TCRs and co-cultured with K562 cells expressing the appropriate HLA antigen pulsed with individual overlapping 15mer peptides spanning the NY-ESO-1 protein. Reactivity of TCR-transfected T cells against the NY-ESO-1 peptides was assayed in IFNγ-ELISPOT assays (FIG. 11).

Remarkably, epitopes of all seven TCRs were localized to amino acids 85-111 of the NY-ESO-1 protein (FIG. 11, 12). This region is known to undergo efficient proteosomal cleavage due to hydrophobic sequences and is processed into multiple epitopes with various HLA restrictions (Valmori, D. et al. (2007), Clin. Immunol. 122, 163-172). By screening serial nonamers, we narrowed down the HLA-B*3508 restricted epitope of $TCR_{CD8}$-NY#5, #6, #8 and #15 to NY-ESO-$1_{92-100}$ (seq. LAMPFATPM) (FIG. 12).

In order to show that NY-ESO-1-specific TCRs isolated from CD8+ T cells are able to mediate cytolytic effector functions, TCR-transgenic IVSB cells were analyzed for specific killing of peptide-pulsed K562-A*6801 cells. As shown in FIG. 13, IVSB effectors were reprogrammed by $TCR_{CD8}$-NY#2 to specifically lyse target cells at different E:T ratios.

Validation of TCRs isolated from CD4+ T cells of two other seropositive NSCLC patients resulted in cloning of 9 independent functional NY-ESO-1-specific TCRs. Determination of restriction elements (FIG. 14) and confinement of epitope localizations (FIG. 15) revealed that 7 of these TCRs recognized epitopes in a peptide stretch comprising aa 117-147 in the context of different HLA class II allelotypes, suggesting a hot spot for T helper cell epitopes (Table 5).

To date, 16 NY-ESO-1-specific TCRs were cloned from CD4+ and CD8+ derived from three different NSCLC patients and characterized regarding HLA restriction and peptide specificity (Table 2).

Example 4: Isolation of TCRs Specific for the Tumor Antigen TPTE

TPTE (Transmembrane Phosphatase with Tensin homology; synonyms: CT44, PTEN2, EC 3.1.3.48, OTTHUMP00000082790), is a sperm cell-specific lipid phosphatase that is aberrantly transcribed in many human cancers (Chen, H. et al. (1999), Hum. Genet. 105, 399-409; Dong, X. Y. et al. (2003), Br. J. Cancer 89, 291-297; Singh, A. P. et al. (2008), Cancer Lett. 259, 28-38), but little is known about its immunogenicity and T cell responses had not been reported so far.

In order to isolate TPTE-specific TCRs, 3 NSCLC patients showing significant absorbance values in the pre-screening by CrELISA were selected for antigen-specific expansion and flow cytometry sorting of TPTE-specific CD8+ and CD4+ T cells.

TCRs isolated from CD8+ T cells were validated for recognition of TPTE expressing target cells and were characterized regarding HLA restriction and epitope specificity as exemplarily shown for $TCR_{CD8}TPT\#3$ in FIG. 16. This TCR was shown to reprogram IVSB cells for specific recognition of K562 cells presenting TPTE peptides on HLA B*3501 (FIG. 16 top). The HLA-B*3501-restricted epitope could be localized to TPTE 15-mers P130, P131 and P132, with highest reactivity to peptide P131 representing amino acids 521-535 of TPTE (FIG. 16 middle). By analyzing serial nonamers covering this region, the novel epitope $TPTE_{527-535}$ (seq. YPSDFAVEI) could be defined, which complies with the requirements of a B*3501 binding motif with proline as an anchor residue at position 2, aspartic acid as a charged residue at position 4 and isoleucine as a hydrophobic amino acid at position 9 (Falk, K. et al. (1993), Immunogenetics 38, 161-162) (FIG. 16 bottom).

Analogously, TCRs isolated from CD4+ T cells were validated for specific recognition of K562 cells expressing TPTE and individual HLA class II alleles of the donor (FIG. 17). After determination of HLA restrictions TPTE-specific TCRs were analyzed for recognition of TPTE 15mer peptides in order to localize the recognized epitopes (FIG. 18).

A total of 31 functional TPTE-reactive TCRs were identified thus far, from which two are derived from CD8+ cells and 29 are derived from CD4+ T cells of three different NSCLC patients (Table 3). Fine mapping of epitopes by the use of single-peptide-pulsed HLA allele-expressing K562 target cells, disclosed that epitopes were distributed all over the TPTE protein sequence (Table 5).

Example 5: Isolation of High-Affinity PLAC1-Specific TCRs from T Cells of Immunized A2.1/DR1 Mice The trophoblast-specific gene PLAC1 (PLACenta-specific 1, synonyms: OTTHUMP00000024066; cancer/testis antigen 92) is a novel member of cancer-associated placental genes (Koslowski M. et al. (2007), Cancer Research 67, 9528-34). PLAC1 is ectopically expressed in a wide range of human malignancies, most frequently in breast cancer, and is essentially involved in cancer cell proliferation, migration, and invasion.

In order to obtain TCRs specific for PLAC1, we changed the source for antigen-specific T cells. As TCRs isolated from the natural repertoire of cancer patients are usually of low affinity owing to central tolerance mechanisms, we applied an alternative approach bypassing tolerance to generate high-affinity T cells specific for PLAC1. T cells of HLA A2.1/DR1 transgenic mice (Pajot A. et al. (2004), Eur. J. Immunol. 34, 3060-69) were primed in vivo against the human PLAC1 antigen by repetitive intranodal immunization using PLAC1-encoding IVT RNA (Kreiter S. et al. (2010), Cancer Research 70, 9031-40). Spleen cells obtained from these mice were rechallenged with PLAC1 overlapping peptides following detection and isolation of antigen-specific T cells based on their activation-induced upregulation of CD137 (FIG. 19). Notably, in all five mice a significant percentage of PLAC1-specific T cells (ranging from 16-48% of CD8+ cells) could be established by intranodal immunization with PLAC1 IVT RNA.

For validation of TCRs cloned from murine CD8+ T cells TCR-engineered IVSB cells were analyzed for specific cytokine secretion in response to PLAC1 peptide-pulsed K562-A*0201 cells by IFNγ-ELISPOT (FIG. 20). A total of 11 TCRs were shown to mediate specific recognition of K562-A*0201 cells pulsed with peptides derived from PLAC1 compared to a control antigen. Remarkably, IFNγ secretion mediated by the PLAC1-specific TCRs was even higher compared to those mediated by the endogenous TCR of IVSB effectors. Epitope mapping by the use single-peptide-pulsed HLA allele-expressing K562 target cells, disclosed that all identified PLAC1-specific TCRs recognize 15mer peptides 7 and 8 representing amino acid 25-43 of PLAC1 (FIG. 21). By screening serial nonamers covering this region, we identified two HLA-A*0201 restricted epitopes: PLAC1 amino acids 28-36 and amino acids 30-41, with best recognition of amino acids 31-39 (FIG. 22, Table 5). Notably, all PLAC1-specific TCRs obtained from 4 different mice were shown to recognize these two epitopes indicating preferential procession of these PLAC1 peptides as well as efficient binding and presentation on HLA A*0201. All TCRs mediated increased IFNγ secretion in response to amino acids 31-39 compared to amino acids 28-36. The latter was properly recognized by some of the TCRs only.

By cloning of 11 PLAC1-specific TCRs (Table 4) and identification of two HLA A*0201-presented immunodominant PLAC1 epitopes (Table 5) we could show that T cells of A2/DR1 mice primed in vivo by intranodal vaccination with antigen-encoding IVT RNA are exploitable as a source for TCR isolation.

CONCLUSION

We were able to establish a versatile platform technology for efficient cloning and rapid characterization of immunologically relevant TCRs from small antigen-specific T cell populations without the need for generation of T cell clones or lines and prior knowledge of restriction elements or T cell epitopes.

Usage of our TCR isolation/validation approach for viral and tumor antigens resulted in the discovery of more than 70 antigen-specific TCRs (Table 1,2,3,4), whereof far more than half were directed against novel HLA presented epitopes (Table 5).

Notably, from single donors several TCR specificities derived from CD8+ as well as CD4+ T lymphocytes were cloned in parallel and shown to reprogram T cell effectors for recognition of the respective antigen.

This approach enables the generation of a large library of TCRs in a timely manner for "off the shelf" use filling the gap between the availability of a large amount of target structures and the small number of suitable TCR candidates for antigen-specific therapy approaches in the field of cancer, autoimmunity and infectious diseases.

Tables

TABLE 1 hCMV pp65-specific TCRs

| Designation | TCR alpha chain[a] | TCR beta chain[a] | HLA class I/II restriction[b] | Recognized region |
|---|---|---|---|---|
| TCR$_{CD8}$-CMV#1 | V1.2 J24_2 C | V3.1 D2 J2.1 C2 | B*3501 | aa 117-139, best 117-131 |
| TCR$_{CD8}$-CMV#4 | V3 J43 C | V6.5 D1 J1.2 C1 | A*0201 | aa 495-503 |
| TCR$_{CD8}$-CMV#8 | V22 J58 C | V10.1 D J1.4 C1 | A*0201 | aa 495-503 |
| TCR$_{CD8}$-CMV#9 | V19 J26 C | V13 D2 J2.1 C2 | pending | pending |
| TCR$_{CD8}$-CMV#10 | V24 J49 C | V6.5 D1 J1.2 C1 | A*0201 | aa 495-503 |
| TCR$_{CD8}$-CMV#11 | V16 J36 C | V25.1 D1 J2.2 C2 | A*0201 | aa 495-503 |
| TCR$_{CD8}$-CMV#12 | V39 J58 C | V9 D2 J2.2 C2 | A*0201 | aa 495-503 |
| TCR$_{CD8}$-CMV#14 | V24 J21 C | V3.1 D2 J2.2 C2 | A*0201 | aa 495-503 |
| TCR$_{CD8}$-CMV#15 | V12.3 J43 C | V12.4 D1 J1.4 C1[c] | A*0201 | aa 495-503 |
| TCR$_{CD8}$-CMV#16 | V13.1_2 J50 C | V25.1 J1.3 C1 | A*0201 | aa 495-503 |
| TCR$_{CD4}$-CMV#1 | V21 J43 C | V3.1 D1 J1.1 C1 | DRB1*0701 | aa 117-139 |
| TCR$_{CD4}$-CMV#3 | V8.6_2 J37_2 C | V6.1 D1 J1.2 C1 | DRB1*0701 | aa 337-359 |
| TCR$_{CD4}$-CMV#5 | V22 J49 C | V6.2 D2 J2.3 C2[d] | DRB1*0701 | aa 337-359 |

TABLE 2

NY-ESO-1-specific TCRs

| Designation | TCR alpha chain[a] | TCR beta chain[a] | HLA class I/II restriction[b] | Recognized region |
|---|---|---|---|---|
| TCR$_{CD8}$-NY#2 | V3 J28 C | V20.1_2 J2.3 C2 | A*6801 | aa 93-107 |
| TCR$_{CD8}$-NY#5 | V24 J3 C | V7.6 D2 J2.2 C2 | B*3508 | aa 92-100 |
| TCR$_{CD8}$-NY#6 | V17 J47_2 C | V12.3 D2 J2.1 C2 | B*3508 | aa 92-100 |
| TCR$_{CD8}$-NY#8 | V8.6_2 J9 C | V28.1 D1 J1.1 C1 | B*3508 | aa 92-100 |
| TCR$_{CD8}$-NY#12 | V1.1 J23 C | V4.1 D2 J2.1 C2 | B*0702 | aa 97-111 |
| TCR$_{CD8}$-NY#13 | V5 J33 C | V5.5_2 D1 J2.5 C2 | A*6801 | aa 93-107 |
| TCR$_{CD8}$-NY#15 | V12.2_2 J53 C | V4.1 D2 J2.5 C2 | B*3508 | aa 92-100 |
| TCR$_{CD4}$-NY#1 | V22 J20 C | V9 D1 J1.1 C1 | DRB1*0401 | aa 165-180 |
| TCR$_{CD4}$-NY#3 | V12.3 J54 C | V11.2 D2 J2.2 C2 | DRB1*0401 | aa 117-139 |
| TCR$_{CD4}$-NY#5 | V8.4_3 J48 C | V4.1 DI J1.5 C1 | DRB1*1101 | aa 117-139 |
| TCR$_{CD4}$-NY#7 | V8.6_2 J13_2 C | V20.1 D2 J2.5 C2 | DRB1*1101 DRB1*1601 | aa 117-139 |
| TCR$_{CD4}$-NY#10 | V9.2_3 J42 C | V7.9_3 D2 J2.7 C2 | DRB5*0202 | aa 85-99 |
| TCR$_{CD4}$-NY#11 | V8.1 J23 C | V11.2 D1 J1.2 C1 | DRB1*1101 | aa 117-139 |
| TCR$_{CD4}$-NY#13 | V21_2 J24_2 C | V7.9_3 D1 J2.3 C2 | DRB5*0202 | aa 129-147 |
| TCR$_{CD4}$-NY#16 | V8.4_3 J10 C | V20.1 D1 J1.5 C1 | DRB3*0201 | aa 117-139 |
| TCR$_{CD4}$-NY#14 | V8.4_3 J37_2 C | V3.1 D2 J1.3 C1 | DRB3*0201 | aa 121-135 |

TABLE 3

TPTE-specific TCRs

| Designation | TCR alpha chain[a] | TCR beta chain[a] | HLA class I/II restriction[b] | Recognized region |
|---|---|---|---|---|
| TCR$_{CD8}$-TPT#3 | V27 J16 C | V7.9 D2 J2.2 C2 | B*3501 | aa 527-535 |
| TCR$_{CD8}$-TPT#35 | V19 J17 C | V6.2/V6.3 D1 J1.2 C1[d] | B*0702 | aa 188-196 |
| TCR$_{CD4}$-TPT#4 | V14/DV4 J48 C | V29.1 D1 J1.2 C1 | DRB4*0101 | aa 405-423 |
| TCR$_{CD4}$-TPT#5 | V38.2/DV8 J40 C | V4.2 D2 J2.7 C2 | DRB1*1401 | aa 417-435 |
| TCR$_{CD4}$-TPT#6 | V12.3 J35 C | V5.4 D1 J1.3 C1 | DRB1*1401 | aa 53-71 |
| TCR$_{CD4}$-TPT#8 | V38.1 J45 C | V3.1 D1 J2.7 C2 | DRB3*0201/2 | aa 181-195 |
| TCR$_{CD4}$-TPT#11 | V17 J27 C | V6.6_2 D1 J2.3 C2 | DRB1*0701 | aa 109-127 |
| TCR$_{CD4}$-TPT#13 | V20_2 J29 C | V19 D2 J2.1 C2 | DRB1*1401 | aa 497-515 |
| TCR$_{CD4}$-TPT#17 | V29/DV5 J49 C | V7.2 D1 J2.7 C2 | DRB5*0202 | aa 177-195 |
| TCR$_{CD4}$-TPT#27 | V13.1_2 J45 C | V19 D1 J1.1 C1 | DRB3*0301 | aa 181-195 |
| TCR$_{CD4}$-TPT#33 | V29/DV5 J42 C | V24.1 D2 J2.1 C2 | DRB5*0202 | aa 217-231 |
| TCR$_{CD4}$-TPT#38 | V39 J18 C | V5.5_2 DI J1.4 C1 | DRB1*1601 | aa 277-291 |
| TCR$_{CD4}$-TPT#42 | V25 J10 C | V7.8 D2 J2.7 C2 | DRB1*1301 | aa 269-283 |
| TCR$_{CD4}$-TPT#45 | V13.2 J23 C | V20.1 D1 J1.2 C1 | DRB1*1501 | aa 413-427 |
| TCR$_{CD4}$-TPT#48 | V8.3 J43 C | V28 DI J1.1 C1 | DRB1*1501 | aa 173-187 |
| TCR$_{CD4}$-TPT#49 | V38.1 J49 C | V19 D2 J2.2 C2 | DRB1*1501 | aa 393-411 |
| TCR$_{CD4}$-TPT#51 | V13.1_2 J53 C | V14 D1 J1.1 C1 | DRB1*1301 | aa 217-231 |
| TCR$_{CD4}$-TPT#52 | V8.3 J54 C | V6.1 D2 J2.7 C2 | DRB1*1501 | aa 117-135 |
| TCR$_{CD4}$-TPT#54[g] | V9.2 J23 C | V20.1 D1 J1.1 C1 | DQB1*0602/03; DQA*0102/03 | aa 53-67 aa 77-91 aa 245-259 |
| TCR$_{CD4}$-TPT#55 | V38.2/DV8 J34 C | V5.1 J2.1 C2 | DRB1*1301 | aa 177-195 |
| TCR$_{CD4}$-TPT#57 | V8.1 J27 C | V5.1 D2 J2.7 C2 | DRB1*1501 | aa 81-95 |
| TCR$_{CD4}$-TPT#59 | V39 J49 C | V7.9_3 D2 J2.4 C2 | DRB1*1301 | aa 141-155 |
| TCR$_{CD4}$-TPT#67 | V12.3 J9 C | V5.1 D2 J2.7 C2 | DRB1*1501 | aa 173-187 |
| TCR$_{CD4}$-TPT#76 | V8.3 J57 C | V19 D2_2 J2.7 C2 | DQA1*0102/DQB1*0602 DQA1*0103/DQB1*0602 DQA1*0103/DQB1*0603 | aa 453-467 |
| TCR$_{CD4}$-TPT#77 | V14/DV4_3 J50 C | V20.1 D2 J2.2 C2 | DRB1*1301 | aa 417-435 |
| TCR$_{CD4}$-TPT#78 | V8.6_2 J21 C | V2 D1 J1.6_2 C1 | DRB1*1301 | aa 221-235 |
| TCR$_{CD4}$-TPT#79[g] | V38.2/DV8 J39 C | V5.1 D2 J2.1 C2 | DRB1*1501 | aa 149-163 aa 157-171 aa 173-187 |
| TCR$_{CD4}$-TPT#82 | V38.2/DV8 J39 C | V19 D1 J2.7 C2 | DRB1*1301 | aa 409-423 |
| TCR$_{CD4}$-TPT#87 | V39 J31 C | V5.1 J2.6 C2 | DRB1*1301 | aa 177-195 |
| TCR$_{CD4}$-TPT#91 | V20_2 J53 C | V6.1 D1 J2.7 C2 | DRB1*1501 | aa 173-187 |
| TCR$_{CD4}$-TPT#9[g] | V23/DV6 J49 C | V3.1 D1 J1.2 C1 | DRB1*0701 | aa 121-135 aa 145-159 |

TABLE 4

PLAC1-specific TCRs

| Designation | TCR alpha chain[a] | TCR beta chain[a] | HLA class I/II restriction[b] | Recognized region |
|---|---|---|---|---|
| TCR$_{CD8}$-mP1#2 | V6D.6_5 J33 C | V2 D1 J1.3 C1 | A*0201 | aa 28-36, 30-41, best 31-39 |
| TCR$_{CD8}$-mP1#8 | V9D.1 J12 C[e] | V5 D2 J2.1 C2 | A*0201 | aa 28-36, 30-41, best 31-39 |
| TCR$_{CD8}$-mP1#9 | V4D.4_2 J44 C | V2 D2 J2.7 C2 | A*0201 | aa 25-43 |
| TCR$_{CD8}$-mP1#11 | V6D.6_2 J9_2 C | V2 D1 J1.3 C1 | A*0201 | aa 28-36, 30-41, best 31-39 |
| TCR$_{CD8}$-mP1#12 | V4D.4_2 J27 C | V30 D1 J2.2 C2 | A*0201 | aa 28-36, 30-41, best 31-39 |
| TCR$_{CD8}$-mP1#14 | V9D.1_2 J12 C | V5 D1 J1.1 C1 | A*0201 | aa 28-36, 30-41, best 31-39 |
| TCR$_{CD8}$-mP1#17 | V14.1 J31 C[f] | V13.2 D2 J2.1 C2 | A*0201 | aa 28-36, 30-41, best 31-39 |
| TCR$_{CD8}$-mP1#19 | V6D.3 J22 C | V13.3 DI J1.6 C1 | A*0201 | aa 28-36, 30-41, best 31-39 |
| TCR$_{CD8}$-mP1#20 | V12.3_3 J38 C | V5 D2 J1.1 C1 | A*0201 | aa 28-36, 30-41, best 31-39 |
| TCR$_{CD8}$-mP1#22 | V13D.2 J34_2 C | V20 D1 J2.1 C2 | A*0201 | aa 28-36, 30-41, best 31-39 |
| TCR$_{CD8}$-mP1#25 | V8.1_3 J21 C | V31 D2 J2.1 C2 | A*0201 | aa 25-43 |

[a]Designations of the TCR V(D)J genes according to the IMGT nomenclature; Example: Vβ7.9 is the ninth gene of Vβ gene subgroup 7, while V7.9_3 is the third allele of gene 9 of subgroup 7. Alleles are only specified by an underline, if they differ from allele 1.
[b]Designations of the HLA alleles begin with HLA- and the locus name, then * and a number of digits specifying the allele. The first two digits specify a group of alleles. The third through fourth digits specify a synonymous allele. Digits five through six denote any synonymous mutations within the coding frame of the gene. The seventh and eighth digits distinguish mutations outside the coding region
[c]The TCR beta gene is V12.4_1 or V12.4_2
[d]The TCR beta gene is V6.2 or V6.3
[e]The TCR alpha gene is V9D.1_1 or V9D.1_2
[f]The TCR alpha gene is J31_1 or J31_2
[g]Promiscuous TCRs recognizing more than one epitope
aa = amino acids

TABLE 5

T cell epitopes derived from the antigens hCMV pp65, NY-ESO-I, TPTE, PLAC1

| Antigen | Epitope | Amino acid sequence | HLA class I/II restriction | SEQ ID NO: |
|---|---|---|---|---|
| hCMV pp65 | aa 117-139, best 117-131 | PLKMLNIPSINVHHYPSAAERKH | B*3501 | 108 |
|  | aa 495-503 | NLVPMVATV | A*0201 | 109 |
|  | aa 117-139 | PLKMLNIPSINVHHYPSAAERKH | DRB1*0701 | 108 |
|  | aa 337-359 | VELRQYDPVAALFFFDIDLLLQR | DRB1*0701 | 110 |
| NY-ESO-I | aa 92-100 | LAMPFATPM | B*3508 | 111 |
|  | aa 93-107 | AMPFATPMEAELARR | A*6801 | 112 |
|  | aa 97-111 | ATPMEAELARRSLAQ | B*0702 | 113 |
|  | aa 85-99 | SRLLEFYLAMPFATP | DRB5*0202 | 114 |
|  | aa 117-139 | PVPGVLLKEFTVSGNILTIRLTA | DRB1*0401 | 115 |
|  | aa 117-139 | PVPGVLLKEFTVSGNILTIRLTA | DRB1*1101 | 115 |
|  | aa 117-139 | PVPGVLLKEFTVSGNILTIRLTA | DRB1*1601 | 115 |
|  | aa 117-139 | PVPGVLLKEFTVSGNILTIRLTA | DRB3*0201 | 115 |
|  | aa 129-147 | SGNILTIRLTAADHRQLQL | DRB5*0202 | 116 |
|  | aa 165-180 | CFLPVFLAQPPSGQRR | DRB1*0401 | 117 |
|  | aa 121-135 | VLLKEFTVSGNILTI | DRB3*0201 | 175 |
| TPTE | aa 185-199 | RNIPRWTHLLRLLRL | B*0702 | 118 |
|  | aa 527-535 | YPSDFAVEI | B*3501 | 119 |
|  | aa 53-71 | SPISESVLARLSKFEVEDA | DRB1*1401 | 120 |
|  | aa 81-95 | IKKIVHSIVSSFAFG | DRB1*1501 | 121 |
|  | aa 109-127 | ILADLIFTDSKLYIPLEYR | DRB1*0701 | 122 |
|  | aa 117-135 | DSKLYIPLEYRSISLAIAL | DRB1*1501 | 123 |
|  | aa 141-155 | VLLRVFVERRQQYFS | DRB1*1301 | 124 |
|  | aa 173-187 | DVVYIFFDIKLLRNI | DRB1*1501 | 125 |
|  | aa 177-191 | IFFDIKLLRNLPRWT | DRB1*1501 | 126 |
|  | aa 177-195 | IFFDIKLLRNIPRWTHLLR | DRB1*1301 | 127 |
|  | aa 177-195 | IFFDIKLLRNIPRWTHLLR | DRB5*0202 | 127 |

TABLE 5 -continued

T cell epitopes derived from the antigens hCMV pp65, NY-ESO-I, TPTE, PLAC1

| Antigen | Epitope | Amino acid sequence | HLA class I/II restriction | SEQ ID NO: |
|---|---|---|---|---|
| | aa 181-195 | IKLLRNIPRWTHLLR | DRB3*0201/2 | 128 |
| | aa 181-195 | IKLLRNIPRWTHLLR | DRB3*0301 | 128 |
| | aa 217-231 | KLIRRRVSENKRRYT | DRB1*1301 | 129 |
| | aa 217-231 | KLIRRRVSENKRRYT | DRB5*0202 | 129 |
| | aa 221-235 | RRVSENKRRYTRDGF | DRB1*1301 | 130 |
| | aa 269-283 | RFLDICKHRNHYRVYN | DRB1*1301 | 131 |
| | aa 277-291 | NHYRVYNLCSERAYD | DRB1*1601 | 132 |
| | aa 393-411 | YVAYFAQVKHLYNWNLPPR | DRB1*1501 | 133 |
| | aa 405-423 | NWNLPPRRILFIICHFITYS | DRB4*0101 | 134 |
| | aa 409-423 | PPRRILFIKHFIIYS | DRB1*1301 | 135 |
| | aa 413-427 | ILFIKHFIIYSIPRY | DRB1*1501 | 136 |
| | aa 417-435 | KHFITYSEPRYVRDLKIQI | DRB1*1301 | 137 |
| | aa 417-435 | KHFITYSLPRYVRDLKIQI | DRB1*1401 | 137 |
| | aa 453-467 | VLDNITTDKILIDVF | DQA1*0102/B1*0602 | 138 |
| | aa 453-467 | VLDNITTDKILIDVF | DQA1*0103/B1*0602 | 138 |
| | aa 453-467 | VLDNITTDKILIDVF | DQA1*0103/B1*0603 | 138 |
| | aa 497-515 | WLHTSFIENNRLYLPKNEL | DRB1*1401 | 139 |
| | aa 102-110 | VLLDVTLIL | A*0201 | 178 |
| | aa 164-172 | AIIVILLLV | A*0201 | 179 |
| | aa 188-196 | PRWTHLLRL | B*0702 | 180 |
| | aa 53-67 | SPISESVLARLSKFE | DQA1*0102/DQB1*0602 | 181 |
| | aa 77-91 | YDSKIKKIVHSIVSS | DQA1*0102/DQB1*0602 | 182 |
| | aa 121-135 | YIPLEYRSISLAIAL | DRB1*0701 | 183 |
| | aa 145-159 | VFVERRQQYFSDLFN | DRB1*0701 | 184 |
| | aa 149-163 | RRQQYFSDLFNILDT | DRB1*1501 | 185 |
| | aa 157-171 | LFNILDTAIIVILLL | DRB1*1501 | 186 |
| | aa 245-259 | RIIAMSFPSSGRQSF | DQA1*0102/DQB1*0602 | 187 |
| PLAC1 | aa 28-36 | VLCSIDWFM | A*0201 | 172 |
| | aa 30-41, best 31-39 | CSIDWFMVTVHP | A*0201 | 173 |
| | aa 25-43 | PMTVLCSIDWFMVTVHPFM | A*0201 | 196 |

In the following, the T cell receptor sequences obtained are shown. The underlined sequences are the CDR sequences, wherein the first sequence in each T cell receptor chain is CDR1, followed by CDR2 and CDR3.

1. hCMV Pp65-Specific T Cell Receptors

TCR$_{CD8}$-CMV#1:
>Vα1.2 J24_2 C(V->A)
SEQ ID NO: 4
MWGAFLLYVSMKMGGTTGQNIDQPTEMTATEGAIVQINCTYQTSGFNGLFWYQQH

AGEAPTFLSYNVLDGLEEKGRFSSFLSRSKGYSYLLLKELQMKDSASYLCAVADSWG

KLQFGAGTQVVVTPDIQNPDPAVYQLRDSKSSDKSVCLFTDFDSQTNVSQSKDSDVY

ITDKTVLDMRSMDFKSNSAVAWSNKSDFACANAFNNSIIPEDTFFPSPESSCDVKLVE

KSFETDTNLNFQNLSVIGFRILLLKVAGFNLLMTLRLWSS*;

>Vβ3.1 D2 J2.1 C2 (C->T)
SEQ ID NO: 5
MGTRLLCCVVFCLLQAGPLDTAVSQTPKYLVTQMGNDKSIKCEQNLGHDTMYWYK

QDSKKFLKIMFSYNNKELIINETVPNRFSPKSPDKAHLNLHINSLELGDSAVYFCASSQ

EGLAGASNNEQFFGPGTRLTVLEDLKNVFPPEVAVFEPSEAEISHTQKATLVCLATGF

YPDHVELSWWVNGKEVHSGVSTDPQPLKEQPALNDSRYCLSSRLRVSATFWQNPRN

HFRCQVQFYGLSENDEWTQDRAKPVTQIVSAEAWGRADCGFTSESYQQGVLSATIL

YEILLGKATLYAVLVSALVLMAMVKRKDSRG*;

TCR<sub>CD8</sub>-CMV#4:
>Vα3 J43 C
SEQ ID NO: 6
MASAPISMLAMLFTLSGLRAQSVAQPEDQVNVAEGNPLTVKCTYS<u>VSGNPY</u>LFWYV QYPNRGLQFLLK<u>YITGDNL</u>VKGSYGFEAEFNKSQTSFHLKKPSALVSDSALYFC<u>AVS</u>

<u>ASNDMR</u>FGAGTRLTVKPNIQNPDPAVYQLRDSKSSDKSVCLFTDFDSQTNVSQSKDS

DVYITDKTVLDMRSMDFKSNSAVAWSNKSDFACANAFNNSIIPEDTFFPSPESSCDVK

LVEKSFETDTNLNFQNLSVIGFRILLLKVAGFNLLMTLRLWSS*;

>Vβ6.5 D1 J1.2 C1 (S->R)
SEQ ID NO: 7
MRIGLLCCAALSLLWAGPVNAGVTQTPKFQVLKTGQSMTLQCAQD<u>MNHEYM</u>SWY

RQDPGMGLRLIHY<u>SVGAGI</u>TDQGEVPNGYNVSRSTTEDFPLRLLSAAPSQTSVYFC<u>AS</u>

<u>SPQTGASFNYGYT</u>FGSGTRLTVVEDLNKVFPPEVAVFEPSEAEISHTQKATLVCLATG

FFPDHVELSWWVNGKEVHSGVSTDPQPLKEQPALNDSRYCLSSRLRVSATFWQNPR

NHFRCQVQFYGLSENDEWTQDRAKPVTQIVSAEAWGRADCGFTSVSYQQGVLSATI

LYEILLGKATLYAVLVSALVLMAMVKRKDF*;

TCR<sub>CD8</sub>-CMV#8:
>Vα22 J58 C
SEQ ID NO: 8
MKRILGALLGLLSAQVCCVRGIQVEQSPPDLILQEGANSTLRCNFS<u>DSVNNL</u>QWFHQ NPWGQLINLFY<u>IPSGT</u>KQNGRLSATTVATERYSLLYISSSQTTDSGVYFC<u>AVVRWETS</u>

<u>GSRLT</u>FGEGTQLTVNPDIQNPDPAVYQLRDSKSSDKSVCLFTDFDSQTNVSQSKDSDV

YITDKTVLDMRSMDFKSNSAVAWSNKSDFACANAFNNSIIPEDTFFPSPESSCDVKLV

EKSFETDTNLNFQNLSVIGFRILLLKVAGFNLLMTLRLWSS*;

>Vβ10.1 D J1.4 C1
SEQ ID NO: 9
MGTRLFFYVAICLLWAGHRDAEITQSPRHKITETGRQVTLACHQT<u>WNHNN</u>MFWYRQ

DLGHGLRLIHYSYGVQDTNKGEVSDGYSVSRSNTEDLPLTLESAASSQTSVYFC<u>ASSD</u>

<u>PTEEKLF</u>FGSGTQLSVLEDLNKVFPPEVAVFEPSEAEISHTQKATLVCLATGFFPDHVE

LSWWVNGKEVHSGVSTDPQPLKEQPALNDSRYCLSSRLRVSATFWQNPRNHFRCQV

QFYGLSENDEWTQDRAKPVTQIVSAEAWGRADCGFTSVSYQQGVLSATILYEILLGK

ATLYAVLVSALVLMAMVKRKDF*;

TCR<sub>CD8</sub>-CMV#9:
>Vα19 J26 C
SEQ ID NO: 10
MLTASLLRAVIASICVVSSMAQKVTQAQTEISVVEKEDVTLDCVYE<u>TRDTTYY</u>LFWY KQPPSGELVFLIR<u>RNSFDEQ</u>NEISGRYSWNFQKSTSSFNFTITASQVVDSAVYFC<u>ALSE</u>

<u>GGSYGQNF</u>VFGPGTRLSVLPYIQNPDPAVYQLRDSKSSDKSVCLFTDFDSQTNVSQSK

DSDVYITDKTVLDMRSMDFKSNSAVAWSNKSDFACANAFNNSIIPEDTFFPSPESSCD

VKLVEKSFETDTNLNFQNLSVIGFRILLLKVAGFNLLMTLRLWSS*;

>Vβ13 D2 J2.1 C2 (MLSLPDSAWN->MG)
SEQ ID NO: 11
MGTRLLCRVMLCLLGAGSVAAGVIQSPRHLIKEKRETATLKCYPI<u>PRHDT</u>VYWYQQ

GPGQDPQFLIS<u>FYEKMQ</u>SDKGSIPDRFSAQQFSDYHSELNMSSLELGDSALYFC<u>ASSL</u>

<u>RDEQF</u>FGPGTRLTVLEDLKNVFPPEVAVFEPSEAEISHTQKATLVCLATGFYPDHVEL

SWWVNGKEVHSGVSTDPQPLKEQPALNDSRYCLSSRLRVSATFWQNPRNHFRCQVQ

FYGLSENDEWTQDRAKPVTQIVSAEAWGRADCGFTSESYQQGVLSATILYEILLGKA

TLYAVLVSALVLMAMVKRKDSRG*;

-continued

TCR<sub>CD8</sub>-CMV#10:
>Vα24 J49 C
SEQ ID NO: 12
MEKNPLAAPLLILWFHLDCVSSILNVEQSPQSLHVQEGDSTNFTCSFP<u>SSNFYA</u>LHWY RWETAKSPEALFV<u>MTLNGD</u>EKKKGRISATLNTKEGYSYLYIKGSQPEDSATYLC<u>ARN</u>

<u>TGNQFY</u>FGTGTSLTVIPNIQNPDPAVYQLRDSKSSDKSVCLFTDFDSQTNVSQSKDSD

VYITDKTVLDMRSMDFKSNSAVAWSNKSDFACANAFNNSIIPEDTFFPSPESSCDVKL

VEKSFETDTNLNFQNLSVIGFRILLLKVAGFNLLMTLRLWSS*;

>Vβ6.5 D1 J1.2 C1
SEQ ID NO: 13
MSIGLLCCAALSLLWAGPVNAGVTQTPKFQVLKTGQSMTLQCAQD<u>MNHEYM</u>SWYR

QDPGMGLRLIHY<u>SVGAGI</u>TDQGEVPNGYNVSRSTTEDFPLRLLSAAPSQTSVYFC<u>ATQ</u>

<u>LATGTNYGYT</u>FGSGTRLTVVEDLNKVFPPEVAVFEPSEAEISHTQKATLVCLATGFFP

DHVELSWWVNGKEVHSGVSTDPQPLKEQPALNDSRYCLSSRLRVSATFWQNPRNHF

RCQVQFYGLSENDEWTQDRAKPVTQIVSAEAWGRADCGFTSVSYQQGVLSATILYEI

LLGKATLYAVLVSALVLMAMVKRKDF*;

TCR<sub>CD8</sub>-CMV#11:
>Vα16 J36 C
SEQ ID NO: 14
MKPTLISVLVIIFILRGTRAQRVTQPEKLLSVFKGAPVELKCNYS<u>YSGSPE</u>LFWYVQYS RQRLQLLLR<u>HISRES</u>IKGFTADLNKGETSFHLKKPFAQEEDSAMYYC<u>ALGWANNL</u>FF

GTGTRLTVIPYIQNPDPAVYQLRDSKSSDKSVCLFTDFDSQTNVSQSKDSDVYITDKT

VLDMRSMDFKSNSAVAWSNKSDFACANAFNNSIIPEDTFFPSPESSCDVKLVEKSFET

DTNLNFQNLSVIGFRILLLKVAGFNLLMTLRLWSS*;

>Vβ25.1 D1 J2.2 C2 (T->G; M->G)
SEQ ID NO: 15
MGTRLLCYGGFYFLGAGLMEADIYQTPRYLVIGTGKKITLECSQT<u>MGHDK</u>MYWYQ

QDPGMELHLIHY<u>SYGVNS</u>TEKGDLSSESTVSRIRTEHFPLTLESARPSHTSQYLC<u>ASTE</u>

<u>GTGHTGELF</u>FGEGSRLTVLEDLKNVFPPEVAVFEPSEAEISHTQKATLVCLATGFYPD

HVELSWWVNGKEVHSGVSTDPQPLKEQPALNDSRYCLSSRLRVSATFWQNPRNHFR

CQVQFYGLSENDEWTQDRAKPVTQIVSAEAWGRADCGFTSESYQQGVLSATILYEIL

LGKATLYAVLVSALVLMAMVKRKDSRG*;

TCR<sub>CD8</sub>-CMV#12:
>Vα39 J58 C
SEQ ID NO: 16
MKKLLAMILWLQLDRLSGELKVEQNPLFLSMQEGKNYTIYCNYS<u>TTSDRL</u>YWYRQD PGKSLESLFV<u>LLSNGA</u>VKQEGRLMASLDTKARLSTLHITAAVHDLSATYFC<u>AVDIETS</u>

<u>GSRLT</u>FGEGTQLTVNPDIQNPDPAVYQLRDSKSSDKSVCLFTDFDSQTNVSQSKDSDV

YITDKTVLDMRSMDFKSNSAVAWSNKSDFACANAFNNSIIPEDTFFPSPESSCDVKLV

EKSFETDTNLNFQNLSVIGFRILLLKVAGFNLLMTLRLWSS*;

>Vβ9 D2 J2.2 C2 (F->T)
SEQ ID NO: 17
MGTRLLCCVAFCLLGAGPVDSGVTQTPKHLITATGQRVTLRCSPR<u>SGDLS</u>VYWYQQS

LDQGLQFLIQ<u>YYNGEE</u>RAKGNILERFSAQQFPDLHSELNLSSLELGDSALYFC<u>ASSAL</u>

<u>GGAGTGELF</u>FGEGSRLTVLEDLKNVFPPEVAVFEPSEAEISHTQKATLVCLATGFYPD

HVELSWWVNGKEVHSGVSTDPQPLKEQPALNDSRYCLSSRLRVSATFWQNPRNHFR

CQVQFYGLSENDEWTQDRAKPVTQIVSAEAWGRADCGFTSESYQQGVLSATILYEIL

LGKATLYAVLVSALVLMAMVKRKDSRG*;

-continued

TCR<sub>CD8</sub>-CMV#14:
>Vα24 J21 C

SEQ ID NO: 18

MEKNPLAAPLLILWFHLDCVSSILNVEQSPQSLHVQEGDSTNFTCSFP<u>SSNFYAL</u>HWY

RWETAKSPEALFV<u>MTLNGD</u>EKKKGRISATLNTKEGYSYLYIKGSQPEDSATYLC<u>AFIN</u>

<u>FNKFY</u>FGSGTKLNVKPNIQNPDPAVYQLRDSKSSDKSVCLFTDFDSQTNVSQSKDSD

VYITDKTVLDMRSMDFKSNSAVAWSNKSDFACANAFNNSIIPEDTFFPSPESSCDVKL

VEKSFETDTNLNFQNLSVIGFRILLLKVAGFNLLMTLRLWSS*;

>Vβ3.1 D2 J2.2 C2 (C->T)

SEQ ID NO: 19

MGTRLLCCVVFCLLQAGPLDTAVSQTPKYLVTQMGNDKSIKCEQN<u>LGHDT</u>MYWYK

QDSKKFLKIMFS<u>YNNKEL</u>IINETVPNRFSPKSPDKAHLNLHINSLELGDSAVYFC<u>ASSQ</u>

<u>VLGPGELF</u>FGEGSRLTVLEDLKNVFPPEVAVFEPSEAEISHTQKATLVCLATGFYPDH

VELSWWVNGKEVHSGVSTDPQPLKEQPALNDSRYCLSSRLRVSATFWQNPRNHFRC

QVQFYGLSENDEWTQDRAKPVTQIVSAEAWGRADCGFTSESYQQGVLSATILYEILL

GKATLYAVLVSALVLMAMVKRKDSRG*;

TCR<sub>CD8</sub>-CMV#15:
>Vα12.3 J43 C

SEQ ID NO: 20

MMKSLRVLLVILWLQLSWVWSQQKEVEQDPGPLSVPEGAIVSLNCTYS<u>NSAFQY</u>FM

WYRQYSRKGPELLMY<u>TYSSGN</u>KEDGRFTAQVDKSSKYISLFIRDSQPSDSATYLC<u>AM</u>

<u>VNNNNDMR</u>FGAGTRLTVKPNIQNPDPAVYQLRDSKSSDKSVCLFTDFDSQTNVSQSK

DSDVYITDKTVLDMRSMDFKSNSAVAWSNKSDFACANAFNNSIIPEDIFFPSPESSCD

VKLVEKSFETDTNLNFQNLSVIGFRILLLKVAGFNLLMTLRLWSS*;

>Vβ12.4 D1 J1.4 C1

SEQ ID NO: 21

MDSWTLCCVSLCILVAKHTDAGVIQSPRHEVTEMGQEVTLRCKPI<u>SGHDY</u>LFWYRQT

MMRGLELLIY<u>FNNNVP</u>IDDSGMPEDRFSAKMPNASFSTLKIQPSEPRDSAVYFC<u>ASSY</u>

<u>GTYEKLF</u>FGSGTQLSVLEDLNKVFPPEVAVFEPSEAEISHTQKATLVCLATGFFPDHV

ELSWWVNGKEVHSGVSTDPQPLKEQPALNDSRYCLSSRLRVSATFWQNPRNHFRCQ

VQFYGLSENDEWTQDRAKPVTQIVSAEAWGRADCGFTSVSYQQGVLSATILYEILLG

KATLYAVLVSALVLMAMVKRKDF*;

TCR<sub>CD8</sub>-CMV#16:
>Vα13.1_2 J50 C

SEQ ID NO: 22

MTSIRAVFIFLWLQLDLVNGENVEQHPSTLSVQEGDSAVIKCTYS<u>DSASNY</u>FPWYKQ

ELGKRPQLLID<u>IRSNV</u>GEKKDQRIAVTLNKTAKHFSLHITETQPEDSAVYFC<u>AATYDK</u>

<u>VI</u>FGPGTSLSVIPNIQNPDPAVYQLRDSKSSDKSVCLFTDFDSQTNVSQSKDSDVYITD

KTVLDMRSMDFKSNSAVAWSNKSDFACANAFNNSIIPEDTFFPSPESSCDVKLVEKSF

ETDTNLNFQNLSVIGFRILLLKVAGFNLLMTLRLWSS*;

>Vβ25.1 J1.3 C1 (TI->GT)

SEQ ID NO: 23

MGTRLLCYMGFYFLGAGLMEADIYQTPRYLVIGTGKKITLECSQT<u>MGHDK</u>MYWYQ

QDPGMELHLIHY<u>SYGVNS</u>TEKGDLSSESTVSRIRTEHFPLTLESARPSHTSQYLC<u>ASSE</u>

<u>TSFSGNTIY</u>FGEGSWLTVVEDLNKVFPPEVAVFEPSEAEISHTQKATLVCLATGFFPDH

VELSWWVNGKEVHSGVSTDPQPLKEQPALNDSRYCLSSRLRVSATFWQNPRNHFRC

QVQFYGLSENDEWTQDRAKPVTQIVSAEAWGRADCGFTSVSYQQGVLSATILYEILL

GKATLYAVLVSALVLMAMVKRKDF*;

-continued

TCR$_{CD4}$-CMV#1:
>Vα21 J43 C
SEQ ID NO: 24

METLLGLLILWLQLQWVSSKQEVTQIPAALSVPEGENLVLNCSFT<u>DSAIYN</u>LQWFRQ

DPGKGLTSLLL<u>IQSSQR</u>EQTSGRLNASLDKSSGRSTLYIAASQPGDSATYLC<u>AVKDND</u>

<u>MR</u>FGAGTRLTVKPNIQNPDPAVYQLRDSKSSDKSVCLFTDFDSQTNVSQSKDSDVYI

TDKTVLDMRSMDFKSNSAVAWSNKSDFACANAFNNSIIPEDTFFPSPESSCDVKLVEK

SFETDTNLNFQNLSVIGFRILLLKVAGFNLLMTLRLWSS*;

>Vβ3.1 D1 J1.1 C1 (C->T)
SEQ ID NO: 25

MGTRLLCCVVFCLLQAGPLDTAVSQTPKYLVTQMGNDKSIKCEQN<u>LGHDT</u>MYWYK

QDSKKFLKIMFS<u>YNNKELI</u>INETVPNRFSPKSPDKAHLNLHINSLELGDSAVYFC<u>ASSQ</u>

<u>EKRGAF</u>FGQGTRLTVVEDLNKVFPPEVAVFEPSEAEISHTQKATLVCLATGFFPDHVE

LSWWVVNGKEVHSGVSTDPQPLKEQPALNDSRYCLSSRLRVSATFWQNPRNHFRCQV

QFYGLSENDEWTQDRAKPVTQIVSAEAWGRADCGFTSVSYQQGVLSATILYEILLGK

ATLYAVLVSALVLMAMVKRKDF*;

TCR$_{CD4}$-CMV#3:
>Vα8.6_2 J37_2 C
SEQ ID NO: 26

MLLLLVPAFQVIFTLGGTRAQSVTQLDSQVPVFEEAPVELRCNYS<u>SSVSVY</u>LFWYVQ

YPNQGLQLLLK<u>YLSGSTL</u>VKGINGFEAEFNKSQTSFHLRKPSVHISDTAEYFC<u>AVSSY</u>

<u>GSSNTGKLI</u>FGQGTTLQVKPDIQNPDPAVYQLRDSKSSDKSVCLFTDFDSQTNVSQSK

DSDVYITDKTVLDMRSMDFKSNSAVAWSNKSDFACANAFNNSIIPEDTFFPSPESSCD

VKLVEKSFETDTNLNFQNLSVIGFRILLLKVAGFNLLMTLRLWSS*;

>Vβ6.1 D1 J1.2 C1 (I->L)
SEQ ID NO: 27

MSLGLLCCVAFSLLWASPVNAGVTQTPKFQVLKTGQSMTLQCAQD<u>MNHNS</u>MYWY

RQDPGMGLRLIYY<u>SASEGT</u>TDKGEVPNGYNVSRLNKREFSLRLESAAPSQTSVYFC<u>A</u>

<u>SSTAGGRNYGYT</u>FGSGTRLTVVEDLNKVFPPEVAVFEPSEAEISHTQKATLVCLATGF

FPDHVELSWWVNGKEVHSGVSTDPQPLKEQPALNDSRYCLSSRLRVSATFWQNPRN

HFRCQVQFYGLSENDEWTQDRAKPVTQIVSAEAWGRADCGFTSVSYQQGVLSATIL

YEILLGKATLYAVLVSALVLMAMVKRKDF*;

TCR$_{CD4}$-CMV#5:
>Vα22 J49 C
SEQ ID NO: 28

MKRILGALLGLLSAQVCCVRGIQVEQSPPDLILQEGANSTLRCNFS<u>DSVNN</u>LQWFHQ

NPWGQLINLFY<u>IPSGT</u>KQNGRLSATTVATERYSLLYISSSQTTDSGVYFC<u>AAGSNTGN</u>

<u>QFY</u>FGTGTSLTVIPNIQNPDPAVYQLRDSKSSDKSVCLFTDFDSQTNVSQSKDSDVYIT

DKTVLDMRSMDFKSNSAVAWSNKSDFACANAFNNSIIPEDTFFPSPESSCDVKLVEKS

FETDTNLNFQNLSVIGFRILLLKVAGFNLLMTLRLWSS*;

>Vβ6.2 D2 J2.3 C2 (G->A)
SEQ ID NO: 29

MSLGLLCCAAFSLLWAGPVNAGVTQTPKFRVLKTGQSMTLLCAQD<u>MNHEY</u>MYWY

RQDPGMGLRLIHY<u>SVGEGT</u>TAKGEVPDGYNVSRLKKQNFLLGLESAAPSQTSVYFC<u>A</u>

<u>SSSRGYGTDTQY</u>FGPGTRLTVEDLKNVFPPEVAVFEPSEAEISHTQKATLVCLATGF

YPDHVELSWVVVNGKEVHSGVSTDPQPLKEQPALNDSRYCLSSRLRVSATFWQNPRN

HFRCQVQFYGLSENDEWTQDRAKPVTQIVSAEAWGRADCGFTSESYQQGVLSATIL

YEILLGKATLYAVLVSALVLMAMVKRKDSRG*;

2. NY-ESO-I-Specific T Cell Receptors

TCR<sub>CD8</sub>-NY#2:
>Vα3 J28 C
SEQ ID NO: 30
MASAPISMLAMLFTLSGLRAQSVAQPEDQVNVAEGNPLTVKCTYS<u>VSGNPYL</u>FWYV QYPNRGLQFLLK<u>YITGDNL</u>VKGSYGFEAEFNKSQTSFHLKKPSALVSDSALYFC<u>AVRP</u>

<u>LYSGAGSYQLT</u>FGKGTKLSVIPNIQNPDPAVYQLRDSKSSDKSVCLFTDFDSQTNVSQ

SKDSDVYITDKTVLDMRSMDFKSNSAVAWSNKSDFACANAFNNSIIPEDTFFPSPESS

CDVKLVEKSFETDTNLNFQNLSVIGFRILLLKVAGFNLLMTLRLWSS*;

>Vβ20.1_2 J2.3 C2
SEQ ID NO: 31
MLLLLLLLGPGSGLGAVVSQHPSRVICKSGTSVKIECRSL<u>DFQATT</u>MFWYRQFPKQSL

MLMAT<u>SNEGSKA</u>TYEQGVEKDKFLINHASLTLSTLTVTSAHPEDSSFYIC<u>SARNLPLT</u>

<u>DTQYF</u>GPGTRLTVLEDLKNVFPPEVAVFEPSEAEISHTQKATLVCLATGFYPDHVELS

WWVNGKEVHSGVSTDPQPLKEQPALNDSRYCLSSRLRVSATFWQNPRNHFRCQVQF

YGLSENDEWTQDRAKPVTQIVSAEAWGRADCGFTSESYQQGVLSATILYEILLGKAT

LYAVLVSALVLMAMVKRKDSRG*;

TCR<sub>CD8</sub>-NY#5:
>Vα24 J3 C
SEQ ID NO: 32
MEKNPLAAPLLILWFHLDCVSSILNVEQSPQSLHVQEGDSTNFTCSFP<u>SSNFYAL</u>HWY RWETAKSPEALFV<u>MTLNGD</u>EKKKGRISATLNTKEGYSYLYIKGSQPEDSATYLC<u>AST</u>

<u>SYSSASKII</u>FGSGTRLSIRPNIQNPDPAVYQLRDSKSSDKSVCLFTDFDSQTNVSQSKDS

DVYITDKTVLDMRSMDFKSNSAVAWSNKSDFACANAFNNSIIPEDTFFPSPESSCDVK

LVEKSFETDTNLNFQNLSVIGFRILLLKVAGFNLLMTLRLWSS*;

>Vβ7.6 D2 J2.2 C2 (S->R)
SEQ ID NO: 33
MGTRLLCWVVLGFLGTDHTGAGVSQSPRYKVTKRGQDVALRCDPI<u>SGHVS</u>LYWYR

QALGQGPEFLTY<u>FNYEAQ</u>QDKSGLPNDRFSAERPEGSISTLTIQRTEQRDSAMYRC<u>AS</u>

<u>SHSSGGAGELF</u>FGEGSRLTVLEDLKNVFPPEVAVFEPSEAEISHTQKATLVCLATGFYP

DHVELSWWVNGKEVHSGVSTDPQPLKEQPALNDSRYCLSSRLRVSATFWQNPRNHF

RCQVQFYGLSENDEWTQDRAKPVTQIVSAEAWGRADCGFTSESYQQGVLSATILYEI

LLGKATLYAVLVSALVLMAMVKRKDSRG*;

TCR<sub>CD8</sub>-NY#6:
>Vα17 J47_2 C
SEQ ID NO: 34
METLLGVSLVILWLQLARVNSQQGEEDPQALSIQEGENATMNCSYK<u>TSINNL</u>QWYR QNSGRGLVHLIL<u>IRSNERE</u>KHSGRLRVTLDTSKKSSSLLITASRAADTASYFC<u>ATDEYG</u>

<u>NKLV</u>FGAGTILRVKSYIQNPDPAVYQLRDSKSSDKSVCLFTDFDSQTNVSQSKDSDV

YITDKTVLDMRSMDFKSNSAVAWSNKSDFACANAFNNSIIPEDTFFPSPESSCDVKLV

EKSFETDTNLNFQNLSVIGFRILLLKVAGFNLLMTLRLWSS*;

>Vβ12.3 D2 J2.1 C2 (F->L)
SEQ ID NO: 35
MDSWILCCVSLCILVAKHTDAGVIQSPRHEVTEMGQEVTLRCKPI<u>SGHNS</u>LFWYRQT

MMRGLELLIY<u>FNNNVP</u>IDDSGMPEDRFSAKMPNASFSTLKIQPSEPRDSAVYFC<u>ASSY</u>

<u>PGFNEQF</u>FGPGTRLTVLEDLKNVFPPEVAVFEPSEAEISHTQKATLVCLATGFYPDHV

-continued

ELSWWVNGKEVHSGVSTDPQPLKEQPALNDSRYCLSSRLRVSATFWQNPRNHFRCQ

VQFYGLSENDEWTQDRAKPVTQIVSAEAWGRADCGFTSESYQQGVLSATILYEILLG

KATLYAVLVSALVLMAMVKRKDSRG*;

TCR<sub>CD8</sub>-NY#8:
>Vα8.6_2 J9 C(A->V)
SEQ ID NO: 36

MLLLLVPVFQVIFTLGGTRAQSVTQLDSQVPVFEEAPVELRCNYS<u>SSVSVY</u>LFWYVQ

YPNQGLQLLLK<u>YLSGSTL</u>VKGINGFEAEFNKSQTSFHLRKPSVHISDTAEYFC<u>AVSDQ</u>

<u>GTGGFKTI</u>FGAGTRLFVKANIQNPDPAVYQLRDSKSSDKSVCLFTDFDSQTNVSQSKD

SDVYITDKTVLDMRSMDFKSNSAVAWSNKSDFACANAFNNSIIPEDTFFPSPESSCDV

KLVEKSFETDTNLNFQNLSVIGFRILLLKVAGFNLLMTLRLWSS*;

>Vβ28.1 D1 J1.1 C1
SEQ ID NO: 37

MGIRLLCRVAFCFLAVGLVDVKVTQSSRYLVKRTGEKVFLECVQD<u>MDHEN</u>MFWYR

QDPGLGLRLIYF<u>SYDVKM</u>KEKGDIPEGYSVSREKKERFSLILESASTNQTSMYLC<u>ASR</u>

<u>GTVTSSLMNTEAF</u>FGQGTRLTVVEDLNKVFPPEVAVFEPSEAEISHTQKATLVCLATG

FFPDHVELSWWVNGKEVHSGVSTDPQPLKEQPALNDSRYCLSSRLRVSATFWQNPR

NHFRCQVQFYGLSENDEWTQDRAKPVTQIVSAEAWGRADCGFTSVSYQQGVLSATI

LYEILLGKATLYAVLVSALVLMAMVKRKDF*;

TCR<sub>CD8</sub>-NY#12:
>Vα1.1 J23 C
SEQ ID NO: 38

MVVGAFLLYVSMKMGGTAGQSLEQPSEVTAVEGAIVQINCTYQ<u>TSGFYG</u>LSWYQQH

DGGAPTFLSY<u>NALDG</u>LEETGRFSSFLSRSDSYGYLLLQELQMKDSASYFC<u>AVRDKQG</u>

<u>GKLI</u>FGQGTELSVKPNIQNPDPAVYQLRDSKSSDKSVCLFTDFDSQTNVSQSKDSDVY

ITDKTVLDMRSMDFKSNSAVAWSNKSDFACANAFNNSIIPEDTFFPSPESSCDVKLVE

KSFETDTNLNFQNLSVIGFRILLLKVAGFNLLMTLRLWSS*;

>Vβ4.1 D2 J2.1 C2 (C->S)
SEQ ID NO: 39

MGSRLLCCAVLCLLGAVPIDTEVTQTPKHLVMGMTNKKSLKCEQH<u>MGHRA</u>MYWY

KQKAKKPPELMFV<u>YSYEKL</u>SINESVPSRFSPECPNSSLLNLHLHALQPEDSALYLC<u>AS</u>

<u>MGKRGGNEQF</u>FGPGTRLTVLEDLKNVFPPEVAVFEPSEAEISHTQKATLVCLATGFYP

DHVELSWWVNGKEVHSGVSTDPQPLKEQPALNDSRYCLSSRLRVSATFWQNPRNHF

RCQVQFYGLSENDEWTQDRAKPVTQIVSAEAWGRADCGFTSESYQQGVLSATILYEI

LLGKATLYAVLVSALVLMAMVKRKDSRG*;

TCR<sub>CD8</sub>-NY#13:
>Vα5 J33 C
SEQ ID NO: 40

MKTFAGFSFLFLWLQLDCMSRGEDVEQSLFLSVREGDSSVINCTYT<u>DSSSTY</u>LYWYK

QEPGAGLQLLTY<u>IFSNMD</u>MKQDQRLTVLLNKKDKHLSLRIADTQTGDSAIYFC<u>AERG</u>

<u>QDSNYQLI</u>WGAGTKLIIKPDIQNPDPAVYQLRDSKSSDKSVCLFTDFDSQTNVSQSKD

SDVYITDKTVLDMRSMDFKSNSAVAWSNKSDFACANAFNNSIIPEDTFFPSPESSCDV

KLVEKSFETDTNLNFQNLSVIGFRILLLKVAGFNLLMTLRLWSS*;

>Vβ5.5_2 D1 J2.5 C2 (PG->TR; C->F)
SEQ ID NO: 41

MGTRLLFWVLLCLLGAGPVDAGVTQSPTHLIKTRGQHVTLRCSPI<u>SGHKS</u>VSWYQQV

LGQGPQFIFQ<u>YYEKEE</u>RGRGNFPDRFSARQFPNYSSELNVNALLLGDSALYLC<u>ASSG</u>

<u>WTGRSFGGGAQY</u>FGPGTRLLVLEDLKNVFPPEVAVFEPSEAEISHTQKATLVCLATGF

```
YPDHVELSWWVNGKEVHSGVSTDPQPLKEQPALNDSRYCLSSRLRVSATFWQNPRN

HFRCQVQFYGLSENDEWTQDRAKPVTQIVSAEAWGRADCGFTSESYQQGVLSATIL

YEILLGKATLYAVLVSALVLMAMVKRKDSRG*;

TCR_CD8-NY#15:
>Vα12.2 2 J53 C(K->I)
                                                SEQ ID NO: 42
MISLRVLLVILWLQLSWVWSQQKEVEQNSGPLSVPEGAIASLNCTYSDRGSQSFFWY

RQYSGKSPELIMSIYSNGDKEDGRFTAQLNKASQYVSLLIRDSQPSDSATYLCAVPYY

WSSGGSNYKLTFGKGILLTVNPNIQNPDPAVYQLRDSKSSDKSVCLFTDFDSQTNVS

QSKDSDVYITDKTVLDMRSMDFKSNSAVAWSNKSDFACANAFNNSIIPEDTFFPSPES

SCDVKLVEKSFETDTNLNFQNLSVIGFRILLLKVAGFNLLMTLRLWSS*;

>Vβ4.1 D2 J2.5 C2 (C->S)
                                                SEQ ID NO: 43
MGSRLLCCAVLCLLGAVPIDTEVTQTPKHLVMGMTNKKSLKCEQHMGHRAMYWY

KQKAKKPPELMFVYSYEKLSINESVPSRFSPECPNSSLLNLHLHALQPEDSALYLCASS

QSGLEETQYFGPGTRLLVLEDLKNVFPPEVAVFEPSEAEISHTQKATLVCLATGFYPD

HVELSWWVNGKEVHSGVSTDPQPLKEQPALNDSRYCLSSRLRVSATFWQNPRNHFR

CQVQFYGLSENDEWTQDRAKPVTQIVSAEAWGRADCGFTSESYQQGVLSATILYEIL

LGKATLYAVLVSALVLMAMVKRKDSRG*;

TCR_CD4-NY#1:
>Vα22 J20 C (Donor SNPN->K)
                                                SEQ ID NO: 44
MKRILGALLGLLSAQVCCVRGIQVEQSPPDLILQEGANSTLRCNFSDSVNNLQWFHQ

NPWGQLINLFYIPSGTKQNGRLSATTVATERYSLLYISSSQTTDSGVYFCAVNDYKLS

FGAGTTVTVRANIQKPDPAVYQLRDSKSSDKSVCLFTDFDSQTNVSQSKDSDVYITD

KTVLDMRSMDFKSNSAVAWSNKSDFACANAFNNSIIPEDTFFPSPESSCDVKLVEKSF

ETDTNLNFQNLSVIGFRILLLKVAGFNLLMTLRLWSS*;

>Vβ9 D1 J1.1 C1 (F->T)
                                                SEQ ID NO: 45
MGTRLLCCVAFCLLGAGPVDSGVTQTPKHLITATGQRVTLRCSPRSGDLSVYWYQQS

LDQGLQFLIQYYNGEERAKGNILERFSAQQFPDLHSELNLSSLELGDSALYFCASSPG

VSGTTEAFFGQGTRLTVVEDLKNVFPPEVAVFEPSEAEISHTQKATLVCLATGFFPDH

VELSWWVNGKEVHSGVSTDPQPLKEQPALNDSRYCLSSRLRVSATFWQNPRNHFRC

QVQFYGLSENDEWTQDRAKPVTQIVSAEAWGRADCGFTSVSYQQGVLSATILYEILL

GKATLYAVLVSALVLMAMVKRKDF*;

TCR_CD4-NY#3:
>Vα12.3 J54 C
                                                SEQ ID NO: 46
MMKSLRVLLVILWLQLSWVWSQQKEVEQDPGPLSVPEGAIVSLNCTYSNSAFQYFM

WYRQYSRKGPELLMYTYSSGNKEDGRFTAQVDKSSKYISLFIRDSQPSDSATYLCAM

SKGAQKLVFGQGTRLTINPNIQNPDPAVYQLRDSKSSDKSVCLFTDFDSQTNVSQSKD

SDVYITDKTVLDMRSMDFKSNSAVAWSNKSDFACANAFNNSIIPEDTFFPSPESSCDV

KLVEKSFETDTNLNFQNLSVIGFRILLLKVAGFNLLMTLRLWSS*;

>Vβ11.2 D2 J2.2 C2
                                                SEQ ID NO: 47
MGTRLLCWAALCLLGAELTEAGVAQSPRYKIIEKRQSVAFWCNPISGHATLYWYQQI

LGQGPKLLIQFQNNGVVDDSQLPKDRFSAERLKGVDSTLKIQPAKLEDSAVYLCASSL

GDSNTGELFFGEGSRLTVLEDLKNVFPPEVAVFEPSEAEISHTQKATLVCLATGFYPD
```

HVELSWWVNGKEVHSGVSTDPQPLKEQPALNDSRYCLSSRLRVSATFWQNPRNHFR

CQVQFYGLSENDEWTQDRAKPVTQIVSAEAWGRADCGFTSESYQQGVLSATILYEIL

LGKATLYAVLVSALVLMAMVKRKDSRG*;

TCR<sub>CD4</sub>-NY#5:
>Vα8.4_3 J48 C
SEQ ID NO: 140

MLLLLVPVLEVIFTLGGTRAQSVTQLGSHVSVSEGALVLLRCNYS<u>SSVPPY</u>LFWYVQ

YPNQGLQLLLK<u>YTTGATLV</u>KGINGFEAEFKKSETSFHLTKPSAHMSDAAEYFC<u>AVSR</u>

<u>ANFGNEKLT</u>FGTGTRLTIIPNIQNPDPAVYQLRDSKSSDKSVCLFTDFDSQTNVSQSKD

SDVYITDKTVLDMRSMDFKSNSAVAWSNKSDFACANAFNNSIIPEDTFFPSPESSCDV

KLVEKSFETDTNLNFQNLSVIGFRILLLKVAGFNLLMTLRLWSS*;

>Vβ4.1 D1 J1.5 C1 (GCKL→SNQV)
SEQ ID NO: 141

MSNQVLCCAVLCLLGAVPIDTEVTQTPKHLVMGMTNKKSLKCEQH<u>MGHRA</u>MYWY

KQKAKKPPELMFV<u>YSYEKL</u>SINESVPSRFSPECPNSSLLNLHLHALQPEDSALYLC<u>ASS</u>

<u>QDPRGGPQH</u>FGDGTRLSILEDLNKVFPPEVAVFEPSEAEISHTQKATLVCLATGFFPDH

VELSWWVNGKEVHSGVSTDPQPLKEQPALNDSRYCLSSRLRVSATFWQNPRNHFRC

QVQFYGLSENDEWTQDRAKPVTQIVSAEAWGRADCGFTSVSYQQGVLSATILYEILL

GKATLYAVLVSALVLMAMVKRKDF*;

TCR<sub>CD4</sub>-NY#7:
>Vα8.6_2 J13_2 C
SEQ ID NO: 142

MLLLLVPAFQVIFTLGGTRAQSVTQLDSQVPVFEEAPVELRCNYS<u>SSVSVY</u>LFWYVQ

YPNQGLQLLLK<u>YLSGSTLV</u>KGINGFEAEFNKSQTSFHLRKPSVHISDTAEYFC<u>AVSKS</u>

<u>GGYQKV</u>TFGTGTKLQVIPNIQNPDPAVYQLRDSKSSDKSVCLFTDFDSQTNVSQSKDS

DVYITDKTVLDMRSMDFKSNSAVAWSNKSDFACANAFNNSHPEDTFFPSPESSCDVK

LVEKSFETDTNLNFQNLSVIGFRILLLKVAGFNLLMTLRLWSS*;

>Vβ20.1 D2 J2.5 C2
SEQ ID NO: 143

MLLLLLLLGPGSGLGAVVSQHPSWVICKSGTSVKIECRSL<u>DFQATT</u>MFWYRQFPKQS

LMLMAT<u>SNEGSKA</u>TYEQGVEKDKFLINHASLTLSTLTVTSAHPEDSSFYIC<u>SAAPGLA</u>

<u>GGQGGSQY</u>FGPGTRLLVLEDLKNVFPPEVAVFEPSEAEISHTQKATLVCLATGFYPDH

VELSWWVNGKEVHSGVSTDPQPLKEQPALNDSRYCLSSRLRVSATFWQNPRNHFRC

QVQFYGLSENDEWTQDRAKPVTQIVSAEAWGRADCGFTSESYQQGVLSATILYEILL

GKATLYAVLVSALVLMAMVKRKDSRG*;

TCR<sub>CD4</sub>-NY#10:
>Vα9.2_3 J42 C
SEQ ID NO: 144

MNYSPGLVSLILLLLGRTRGDSVTQMEGPVTLSEEAFLTINCTYT<u>ATGYPS</u>LFWYVQY

PGEGLQLLLK<u>ATKADDK</u>GSNKGFEATYRKETTSFHLEKGSVQVSDSAVYFC<u>ARAVN</u>

<u>YGGSQGNLI</u>FGKGTKLSVKPNIQNPDPAVYQLRDSKSSDKSVCLFTDFDSQTNVSQSK

DSDVYITDKTVLDMRSMDFKSNSAVAWSNKSDFACANAFNNSIIPEDTFFPSPESSCD

VKLVEKSFETDTNLNFQNLSVIGFRILLLKVAGFNLLMTLRLWSS*;

>Vβ7.9_3 D2 J2.7 C2 (S→R)
SEQ ID NO: 145

MGTRLLCWMALCLLGADHADTGVSQDPRHKITKRGQNVTFRCDPI<u>SEHNR</u>LYWYR

QTLGQGPEFLTY<u>FQNEAQ</u>LEKSRLLSDRFSAERPKGSFSTLEIQRTEQGDSAMYLC<u>AS</u>

<u>SLGHEQY</u>FGPGTRLTVTEDLKNVFPPEVAVFEPSEAEISHTQKATLVCLATGFYPDHV

-continued

ELSWWVNGKEVHSGVSTDPQPLKEQPALNDSRYCLSSRLRVSATFWQNPRNHFRCQ

VQFYGLSENDEWTQDRAKPVTQIVSAEAWGRADCGFTSESYQQGVLSATILYEILLG

KATLYAVLVSALVLMAMVKRKDSRG*;

TCR$_{CD4}$-NY11:
>Vα8.1 J23 C
    SEQ ID NO: 146

MLLLLIPVLGMIFALRDARAQSVSQHNHHVILSEAASLELGCNYS<u>YGGTVN</u>LFWYVQ

YPGQHLQLLLK<u>YFSGDPLV</u>KGIKGFEAEFIKSKFSFNLRKPSVQWSDTAEYFC<u>AVNRR</u>

<u>TGNQGGKLI</u>FGQGTELSVKPNIQNPDPAVYQLRDSKSSDKSVCLFTDFDSQTNVSQSK

DSDVYITDKTVLDMRSMDFKSNSAVAWSNKSDFACANAFNNSIIPEDTFFPSPESSCD

VKLVEKSFETDTNLNFQNLSVIGFRILLLKVAGFNLLMTLRLWSS*;

>Vβ11.2 D1 J1.2 C1
    SEQ ID NO: 147

MGTRLLCWAALCLLGAELTEAGVAQSPRYKIIEKRQSVAFWCNPI<u>SGHAT</u>LYWYQQI

LGQGPKLLIQ<u>FQNNGV</u>VDDSQLPKDRFSAERLKGVDSTLKIQPAKLEDSAVYLC<u>ASSL</u>

<u>GPYIDGAGCT</u>FGSGTRLTVVEDLNKVFPPEVAVFEPSEAEISHTQKATLVCLATGFFP

DHVELSWWVNGKEVHSGVSTDPQPLKEQPALNDSRYCLSSRLRVSATFWQNPRNHF

RCQVQFYGLSENDEWTQDRAKPVTQIVSAEAWGRADCGFTSVSYQQGVLSATILYEI

LLGKATLYAVLVSALVLMAMVKRKDF*;

TCR$_{CD4}$-NY#13:
>Vα21_2 J24_2 C
    SEQ ID NO: 148

METLLGLLILWLQLQWVSSKQEVTQIPAALSVPEGENLVLNCSFT<u>DSAIYN</u>LQWFRQ

DPGKGLTSLLL<u>IQSSQRE</u>QTSGRLNASLDKSSGRSTLYIAASQPGDSATYLC<u>AVPTDS</u>

<u>WGKLQ</u>FGAGTQVVVTPDIQNPDPAVYQLRDSKSSDKSVCLFTDFDSQTNVSQSKDSD

VYITDKTVLDMRSMDFKSNSAVAWSNKSDFACANAFNNSIIPEDTFFPSPESSCDVKL

VEKSFETDTNLNFQNLSVIGFRILLLKVAGFNLLMTLRLWSS*;

>Vβ7.9_3 D1 J2.3 C2 (S→R)
    SEQ ID NO: 149

MGTRLLCWMALCLLGADHADTGVSQDPRHKITKRGQNVTFRCDPI<u>SEHNR</u>LYWYR

QTLGQGPEFLTY<u>FQNEAQ</u>LEKSRLLSDRFSAERPKGSFSTLEIQRTEQGDSAMYLC<u>AS</u>

<u>SSKLTGIPEGTDTQ</u>YFGPGTRLTVLEDLKNVFPPEVAVFEPSEAEISHTQKATLVCLAT

GFYPDHVELSWVVVNGKEVHSGVSTDPQPLKEQPALNDSRYCLSSRLRVSATFWQNP

RNHFRCQVQFYGLSENDEWTQDRAKPVTQIVSAEAWGRADCGFTSESYQQGVLSAT

ILYEILLGKATLYAVLVSALVLMAMVKRKDSRG*;

TCR$_{CD4}$-NY#16:
>Vα8.4_3 J10 C
    SEQ ID NO: 150

MLLLLVPVLEVIFTLGGTRAQSVTQLGSHVSVSEGALVLLRCNYS<u>SSVPPYL</u>FWYVQ

YPNQGLQLLLK<u>YTTGATLV</u>KGINGFEAEFKKSETSFHLTKPSAHMSDAAEYFC<u>AVKK</u>

<u>GGGNKLT</u>FGTGTQLKVELNIQNPDPAVYQLRDSKSSDKSVCLFTDFDSQTNVSQSKD

SDVYITDKTVLDMRSMDFKSNSAVAWSNKSDFACANAFNNSIIPEDTFFPSPESSCDV

KLVEKSFETDTNLNFQNLSVIGFRILLLKVAGFNLLMTLRLWSS*;

>Vβ20.1 D1 J1.5 C1
    SEQ ID NO: 151

MLLLLLLLGPGSGLGAVVSQHPSWVICKSGTSVKIECRSL<u>DFQATT</u>MFWYRQFPKQS

LMLMAT<u>SNEGSKA</u>TYEQGVEKDKFLINHASLTLSTLTVTSAHPEDSSFYIC<u>SATGPSE</u>

<u>HQPQH</u>FGDGTRLSILEDLNKVFPPEVAVFEPSEAEISHTQKATLVCLATGFFPDHVELS

-continued

WWVNGKEVHSGVSTDPQPLKEQPALNDSRYCLSSRLRVSATFWQNPRNHFRCQVQF

YGLSENDEWTQDRAKPVTQIVSAEAWGRADCGFTSVSYQQGVLSATILYEILLGKAT

LYAVLVSALVLMAMVKRKDF*;

TCR$_{CD4}$-NY#14: .
>Vα8.4_3 J372 C

SEQ ID NO: 176

MLLLLVPVLEVIFTLGGTRAQSVTQLGSHVSVSEGALVLLRCNYS<u>SSVPPY</u>LFWYVQ

YPNQGLQLLLK<u>YTTGATLV</u>KGINGFEAEFKKSETSFHLTKPSAHMSDAAEYFC<u>AVSK</u>

<u>GSSNTGKLI</u>FGQGTTLQVKPDIQNPDPAVYQLRDSKSSDKSVCLFTDFDSQTNVSQSK

DSDVYITDKTVLDMRSMDFKSNSAVAWSNKSDFACANAFNNSIIPEDTFFPSPESSCD

VKLVEKSFETDTNLNFQNLSVIGFRILLLKVAGFNLLMTLRLWSS*;

>Vβ3.1 D2 J1.3 C1

SEQ ID NO: 177

MGTRLLCCVVFCLLQAGPLDTAVSQTPKYLVTQMGNDKSIKCEQN<u>LGHDT</u>MYWYK

QDSKKFLKIMFS<u>YNNKELI</u>INETVPNRFSPKSPDKAHLNLHINSLELGDSAVYFC<u>ASSQ</u>

<u>DPGGAGNTIY</u>FGEGSWLTVVEDLNKVFPPEVAVFEPSEAEISHTQKATLVCLATGFFP

DHVELSWWVNGKEVHSGVSTDPQPLKEQPALNDSRYCLSSRLRVSATFWQNPRNHF

RCQVQFYGLSENDEWTQDRAKPVTQIVSAEAWGRADCGFTSVSYQQGVLSATILYEI

LLGKATLYAVLVSALVLMAMVKRKDF*;

3. TPTE-Specific T Cell Receptors:

TCR$_{CD8}$-TPT#3:
>Vα27 J16 C

SEQ ID NO: 48

MVLKFSVSILWIQLAWVSTQLLEQSPQFLSIQEGENLTVYCNSS<u>SVFSS</u>LQWYRQEPG

EGPVLLVT<u>VVTGGE</u>VKKLKRLTFQFGDARKDSSLHITAAQPGDTGLYLC<u>AGAQGQK</u>

<u>LL</u>FARGTMLKVDLNIQNPDPAVYQLRDSKSSDKSVCLFTDFDSQTNVSQSKDSDVYI

TDKTVLDMRSMDFKSNSAVAWSNKSDFACANAFNNSIIPEDTFFPSPESSCDVKLVEK

SFETDTNLNFQNLSVIGFRILLLKVAGFNLLMTLRLWSS*;

>Vβ7.9 D2 J2.2 C2

SEQ ID NO: 49

MGTRLLCWMALCLLGADHADTGVSQNPRHKITKRGQNVTFRCDPI<u>SEHNR</u>LYWYR

QTLGQGPEFLTY<u>FQNEAQ</u>LEKSRLLSDRFSAERPKGSFSTLEIQRTEQGDSAMYLC<u>AS</u>

<u>SHLAGGNTGELF</u>FGEGSRLTVLEDLKNVFPPEVAVFEPSEAEISHTQKATLVCLATGF

YPDHVELSWWVNGKEVHSGVSTDPQPLKEQPALNDSRYCLSSRLRVSATFWQNPRN

HFRCQVQFYGLSENDEWTQDRAKPVTQIVSAEAWGRADCGFTSESYQQGVLSATIL

YEILLGKATLYAVLVSALVLMAMVKRKDSRG*;

TCR$_{CD8}$-TPT#35:
>Vα19 J17 C

SEQ ID NO: 50

MLTASLLRAVIASICVVSSMAQKVTQAQTEISVVEKEDVTLDCVYE<u>TRDTTYY</u>LFWY

KQPPSGELVFLIR<u>RNSFDEQ</u>NEISGRYSWNFQKSTSSFNFTITASQVVDSAVYFC<u>ALIE</u>

<u>AAAGNKLT</u>FGGGTRVLVKPNIQNPDPAVYQLRDSKSSDKSVCLFTDFDSQTNVSQSK

DSDVYITDKTVLDMRSMDFKSNSAVAWSNKSDFACANAFNNSIIPEDTFFPSPESSCD

VKLVEKSFETDTNLNFQNLSVIGFRILLLKVAGFNLLMTLRLWSS*;

-continued

>Vβ12.4 D2 J2.7 C2 (L->F)
SEQ ID NO: 51
MDSWTFCCVSLCILVAKHTDAGVIQSPRHEVTEMGQEVTLRCKPISGHDYLFWYRQT

MMRGLELLIYFNNNVPIDDSGMPEDRFSAKMPNASFSTLKIQPSEPRDSAVYFCAGSL

RLAGAAEQYFGPGTRLTVTEDLKNVFPPEVAVFEPSEAEISHTQKATLVCLATGFYPD

HVELSWWVNGKEVHSGVSTDPQPLKEQPALNDSRYCLSSRLRVSATFWQNPRNHFR

CQVQFYGLSENDEWTQDRAKPVTQIVSAEAWGRADCGFTSESYQQGVLSATILYEIL

LGKATLYAVLVSALVLMAMVKRKDSRG*;

TCR<sub>CD4</sub>-TPT#4:
>Vα14/DV4 J48 C
SEQ ID NO: 52
MSLSSLLKVVTASLWLGPGIAQKITQTQPGMFVQEKEAVTLDCTYDTSDPSYGLFWY

KQPSSGEMIFLIYQGSYDQQNATEGRYSLNFQKARKSANLVISASQLGDSAMYFCAT

ASNFGNEKLTFGTGTRLTIIPNIQNPDPAVYQLRDSKSSDKSVCLFTDFDSQTNVSQSK

DSDVYITDKTVLDMRSMDFKSNSAVAWSNKSDFACANAFNNSIIPEDTFFPSPESSCD

VKLVEKSFETDTNLNFQNLSVIGFRILLLKVAGFNLLMTLRLWSS*;

>Vβ29.1 D1 J1.2 C1
SEQ ID NO: 53
MLSLLLLLLGLGSVFSAVISQKPSRDICQRGTSLTIQCQVDSQVTMMFWYRQQPGQSL

TLIATANQGSEATYESGFVIDKFPISRPNLTFSTLTVSNMSPEDSSIYLCSVDRDREDGY

TFGSGTRLTVVEDLNKVFPPEVAVFEPSEAEISHTQKATLVCLATGFFPDHVELSWWV

NGKEVHSGVSTDPQPLKEQPALNDSRYCLSSRLRVSATFWQNPRNHFRCQVQFYGLS

ENDEWTQDRAKPVTQIVSAEAWGRADCGFTSVSYQQGVLSATILYEILLGKATLYAV

LVSALVLMAIVIVKRKDF*;

TCR<sub>CD4</sub>-TPT#5:
>Vα38.2/DV8 J40 C
SEQ ID NO: 54
MACPGFLWALVISTCLEFSMAQTVTQSQPEMSVQEAETVTLSCTYDTSESDYYLFWY

KQPPSRQMILVIRQEAYKQQNATENRFSVNFQKAAKSFSLKISDSQLGDAAMYFCAY

SRTSGTYKYIFGTGTRLKVLANIQNPDPAVYQLRDSKSSDKSVCLFTDFDSQTNVSQS

KDSDVYITDKTVLDMRSMDFKSNSAVAWSNKSDFACANAFNNSIIPEDTFFPSPESSC

DVKLVEKSFETDTNLNFQNLSVIGFRILLLKVAGFNLLMTLRLWSS*;

>Vβ4.2 D2 J2.7 C2 (GCRL->SNQV)
SEQ ID NO: 55
MSNQVLCCAVLCLLGAVPMETGVTQTPRHLVMGMTNKKSLKCEQHLGHNAMYWY

KQSAKKPLELMFVYNFKEQTENNSVPSRFSPECPNSSHLFLHLHTLQPEDSALYLCAS

SQEISGSSYEQYFGPGTRLTVTEDLKNVFPPEVAVFEPSEAEISHTQKATLVCLATGFY

PDHVELSWWVNGKEVHSGVSTDPQPLKEQPALNDSRYCLSSRLRVSATFWQNPRNH

FRCQVQFYGLSENDEWTQDRAKPVTQIVSAEAWGRADCGFTSESYQQGVLSATILYE

ILLGKATLYAVLVSALVLMAMVKRKDSRG*;

TCR<sub>CD4</sub>-TPT#6:
>Vα12.3 J35 C
SEQ ID NO: 56
MMKSLRVLLVILWLQLSWVWSQQKEVEQDPGPLSVPEGAIVSLNCTYSNSAFQYFM

WYRQYSRKGPELLMYTYSSGNKEDGRFTAQVDKSSKYISLFIRDSQPSDSATYLCAM

SAVSFGNVLHCGSGTQVIVLPHIQNPDPAVYQLRDSKSSDKSVCLFTDFDSQTNVSQS

KDSDVYITDKTVLDMRSMDFKSNSAVAWSNKSDFACANAFNNSIIPEDTFFPSPESSC

DVKLVEKSFETDTNLNFQNLSVIGFRILLLKVAGFNLLMTLRLWSS*;

-continued

\>Vβ5.4 D1 J1.3 C1 (PG->TR)
SEQ ID NO: 57
MGTRLLCWVLLCLLGAGSVETGVTQSPTHLIKTRGQQVTLRCSSQSGHNTVSWYQQ

ALGQGPQFIFQYYREEENGRGNFPPRFSGLQFPNYSSELNVNALELDDSALYLCASSF

GENTIYFGEGSWLTVVEDLNKVFPPEVAVFEPSEAEISHTQKATLVCLATGFFPDHVE

LSWWVNGKEVHSGVSTDPQPLKEQPALNDSRYCLSSRLRVSATFWQNPRNHFRCQV

QFYGLSENDEWTQDRAKPVTQIVSAEAWGRADCGFTSVSYQQGVLSATILYEILLGK

ATLYAVLVSALVLMAMVKRKDF*;

$TCR_{CD4}$-TPT#8:
\>Vα38.1 J45 C
SEQ ID NO: 58
MTRVSLLWAVVVSTCLESGMAQTVTQSQPEMSVQEAETVTLSCTYDTSENNYYLFW

YKQPPSRQMILVIRQEAYKQQNATENRFSVNFQKAAKSFSLKISDSQLGDTAMYFCA

FMKHPSGGGADGLTFGKGTHLIIQPYIQNPDPAVYQLRDSKSSDKSVCLFTDFDSQTN

VSQSKDSDVYITDKTVLDMRSMDFKSNSAVAWSNKSDFACANAFNNSIIPEDTFFPSP

ESSCDVKLVEKSFETDTNLNFQNLSVIGFRILLLKVAGFNLLMTLRLWSS*;

\>Vβ3.1 D1 J2.7 C2 (C->T)
SEQ ID NO: 59
MGTRLLCCVVFCLLQAGPLDTAVSQTPKYLVTQMGNDKSIKCEQNLGHDTMYWYK

QDSKKFLKIMFSYNNKELIINETVPNRFSPKSPDKAHLNLHINSLELGDSAVYFCASSH

ERGGAYEQYFGPGTRLTVTEDLKNVFPPEVAVFEPSEAEISHTQKATLVCLATGFYPD

HVELSWWVN GKEVHSGVSTDPQPLKEQPALNDSRYCLSSRLRVSATFWQNPRNHFR

CQVQFYGLSENDEWTQDRAKPVTQIVSAEAWGRADCGFTSESYQQGVLSATILYEIL

LGKATLYAVLVSALVLMAMVKRKDSRG*;

$TCR_{CD4}$-TPT#11:
\>Vα17 J27 C
SEQ ID NO: 60
METLLGVSLVILWLQLARVNSQQGEEDPQALSIQEGENATMNCSYKTSINNLQWYR

QNSGRGLVHLILIRSNEREKHSGRLRVTLDTSKKSSSLLITASRAADTASYFCAGYNT

NAGKSTFGDGTTLTVKPNIQNPDPAVYQLRDSKSSDKSVCLFTDFDSQTNVSQSKDS

DVYITDKTVLDMRSMDFKSNSAVAWSNKSDFACANAFNNSIIPEDTFFPSPESSCDVK

LVEKSFETDTNLNFQNLSVIGFRILLLKVAGFNLLMTLRLWSS*;

\>Vβ6.6_2 D1 J2.3 C2 (IS->LG)
SEQ ID NO: 61
MSLGLLCCAAFPLLWAGPVNAGVTQTPKFRILKIGQSMTLQCAQDMNHNYMYWYR

QDPGMGLKLIYYSVGAGITDKGEVPNGYNVSRSTTEDFPLRLELAAPSQTSVYFCASS

FGQVWADTQYFGPGTRLTVLEDLKNVFPPEVAVFEPSEAEISHTQKATLVCLATGFY

PDHVELSWWVNGKEVHSGVSTDPQPLKEQPALNDSRYCLSSRLRVSATFWQNPRNH

FRCQVQFYGLSENDEWTQDRAKPVTQIVSAEAWGRADCGFTSESYQQGVLSATILYE

ILLGKATLYAVLVSALVLMAMVKRKDSRG*;

$TCR_{CD4}$-TPT#13:
\>Vα20_2 J29 C
SEQ ID NO: 62
MEKMLECAFIVLWLQLGWLSGEDQVTQSPEALRLQEGESSSLNCSYTVSGLRGLFW

YRQHPGKGPEFLFTLYSAGEEKEKERLKATLTKKESFLHITAPKPEDSATYLCAVQAS

NSGNTPLVFGKGTRLSVIANIQNPDPAVYQLRDSKSSDKSVCLFTDFDSQTNVSQSKD

SDVYITDKTVLDMRSMDFKSNSAVAWSNKSDFACANAFNNSIIPEDTFFPSPESSCDV

KLVEKSFETDTNLNFQNLSVIGFRILLLKVAGFNLLMTLRLWSS*;

-continued

>Vβ19 D2 J2.1 C2
SEQ ID NO: 63
MSNQVLCCVVLCFLGANTVDGGITQSPKYLFRKEGQNVTLSCEQNLNHDAMYWYR

QDPGQGLRLIYYSQIVNDFQKGDIAEGYSVSREKKESFPLTVTSAQKNPTAFYLCASS

APHQRGTNEQFFGPGTRLTVLEDLKNVFPPEVAVFEPSEAEISHTQKATLVCLATGFY

PDHVELSWWVNGKEVHSGVSTDPQPLKEQPALNDSRYCLSSRLRVSATFWQNPRNH

FRCQVQFYGLSENDEWTQDRAKPVTQIVSAEAWGRADCGFTSESYQQGVLSATILYE

ILLGKATLYAVLVSALVLMAMVKRKDSRG*;

TCR$_{CD4}$-TPT#17:
>Vα29/DV5 J49 C
SEQ ID NO: 64
MAMLLGASVLILWLQPDWVNSQQKNDDQQVKQNSPSLSVQEGRISILNCDYTNSMF

DYFLWYKKYPAEGPTFLISISSIKDKNEDGRFTVFLNKSAKHLSLHIVPSQPGDSAVYF

CAASPNTGNQFYFGTGTSLTVIPNIQNPDPAVYQLRDSKSSDKSVCLFTDFDSQTNVS

QSKDSDVYITDKTVLDMRSMDFKSNSAVAWSNKSDFACANAFNNSIIPEDTFFPSPES

SCDVKLVEKSFETDTNLNFQNLSVIGFRILLLKVAGFNLLMTLRLWSS*;

>Vβ7.2 D1 J2.7 C2
SEQ ID NO: 65
MGTRLLFWVAFCLLGADHTGAGVSQSPSNKVTEKGKDVELRCDPISGHTALYWYRQ

SLGQGLEFLIYFQGNSAPDKSGLPSDRFSAERTGGSVSTLTIQRTQQEDSAVYLCASSL

TGGPYEQYFGPGTRLTVTEDLKNVFPPEVAVFEPSEAEISHTQKATLVCLATGFYPDH

VELSWVVVNGKEVHSGVSTDPQPLKEQPALNDSRYCLSSRLRVSATFWQNPRNHFRC

QVQFYGLSENDEWTQDRAKPVTQIVSAEAWGRADCGFTSESYQQGVLSATILYEILL

GKATLYAVLVSALVLMAMVKRKDSRG*;

TCR$_{CD4}$-TPT#27:
>Vα13.1_2 J45 C (Donor SNP N->K)
SEQ ID NO: 66
MTSIRAVFIFLWLQLDLVNGENVEQHPSTLSVQEGDSAVIKCTYSDSASNYFPWYKQ

ELGKRPQLIIDIRSNVGEKKDQRIAVTLNKTAKHFSLHITETQPEDSAVYFCAALYSGG

GADGLTFGKGTHLIIQPYIQKPDPAVYQLRDSKSSDKSVCLFTDFDSQTNVSQSKDSD

VYITDKTVLDMRSMDFKSNSAVAWSNKSDFACANAFNNSIIPEDTFFPSPESSCDVKL

VEKSFETD TNLNFQNLSVIGFRILLLKVAGFNLLMTLRLWSS*;

>Vβ19 D1 J1.1 C1
SEQ ID NO: 67
MSNQVLCCVVLCFLGANTVDGGITQSPKYLFRKEGQNVTLSCEQNLNHDAMYWYR

QDPGQGLRLIYYSQIVNDFQKGDIAEGYSVSREKKESFPLTVTSAQKNPTAFYLCASSI

GGGVNTEAFFGQGTRLTVVEDLNKVFPPEVAVFEPSEAEISHTQKATLVCLATGFFPD

HVELSWWVNGKEVHSGVSTDPQPLKEQPALNDSRYCLSSRLRVSATFWQNPRNHFR

CQVQFYGLSENDEWTQDRAKPVTQIVSAEAWGRADCGFTSVSYQQGVLSATILYEIL

LGKATLYAVLVSALVLMAMVKRKDF*;

TCR$_{CD4}$-TPT#33:
>Vα29/DV5 J42 C (Donor SNP N->K)
SEQ ID NO: 68
MAMLLGASVLILWLQPDWVNSQQKNDDQQVKQNSPSLSVQEGRISILNCDYTNSMF

DYFLWYKKYPAEGPTFLISISSIKDKNEDGRFTVFLNKSAKHLSLHIVPSQPGDSAVYF

CAARSYGGSQGNLIFGKGTKLSVKPNIQKPDPAVYQLRDSKSSDKSVCLFTDFDSQTN

VSQSKDSDVYITDKTVLDMRSMDFKSNSAVAWSNKSDFACANAFNNSIIPEDTFFPSP

ESSCDVKLVEKSFETDTNLNFQNLSVIGFRILLLKVAGFNLLMTLRLWSS*;

-continued

>Vβ24.1 D2 J2.1 C2
SEQ ID NO: 69
MASLLFFCGAFHLLGTGSMDADVTQTPRNRITKTGKRIMLECSQT<u>KGHDR</u>MYWYRQ

DPGLGLRLIYY<u>SFDVKD</u>INKGEISDGYSVSRQAQAKFSLSLESAIPNQTALYFC<u>ATSDT</u>

<u>GTSRNEQF</u>FGPGTRLTVLEDLKNVFPPEVAVFEPSEAEISHTQKATLVCLATGFYPDH

VELSWWVNGKEVHSGVSTDPQPLKEQPALNDSRYCLSSRLRVSATFWQNPRNHFRC

QVQFYGLSENDEWTQDRAKPVTQIVSAEAWGRADCGFTSESYQQGVLSATILYEILL

GKATLYAVLVSALVLMAMVKRKDSRG*;

TCR<sub>CD4</sub>-TPT#38:
>Vα39 J18 C(Donor SNPN->K)
SEQ ID NO: 70
MKKLLAMILWLQLDRLSGELKVEQNPLFLSMQEGKNYTIYCNYS<u>TTSDRL</u>YWYRQD PGKSLESLFV<u>LLSNGA</u>VKQEGRLMASLDTKARLSTLHITAAVHDLSATYFC<u>AVGFRG</u>

<u>STLGRLY</u>FGRGTQLTVWPDIQKPDPAVYQLRDSKSSDKSVCLFTDFDSQTNVSQSKD

SDVYITDKTVLDMRSMDFKSNSAVAWSNKSDFACANAFNNSIIPEDTFFPSPESSCDV

KLVEKSFETDTNLNFQNLSVIGFRILLLKVAGFNLLMTLRLWSS*;

>Vβ5.5_2 D1 J1.4 C1 (PG->TR)
SEQ ID NO: 71
MGTRLLCWVLLCLLGAGPVDAGVTQPTHLIKTRGQHVTLRCSPI<u>SGHKS</u>VSWYQQ

VLGQGPQFIFQ<u>YYEKEE</u>RGRGNFPDRFSARQFPNYSSELNVNALLLGDSALYLC<u>ASS</u>

<u>WGQGNEKLF</u>FGSGTQLSVLEDLNKVFPPEVAVFEPSEAEISHTQKATLVCLATGFFPD

HVELSWWVNGKEVHSGVSTDPQPLKEQPALNDSRYCLSSRLRVSATFWQNPRNHFR

CQVQFYGLSENDEWTQDRAKPVTQIVSAEAWGRADCGFTSVSYQQGVLSATILYEIL

LGKATLYAVLVSALVLMAMVKRKDF*;

TCR<sub>CD4</sub>-TPT#42:
>Vα25 J10 C
SEQ ID NO: 72
MLLITSMLVLWMQLSQVNGQQVMQIPQYQHVQEGEDFTTYCNS<u>STTLSN</u>IQWYKQR PGGHPVFLIQ<u>LVKSGE</u>VKKQKRLTFQFGEAKKNSSLHITATQTTDVGTYFC<u>AGSTGG</u>

<u>GNKLT</u>FGTGTQLKVELNIQNPDPAVYQLRDSKSSDKSVCLFTDFDSQINVSQSKDSD

VYITDKTVLDMRSMDFKSNSAVAWSNKSDFACANAFNNSIIPEDTFFPSPESSCDVKL

VEKSFETDTNLNFQNLSVIGFRILLLKVAGFNLLMTLRLWSS*;

>Vβ7.8 D2 J2.7 C2 (GTR->DIW; L->V)
SEQ ID NO: 73
MD1WLVCWVVLGFLGTDHTGAGVSQSPRYKVAKRGQDVALRCDPI<u>SGHVS</u>LFWYQ

QALGQGPEFLTY<u>FQNEAQ</u>LDKSGLPSDRFFAERPEGSVSTLKIQRTQQEDSAVYLC<u>AS</u>

<u>SDFYEQY</u>FGPGTRLTVTEDLKNVFPPEVAVFEPSEAEISHTQKATLVCLATGFYPDHV

ELSWVVVNGKEVHSGVSTDPQPLKEQPALNDSRYCLSSRLRVSATFWQNPRNHFRCQ

VQFYGLSENDEWTQDRAKPVTQIVSAEAWGRADCGFTSESYQQGVLSATILYEILLG

KATLYAVLVSALVLMAMVKRKDSRG*;

TCR<sub>CD4</sub>-TPT#45:
>Vα13.2 J23 C
SEQ ID NO: 74
MAGIRALFMYLWLQLDWVSRGESVGLHLPTLSVQEGDNSIINCAYS<u>NSASDY</u>FIWYK QESGKGPQFIID<u>IRSNMD</u>KRQGQRVTVLLNKTVKHLSLQIAATQPGDSAVYFC<u>AETRQ</u>

<u>GGKLI</u>FGQGTELSVKPNIQNPDPAVYQLRDSKSSDKSVCLFTDFDSQTNVSQSKDSDV

YITDKTVLDMRSMDFKSNSAVAWSNKSDFACANAFNNSIIPEDTFFPSPESSCDVKLV

EKSFETDTNLNFQNLSVIGFRILLLKVAGFNLLMTLRLWSS*;

-continued

\>Vβ20.1 D1 J1.2 C1 (ISLLLPGSLAG missing following GPG)
SEQ ID NO: 75
MLLLLLLL<u>GPGS</u>GLGAVVSQHPSWVICKSGTSVKIECRSL<u>DFQATT</u>MFWYRQFPKQS LMLMAT<u>SNEGSKA</u>TYEQGVEKDKFLINHASLTLSTLTVTSAHPEDSSFYIC<u>SAPPGVT</u>

<u>VRAYGYT</u>FGSGTRLTVVEDLNKVFPPEVAVFEPSEAEISHTQKATLVCLATGFFPDHV

ELSWWVNGKEVHSGVSTDPQPLKEQPALNDSRYCLSSRLRVSATFWQNPRNHFRCQ

VQFYGLSENDEWTQDRAKPVTQIVSAEAWGRADCGFTSVSYQQGVLSATILYEILLG

KATLYAVLVSALVLMAMVKRKDF\*;

TCR$_{CD4}$-TPT#48:
\>Vα38.2/DV8 J42 C
SEQ ID NO: 76
MACPGFLWALVISTCLEFSMAQTVTQSQPEMSVQEAETVTLSCTYD<u>TSESDYY</u>LFWY

KQPPSRQMILVIR<u>QEAYKQQ</u>NATENRFSVNFQKAAKSFSLKISDSQLGDAAMYFC<u>AY</u>

<u>RNYGGSQGNLI</u>FGKGTKLSVKPNIQNPDPAVYQLRDSKSSDKSVCLFTDFDSQTNVS

QSKDSDVYITDKTVLDMRSMDFKSNSAVAWSNKSDFACANAFNNSIIPEDTFFPSPES

SCDVKLVEKSFETDTNLNFQNLSVIGFRILLLKVAGFNLLMTLRLWSS\*;

\>Vα28 D1 J1.1 C1
SEQ ID NO: 77
MGIRLLCRVAFCFLAVGLVDVKVTQSSRYLVKRTGEKVFLECVQD<u>MDHEN</u>MFWYR

QDPGLGLRLIYF<u>SYDVKM</u>KEKGDIPEGYSVSREKKERFSLILESASTNQTSMYLC<u>ASN</u>

<u>RLNTEAF</u>FGQGTRLTVVEDLNKVFPPEVAVFEPSEAEISHTQKATLVCLATGFFPDHV

ELSWWVNGKEVHSGVSTDPQPLKEQPALNDSRYCLSSRLRVSATFWQNPRNHFRCQ

VQFYGLSENDEWTQDRAKPVTQIVSAEAWGRADCGFTSVSYQQGVLSATILYEILLG

KATLYAVLVSALVLMAMVKRKDF\*;

TCR$_{CD4}$-TPT#49:
\>Vα38.1 J49 C
SEQ ID NO: 78
MTRVSLLWAVVVSTCLESGMAQTVTQSQPEMSVQEAETVTLSCTYD<u>TSENNYY</u>LFW

YKQPPSRQMILVIR<u>QEAYKQQ</u>NATENRFSVNFQKAAKSFSLKISDSQLGDTAMYFC<u>A</u>

<u>FMKNTGNQFY</u>FGTGTSLTVIPNIQNPDPAVYQLRDSKSSDKSVCLFTDFDSQTNVSQS

KDSDVYITDKTVLDMRSMDFKSNSAVAWSNKSDFACANAFNNSIIPEDTFFPSPESSC

DVKLVEKSFETDTNLNFQNLSVIGFRILLLKVAGFNLLMTLRLWSS\*;

\>Vβ19 D2 J2.2 C2
SEQ ID NO: 79
MSNQVLCCVVLCFLGANTVDGGITQSPKYLFRKEGQNVTLSCEQN<u>LNHDA</u>MYWYR

QDPGQGLRLIYY<u>SQIVND</u>FQKGDIAEGYSVSREKKESFPLTVTSAQKNPTAFYLC<u>ASR</u>

<u>RLDGLGIGELF</u>FGEGSRLTVLEDLKNVFPPEVAVFEPSEAEISHTQKATLVCLATGFYP

DHVELSWWVNGKEVHSGVSTDPQPLKEQPALNDSRYCLSSRLRVSATFWQNPRNHF

RCQVQFYGLSENDEWTQDRAKPVTQIVSAEAWGRADCGFTSESYQQGVLSATILYEI

LLGKATLYAVLVSALVLMAMVKRKDSRG\*;

TCR$_{CD4}$-TPT#51:
\>Vα13.1 2 J53 C
SEQ ID NO: 80
MTSIRAVFIFLWLQLDLVNGENVEQHPSTLSVQEGDSAVIKCTYS<u>DSASNY</u>FPWYKQ

ELGKRPQLIID<u>IRSNV</u>GEKKDQRIAVTLNKTAKHFSLHITETQPEDSAVYFC<u>AALSGGS</u>

<u>NYKLT</u>FGKGTLLTVNPNIQNPDPAVYQLRDSKSSDKSVCLFTDFDSQTNVSQSKDSD

VYITDKTVLDMRSMDFKSNSAVAWSNKSDFACANAFNNSIIPEDTFFPSPESSCDVKL

VEKSFETDTNLNFQNLSVIGFRILLLKVAGFNLLMTLRLWSS\*;

-continued

>Vβ14 D1 J1.1 C1
SEQ ID NO: 81
MVSRLLSLVSLCLLGAKHIEAGVTQFPSHSVIEKGQTVTLRCDPI<u>SGHDN</u>LYWYRRV

MGKEIKFLLH<u>FVKESK</u>QDESGMPNNRFLAERTGGTYSTLKVQPAELEDSGVYFC<u>ASS</u>

<u>QQENTEAF</u>FGQGTRLTVVEDLNKVFPPEVAVFEPSEAEISHTQKATLVCLATGFFPDH

VELSWWVNGKEVHSGVSTDPQPLKEQPALNDSRYCLSSRLRVSATFWQNPRNHFRC

QVQFYGLSENDEWTQDRAKPVTQIVSAEAWGRADCGFTSVSYQQGVLSATILYEILL

GKATLYAVLVSALVLMAMVKRKDF*;

TCR<sub>CD4</sub>-TPT#52:
>Vα8.3 J54 C (Additional MA)
SEQ ID NO: 82
MAMLLELIPLLGIHFVLRTARAQSVTQPDIHITVSEGASLELRCNYS<u>YGATPYL</u>FWYV QSPGQGLQLLLK<u>YFSGDTL</u>VQGIKGFEAEFKRSQSSFNLRKPSVHWSDAAEYFC<u>AVG</u>

<u>AQGAQKLV</u>FGQGTRLTINPNIQNPDPAVYQLRDSKSSDKSVCLFTDFDSQTNVSQSK

DSDVYITDKTVLDMRSMDFKSNSAVAWSNKSDFACANAFNNSIIPEDTFFPSPESSCD

VKLVEKSFETDTNLNFQNLSVIGFRILLLKVAGFNLLMTLRLWSS*;

>Vβ6.1 D2 J2.7 C2 (I->L)
SEQ ID NO: 83
MSLGLLCCVAFSLLWASPVNAGVTQTPKFQVLKTGQSMTLQCAQD<u>MNHNS</u>MYWY

RQDPGMGLRLIYY<u>SASEGT</u>TDKGEVPNGYNVSRLNKREFSLRLESAAPSQTSVYFC<u>A</u>

<u>SSEAGGSSFEQY</u>FGPGTRLTVTEDLNKVFPPEVAVFEPSEAEISHTQKATLVCLATGFY

PDHVELSWWVNGKEVHSGVSTDPQPLKEQPALNDSRYCLSSRLRVSATFWQNPRNH

FRCQVQFYGLSENDEWTQDRAKPVTQNSAEAWGRADCGFTSESYQQGVLSATILYE

ILLGKATLYAVLVSALVLMAMVKRKDSRG*;

TCR<sub>CD4</sub>-TPT#54:
>Vα9.2 J23 C
SEQ ID NO: 84
MNYSPGLVSLILLLLGRTRGNSVTQMEGPVTLSEEAFLTINCTYT<u>ATGYPS</u>LFWYVQY PGEGLQLLLK<u>ATKADD</u>KGSNKGFEATYRKETTSFHLEKGSVQVSDSAVYFC<u>ALGRG</u>

<u>KLI</u>FGQGTELSVKPNIQNPDPAVYQLRDSKSSDKSVCLFTDFDSQTNVSQSKDSDVYI

TDKTVLDMRSMDFKSNSAVAWSNKSDFACANAFNNSIIPEDTFFPSPESSCDVKLVEK

SFETDTNLNFQNLSVIGFRILLLKVAGFNLLMTLRLWSS*;

>Vβ20.1 D1 J1.1 C1 (ISLLLPGSLAG missing following GPG)
SEQ ID NO: 85
MLLLLLLLGPGSGLGAVVSQHPSWVICKSGTSVKIECRSL<u>DFQATT</u>MFWYRQFPKQS LMLMAT<u>SNEGSKA</u>TYEQGVEKDKFLINHASLTLSTLTVTSAHPEDSSFYIC<u>SAVDSDL</u>

<u>EAF</u>FGQGTRLTVVEDLNKVFPPEVAVFEPSEAEISHTQKATLVCLATGFFPDHVELSW

WVNGKEVHSGVSTDPQPLKEQPALNDSRYCLSSRLRVSATFWQNPRNHFRCQVQFY

GLSENDEWTQDRAKPVTQIVSAEAWGRADCGFTSVSYQQGVLSATILYEILLGKATL

YAVLVSALVLMAMVKRKDF*;

TCR<sub>CD4</sub>-TPT#55:
>Vα38.2/DV8 J34 C
SEQ ID NO: 86
MACPGFLWALVISTCLEFSMAQTVTQSQPEMSVQEAETVTLSCTYD<u>TSESDYY</u>LFWY KQPPSRQMILVIR<u>QEAYKQQ</u>NATENRFSVNFQKAAKSFSLKISDSQLGDAAMYFC<u>AY</u>

<u>RSAVYNTDKLI</u>FGTGTRLQVFPNIQNPDPAVYQLRDSKSSDKSVCLFTDFDSQTNVSQ

SKDSDVYITDKTVLDMRSMDFKSNSAVAWSNKSDFACANAFNNSIIPEDTFFPSPESS

CDVKLVEKSFETDTNLNFQNLSVIGFRILLLKVAGFNLLMTLRLWSS*;

-continued

>Vβ5.1 J2.1 C2
SEQ ID NO: 87
MGSRLLCWVLLCLLGAGPVKAGVTQTPRYLIKTRGQQVTLSCSPIS<u>GHRS</u>VSWYQQT
PGQGLQFLFE<u>YFSETQR</u>NKGNFPGRFSGRQFSNSRSEMNVSTLELGDSALYLC<u>ASSFS</u>
<u>SYNEQ</u>FFGPGTRLTVLEDLKNVFPPEVAVFEPSEAEISHTQKATLVCLATGFYPDHVE
LSWWVNGKEVHSGVSTDPQPLKEQPALNDSRYCLSSRLRVSATFWQNPRNHFRCQV
QFYGLSENDEWTQDRAKPVTQIVSAEAWGRADCGFTSESYQQGVLSATILYEILLGK
ATLYAVLVSALVLMAMVKRKDSRG*;

TCR<sub>CD4</sub>-TPT#57:
>Vα8.1 J27 C
SEQ ID NO: 88
MLLLLIPVLGMIFALRDARAQSVSQHNHHVILSEAASLELGCNYS<u>YGGTVN</u>LFWYVQ
YPGQHLQLLLK<u>YFSGDPL</u>VKGIKGFEAEFIKSKFSFNLRKPSVQWSDTAEYFC<u>AVNAR</u>
<u>DNAGKS</u>TFGDGTTLTVKPNIQNPDPAVYQLRDSKSSDKSVCLFTDFDSQTNVSQSKD
SDVYITDKTVLDMRSMDFKSNSAVAWSNKSDFACANAFNNSIIPEDTFFPSPESSCDV
KLVEKSFETDTNLNFQNLSVIGFRILLLKVAGFNLLMTLRLWSS*;

>Vβ5.1 D2 J2.7 C2
SEQ ID NO: 89
MGSRLLCWVLLCLLGAGPVKAGVTQTPRYLIKTRGQQVTLSCSPIS<u>GHRS</u>VSWYQQT
PGQGLQFLFE<u>YFSETQR</u>NKGNFPGRFSGRQFSNSRSEMNVSTLELGDSALYLC<u>ASRGE</u>
<u>PSSYEQY</u>FGPGTRLTVTEDLKNVFPPEVAVFEPSEAEISHTQKATLVCLATGFYPDHV
ELSWWVNGKEVHSGVSTDPQPLKEQPALNDSRYCLSSRLRVSATFWQNPRNHFRCQ
VQFYGLSENDEWTQDRAKPVTQIVSAEAWGRADCGFTSESYQQGVLSATILYEILLG
KATLYAVLVSALVLMAMVKRKDSRG*;

TCR<sub>CD4</sub>-TPT#59:
>Vα39 J49 C
SEQ ID NO: 90
MKKLLAMILWLQLDRLSGELKVEQNPLFLSMQEGKNYTIYCNYS<u>TTSDRL</u>YWYRQD
PGKSLESLFV<u>LLSNGA</u>VKQEGRLMASLDTKARLSTLHITAAVHDLSATYFC<u>AVDNEF</u>
<u>YF</u>GTGTSLTVIPNIQNPDPAVYQLRDSKSSDKSVCLFTDFDSQTNVSQSKDSDVYITD
KTVLDMRSMDFKSNSAVAWSNKSDFACANAFNNSIIPEDTFFPSPESSCDVKLVEKSF
ETDTNLNFQNLSVIGFRILLLKVAGFNLLMTLRLWSS*;

>Vβ7.93 D2 J2.4 C2 (S->R)
SEQ ID NO: 91
MGTRLLCWMALCLLGADHADTGVSQDPRHKITKRGQNVTFRCDPIS<u>EHNRL</u>YWYR
QTLGQGPEFLTY<u>FQNEAQ</u>LEKSRLLSDRFSAERPKGSFSTLEIQRTEQGDSAMYLC<u>AS</u>
<u>SLLGAGNIQY</u>FGAGTRLSVLEDLKNVFPPEVAVFEPSEAEISHTQKATLVCLATGFYP
DHVELSWWVNGKEVHSGVSTDPQPLKEQPALNDSRYCLSSRLRVSATFWQNPRNHF
RCQVQFYGLSENDEWTQDRAKPVTQNSAEAWGRADCGFTSESYQQGVLSATILYEI
LLGKATLYAVLVSALVLMAMVKRKDSRG*;

TCR<sub>CD4</sub>-TPT#67:
>Vα12.3 J9 C
SEQ ID NO: 92
MMKSLRVLLVILWLQLSWVWSQQKEVEQDPGPLSVPEGAIVSLNCTYS<u>NSAFQY</u>FM
WYRQYSRKGPELLMY<u>TYSSG</u>NKEDGRFTAQVDKSSKYISLFIRDSQPSDSATYLC<u>AL</u>
<u>YTGGFKTI</u>FGAGTRLFVKANIQNPDPAVYQLRDSKSSDKSVCLFTDFDSQTNVSQSKD
SDVYITDKTVLDMRSMDFKSNSAVAWSNKSDFACANAFNNSIIPEDTFFPSPESSCDV
KLVEKSFETDTNLNFQNLSVIGFRILLLKVAGFNLLMTLRLWSS*;

-continued

>Vβ5.1 D2 J2.7 C2
SEQ ID NO: 93
MGSRLLCWVLLCLLGAGPVKAGVTQTPRYLIKTRGQQVTLSCSPI<u>SGHRS</u>VSWYQQT

PGQGLQFLFE<u>YFSETQ</u>RNKGNFPGRFSGRQFSNSRSEMNVSTLELGDSALYLC<u>ASSFM</u>

<u>GTEQY</u>FGPGTRLTVTEDLKNVFPPEVAVFEPSEAEISHTQKATLVCLATGFYPDHVEL

SWWVNGKEVHSGVSTDPQPLKEQPALNDSRYCLSSRLRVSATFWQNPRNHFRCQVQ

FYGLSENDEWTQDRAKPVTQIVSAEAWGRADCGFTSESYQQGVLSATILYEILLGKA

TLYAVLVSALVLMAMVKRKDSRG*;

TCR$_{CD4}$-TPT#76:
>Vα8.3 J57 C
SEQ ID NO: 94
MLLELIPLLGIHFVLRTARAQSVTQPDIHITVSEGASLELRCNYS<u>YGATPYL</u>FWYVQSP

GQGLQLLLK<u>YFSGDTL</u>VQGIKGFEAEFKRSQSSFNLRKPSVHWSDAAEYFC<u>AVGAFT</u>

<u>RGGSEKLV</u>FGKGMKLTVNPYIQNPDPAVYQLRDSKSSDKSVCLFTDFDSQTNVSQSK

DSDVYITDKTVLDMRSMDFKSNSAVAWSNKSDFACANAFNNSIIPEDTFFPSPESSCD

VKLVEKSFETDTNLNFQNLSVIGFRILLLKVAGFNLLMTLRLWSS*;

>V19 D2_2 J2.7 C2
SEQ ID NO: 95
MSNQVLCCVVLCFLGANTVDGGITQSPKYLFRKEGQNVTLSCEQN<u>LNHDA</u>MYWYR

QDPGQGLRLIYY<u>SQIVND</u>FQKGDIAEGYSVSREKKESFPLTVTSAQKNPTAFYLC<u>ATG</u>

<u>SYVGYEQY</u>FGPGTRLTVTEDLKNVFPPEVAVFEPSEAEISHTQKATLVCLATGFYPDH

VELSWWVNGKEVHSGVSTDPQPLKEQPALNDSRYCLSSRLRVSATFWQNPRNHFRC

QVQFYGLSENDEWTQDRAKPVTQIVSAEAWGRADCGFTSESYQQGVLSATILYEILL

GKATLYAVLVSALVLMAMVKRKDSRG*;

TCR$_{CD4}$-TPT#77:
>Vα14/DV4_3 J50 C
SEQ ID NO: 96
MSLSSLLKVVTASLWLGPGIAQKITQTQPGMFVQEKEAVTLDCTYD<u>TSDPSYG</u>LFWY

KQPSSGEMIFLIY<u>QGSYDQQ</u>NATEGRYSLNFQKARKSANLVISASQLGDSAMYFC<u>AM</u>

<u>REGLAKTSYDKVI</u>FGPGTSLSVIPNIQNPDPAVYQLRDSKSSDKSVCLFTDFDSQTNVS

QSKDSDVYITDKTVLDMRSMDFKSNSAVAWSNKSDFACANAFNNSIIPEDTFFPSPES

SCDVKLVEKSFETDTNLNFQNLSVIGFRILLLKVAGFNLLMTLRLWSS*;

>Vβ20.1 D2 J2.2 C2 (ISLLLPGSLAG is missing following GPG)
SEQ ID NO: 97
MLLLLLLLGPGSGLGAVVSQHPSWVICKSGTSVKIECRSL<u>DFQATT</u>MFWYRQFPKQS LMLMAT<u>SNEGSKA</u>TYEQGVEKDKFLINHASLTLSTLTVTSAHPEDSSFYIC<u>SAPGTGH</u>

<u>SAGELF</u>FGEGSRLTVLEDLKNVFPPEVAVFEPSEAEISHTQKATLVCLATGFYPDHVE

LSWWVNGKEVHSGVSTDPQPLKEQPALNDSRYCLSSRLRVSATFWQNPRNHFRCQV

QFYGLSENDEWTQDRAKPVTQIVSAEAWGRADCGFTSESYQQGVLSATILYEILLGK

ATLYAVLVSALVLMAMVKRKDSRG*;

TCR$_{CD4}$-TPT#78:
>Vα8.6_2 J21 C
SEQ ID NO: 98
MLLLLVPAFQVIFTLGGTRAQSVTQLDSQVPVFEEAPVELRCNYS<u>SSVSVY</u>LFWYVQ

YPNQGLQLLLK<u>YLSGSTL</u>VKGINGFEAEFNKSQTSFHLRKPSVHISDTAEYFC<u>AVGPN</u>

<u>NFNKFY</u>FGSGTKLNVKPNIQNPDPAVYQLRDSKSSDKSVCLFTDFDSQTNVSQSKDS

DVYITDKTVLDMRSMDFKSNSAVAWSNKSDFACANAFNNSIIPEDTFFPSPESSCDVK

LVEKSFETDTNLNFQNLSVIGFRILLLKVAGFNLLMTLRLWSS*;

-continued

>Vβ2 D1 J1.6_2 C1 (L->I)
SEQ ID NO: 99
MDIWLVCWAIFSLLKAGLTEPEVTQTPSHQVTQMGQEVILRCVPI<u>SNHLY</u>FYWYRQI
LGQKVEFLVS<u>FYNNEI</u>SEKSEIFDDQFSVERPDGSNFTLKIRSTKLEDSAMYFC<u>ASSPV</u>
<u>GGYNSPLH</u>FGNGTRLTVTEDLNKVFPPEVAVFEPSEAEISHTQKATLVCLATGFFPDH
VELSWWVNGKEVHSGVSTDPQPLKEQPALNDSRYCLSSRLRVSATFWQNPRNHFRC
QVQFYGLSENDEWTQDRAKPVTQIVSAEAWGRADCGFTSVSYQQGVLSATILYEILL
GKATLYAVLVSALVLMAMVKRKDF*;

TCR<sub>CD4</sub>-TPT#79:
>Vα38.2/DV8 J39 C
SEQ ID NO: 100
MACPGFLWALVISTCLEFSMAQTVTQSQPEMSVQEAETVTLSCTYD<u>TSESDYY</u>LFWY
KQPPSRQMILVIR<u>QEAYKQQ</u>NATENRFSVNFQKAAKSFSLKISDSQLGDAAMYFC<u>AY</u>
<u>RSYNAGNMLT</u>FGGGTRLMVKPHIQNPDPAVYQLRDSKSSDKSVCLFTDFDSQTNVS
QSKDSDVYITDKTVLDMRSMDFKSNSAVAWSNKSDFACANAFNNSIIPEDTFFPSPES
SCDVKLVEKSFETDTNLNFQNLSVIGFRILLLKVAGFNLLMTLRLWSS*;

>Vβ5.1 D2 J2.1 C2
SEQ ID NO: 101
MGSRLLCLVLLCLLGAGPVKAGVTQTPRYLIKTRGQQVTLSCSPI<u>SGHRS</u>VSWYQQT
PGQGLQFLFE<u>YFSETQR</u>NKGNFPGRFSGRQFSNSRSEMNVSTLELGDSALYLC<u>ASSDT</u>
<u>SGGGGEQF</u>FGPGTRLTVLEDLKNVFPPEVAVFEPSEAEISHTQKATLVCLATGFYPDH
VELSWWVNGKEVHSGVSTDPQPLKEQPALNDSRYCLSSRLRVSATFWQNPRNHFRC
QVQFYGLSENDEWTQDRAKPVTQIVSAEAWGRADCGFTSESYQQGVLSATILYEILL
GKATLYAVLVSALVLMAMVKRKDSRG*;

TCR<sub>CD4</sub>-TPT#82:
>Vα38.2/DV8 J39 C
SEQ ID NO: 102
MACPGFLWALVISTCLEFSMAQTVTQSQPEMSVQEAETVTLSCTYD<u>TSESDYY</u>LFWY
KQPPSRQMILVIR<u>QEAYKQQ</u>NATENRFSVNFQKAAKSFSLKISDSQLGDAAMYFC<u>AY</u>
<u>RSAGLLLT</u>FGGGTRLMVKPHIQNPDPAVYQLRDSKSSDKSVCLFTDFDSQTNVSQSK
DSDVYITDKTVLDMRSMDFKSNSAVAWSNKSDFACANAFNNSIIPEDTFFPSPESSCD
VKLVEKSFETDTNLNFQNLSVIGFRILLLKVAGFNLLMTLRLWSS*;

>Vβ 19 D1 J2.7 C2
SEQ ID NO: 103
MSNQVLCCVVLCFLGANTVDGGITQSPKYLFRKEGQNVTLSCEQN<u>LNHDA</u>MYWYR
QDPGQGLRLIYY<u>SQIVNDF</u>QKGDIAEGYSVSREKKESFPLTVTSAQKNPTAFYLC<u>ASS</u>
<u>KAPGQGNTQGWEQY</u>FGPGTRLTVTEDLKNVFPPEVAVFEPSEAEISHTQKATLVCLA
TGFYPDHVELSWWVNGKEVHSGVSTDPQPLKEQPALNDSRYCLSSRLRVSATFWQN
PRNHFRCQVQFYGLSENDEWTQDRAKPVTQIVSAEAWGRADCGFTSESYQQGVLSA
TILYEILLGKATLYAVLVSALVLMAMVKRKDSRG*;

TCR<sub>CD4</sub>-TPT#87:
>Vα39 J31 C
SEQ ID NO: 104
MKKLLAMILWLQLDRLSGELKVEQNPLFLSMQEGKNYTIYCNYS<u>TTSDRL</u>YWYRQD
PGKSLESLFV<u>LLSNGA</u>VKQEGRLMASLDTKARLSTLHITAAVHDLSATYFC<u>AVDMW</u>
<u>NNNARLMF</u>GDGTQLVVKPNIQNPDPAVYQLRDSKSSDKSVCLFTDFDSQTNVSQSK
DSDVYITDKTVLDMRSMDFKSNSAVAWSNKSDFACANAFNNSIIPEDTFFPSPESSCD
VKLVEKSFETDTNLNFQNLSVIGFRILLLKVAGFNLLMTLRLWSS*;

-continued

>Vβ5.1 J2.6 C2

SEQ ID NO: 105

MGSRLLCWVLLCLLGAGPVKAGVTQTPRYLIKTRGQQVTLSCSPIS<u>GHRS</u>VSWYQQT

PGQGLQFLFE<u>YFSETQ</u>RNKGNFPGRFSGRQFSNSRSEMNVSTLELGDSALYLC<u>ASSLA</u>

<u>QSGANVLT</u>FGAGSRLTVLEDLKNVFPPEVAVFEPSEAEISHTQKATLVCLATGFYPDH

VELSWWVNGKEVHSGVSTDPQPLKEQPALNDSRYCLSSRLRVSATFWQNPRNHFRC

QVQFYGLSENDEWTQDRAKPVTQIVSAEAWGRADCGFTSESYQQGVLSATILYEILL

GKATLYAVLVSALVLMAMVKRKDSRG*;

TCR$_{CD4}$-TPT#91:
>Vα20_2 J53 C

SEQ ID NO: 106

MEKMLECAFIVLWLQLGWLSGEDQVTQSPEALRLQEGESSSLNCSYT<u>VSGLRG</u>LFW

YRQDPGKGPEFLFT<u>LYSAGEE</u>KEKERLKATLTKKESFLHITAPKPEDSATYLC<u>AVLGG</u>

<u>SNYKLT</u>FGKGTLLTVNPNIQNPDPAVYQLRDSKSSDKSVCLFTDFDSQTNVSQSKDSD

VYITDKTVLDMRSMDFKSNSAVAWSNKSDFACANAFNNSIIPEDTFFPSPESSCDVKL

VEKSFETDTNLNFQNLSVIGFRILLLKVAGFNLLMTLRLWSS*;

>Vβ6.1 D1 J2.7 C2 (I->L)

SEQ ID NO: 107

MSLGLLCCVAFSLLWASPVNAGVTQTPKFQVLKTGQSMTLQCAQD<u>MNHNS</u>MYWY

RQDPGMGLRLIYY<u>SASEGT</u>TDKGEVPNGYNVSRLNKREFSLRLESAAPSQTSVYFC<u>AI</u>

<u>SRDSYEQY</u>FGPGTRLTVTEDLKNVFPPEVAVFEPSEAEISHTQKATLVCLATGFYPDH

VELSWWVNGKEVHSGVSTDPQPLKEQPALNDSRYCLSSRLRVSATFWQNPRNHFRC

QVQFYGLSENDEWTQDRAKPVTQIVSAEAWGRADCGFTSESYQQGVLSATILYEILL

GKATLYAVLVSALVLMAMVKRKDSRG*;

TCR$_{CD8}$-TPT#35/2:
>Vα19 J17 C

SEQ ID NO: 188

MLTASLLRAVIASICVVSSMAQKVTQAQTEISVVEKEDVTLDCVYE<u>TRDTTYY</u>LFWY

KQPPSGELVFLIR<u>RNSFDEQN</u>EISGRYSWNFQKSTSSFNFTITASQVVDSAVYFC<u>ALIE</u>

<u>AAAGNKLT</u>FGGGTRVLVKPNIQNPDPAVYQLRDSKSSDKSVCLFTDFDSQTNVSQSK

DSDVYITDKTVLDMRSMDFKSNSAVAWSNKSDFACANAFNNSIIPEDTFFPSPESSCD

VKLVEKSFETDTNLNFQNLSVIGFRILLLKVAGFNLLMTLRLWSS*;

>Vβ6.2 oder V136.3 D1 J1.2 C1 (A→V)

SEQ ID NO: 189

MSLGLLCCGVFSLLWAGPVNAGVTQTPKFRVLKTGQSMTLLCAQD<u>MNHEY</u>MYWY

RQDPGMGLRLIHY<u>SVGEGT</u>TAKGEVPDGYNVSRLKKQNFLLGLESAAPSQTSVYFC<u>A</u>

<u>SSDGYGYT</u>FGSGTRLTVVEDLNKVFPPEVAVFEPSEAEISHTQKATLVCLATGFFPDH

VELSWWVNGKEVHSGVSTDPQPLKEQPALNDSRYCLSSRLRVSATFWQNPRNHFRC

QVQFYGLSENDEWTQDRAKPVTQIVSAEAWGRADCGFTSVSYQQGVLSATILYEILL

GKATLYAVLVSALVLMAMVKRKDF*;

TCR$_{CD4}$-TPT#9:
>Vα23/DV6 J49 C

SEQ ID NO: 190

MDKILGASFLVLWLQLCWVSGQQKEKSDQQQVKQSPQSLIVQKGGISIINCAYE<u>NTA</u>

<u>FDYF</u>PWYQQFPGKGPALLIA<u>IRPDVSE</u>KKEGRFTISFNKSAKQFSLHIMDSQPGDSATY

FC<u>AASFYIGNQFY</u>FGTGTSLTVIPNIQNPDPAVYQLRDSKSSDKSVCLFTDFDSQTNV

SQSKDSDVYITDKTVLDMRSMDFKSNSAVAWSNKSDFACANAFNNSIIPEDTFFPSPE

SSCDVKLVEKSFETDTNLNFQNLSVIGFRILLLKVAGFNLLMTLRLWSS*;

-continued

>Vβ3.1 D1 J1.2 C1 (C→T)
SEQ ID NO: 191

MGTRLLCCVVFCLLQAGPLDTAVSQTPKYLVTQMGNDKSIKCEQNLGHDTMYWYK

QDSKKFLKIMPSYNNKELIINETVPNRFSPKSPDKAHLNLHINSLELGDSAVYFCASSQ

EALGGGYGYTFGSGTRLTVVEDLNKVFPPEVAVFEPSEAEISHTQKATLVCLATGFFP

DHVELSWVVVNGKEVHSGVSTDPQPLKEQPALNDSRYCLSSRLRVSATFWQNPRNHF

RCQVQFYGLSENDEWTQDRAKPVTQIVSAEAWGRADCGFTSVSYQQGVLSATILYEI

LLGKATLYAVLVSALVLMAMVKRKDF*;

TCR$_{CD4}$-TPT#48/2:
>Vα8.3 J43 C(E→V)
SEQ ID NO: 192

MLLVLIPLLGIHFVLRTARAQSVTQPDIHITVSEGASLELRCNYSYGATPYLFWYVQSP

GQGLQLLLKYFSGDTLVQGIKGFEAEFKRSQSSFNLRKPSVHWSDAAEYFCAVGAYD

MRFGAGTRLTVKPNIQNPDPAVYQLRDSKSSDKSVCLFTDFDSQTNVSQSKDSDVYI

TDKTVLDMRSMDFKSNSAVAWSNKSDFACANAFNNSIIPEDTFFPSPESSCDVKLVEK

SFETDTNLNFQNLSVIGFRILLLKVAGFNLLMTLRLWSS*;

>Vβ28 D1 J1.1 C1
SEQ ID NO: 193

MGIRLLCRVAFCFLAVGLVDVKVTQSSRYLVKRTGEKVFLECVQDMDHENMFWYR

QDPGLGLRLIYFSYDVKMKEKGDrPEGYSVSREKKERFSLILESASTNQTSMYLCASN

RLNTEAFFGQGTRLTVVEDLNKVFPPEVAVFEPSEAEISHTQKATLVCLATGFFPDHV

ELSWWVNGKEVHSGVSTDPQPLKEQPALNDSRYCLSSRLRVSATFWQNPRNHFRCQ

VQFYGLSENDEWTQDRAKPVTQIVSAEAWGRADCGFTSVSYQQGVLSATILYEILLG

KATLYAVLVSALVLMAMVKRKDF*;

4. PLAC1-Specific T Cell Receptors

TCR$_{CD8}$-mPL#2:
>Vα6D.6_5 J33 C (DFS oder DSS→NSF)
SEQ ID NO: 152

MNSFPGFVAVILLILGRTHGDSVTQTEGQVTVSESKSLIINCTYSATSIGYPNLFWYVR

YPGEGLQLLLKVITAGQKGSSRGFEATYNKEATSFHLQKASVQESDSAVYYCALSDS

NYQLIWGSGTKLIIKPDIQNPEPAVYQLKDPRSQDSTLCLFTDFDSQINVPKTMESGTFI

TDKTVLDMKAMDSKSNGAIAWSNQTSFTCQDIFKETNATYPSSDVPCDATLTEKSFE

TDMNLNFQNLSVMGLRILLLKVAGFNLLMTLRLWSS*;

>Vβ2 D1 J1.3 C1
SEQ ID NO: 153

MGSIFLSCLAVCLLVAGPVDPKIIQKPKYLVAVTGSEKILICEQYLGHNAMYWYRQS

AKKPLEFMFSYSYQKLMDNQTASSRFQPQSSKKNHLDLQITALKPDDSATYFCASSP

DNSGNTLYFGEGSRLIVVEDLRNVTPPKVSLFEPSKAEIANKQKATLVCLARGFFPDH

VELSWWVNGKEVHSGVSTDPQAYKESNYSYCLSSRLRVSATFWHNPRNHFRCQVQF

HGLSEEDKWPEGSPKPVTQNISAEAWGRADCGITSASYQQGVLSATILYEILLGKATL

YAVLVSTLVVMAMVKRKNS*;

TCR$_{CD8}$-mPL#8:
>Vα9D.1_1 or V9D.1_2 J12 C(L→F)
SEQ ID NO: 154

MLLVFISFLGIHFFLDVQTQTVSQSDAHVTVFEGDSVELRCNYSYGGSIYLSWYIQHH

GRGLQFLLKYYSGNPVVQGVNGFKAEFSKSDSSFHLRKASVHWSDSAVYFCAVSAG

GYKVVFGSGTRLLVSPDIQNPEPAVYQLKDPRSQDSTLCLFTDFDSQINVPKTMESGT

-continued

FITDKTVLDMKAMDSKSNGAIAWSNQTSFTCQDIFKETNATYPSSDVPCDATLTEKSF

ETDMNLNFQNLSVMGLRILLLKVAGFNLLMTLRLWSS*;

>Vβ5 D2 J2.1 C2
SEQ ID NO: 155
MSCRLLLYVSLCLVETALMNTKITQSPRYLILGRANKSLECEQ<u>LGHNA</u>MYWYKQS

AEKPPELMFL<u>YNLKQL</u>IRNETVPSRFIPECPDSSKLLLHISAVDPEDSAVYFC<u>ASSPGG</u>

<u>AEQF</u>FGPGTRLTVLEDLRNVTPPKVSLFEPSKAEIANKQKATLVCLARGFFPDHVELS

WWVNGKEVHSGVSTDPQAYKESNYSYCLSSRLRVSATFWHNPRNHFRCQVQFHGL

SEEDKWPEGSPKPVTQNISAEAWGRADCGITSASYHQGVLSATILYEILLGKATLYAV

LVSGLVLMAMVKIKKNS*;

TCR$_{CD8}$-mPL#9:
>Vα4D.4_2 J44 C(Q→E)
SEQ ID NO: 156
MERNLGAVLGILWVQICWVRGDQVEQSPSALSLHEGTGSALRCNFT<u>TTMRA</u>VQWFQ

QNSRGSLINLFY<u>LASGT</u>KENGRLKSTFNSKESYSTLHIRDAQLEDSGTYFC<u>AAPFVTGS</u>

<u>GGKL</u>TLGAGTRLQVNLDIQNPEPAVYQLKDPRSQDSTLCLFTDFDSQINVPKTMESGT

FITDKTVLDMKAMDSKSNGAIAWSNQTSFTCQDIFKETNATYPSSDVPCDATLTEKSF

ETDMNLNFQNLSVMGLRILLLKVAGFNLLMTLRLWSS*;

>Vβ2 D2 J2.7 C2
SEQ ID NO: 157
MGSIFLSCLAVCLLVAGPVDPKIIQKPKYLVAVTGSEKILICEQ<u>YLGHNA</u>MYWYRQS

AKKPLEFMFS<u>YSYQKL</u>MDNQTASSRFQPQSSKKNHLDLQITALKPDDSATYFC<u>ASSQ</u>

<u>DGWGYEQY</u>FGPGTRLTVLEDLRNVTPPKVSLFEPSKAEIANKQKATLVCLARGFFPD

HVELSWWVNGKEVHSGVSTDPQAYKESNYSYCLSSRLRVSATFWHNPRNHFRCQV

QFHGLSEEDKWPEGSPKPVTQNISAEAWGRADCGITSASYHQGVLSATILYEILLGKA

TLYAVLVSGLVLMAMVKKKNS*;

TCR$_{CD8}$-mPL#11:
>Vα6D.6_2 J9_2 C(DF→NS)
SEQ ID NO: 158
MNSSPGFVAVILLILGRTHGDSVTQTEGPVTVSESESLIINCTYS<u>ATSIAYPN</u>LFWYVR

YPGEGLQLLLK<u>VITAGQK</u>GSSRGFEATYNKETTSFHLQKASVQESDSAVYYC<u>ALGLG</u>

<u>YKLT</u>FGTGTSLLVDPNIQNPEPAVYQLKDPRSQDSTLCLFTDFDSQINVPKTMESGTFI

TDKTVLDMKAMDSKSNGAIAWSNQTSFTCQDIFKETNATYPSSDVPCDATLTEKSFE

TDMNLNFQNLSVMGLRILLLKVAGFNLLMTLRLWSS*;

>Vβ2 D1 J1.3 C1
SEQ ID NO: 159
MGSIFLSCLAVCLLVAGPVDPKIIQKPKYLVAVTGSEKILICEQ<u>YLGHNA</u>MYWYRQS

AKKPLEFMFS<u>YSYQKL</u>MDNQTASSRFQPQSSKKNHLDLQITALKPDDSATYFC<u>ASSG</u>

<u>DNSGNTLY</u>FGEGSRLIVVEDLRNVTPPKVSLFEPSKAEIANKQKATLVCLARGFFPDH

VELSWWVNGKEVHSGVSTDPQAYKESNYSYCLSSRLRVSATFWHNPRNHFRCQVQF

HGLSEEDKWPEGSPKPVTQNISAEAWGRADCGITSASYQQGVLSATILYEILLGKATL

YAVLVSTLVVMAMVKRKNS*;

TCR$_{CD8}$-mPL#12:
>Vα4D.4_2 J27 C(Q→E)
SEQ ID NO: 160
MERNLGAVLGILWVQICWVRGDQVEQSPSALSLHEGTGSALRCNFT<u>TTMRA</u>VQWFQ

QNSRGSLINLFY<u>LASGT</u>KENGRLKSTFNSKESYSTLHIRDAQLEDSGTYFC<u>AAVNTNT</u>

<u>GKLT</u>FGDGTVLTVKPNIQNPEPAVYQLKDPRSQDSTLCLFTDFDSQINVPKTMESGTFI

-continued

TDKTVLDMKAMDSKSNGAIAWSNQTSFTCQDIFKETNATYPSSDVPCDATLTEKSFE

TDMNLNFQNLSVMGLRILLLKVAGFNLLMTLRLWSS*;

>Vβ30 D1 J2.2 C2                                               SEQ ID NO: 161

MWTFLLLLWSQGSVFSVLLYQKPNRDICQSGTSLKIQCVAD<u>SQVVS</u>MFWYQQFQEQ

SLMLMAT<u>ANEGSEA</u>TYESGFTKDKFPISRPNLTFSTLTVNNARPGDSSIYFC<u>SSRTPNT</u>

<u>GQLY</u>FGEGSKLTVLEDLRNVTPPKVSLFEPSKAEIANKQKATLVCLARGFFPDHVELS

WWVNGKEVHSGVSTDPQAYKESNYSYCLSSRLRVSATFWHNPRNHFRCQVQFHGL

SEEDKWPEGSPKPVTQNISAEAWGRADCGITSASYHQGVLSATILYEILLGKATLYAV

LVSGLVLMAMVKKKNS*;

TCR<sub>CD8</sub>-mPL#14:
>Vα9D.1_2 J12 C                                                SEQ ID NO: 162

MLLVLISFLGIHFFLDVQTQTVSQSDAHVTVFEGDSVELRCNYS<u>YGGSIY</u>LSWYIQHH

GHGLQFLLK<u>YYSGNPVV</u>QGVNGFEAEFSKSDSSFHLRKASVHWSDSAVYFC<u>AVSSG</u>

<u>GYKVV</u>FGSGTRLLVSPDIQNPEPAVYQLKDPRSQDSTLCLFTDFDSQINVPKTMESGT

FITDKTVLDMKAMDSKSNGAIAWSNQTSFTCQDIFKETNATYPSSDVPCDATLTEKSF

ETDMNLNFQNLSVMGLRILLLKVAGFNLLMTLRLWSS*;

>Vβ5 D1 J1.1 C1                                                SEQ ID NO: 163

MSCRLLLYVSLCLVETALMNTKITQSPRYLILGRANKSLECEQH<u>LGHNA</u>MYWYKQS

AEKPPELMFL<u>YNLKQL</u>IRNETVPSRFIPECPDSSKLLLHISAVDPEDSAVYFC<u>ASSQGG</u>

<u>TEVF</u>FGKGTRLTVVEDLRNVTPPKVSLFEPSKAEIANKQKATLVCLARGFFPDHVELS

WWVNGKEVHSGVSTDPQAYKESNYSYCLSSRLRVSATFWHNPRNHFRCQVQFHGL

SEEDKWPEGSPKPVTQNISAEAWGRADCGITSASYQQGVLSATILYEILLGKATLYAV

LVSTLVVMAMVKRKNS*;

TCR<sub>CD8</sub>-mPL#17:
>Vα14.1 J31_1 oder_2 C                                         SEQ ID NO: 164

MDKILTATFLLLGLHLAGVNGQQQEKRDQQQVRQSPQSLTVWEGETAILNCSYE<u>DST</u>

<u>FNYF</u>PWYQQFPGEGPALLIS<u>IRSVSDK</u>KEDGRFTIFFNKREKKLSLHITDSQPGDSATY

FC<u>APNNRIF</u>FGDGTQLVVKPNIQNPEPAVYQLKDPRSQDSTLCLFTDFDSQINVPKTM

ESGTFITDKTVLDMKAMDSKSNGAIAWSNQTSFTCQDIFKETNATYPSSDVPCDATLT

EKSFETDMNLNFQNLSVMGLRILLLKVAGFNLLMTLRLWSS*;

>Vβ13.2 D2 J2.1 C2                                             SEQ ID NO: 165

MGSRLFFVLSSLLCSKHMEAAVTQSPRNKVAVTGGKVTLSCNQT<u>NNHNN</u>MYWYRQ

DTGHGLRLIHY<u>SYGAGS</u>TEKGDIPDGYKASRPSQENFSLILELATPSQTSVYFC<u>ASLGY</u>

NYAEQFFGPGTRLTVLEDLRNVTPPKVSLFEPSKAEIANKQKATLVCLARGFFPDHVE

LSWWVNGKEVHSGVSTDPQAYKESNYSYCLSSRLRVSATFWHNPRNHFRCQVQFH

GLSEEDKWPEGSPKPVTQNISAEAWGRADCGITSASYHQGVLSATILYEILLGKATLY

AVLVSGLVLMAMVKKKNS*;

TCR<sub>CD8</sub>-mPL#19:
>Vα6D.3 J22 C                                                  SEQ ID NO: 166

MNNSPALVTVMLFILGRTHGDSVIQMGQVTLSENDFLFINCTYS<u>TTGYPT</u>LFWYVQ

YSGEGPQLLLQ<u>VTTANNK</u>GSSRGFEATYDKGTTSFHLQKTSVQEIDSAVYYC<u>AMSDA</u>

<u>SGSWQL</u>IFGSGTQLTVMPDIQNPEPAVYQLKDPRSQDSTLCLFTDFDSQINVPKTMES

```
GTFITDKTVLDMKAMDSKSNGAIAWSNQTSFTCQDIFKETNATYPSSDVPCDATLTE

KSFETDMNLNFQNLSVMGLRILLLKVAGFNLLMTLRLWSS*;

>Vβ13.3 D1 J1.6 C1
                                                    SEQ ID NO: 167
MGSRLFFVVLILLLCAKHMEAAVTQSPRSKVAVTGGKVTLSCHQTNNHDYMYWYRQ

DTGHGLRLIHYSYVADSTEKGDIPDGYKASRPSQENFSLILELASLSQTAVYFCASSPD

RPSYNSPLYFAAGTRLTVTEDLRNVTPPKVSLFEPSKAEIANKQKATLVCLARGFFPD

HVELSWWVNGKEVHSGVSTDPQAYKESNYSYCLSSRLRVSATFWHNPRNHFRCQV

QFHGLSEEDKWPEGSPKPVTQNISAEAWGRADCGITSASYQQGVLSATILYEILLGKA

TLYAVLVSTLVVMAMVKRKNS*;

TCR<sub>CD8</sub>-mPL#20:
>Vα12.3_3 J38 C
                                                    SEQ ID NO: 168
MRPGTCSVLVLLLMLRRSNGDGDSVTQKEGLVTLTEGLPVMLNCTYQTIYSNAFLF

WYVHYLNESPRLLLKSSTDNKRTEHQGFHATLHKSSSSFHLQKSSAQLSDSALYYCA

LNNVGDNSKLIWGLGTSLVVNPNIQNPEPAVYQLKDPRSQDSTLCLFTDFDSQINVPK

TMESGTFITDKTVLDMKAMDSKSNGAIAWSNQTSFTCQDIFKETNATYPSSDVPCDA

TLTEKSFETDMNLNFQNLSVMGLRILLLKVAGFNLLMTLRLWSS*;

>Vβ5 D2 J1.1 C1
                                                    SEQ ID NO: 169
MSCRLLLYVSLCLVETALMNTKITQSPRYLILGRANKSLECEQHLGHNAMYWYKQS

AEKPPELMFLYNLKQLIRNETVPSRFIPECPDSSKLLLHISAVDPEDSAVYFCASSQYG

GANTEVFFGKGTRLTVVEDLRNVTPPKVSLFEPSKAEIANKQKATLVCLARGFFPDH

VELSWWVNGKEVHSGVSTDPQAYKESNYSYCLSSRLRVSATFWHNPRNHFRCQVQF

HGLSEEDKWPEGSPKPVTQNISAEAWGRADCGITSASYQQGVLSATILYEILLGKATL

YAVLVSTLVVMAMVKRKNS*;

TCR<sub>CD8</sub>-mPL#22:
>Vα 13D.2 J34_2 C(V→L)
                                                    SEQ ID NO: 170
MKRLLCSLLGLLCTQVCWVKGQQVQQSPASLVLQEGENAELQCNFSSTATRLQWFY

QHPGGRLVSLFYNPSGTKHTGRLTSTTVTNERRSSLHISSSQTTDSGTYFCAAASNTN

KVVFGTGTRLQVLPNIQNPEPAVYQLKDPRSQDSTLCLFTDFDSQINVPKTMESGTFIT

DKTVLDMKAMDSKSNGAIAWSNQTSFTCQDIFKETNATYPSSDVPCDATLTEKSFET

DMNLNFQNLSVMGLRILLLKVAGFNLLMTLRLWSS*;

>Vβ20 D1 J2.1 C2
                                                    SEQ ID NO: 171
MLLLLLLLGPGCGLGALVYQYPRRTICKSGTSMRMECQAVGFQATSVAWYRQSPQK

TFELIALSTVNSAIKYEQNFTQEKFPISHPNLSFSSMTVLNAYLEDRGLYLCGVDRANY

AEQFFGPGTRLTVLEDLRNVTPPKVSLFEPSKAEIANKQKATLVCLARGFFPDHVELS

WWVNGKEVHSGVSTDPQAYKESNYSYCLSSRLRVSATFWHNPRNHFRCQVQFHGL

SEEDKWPEGSPKPVTQNISAEAWGRADCGITSASYHQGVLSATILYEILLGKATLYAV

LVSGLVLMAMVKKKNS*;

TCR<sub>CD8</sub>-mPL#25:
>Vα8.1_3 J21 C
                                                    SEQ ID NO: 194
MHSLLGLLLWLQLTRVNSQLAEENSWALSVHEGESVTVNCSYKTSITALQWYRQKS

GKGPAQLILIRSNEREKRNGRLRATLDTSSQSSSLSITATRCEDTAVYFCATDNVLYFG

SGTKLTVEPNIQNPEPAVYQLKDPRSQDSTLCLFTDFDSQINVPKTMESGTFITDKTVL
```

-continued

DMKAMDSKSNGAIAWSNQTSFTCQDIFKETNATYPSSDVPCDATLTEKSFETDMNLN

FQNLSVMGLRILLLKVAGFNLLMTLRLWSS*;

>Vβ31 D2 J2.1 C2

SEQ ID NO: 195

MLYSLLAFLLGMFLGVSAQTIHQWPVAEIKAVGSPLSLGCTIK<u>GKSSPN</u>LYWYWQAT

GGTLQQLFY<u>SITVG</u>QVESVVQLNLSASRPKDDQFILSTEKLLLSHSGFYLC<u>AWKLGNY</u>

<u>AEQF</u>FGPGTRLTVLEDLRNVTPPKVSLFEPSKAEIANKQKATLVCLARGFFPDHVELS

WWVNGKEVHSGVSTDPQAYKESNYSYCLSSRLRVSATFWHNPRNHFRCQVQFHGL

SEEDKWPEGSPKPVTQNISAEAWGRADCGITSASYHQGVLSATILYEILLGKATLYAV

LVSGLVLMAMVKKKNS*;

---

The invention claimed is:

1. An antigen-specific lymphoid cell produced by transferring into a lymphoid cell:
   (i) a nucleic acid encoding a T cell receptor α-chain comprising a T cell receptor α-chain sequence selected from SEQ ID NOs: 4, 6, 8, 10, 12, 14, 16, 18, 20, 22, 24, 26, 28, 30, 32, 34, 36, 38, 40, 42, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 140, 142, 144, 146, 148, 150, 152, 154, 156, 158, 160, 162, 164, 166, 168, 170, 176, 188, 190, 192, and 194 and a nucleic acid encoding a T cell receptor β-chain comprising a T cell receptor β-chain sequence selected from SEQ ID NOs: 5, 7, 9, 1 1, 13, 15, 17, 19, 21, 23, 25, 27, 29, 31 , 33, 35, 37, 39, 41 , 43, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 141, 143, 145, 147, 149, 151 , 153, 155, 157, 159, 161, 163, 165, 167, 169, 171, 177, 189, 191, 193, and 195; or
   (ii) a nucleic acid encoding a T cell receptor α-chain comprising a T cell receptor α-chain sequence selected from SEQ ID NOs: 4, 6, 8, 10, 12, 14, 16, 18, 20, 22, 24, 26, 28, 30, 32, 34, 36, 38, 40, 42, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 140, 142, 144, 146, 148, 150, 152, 154, 156, 158, 160, 162, 164, 166, 168, 170, 176, 188, 190, 192, and 194 and a T cell receptor β-chain sequence selected from SEQ ID NOs: 5, 7, 9, 1 1, 13, 15, 17, 19, 21, 23, 25, 27, 29, 31 , 33, 35, 37, 39, 41 , 43, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 141, 143, 145, 147, 149, 151 , 153, 155, 157, 159, 161, 163, 165, 167, 169, 171, 177, 189, 191, 193, and 195, wherein the lymphoid cell is a T cell lacking endogenous expression of a T cell receptor.

2. A pharmaceutical composition comprising the antigen-specific lymphoid cell of claim 1.

3. An antigen-specific lymphoid cell produced by transferring into a lymphoid cell
   (i) a nucleic acid encoding a T cell receptor a-chain comprising all three of the CDR sequences of a T cell receptor a-chain sequence selected from SEQ ID NOs: 4, 6, 8, 10, 12, 14, 16, 18, 20, 22, 24, 26, 28, 30, 32, 34, 36, 38, 40, 42, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 140, 142, 144, 146, 148, 150, 152, 154, 156, 158, 160, 162, 164, 166, 168, 170, 176, 188, 190, 192, and 194 and a nucleic acid encoding a T cell receptor β-chain comprising all three of the CDR sequences of a T cell receptor β-chain sequence selected from SEQ ID NOs: 5, 7, 9, 1 1 , 13, 15, 17, 19, 21, 23, 25, 27, 29, 31 , 33, 35, 37, 39, 41 , 43, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 141, 143, 145, 147, 149, 151 , 153, 155, 157, 159, 161, 163, 165, 167, 169, 171, 177, 189, 191 , 193, and 195 or (ii) a nucleic acid encoding a T cell receptor comprising all three of the CDR sequences of a T cell receptor a-chain sequence selected from SEQ ID NOs: 4, 6, 8, 10, 12, 14, 16, 18, 20, 22, 24, 26, 28, 30, 32, 34, 36, 38, 40, 42, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 140, 142, 144, 146, 148, 150, 152, 154, 156, 158, 160, 162, 164, 166, 168, 170, 176, 188, 190, 192, and 194 and all three of the CDR sequences of a T cell receptor β-chain sequence selected from SEQ ID NOs: 5, 7, 9, 1 1 , 13, 15, 17, 19, 21, 23, 25, 27, 29, 31 , 33, 35, 37, 39, 41, 43, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 141, 143, 145, 147, 149, 151 , 153, 155, 157, 159, 161, 163, 165, 167, 169, 171, 177, 189, 191 , 193, and 195.

4. A pharmaceutical composition comprising the antigen-specific lymphoid cell of claim 3.

5. The antigen-specific lymphoid cell of claim 1, wherein the nucleic acid is RNA.

6. The antigen-specific lymphoid cell of claim 5, wherein the RNA is in vitro transcribed RNA (IVT RNA).

7. The antigen-specific lymphoid cell of claim 1, wherein the lymphoid cell is a lymphocyte or a lymphoblast.

8. The antigen-specific lymphoid cell of claim 3, wherein the nucleic acid is RNA.

9. The antigen-specific lymphoid cell of claim 3, wherein the RNA is in vitro transcribed RNA (IVT RNA).

10. The antigen-specific lymphoid cell of claim 3, wherein the lymphoid cell is a lymphocyte or a lymphoblast.

11. The antigen-specific lymphoid cell of claim 1, wherein the T cell receptor a-chain sequence is selected from SEQ ID NOs : 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 188, 190, and 192 and the T cell receptor β-chain sequence is selected from SEQ ID NOs: 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 189, 191, and 193.

12. The antigen-specific lymphoid cell of claim 11, wherein the T cell receptor α-chain sequence is selected from SEQ ID NOs: 48, 50, 92, 104, and 106 and the T cell receptor β-chain sequence is selected from SEQ ID NOs: 49, 51, 93, 105, and 107.

13. The antigen-specific lymphoid cell of claim 12, wherein the T cell receptor α-chain sequence is SEQ ID NO: 48, and the T cell receptor β-chain sequence is SEQ ID NO: 49.

14. The antigen-specific lymphoid cell of claim 3, wherein the T cell receptor α-chain sequence is selected from SEQ ID NOs : 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 188, 190, and 192 and the T cell receptor β-chain sequence is selected from SEQ ID NOs: 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 189, 191, and 193.

15. The antigen-specific lymphoid cell of claim 14, wherein the T cell receptor α-chain sequence is selected from SEQ ID NOs: 48, 50, 92, 104, and 106 and the T cell receptor β-chain sequence is selected from SEQ ID NOs: 49, 51, 93, 105, and 107.

16. The antigen-specific lymphoid cell of claim 15, wherein the T cell receptor α-chain sequence is SEQ ID NO: 48, and the T cell receptor β-chain sequence is SEQ ID NO: 49.

* * * * *

SEQUENCE LISTING

<160> NUMBER OF SEQ ID NOS: 196

<210> SEQ ID NO 1
<211> LENGTH: 561
<212> TYPE: PRT
<213> ORGANISM: Cytomegalovirus

<400> SEQUENCE: 1

Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp
    50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
            100                 105                 110

Val Tyr Ala Leu Pro Leu Lys Met Leu Asn Ile Pro Ser Ile Asn Val
        115                 120                 125

His His Tyr Pro Ser Ala Ala Glu Arg Lys His Arg His Leu Pro Val
    130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
            180                 185                 190

Val Ala Leu Arg His Val Val Cys Ala His Glu Leu Val Cys Ser Met
        195                 200                 205

Glu Asn Thr Arg Ala Thr Lys Met Gln Val Ile Gly Asp Gln Tyr Val
    210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

```
Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
        275                 280                 285

His Ile Met Leu Asp Val Ala Phe Thr Ser His Glu His Phe Gly Leu
    290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
        355                 360                 365

Phe Thr Ser Gln Tyr Arg Ile Gln Gly Lys Leu Glu Tyr Arg His Thr
    370                 375                 380

Trp Asp Arg His Asp Glu Gly Ala Ala Gln Gly Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Ala Met Ala Gly Ala Ser Thr Ser
            420                 425                 430

Ala Gly Arg Lys Arg Lys Ser Ala Ser Ser Ala Thr Ala Cys Thr Ser
        435                 440                 445

Gly Val Met Thr Arg Gly Arg Leu Lys Ala Glu Ser Thr Val Ala Pro
    450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
                485                 490                 495

Val Pro Met Val Ala Thr Val Gln Gly Gln Asn Leu Lys Tyr Gln Glu
            500                 505                 510

Phe Phe Trp Asp Ala Asn Asp Ile Tyr Arg Ile Phe Ala Glu Leu Glu
        515                 520                 525

Gly Val Trp Gln Pro Ala Ala Gln Pro Lys Arg Arg Arg His Arg Gln
    530                 535                 540

Asp Ala Leu Pro Gly Pro Cys Ile Ala Ser Thr Pro Lys Lys His Arg
545                 550                 555                 560

Gly

<210> SEQ ID NO 2
<211> LENGTH: 180
<212> TYPE: PRT
<213> ORGANISM: Homo sapiens

<400> SEQUENCE: 2

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Gly Ala Pro Arg Gly Pro
    50                  55                  60
```

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
            115                 120                 125

Ser Gly Asn Ile Leu Thr Ile Arg Leu Thr Ala Ala Asp His Arg Gln
        130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

<210> SEQ ID NO 3
<211> LENGTH: 551
<212> TYPE: PRT
<213> ORGANISM: Homo sapiens

<400> SEQUENCE: 3

Met Asn Glu Ser Pro Asp Pro Thr Asp Leu Ala Gly Val Ile Ile Glu
1               5                   10                  15

Leu Gly Pro Asn Asp Ser Pro Gln Thr Ser Glu Phe Lys Gly Ala Thr
                20                  25                  30

Glu Glu Ala Pro Ala Lys Glu Ser Pro His Thr Ser Glu Phe Lys Gly
            35                  40                  45

Ala Ala Arg Val Ser Pro Ile Ser Glu Ser Val Leu Ala Arg Leu Ser
        50                  55                  60

Lys Phe Glu Val Glu Asp Ala Glu Asn Val Ala Ser Tyr Asp Ser Lys
65                  70                  75                  80

Ile Lys Lys Ile Val His Ser Ile Val Ser Ser Phe Ala Phe Gly Leu
                85                  90                  95

Phe Gly Val Phe Leu Val Leu Leu Asp Val Thr Leu Ile Leu Ala Asp
            100                 105                 110

Leu Ile Phe Thr Asp Ser Lys Leu Tyr Ile Pro Leu Glu Tyr Arg Ser
        115                 120                 125

Ile Ser Leu Ala Ile Ala Leu Phe Phe Leu Met Asp Val Leu Leu Arg
130                 135                 140

Val Phe Val Glu Arg Arg Gln Gln Tyr Phe Ser Asp Leu Phe Asn Ile
145                 150                 155                 160

Leu Asp Thr Ala Ile Ile Val Ile Leu Leu Val Asp Val Val Tyr
            165                 170                 175

Ile Phe Phe Asp Ile Lys Leu Leu Arg Asn Ile Pro Arg Trp Thr His
        180                 185                 190

Leu Leu Arg Leu Leu Arg Leu Ile Ile Leu Leu Arg Ile Phe His Leu
    195                 200                 205

Phe His Gln Lys Arg Gln Leu Glu Lys Leu Ile Arg Arg Val Ser
210                 215                 220

Glu Asn Lys Arg Arg Tyr Thr Arg Asp Gly Phe Asp Leu Asp Leu Thr
225                 230                 235                 240

Tyr Val Thr Glu Arg Ile Ile Ala Met Ser Phe Pro Ser Ser Gly Arg
            245                 250                 255

-continued

```
Gln Ser Phe Tyr Arg Asn Pro Ile Lys Glu Val Val Arg Phe Leu Asp
            260                 265                 270

Lys Lys His Arg Asn His Tyr Arg Val Tyr Asn Leu Cys Ser Glu Arg
        275                 280                 285

Ala Tyr Asp Pro Lys His Phe His Asn Arg Val Arg Ile Met Ile
    290                 295                 300

Asp Asp His Asn Val Pro Thr Leu His Gln Met Val Val Phe Thr Lys
305                 310                 315                 320

Glu Val Asn Glu Trp Met Ala Gln Asp Leu Glu Asn Ile Val Ala Ile
                325                 330                 335

His Cys Lys Gly Gly Thr Asp Arg Thr Gly Thr Met Val Cys Ala Phe
                340                 345                 350

Leu Ile Ala Ser Glu Ile Cys Ser Thr Ala Lys Glu Ser Leu Tyr Tyr
            355                 360                 365

Phe Gly Glu Arg Arg Thr Asp Lys Thr His Ser Glu Lys Phe Gln Gly
    370                 375                 380

Val Glu Thr Pro Ser Gln Lys Arg Tyr Val Ala Tyr Phe Ala Gln Val
385                 390                 395                 400

Lys His Leu Tyr Asn Trp Asn Leu Pro Pro Arg Arg Ile Leu Phe Ile
                405                 410                 415

Lys His Phe Ile Ile Tyr Ser Ile Pro Arg Tyr Val Arg Asp Leu Lys
                420                 425                 430

Ile Gln Ile Glu Met Glu Lys Lys Val Val Phe Ser Thr Ile Ser Leu
            435                 440                 445

Gly Lys Cys Ser Val Leu Asp Asn Ile Thr Thr Asp Lys Ile Leu Ile
    450                 455                 460

Asp Val Phe Asp Gly Pro Pro Leu Tyr Asp Val Lys Val Gln Phe
465                 470                 475                 480

Phe Tyr Ser Asn Leu Pro Thr Tyr Tyr Asp Asn Cys Ser Phe Tyr Phe
                485                 490                 495

Trp Leu His Thr Ser Phe Ile Glu Asn Asn Arg Leu Tyr Leu Pro Lys
            500                 505                 510

Asn Glu Leu Asp Asn Leu His Lys Gln Lys Ala Arg Arg Ile Tyr Pro
    515                 520                 525

Ser Asp Phe Ala Val Glu Ile Leu Phe Gly Glu Lys Met Thr Ser Ser
530                 535                 540

Asp Val Val Ala Gly Ser Asp
545                 550

<210> SEQ ID NO 4
<211> LENGTH: 267
<212> TYPE: PRT
<213> ORGANISM: Homo sapiens

<400> SEQUENCE: 4

Met Trp Gly Ala Phe Leu Leu Tyr Val Ser Met Lys Met Gly Gly Thr
1               5                   10                  15

Thr Gly Gln Asn Ile Asp Gln Pro Thr Glu Met Thr Ala Thr Glu Gly
            20                  25                  30

Ala Ile Val Gln Ile Asn Cys Thr Tyr Gln Thr Ser Gly Phe Asn Gly
        35                  40                  45

Leu Phe Trp Tyr Gln Gln His Ala Gly Glu Ala Pro Thr Phe Leu Ser
    50                  55                  60

Tyr Asn Val Leu Asp Gly Leu Glu Glu Lys Gly Arg Phe Ser Ser Phe
```

```
                65                  70                  75                  80
Leu Ser Arg Ser Lys Gly Tyr Ser Tyr Leu Leu Leu Lys Glu Leu Gln
                    85                  90                  95

Met Lys Asp Ser Ala Ser Tyr Leu Cys Ala Val Ala Asp Ser Trp Gly
                100                 105                 110

Lys Leu Gln Phe Gly Ala Gly Thr Gln Val Val Val Thr Pro Asp Ile
                115                 120                 125

Gln Asn Pro Asp Pro Ala Val Tyr Gln Leu Arg Asp Ser Lys Ser Ser
            130                 135                 140

Asp Lys Ser Val Cys Leu Phe Thr Asp Phe Asp Ser Gln Thr Asn Val
145                 150                 155                 160

Ser Gln Ser Lys Asp Ser Asp Val Tyr Ile Thr Asp Lys Thr Val Leu
                165                 170                 175

Asp Met Arg Ser Met Asp Phe Lys Ser Asn Ser Ala Val Ala Trp Ser
            180                 185                 190

Asn Lys Ser Asp Phe Ala Cys Ala Asn Ala Phe Asn Asn Ser Ile Ile
                195                 200                 205

Pro Glu Asp Thr Phe Phe Pro Ser Pro Glu Ser Ser Cys Asp Val Lys
            210                 215                 220

Leu Val Glu Lys Ser Phe Glu Thr Asp Thr Asn Leu Asn Phe Gln Asn
225                 230                 235                 240

Leu Ser Val Ile Gly Phe Arg Ile Leu Leu Leu Lys Val Ala Gly Phe
                245                 250                 255

Asn Leu Leu Met Thr Leu Arg Leu Trp Ser Ser
            260                 265

<210> SEQ ID NO 5
<211> LENGTH: 315
<212> TYPE: PRT
<213> ORGANISM: Homo sapiens

<400> SEQUENCE: 5

Met Gly Thr Arg Leu Leu Cys Cys Val Val Phe Cys Leu Leu Gln Ala
1               5                   10                  15

Gly Pro Leu Asp Thr Ala Val Ser Gln Thr Pro Lys Tyr Leu Val Thr
                20                  25                  30

Gln Met Gly Asn Asp Lys Ser Ile Lys Cys Glu Gln Asn Leu Gly His
            35                  40                  45

Asp Thr Met Tyr Trp Tyr Lys Gln Asp Ser Lys Lys Phe Leu Lys Ile
        50                  55                  60

Met Phe Ser Tyr Asn Asn Lys Glu Leu Ile Ile Asn Glu Thr Val Pro
65                  70                  75                  80

Asn Arg Phe Ser Pro Lys Ser Pro Asp Lys Ala His Leu Asn Leu His
                85                  90                  95

Ile Asn Ser Leu Glu Leu Gly Asp Ser Ala Val Tyr Phe Cys Ala Ser
                100                 105                 110

Ser Gln Glu Gly Leu Ala Gly Ala Ser Asn Asn Glu Gln Phe Phe Gly
            115                 120                 125

Pro Gly Thr Arg Leu Thr Val Leu Glu Asp Leu Lys Asn Val Phe Pro
            130                 135                 140

Pro Glu Val Ala Val Phe Glu Pro Ser Glu Ala Glu Ile Ser His Thr
145                 150                 155                 160

Gln Lys Ala Thr Leu Val Cys Leu Ala Thr Gly Phe Tyr Pro Asp His
                165                 170                 175
```

```
Val Glu Leu Ser Trp Trp Val Asn Gly Lys Glu Val His Ser Gly Val
            180                 185                 190

Ser Thr Asp Pro Gln Pro Leu Lys Glu Gln Pro Ala Leu Asn Asp Ser
            195                 200                 205

Arg Tyr Cys Leu Ser Ser Arg Leu Arg Val Ser Ala Thr Phe Trp Gln
            210                 215                 220

Asn Pro Arg Asn His Phe Arg Cys Gln Val Gln Phe Tyr Gly Leu Ser
225                 230                 235                 240

Glu Asn Asp Glu Trp Thr Gln Asp Arg Ala Lys Pro Val Thr Gln Ile
                245                 250                 255

Val Ser Ala Glu Ala Trp Gly Arg Ala Asp Cys Gly Phe Thr Ser Glu
            260                 265                 270

Ser Tyr Gln Gln Gly Val Leu Ser Ala Thr Ile Leu Tyr Glu Ile Leu
            275                 280                 285

Leu Gly Lys Ala Thr Leu Tyr Ala Val Leu Val Ser Ala Leu Val Leu
            290                 295                 300

Met Ala Met Val Lys Arg Lys Asp Ser Arg Gly
305                 310                 315

<210> SEQ ID NO 6
<211> LENGTH: 271
<212> TYPE: PRT
<213> ORGANISM: Homo sapiens

<400> SEQUENCE: 6

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
            35                  40                  45

Asn Pro Tyr Leu Phe Trp Tyr Val Gln Tyr Pro Asn Arg Gly Leu Gln
            50                  55                  60

Phe Leu Leu Lys Tyr Ile Thr Gly Asp Asn Leu Val Lys Gly Ser Tyr
65              70                  75                  80

Gly Phe Glu Ala Glu Phe Asn Lys Ser Gln Thr Ser Phe His Leu Lys
            85                  90                  95

Lys Pro Ser Ala Leu Val Ser Asp Ser Ala Leu Tyr Phe Cys Ala Val
            100                 105                 110

Ser Ala Ser Asn Asp Met Arg Phe Gly Ala Gly Thr Arg Leu Thr Val
            115                 120                 125

Lys Pro Asn Ile Gln Asn Pro Asp Pro Ala Val Tyr Gln Leu Arg Asp
            130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
            165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
            195                 200                 205

Asn Ser Ile Ile Pro Glu Asp Thr Phe Phe Pro Ser Pro Glu Ser Ser
            210                 215                 220

Cys Asp Val Lys Leu Val Glu Lys Ser Phe Glu Thr Asp Thr Asn Leu
225                 230                 235                 240
```

Asn Phe Gln Asn Leu Ser Val Ile Gly Phe Arg Ile Leu Leu Leu Lys
            245                 250                 255

Val Ala Gly Phe Asn Leu Leu Met Thr Leu Arg Leu Trp Ser Ser
            260                 265                 270

<210> SEQ ID NO 7
<211> LENGTH: 312
<212> TYPE: PRT
<213> ORGANISM: Homo sapiens

<400> SEQUENCE: 7

Met Arg Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Pro Gln Thr Gly Ala Ser Phe Asn Tyr Gly Tyr Thr Phe Gly Ser
        115                 120                 125

Gly Thr Arg Leu Thr Val Val Glu Asp Leu Asn Lys Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Phe Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Val Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Phe
305                 310

<210> SEQ ID NO 8
<211> LENGTH: 272
<212> TYPE: PRT

<213> ORGANISM: Homo sapiens

<400> SEQUENCE: 8

Met Lys Arg Ile Leu Gly Ala Leu Leu Gly Leu Leu Ser Ala Gln Val
1               5                   10                  15

Cys Cys Val Arg Gly Ile Gln Val Glu Gln Ser Pro Pro Asp Leu Ile
            20                  25                  30

Leu Gln Glu Gly Ala Asn Ser Thr Leu Arg Cys Asn Phe Ser Asp Ser
        35                  40                  45

Val Asn Asn Leu Gln Trp Phe His Gln Asn Pro Trp Gly Gln Leu Ile
50                  55                  60

Asn Leu Phe Tyr Ile Pro Ser Gly Thr Lys Gln Asn Gly Arg Leu Ser
65                  70                  75                  80

Ala Thr Thr Val Ala Thr Glu Arg Tyr Ser Leu Leu Tyr Ile Ser Ser
                85                  90                  95

Ser Gln Thr Thr Asp Ser Gly Val Tyr Phe Cys Ala Val Val Arg Trp
            100                 105                 110

Glu Thr Ser Gly Ser Arg Leu Thr Phe Gly Glu Gly Thr Gln Leu Thr
        115                 120                 125

Val Asn Pro Asp Ile Gln Asn Pro Asp Pro Ala Val Tyr Gln Leu Arg
130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 9
<211> LENGTH: 308
<212> TYPE: PRT
<213> ORGANISM: Homo sapiens

<400> SEQUENCE: 9

Met Gly Thr Arg Leu Phe Phe Tyr Val Ala Ile Cys Leu Leu Trp Ala
1               5                   10                  15

Gly His Arg Asp Ala Glu Ile Thr Gln Ser Pro Arg His Lys Ile Thr
            20                  25                  30

Glu Thr Gly Arg Gln Val Thr Leu Ala Cys His Gln Thr Trp Asn His
        35                  40                  45

Asn Asn Met Phe Trp Tyr Arg Gln Asp Leu Gly His Gly Leu Arg Leu
50                  55                  60

Ile His Tyr Ser Tyr Gly Val Gln Asp Thr Asn Lys Gly Glu Val Ser
65                  70                  75                  80

Asp Gly Tyr Ser Val Ser Arg Ser Asn Thr Glu Asp Leu Pro Leu Thr

```
                    85                  90                  95
Leu Glu Ser Ala Ala Ser Ser Gln Thr Ser Val Tyr Phe Cys Ala Ser
                100                 105                 110

Ser Asp Pro Thr Glu Glu Lys Leu Phe Phe Gly Ser Gly Thr Gln Leu
            115                 120                 125

Ser Val Leu Glu Asp Leu Asn Lys Val Phe Pro Pro Glu Val Ala Val
        130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
                180                 185                 190

Pro Leu Lys Glu Gln Pro Ala Leu Asn Asp Ser Arg Tyr Cys Leu Ser
            195                 200                 205

Ser Arg Leu Arg Val Ser Ala Thr Phe Trp Gln Asn Pro Arg Asn His
        210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Val Ser Tyr Gln Gln Gly
                260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
        290                 295                 300

Arg Lys Asp Phe
305

<210> SEQ ID NO 10
<211> LENGTH: 277
<212> TYPE: PRT
<213> ORGANISM: Homo sapiens

<400> SEQUENCE: 10

Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
                20                  25                  30

Val Val Glu Lys Glu Asp Val Thr Leu Asp Cys Val Tyr Glu Thr Arg
            35                  40                  45

Asp Thr Thr Tyr Tyr Leu Phe Trp Tyr Lys Gln Pro Pro Ser Gly Glu
        50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
                100                 105                 110

Ala Leu Ser Glu Gly Gly Ser Tyr Gly Gln Asn Phe Val Phe Gly Pro
            115                 120                 125

Gly Thr Arg Leu Ser Val Leu Pro Tyr Ile Gln Asn Pro Asp Pro Ala
        130                 135                 140
```

```
Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
            275

<210> SEQ ID NO 11
<211> LENGTH: 308
<212> TYPE: PRT
<213> ORGANISM: Homo sapiens

<400> SEQUENCE: 11

Met Gly Thr Arg Leu Leu Cys Arg Val Met Leu Cys Leu Leu Gly Ala
1               5                   10                  15

Gly Ser Val Ala Ala Gly Val Ile Gln Ser Pro Arg His Leu Ile Lys
                20                  25                  30

Glu Lys Arg Glu Thr Ala Thr Leu Lys Cys Tyr Pro Ile Pro Arg His
            35                  40                  45

Asp Thr Val Tyr Trp Tyr Gln Gln Gly Pro Gly Gln Asp Pro Gln Phe
        50                  55                  60

Leu Ile Ser Phe Tyr Glu Lys Met Gln Ser Asp Lys Gly Ser Ile Pro
65                  70                  75                  80

Asp Arg Phe Ser Ala Gln Gln Phe Ser Asp Tyr His Ser Glu Leu Asn
                85                  90                  95

Met Ser Ser Leu Glu Leu Gly Asp Ser Ala Leu Tyr Phe Cys Ala Ser
                100                 105                 110

Ser Leu Arg Asp Glu Gln Phe Phe Gly Pro Gly Thr Arg Leu Thr Val
            115                 120                 125

Leu Glu Asp Leu Lys Asn Val Phe Pro Pro Glu Val Ala Val Phe Glu
130                 135                 140

Pro Ser Glu Ala Glu Ile Ser His Thr Gln Lys Ala Thr Leu Val Cys
145                 150                 155                 160

Leu Ala Thr Gly Phe Tyr Pro Asp His Val Glu Leu Ser Trp Trp Val
                165                 170                 175

Asn Gly Lys Glu Val His Ser Gly Val Ser Thr Asp Pro Gln Pro Leu
            180                 185                 190

Lys Glu Gln Pro Ala Leu Asn Asp Ser Arg Tyr Cys Leu Ser Ser Arg
        195                 200                 205

Leu Arg Val Ser Ala Thr Phe Trp Gln Asn Pro Arg Asn His Phe Arg
    210                 215                 220

Cys Gln Val Gln Phe Tyr Gly Leu Ser Glu Asn Asp Glu Trp Thr Gln
225                 230                 235                 240
```

Asp Arg Ala Lys Pro Val Thr Gln Ile Val Ser Ala Glu Ala Trp Gly
            245                 250                 255

Arg Ala Asp Cys Gly Phe Thr Ser Glu Ser Tyr Gln Gln Gly Val Leu
            260                 265                 270

Ser Ala Thr Ile Leu Tyr Glu Ile Leu Leu Gly Lys Ala Thr Leu Tyr
            275                 280                 285

Ala Val Leu Val Ser Ala Leu Val Leu Met Ala Met Val Lys Arg Lys
290                 295                 300

Asp Ser Arg Gly
305

<210> SEQ ID NO 12
<211> LENGTH: 273
<212> TYPE: PRT
<213> ORGANISM: Homo sapiens

<400> SEQUENCE: 12

Met Glu Lys Asn Pro Leu Ala Ala Pro Leu Leu Ile Leu Trp Phe His
1               5                   10                  15

Leu Asp Cys Val Ser Ser Ile Leu Asn Val Glu Gln Ser Pro Gln Ser
            20                  25                  30

Leu His Val Gln Glu Gly Asp Ser Thr Asn Phe Thr Cys Ser Phe Pro
        35                  40                  45

Ser Ser Asn Phe Tyr Ala Leu His Trp Tyr Arg Trp Glu Thr Ala Lys
    50                  55                  60

Ser Pro Glu Ala Leu Phe Val Met Thr Leu Asn Gly Asp Glu Lys Lys
65                  70                  75                  80

Lys Gly Arg Ile Ser Ala Thr Leu Asn Thr Lys Glu Gly Tyr Ser Tyr
                85                  90                  95

Leu Tyr Ile Lys Gly Ser Gln Pro Glu Asp Ser Ala Thr Tyr Leu Cys
            100                 105                 110

Ala Arg Asn Thr Gly Asn Gln Phe Tyr Phe Gly Thr Gly Thr Ser Leu
        115                 120                 125

Thr Val Ile Pro Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 13

```
<211> LENGTH: 310
<212> TYPE: PRT
<213> ORGANISM: Homo sapiens

<400> SEQUENCE: 13

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Thr
            100                 105                 110

Gln Leu Ala Thr Gly Thr Asn Tyr Gly Tyr Thr Phe Gly Ser Gly Thr
        115                 120                 125

Arg Leu Thr Val Val Glu Asp Leu Asn Lys Val Phe Pro Pro Glu Val
130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Phe
305                 310

<210> SEQ ID NO 14
<211> LENGTH: 267
<212> TYPE: PRT
<213> ORGANISM: Homo sapiens

<400> SEQUENCE: 14

Met Lys Pro Thr Leu Ile Ser Val Leu Val Ile Ile Phe Ile Leu Arg
1               5                   10                  15

Gly Thr Arg Ala Gln Arg Val Thr Gln Pro Glu Lys Leu Leu Ser Val
            20                  25                  30
```

```
Phe Lys Gly Ala Pro Val Glu Leu Lys Cys Asn Tyr Ser Tyr Ser Gly
            35                  40                  45

Ser Pro Glu Leu Phe Trp Tyr Val Gln Tyr Ser Gln Arg Leu Gln
 50                  55                  60

Leu Leu Leu Arg His Ile Ser Arg Glu Ser Ile Lys Gly Phe Thr Ala
 65                  70                  75                  80

Asp Leu Asn Lys Gly Glu Thr Ser Phe His Leu Lys Lys Pro Phe Ala
                 85                  90                  95

Gln Glu Glu Asp Ser Ala Met Tyr Tyr Cys Ala Leu Gly Trp Ala Asn
             100                 105                 110

Asn Leu Phe Phe Gly Thr Gly Thr Arg Leu Thr Val Ile Pro Tyr Ile
         115                 120                 125

Gln Asn Pro Asp Pro Ala Val Tyr Gln Leu Arg Asp Ser Lys Ser Ser
     130                 135                 140

Asp Lys Ser Val Cys Leu Phe Thr Asp Phe Asp Ser Gln Thr Asn Val
145                 150                 155                 160

Ser Gln Ser Lys Asp Ser Asp Val Tyr Ile Thr Asp Lys Thr Val Leu
                165                 170                 175

Asp Met Arg Ser Met Asp Phe Lys Ser Asn Ser Ala Val Ala Trp Ser
            180                 185                 190

Asn Lys Ser Asp Phe Ala Cys Ala Asn Ala Phe Asn Asn Ser Ile Ile
        195                 200                 205

Pro Glu Asp Thr Phe Phe Pro Ser Pro Glu Ser Ser Cys Asp Val Lys
    210                 215                 220

Leu Val Glu Lys Ser Phe Glu Thr Asp Thr Asn Leu Asn Phe Gln Asn
225                 230                 235                 240

Leu Ser Val Ile Gly Phe Arg Ile Leu Leu Leu Lys Val Ala Gly Phe
                245                 250                 255

Asn Leu Leu Met Thr Leu Arg Leu Trp Ser Ser
            260                 265

<210> SEQ ID NO 15
<211> LENGTH: 312
<212> TYPE: PRT
<213> ORGANISM: Homo sapiens

<400> SEQUENCE: 15

Met Gly Thr Arg Leu Leu Cys Tyr Gly Gly Phe Tyr Phe Leu Gly Ala
1               5                   10                  15

Gly Leu Met Glu Ala Asp Ile Tyr Gln Thr Pro Arg Tyr Leu Val Ile
            20                  25                  30

Gly Thr Gly Lys Lys Ile Thr Leu Glu Cys Ser Gln Thr Met Gly His
        35                  40                  45

Asp Lys Met Tyr Trp Tyr Gln Gln Asp Pro Gly Met Glu Leu His Leu
    50                  55                  60

Ile His Tyr Ser Tyr Gly Val Asn Ser Thr Glu Lys Gly Asp Leu Ser
65                  70                  75                  80

Ser Glu Ser Thr Val Ser Arg Ile Arg Thr Glu His Phe Pro Leu Thr
                85                  90                  95

Leu Glu Ser Ala Arg Pro Ser His Thr Ser Gln Tyr Leu Cys Ala Ser
            100                 105                 110

Thr Glu Gly Thr Gly His Thr Gly Glu Leu Phe Phe Gly Glu Gly Ser
        115                 120                 125

Arg Leu Thr Val Leu Glu Asp Leu Lys Asn Val Phe Pro Pro Glu Val
```

```
                130                 135                 140
Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
                180                 185                 190

Pro Gln Pro Leu Lys Glu Gln Pro Ala Leu Asn Asp Ser Arg Tyr Cys
                195                 200                 205

Leu Ser Ser Arg Leu Arg Val Ser Ala Thr Phe Trp Gln Asn Pro Arg
                210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
                260                 265                 270

Gln Gly Val Leu Ser Ala Thr Ile Leu Tyr Glu Ile Leu Leu Gly Lys
                275                 280                 285

Ala Thr Leu Tyr Ala Val Leu Val Ser Ala Leu Val Leu Met Ala Met
290                 295                 300

Val Lys Arg Lys Asp Ser Arg Gly
305                 310

<210> SEQ ID NO 16
<211> LENGTH: 271
<212> TYPE: PRT
<213> ORGANISM: Homo sapiens

<400> SEQUENCE: 16

Met Lys Lys Leu Leu Ala Met Ile Leu Trp Leu Gln Leu Asp Arg Leu
1               5                   10                  15

Ser Gly Glu Leu Lys Val Glu Gln Asn Pro Leu Phe Leu Ser Met Gln
                20                  25                  30

Glu Gly Lys Asn Tyr Thr Ile Tyr Cys Asn Tyr Ser Thr Thr Ser Asp
                35                  40                  45

Arg Leu Tyr Trp Tyr Arg Gln Asp Pro Gly Lys Ser Leu Glu Ser Leu
                50                  55                  60

Phe Val Leu Leu Ser Asn Gly Ala Val Lys Gln Glu Gly Arg Leu Met
65                  70                  75                  80

Ala Ser Leu Asp Thr Lys Ala Arg Leu Ser Thr Leu His Ile Thr Ala
                85                  90                  95

Ala Val His Asp Leu Ser Ala Thr Tyr Phe Cys Ala Val Asp Ile Glu
                100                 105                 110

Thr Ser Gly Ser Arg Leu Thr Phe Gly Glu Gly Thr Gln Leu Thr Val
                115                 120                 125

Asn Pro Asp Ile Gln Asn Pro Asp Pro Ala Val Tyr Gln Leu Arg Asp
                130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
                180                 185                 190
```

```
Val Ala Trp Ser Asn Lys Ser Asp Phe Ala Cys Ala Asn Ala Phe Asn
            195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 17
<211> LENGTH: 313
<212> TYPE: PRT
<213> ORGANISM: Homo sapiens

<400> SEQUENCE: 17

Met Gly Thr Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Ala Leu Gly Gly Ala Gly Thr Gly Glu Leu Phe Phe Gly Glu Gly
        115                 120                 125

Ser Arg Leu Thr Val Leu Glu Asp Leu Lys Asn Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Glu Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
    290                 295                 300
```

```
Met Val Lys Arg Lys Asp Ser Arg Gly
305                 310
```

```
<210> SEQ ID NO 18
<211> LENGTH: 273
<212> TYPE: PRT
<213> ORGANISM: Homo sapiens

<400> SEQUENCE: 18
```

```
Met Glu Lys Asn Pro Leu Ala Ala Pro Leu Leu Ile Leu Trp Phe His
1               5                   10                  15

Leu Asp Cys Val Ser Ser Ile Leu Asn Val Glu Gln Ser Pro Gln Ser
            20                  25                  30

Leu His Val Gln Glu Gly Asp Ser Thr Asn Phe Thr Cys Ser Phe Pro
        35                  40                  45

Ser Ser Asn Phe Tyr Ala Leu His Trp Tyr Arg Trp Glu Thr Ala Lys
    50                  55                  60

Ser Pro Glu Ala Leu Phe Val Met Thr Leu Asn Gly Asp Glu Lys Lys
65                  70                  75                  80

Lys Gly Arg Ile Ser Ala Thr Leu Asn Thr Lys Glu Gly Tyr Ser Tyr
                85                  90                  95

Leu Tyr Ile Lys Gly Ser Gln Pro Glu Asp Ser Ala Thr Tyr Leu Cys
            100                 105                 110

Ala Phe Ile Asn Phe Asn Lys Phe Tyr Phe Gly Ser Gly Thr Lys Leu
        115                 120                 125

Asn Val Lys Pro Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser
```

```
<210> SEQ ID NO 19
<211> LENGTH: 311
<212> TYPE: PRT
<213> ORGANISM: Homo sapiens

<400> SEQUENCE: 19
```

```
Met Gly Thr Arg Leu Leu Cys Cys Val Val Phe Cys Leu Leu Gln Ala
1               5                   10                  15

Gly Pro Leu Asp Thr Ala Val Ser Gln Thr Pro Lys Tyr Leu Val Thr
            20                  25                  30
```

```
Gln Met Gly Asn Asp Lys Ser Ile Lys Cys Glu Gln Asn Leu Gly His
         35                  40                  45

Asp Thr Met Tyr Trp Tyr Lys Gln Asp Ser Lys Phe Leu Lys Ile
 50                  55                  60

Met Phe Ser Tyr Asn Asn Lys Glu Leu Ile Ile Asn Glu Thr Val Pro
 65                  70                  75                  80

Asn Arg Phe Ser Pro Lys Ser Pro Asp Lys Ala His Leu Asn Leu His
                 85                  90                  95

Ile Asn Ser Leu Glu Leu Gly Asp Ser Ala Val Tyr Phe Cys Ala Ser
            100                 105                 110

Ser Gln Val Leu Gly Pro Gly Glu Leu Phe Phe Gly Glu Gly Ser Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 20
<211> LENGTH: 273
<212> TYPE: PRT
<213> ORGANISM: Homo sapiens

<400> SEQUENCE: 20

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95
```

```
Phe Ile Arg Asp Ser Gln Pro Ser Asp Ser Ala Thr Tyr Leu Cys Ala
                100                 105                 110
Met Val Asn Asn Asn Asp Met Arg Phe Gly Ala Gly Thr Arg Leu
            115                 120                 125
Thr Val Lys Pro Asn Ile Gln Asn Pro Asp Pro Ala Val Tyr Gln Leu
            130                 135                 140
Arg Asp Ser Lys Ser Ser Asp Lys Ser Val Cys Leu Phe Thr Asp Phe
145                 150                 155                 160
Asp Ser Gln Thr Asn Val Ser Gln Ser Lys Asp Ser Asp Val Tyr Ile
                165                 170                 175
Thr Asp Lys Thr Val Leu Asp Met Arg Ser Met Asp Phe Lys Ser Asn
            180                 185                 190
Ser Ala Val Ala Trp Ser Asn Lys Ser Asp Phe Ala Cys Ala Asn Ala
            195                 200                 205
Phe Asn Asn Ser Ile Ile Pro Glu Asp Thr Phe Phe Pro Ser Pro Glu
            210                 215                 220
Ser Ser Cys Asp Val Lys Leu Val Glu Lys Ser Phe Glu Thr Asp Thr
225                 230                 235                 240
Asn Leu Asn Phe Gln Asn Leu Ser Val Ile Gly Phe Arg Ile Leu Leu
                245                 250                 255
Leu Lys Val Ala Gly Phe Asn Leu Leu Met Thr Leu Arg Leu Trp Ser
            260                 265                 270
Ser

<210> SEQ ID NO 21
<211> LENGTH: 309
<212> TYPE: PRT
<213> ORGANISM: Homo sapiens

<400> SEQUENCE: 21

Met Asp Ser Trp Thr Leu Cys Cys Val Ser Leu Cys Ile Leu Val Ala
1               5                   10                  15
Lys His Thr Asp Ala Gly Val Ile Gln Ser Pro Arg His Glu Val Thr
                20                  25                  30
Glu Met Gly Gln Glu Val Thr Leu Arg Cys Lys Pro Ile Ser Gly His
            35                  40                  45
Asp Tyr Leu Phe Trp Tyr Arg Gln Thr Met Met Arg Gly Leu Glu Leu
        50                  55                  60
Leu Ile Tyr Phe Asn Asn Asn Val Pro Ile Asp Asp Ser Gly Met Pro
65                  70                  75                  80
Glu Asp Arg Phe Ser Ala Lys Met Pro Asn Ala Ser Phe Ser Thr Leu
                85                  90                  95
Lys Ile Gln Pro Ser Glu Pro Arg Asp Ser Ala Val Tyr Phe Cys Ala
                100                 105                 110
Ser Ser Tyr Gly Thr Tyr Glu Lys Leu Phe Phe Gly Ser Gly Thr Gln
            115                 120                 125
Leu Ser Val Leu Glu Asp Leu Asn Lys Val Phe Pro Pro Glu Val Ala
            130                 135                 140
Val Phe Glu Pro Ser Glu Ala Glu Ile Ser His Thr Gln Lys Ala Thr
145                 150                 155                 160
Leu Val Cys Leu Ala Thr Gly Phe Phe Pro Asp His Val Glu Leu Ser
                165                 170                 175
Trp Trp Val Asn Gly Lys Glu Val His Ser Gly Val Ser Thr Asp Pro
            180                 185                 190
```

-continued

```
Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
            245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
            290                 295                 300

Lys Arg Lys Asp Phe
305

<210> SEQ ID NO 22
<211> LENGTH: 269
<212> TYPE: PRT
<213> ORGANISM: Homo sapiens

<400> SEQUENCE: 22

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Arg Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Thr
            100                 105                 110

Tyr Asp Lys Val Ile Phe Gly Pro Gly Thr Ser Leu Ser Val Ile Pro
        115                 120                 125

Asn Ile Gln Asn Pro Asp Pro Ala Val Tyr Gln Leu Arg Asp Ser Lys
    130                 135                 140

Ser Ser Asp Lys Ser Val Cys Leu Phe Thr Asp Phe Asp Ser Gln Thr
145                 150                 155                 160

Asn Val Ser Gln Ser Lys Asp Ser Asp Val Tyr Ile Thr Asp Lys Thr
                165                 170                 175

Val Leu Asp Met Arg Ser Met Asp Phe Lys Ser Asn Ser Ala Val Ala
            180                 185                 190

Trp Ser Asn Lys Ser Asp Phe Ala Cys Ala Asn Ala Phe Asn Asn Ser
        195                 200                 205

Ile Ile Pro Glu Asp Thr Phe Phe Pro Ser Pro Glu Ser Ser Cys Asp
    210                 215                 220

Val Lys Leu Val Glu Lys Ser Phe Glu Thr Asp Thr Asn Leu Asn Phe
225                 230                 235                 240

Gln Asn Leu Ser Val Ile Gly Phe Arg Ile Leu Leu Leu Lys Val Ala
```

```
<210> SEQ ID NO 23
<211> LENGTH: 310
<212> TYPE: PRT
<213> ORGANISM: Homo sapiens

<400> SEQUENCE: 23

Met Gly Thr Arg Leu Leu Cys Tyr Met Gly Phe Tyr Phe Leu Gly Ala
1               5                   10                  15
Gly Leu Met Glu Ala Asp Ile Tyr Gln Thr Pro Arg Tyr Leu Val Ile
            20                  25                  30
Gly Thr Gly Lys Lys Ile Thr Leu Glu Cys Ser Gln Thr Met Gly His
        35                  40                  45
Asp Lys Met Tyr Trp Tyr Gln Gln Asp Pro Gly Met Glu Leu His Leu
    50                  55                  60
Ile His Tyr Ser Tyr Gly Val Asn Ser Thr Glu Lys Gly Asp Leu Ser
65                  70                  75                  80
Ser Glu Ser Thr Val Ser Arg Ile Arg Thr Glu His Phe Pro Leu Thr
                85                  90                  95
Leu Glu Ser Ala Arg Pro Ser His Thr Ser Gln Tyr Leu Cys Ala Ser
            100                 105                 110
Ser Glu Thr Ser Phe Ser Gly Asn Thr Ile Tyr Phe Gly Glu Gly Ser
        115                 120                 125
Trp Leu Thr Val Val Glu Asp Leu Asn Lys Val Phe Pro Pro Glu Val
    130                 135                 140
Ala Val Phe Glu Pro Ser Glu Ala Glu Ile Ser His Thr Gln Lys Ala
145                 150                 155                 160
Thr Leu Val Cys Leu Ala Thr Gly Phe Phe Pro Asp His Val Glu Leu
                165                 170                 175
Ser Trp Trp Val Asn Gly Lys Glu Val His Ser Gly Val Ser Thr Asp
            180                 185                 190
Pro Gln Pro Leu Lys Glu Gln Pro Ala Leu Asn Asp Ser Arg Tyr Cys
        195                 200                 205
Leu Ser Ser Arg Leu Arg Val Ser Ala Thr Phe Trp Gln Asn Pro Arg
    210                 215                 220
Asn His Phe Arg Cys Gln Val Gln Phe Tyr Gly Leu Ser Glu Asn Asp
225                 230                 235                 240
Glu Trp Thr Gln Asp Arg Ala Lys Pro Val Thr Gln Ile Val Ser Ala
                245                 250                 255
Glu Ala Trp Gly Arg Ala Asp Cys Gly Phe Thr Ser Val Ser Tyr Gln
            260                 265                 270
Gln Gly Val Leu Ser Ala Thr Ile Leu Tyr Glu Ile Leu Leu Gly Lys
        275                 280                 285
Ala Thr Leu Tyr Ala Val Leu Val Ser Ala Leu Val Leu Met Ala Met
    290                 295                 300
Val Lys Arg Lys Asp Phe
305                 310

<210> SEQ ID NO 24
<211> LENGTH: 269
<212> TYPE: PRT
<213> ORGANISM: Homo sapiens
```

Preceding continuation (top of page):
```
                    245                 250                 255
Gly Phe Asn Leu Leu Met Thr Leu Arg Leu Trp Ser Ser
            260                 265
```

<400> SEQUENCE: 24

```
Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Lys
            100                 105                 110

Asp Asn Asp Met Arg Phe Gly Ala Gly Thr Arg Leu Thr Val Lys Pro
        115                 120                 125

Asn Ile Gln Asn Pro Asp Pro Ala Val Tyr Gln Leu Arg Asp Ser Lys
    130                 135                 140

Ser Ser Asp Lys Ser Val Cys Leu Phe Thr Asp Phe Asp Ser Gln Thr
145                 150                 155                 160

Asn Val Ser Gln Ser Lys Asp Ser Asp Val Tyr Ile Thr Asp Lys Thr
                165                 170                 175

Val Leu Asp Met Arg Ser Met Asp Phe Lys Ser Asn Ser Ala Val Ala
            180                 185                 190

Trp Ser Asn Lys Ser Asp Phe Ala Cys Ala Asn Ala Phe Asn Asn Ser
        195                 200                 205

Ile Ile Pro Glu Asp Thr Phe Phe Pro Ser Pro Glu Ser Ser Cys Asp
    210                 215                 220

Val Lys Leu Val Glu Lys Ser Phe Glu Thr Asp Thr Asn Leu Asn Phe
225                 230                 235                 240

Gln Asn Leu Ser Val Ile Gly Phe Arg Ile Leu Leu Leu Lys Val Ala
                245                 250                 255

Gly Phe Asn Leu Leu Met Thr Leu Arg Leu Trp Ser Ser
            260                 265
```

<210> SEQ ID NO 25
<211> LENGTH: 307
<212> TYPE: PRT
<213> ORGANISM: Homo sapiens

<400> SEQUENCE: 25

```
Met Gly Thr Arg Leu Leu Cys Cys Val Val Phe Cys Leu Leu Gln Ala
1               5                   10                  15

Gly Pro Leu Asp Thr Ala Val Ser Gln Thr Pro Lys Tyr Leu Val Thr
            20                  25                  30

Gln Met Gly Asn Asp Lys Ser Ile Lys Cys Glu Gln Asn Leu Gly His
        35                  40                  45

Asp Thr Met Tyr Trp Tyr Lys Gln Asp Ser Lys Lys Phe Leu Lys Ile
    50                  55                  60

Met Phe Ser Tyr Asn Asn Lys Glu Leu Ile Ile Asn Glu Thr Val Pro
65                  70                  75                  80

Asn Arg Phe Ser Pro Lys Ser Pro Asp Lys Ala His Leu Asn Leu His
                85                  90                  95
```

```
Ile Asn Ser Leu Glu Leu Gly Asp Ser Ala Val Tyr Phe Cys Ala Ser
            100                 105                 110

Ser Gln Glu Lys Arg Gly Ala Phe Phe Gly Gln Gly Thr Arg Leu Thr
        115                 120                 125

Val Val Glu Asp Leu Asn Lys Val Phe Pro Pro Glu Val Ala Val Phe
130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
290                 295                 300

Lys Asp Phe
305

<210> SEQ ID NO 26
<211> LENGTH: 276
<212> TYPE: PRT
<213> ORGANISM: Homo sapiens

<400> SEQUENCE: 26

Met Leu Leu Leu Leu Val Pro Ala Phe Gln Val Ile Phe Thr Leu Gly
1               5                   10                  15

Gly Thr Arg Ala Gln Ser Val Thr Gln Leu Asp Ser Gln Val Pro Val
            20                  25                  30

Phe Glu Glu Ala Pro Val Glu Leu Arg Cys Asn Tyr Ser Ser Ser Val
        35                  40                  45

Ser Val Tyr Leu Phe Trp Tyr Val Gln Tyr Pro Asn Gln Gly Leu Gln
50                  55                  60

Leu Leu Leu Lys Tyr Leu Ser Gly Ser Thr Leu Val Lys Gly Ile Asn
65                  70                  75                  80

Gly Phe Glu Ala Glu Phe Asn Lys Ser Gln Thr Ser Phe His Leu Arg
                85                  90                  95

Lys Pro Ser Val His Ile Ser Asp Thr Ala Glu Tyr Phe Cys Ala Val
            100                 105                 110

Ser Ser Tyr Gly Ser Ser Asn Thr Gly Lys Leu Ile Phe Gly Gln Gly
        115                 120                 125

Thr Thr Leu Gln Val Lys Pro Asp Ile Gln Asn Pro Asp Pro Ala Val
130                 135                 140

Tyr Gln Leu Arg Asp Ser Lys Ser Ser Asp Lys Ser Val Cys Leu Phe
145                 150                 155                 160
```

-continued

Thr Asp Phe Asp Ser Gln Thr Asn Val Ser Gln Ser Lys Asp Ser Asp
              165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
            195                 200                 205

Ala Asn Ala Phe Asn Asn Ser Ile Ile Pro Glu Asp Thr Phe Phe Pro
210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
                260                 265                 270

Leu Trp Ser Ser
            275

<210> SEQ ID NO 27
<211> LENGTH: 310
<212> TYPE: PRT
<213> ORGANISM: Homo sapiens

<400> SEQUENCE: 27

Met Ser Leu Gly Leu Leu Cys Cys Val Ala Phe Ser Leu Leu Trp Ala
1               5                   10                  15

Ser Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Asn Ser Met Tyr Trp Tyr Arg Gln Asp Pro Gly Met Gly Leu Arg Leu
    50                  55                  60

Ile Tyr Tyr Ser Ala Ser Glu Gly Thr Thr Asp Lys Gly Glu Val Pro
65                  70                  75                  80

Asn Gly Tyr Asn Val Ser Arg Leu Asn Lys Arg Glu Phe Ser Leu Arg
                85                  90                  95

Leu Glu Ser Ala Ala Pro Ser Gln Thr Ser Val Tyr Phe Cys Ala Ser
            100                 105                 110

Ser Thr Ala Gly Gly Arg Asn Tyr Gly Tyr Thr Phe Gly Ser Gly Thr
        115                 120                 125

Arg Leu Thr Val Val Glu Asp Leu Asn Lys Val Phe Pro Pro Glu Val
130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala

```
                     245                 250                 255
Glu Ala Trp Gly Arg Ala Asp Cys Gly Phe Thr Ser Val Ser Tyr Gln
                260                 265                 270

Gln Gly Val Leu Ser Ala Thr Ile Leu Tyr Glu Ile Leu Leu Gly Lys
            275                 280                 285

Ala Thr Leu Tyr Ala Val Leu Val Ser Ala Leu Val Leu Met Ala Met
        290                 295                 300

Val Lys Arg Lys Asp Phe
305                 310

<210> SEQ ID NO 28
<211> LENGTH: 270
<212> TYPE: PRT
<213> ORGANISM: Homo sapiens

<400> SEQUENCE: 28

Met Lys Arg Ile Leu Gly Ala Leu Leu Gly Leu Leu Ser Ala Gln Val
1               5                   10                  15

Cys Cys Val Arg Gly Ile Gln Val Glu Gln Ser Pro Pro Asp Leu Ile
            20                  25                  30

Leu Gln Glu Gly Ala Asn Ser Thr Leu Arg Cys Asn Phe Ser Asp Ser
        35                  40                  45

Val Asn Asn Leu Gln Trp Phe His Gln Asn Pro Trp Gly Gln Leu Ile
    50                  55                  60

Asn Leu Phe Tyr Ile Pro Ser Gly Thr Lys Gln Asn Gly Arg Leu Ser
65                  70                  75                  80

Ala Thr Thr Val Ala Thr Glu Arg Tyr Ser Leu Leu Tyr Ile Ser Ser
                85                  90                  95

Ser Gln Thr Thr Asp Ser Gly Val Tyr Phe Cys Ala Ala Gly Ser Asn
            100                 105                 110

Thr Gly Asn Gln Phe Tyr Phe Gly Thr Gly Thr Ser Leu Thr Val Ile
        115                 120                 125

Pro Asn Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 29
<211> LENGTH: 312
<212> TYPE: PRT
<213> ORGANISM: Homo sapiens
```

-continued

```
<400> SEQUENCE: 29

Met Ser Leu Gly Leu Leu Cys Cys Ala Ala Phe Ser Leu Leu Trp Ala
1               5                   10                  15

Gly Pro Val Asn Ala Gly Val Thr Gln Thr Pro Lys Phe Arg Val Leu
            20                  25                  30

Lys Thr Gly Gln Ser Met Thr Leu Leu Cys Ala Gln Asp Met Asn His
        35                  40                  45

Glu Tyr Met Tyr Trp Tyr Arg Gln Asp Pro Gly Met Gly Leu Arg Leu
    50                  55                  60

Ile His Tyr Ser Val Gly Glu Gly Thr Thr Ala Lys Gly Glu Val Pro
65                  70                  75                  80

Asp Gly Tyr Asn Val Ser Arg Leu Lys Lys Gln Asn Phe Leu Leu Gly
                85                  90                  95

Leu Glu Ser Ala Ala Pro Ser Gln Thr Ser Val Tyr Phe Cys Ala Ser
            100                 105                 110

Ser Ser Arg Gly Tyr Gly Thr Asp Thr Gln Tyr Phe Gly Pro Gly Thr
        115                 120                 125

Arg Leu Thr Val Leu Glu Asp Leu Lys Asn Val Phe Pro Pro Glu Val
130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310

<210> SEQ ID NO 30
<211> LENGTH: 277
<212> TYPE: PRT
<213> ORGANISM: Homo sapiens

<400> SEQUENCE: 30

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45
```

Asn Pro Tyr Leu Phe Trp Tyr Val Gln Tyr Pro Asn Arg Gly Leu Gln
        50                  55                  60

Phe Leu Leu Lys Tyr Ile Thr Gly Asp Asn Leu Val Lys Gly Ser Tyr
 65                  70                  75                  80

Gly Phe Glu Ala Glu Phe Asn Lys Ser Gln Thr Ser Phe His Leu Lys
                 85                  90                  95

Lys Pro Ser Ala Leu Val Ser Asp Ser Ala Leu Tyr Phe Cys Ala Val
            100                 105                 110

Arg Pro Leu Tyr Ser Gly Ala Gly Ser Tyr Gln Leu Thr Phe Gly Lys
            115                 120                 125

Gly Thr Lys Leu Ser Val Ile Pro Asn Ile Gln Asn Pro Asp Pro Ala
130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
            195                 200                 205

Cys Ala Asn Ala Phe Asn Asn Ser Ile Ile Pro Glu Asp Thr Phe Phe
210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
            275

<210> SEQ ID NO 31
<211> LENGTH: 309
<212> TYPE: PRT
<213> ORGANISM: Homo sapiens

<400> SEQUENCE: 31

Met Leu Leu Leu Leu Leu Leu Gly Pro Gly Ser Gly Leu Gly Ala
 1               5                  10                  15

Val Val Ser Gln His Pro Ser Arg Val Ile Cys Lys Ser Gly Thr Ser
                 20                  25                  30

Val Lys Ile Glu Cys Arg Ser Leu Asp Phe Gln Ala Thr Thr Met Phe
             35                  40                  45

Trp Tyr Arg Gln Phe Pro Lys Gln Ser Leu Met Leu Met Ala Thr Ser
         50                  55                  60

Asn Glu Gly Ser Lys Ala Thr Tyr Glu Gln Gly Val Glu Lys Asp Lys
 65                  70                  75                  80

Phe Leu Ile Asn His Ala Ser Leu Thr Leu Ser Thr Leu Thr Val Thr
                 85                  90                  95

Ser Ala His Pro Glu Asp Ser Ser Phe Tyr Ile Cys Ser Ala Arg Asn
            100                 105                 110

Leu Pro Leu Thr Asp Thr Gln Tyr Phe Gly Pro Gly Thr Arg Leu Thr
            115                 120                 125

Val Leu Glu Asp Leu Lys Asn Val Phe Pro Pro Glu Val Ala Val Phe
            130                 135                 140

-continued

Glu Pro Ser Glu Ala Glu Ile Ser His Thr Gln Lys Ala Thr Leu Val
145                 150                 155                 160

Cys Leu Ala Thr Gly Phe Tyr Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Glu Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
290                 295                 300

Lys Asp Ser Arg Gly
305

<210> SEQ ID NO 32
<211> LENGTH: 276
<212> TYPE: PRT
<213> ORGANISM: Homo sapiens

<400> SEQUENCE: 32

Met Glu Lys Asn Pro Leu Ala Ala Pro Leu Leu Ile Leu Trp Phe His
1               5                   10                  15

Leu Asp Cys Val Ser Ser Ile Leu Asn Val Glu Gln Ser Pro Gln Ser
                20                  25                  30

Leu His Val Gln Glu Gly Asp Ser Thr Asn Phe Thr Cys Ser Phe Pro
            35                  40                  45

Ser Ser Asn Phe Tyr Ala Leu His Trp Tyr Arg Trp Glu Thr Ala Lys
50                  55                  60

Ser Pro Glu Ala Leu Phe Val Met Thr Leu Asn Gly Asp Glu Lys Lys
65                  70                  75                  80

Lys Gly Arg Ile Ser Ala Thr Leu Asn Thr Lys Glu Gly Tyr Ser Tyr
                85                  90                  95

Leu Tyr Ile Lys Gly Ser Gln Pro Glu Asp Ser Ala Thr Tyr Leu Cys
            100                 105                 110

Ala Ser Thr Ser Tyr Ser Ser Ala Ser Lys Ile Ile Phe Gly Ser Gly
        115                 120                 125

Thr Arg Leu Ser Ile Arg Pro Asn Ile Gln Asn Pro Asp Pro Ala Val
130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys

```
            195                 200                 205
Ala Asn Ala Phe Asn Asn Ser Ile Ile Pro Glu Asp Thr Phe Phe Pro
        210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
            275

<210> SEQ ID NO 33
<211> LENGTH: 313
<212> TYPE: PRT
<213> ORGANISM: Homo sapiens

<400> SEQUENCE: 33

Met Gly Thr Arg Leu Leu Cys Trp Val Val Leu Gly Phe Leu Gly Thr
1               5                   10                  15

Asp His Thr Gly Ala Gly Val Ser Gln Ser Pro Arg Tyr Lys Val Thr
                20                  25                  30

Lys Arg Gly Gln Asp Val Ala Leu Arg Cys Asp Pro Ile Ser Gly His
            35                  40                  45

Val Ser Leu Tyr Trp Tyr Arg Gln Ala Leu Gly Gln Gly Pro Glu Phe
        50                  55                  60

Leu Thr Tyr Phe Asn Tyr Glu Ala Gln Gln Asp Lys Ser Gly Leu Pro
65                  70                  75                  80

Asn Asp Arg Phe Ser Ala Glu Arg Pro Glu Gly Ser Ile Ser Thr Leu
                85                  90                  95

Thr Ile Gln Arg Thr Glu Gln Arg Asp Ser Ala Met Tyr Arg Cys Ala
            100                 105                 110

Ser Ser His Ser Ser Gly Gly Ala Gly Glu Leu Phe Phe Gly Glu Gly
        115                 120                 125

Ser Arg Leu Thr Val Leu Glu Asp Leu Lys Asn Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Glu Ser Tyr
            260                 265                 270

Gln Gln Gly Val Leu Ser Ala Thr Ile Leu Tyr Glu Ile Leu Leu Gly
        275                 280                 285
```

```
Lys Ala Thr Leu Tyr Ala Val Leu Val Ser Ala Leu Val Leu Met Ala
            290                 295                 300

Met Val Lys Arg Lys Asp Ser Arg Gly
305                 310

<210> SEQ ID NO 34
<211> LENGTH: 271
<212> TYPE: PRT
<213> ORGANISM: Homo sapiens

<400> SEQUENCE: 34

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
                85                  90                  95

Thr Ala Ser Arg Ala Ala Asp Thr Ala Ser Tyr Phe Cys Ala Thr Asp
            100                 105                 110

Glu Tyr Gly Asn Lys Leu Val Phe Gly Ala Gly Thr Ile Leu Arg Val
        115                 120                 125

Lys Ser Tyr Ile Gln Asn Pro Asp Pro Ala Val Tyr Gln Leu Arg Asp
    130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 35
<211> LENGTH: 311
<212> TYPE: PRT
<213> ORGANISM: Homo sapiens

<400> SEQUENCE: 35

Met Asp Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30
```

-continued

Glu Met Gly Gln Glu Val Thr Leu Arg Cys Lys Pro Ile Ser Gly His
         35                  40                  45

Asn Ser Leu Phe Trp Tyr Arg Gln Thr Met Met Arg Gly Leu Glu Leu
 50                  55                  60

Leu Ile Tyr Phe Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
             85                  90                  95

Lys Ile Gln Pro Ser Glu Pro Arg Asp Ser Ala Val Tyr Phe Cys Ala
             100                 105                 110

Ser Ser Tyr Pro Gly Phe Asn Glu Gln Phe Phe Gly Pro Gly Thr Arg
         115                 120                 125

Leu Thr Val Leu Glu Asp Leu Lys Asn Val Phe Pro Pro Glu Val Ala
     130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                 165                 170                 175

Trp Trp Val Asn Gly Lys Glu Val His Ser Gly Val Ser Thr Asp Pro
             180                 185                 190

Gln Pro Leu Lys Glu Gln Pro Ala Leu Asn Asp Ser Arg Tyr Cys Leu
         195                 200                 205

Ser Ser Arg Leu Arg Val Ser Ala Thr Phe Trp Gln Asn Pro Arg Asn
     210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                 245                 250                 255

Ala Trp Gly Arg Ala Asp Cys Gly Phe Thr Ser Glu Ser Tyr Gln Gln
             260                 265                 270

Gly Val Leu Ser Ala Thr Ile Leu Tyr Glu Ile Leu Leu Gly Lys Ala
         275                 280                 285

Thr Leu Tyr Ala Val Leu Val Ser Ala Leu Val Leu Met Ala Met Val
     290                 295                 300

Lys Arg Lys Asp Ser Arg Gly
305                 310

<210> SEQ ID NO 36
<211> LENGTH: 275
<212> TYPE: PRT
<213> ORGANISM: Homo sapiens

<400> SEQUENCE: 36

Met Leu Leu Leu Leu Val Pro Val Phe Gln Val Ile Phe Thr Leu Gly
1               5                   10                  15

Gly Thr Arg Ala Gln Ser Val Thr Gln Leu Asp Ser Gln Val Pro Val
             20                  25                  30

Phe Glu Glu Ala Pro Val Glu Leu Arg Cys Asn Tyr Ser Ser Ser Val
         35                  40                  45

Ser Val Tyr Leu Phe Trp Tyr Val Gln Tyr Pro Asn Gln Gly Leu Gln
     50                  55                  60

Leu Leu Leu Lys Tyr Leu Ser Gly Ser Thr Leu Val Lys Gly Ile Asn
65                  70                  75                  80

Gly Phe Glu Ala Glu Phe Asn Lys Ser Gln Thr Ser Phe His Leu Arg
             85                  90                  95

Lys Pro Ser Val His Ile Ser Asp Thr Ala Glu Tyr Phe Cys Ala Val
            100                 105                 110

Ser Asp Gln Gly Thr Gly Gly Phe Lys Thr Ile Phe Gly Ala Gly Thr
            115                 120                 125

Arg Leu Phe Val Lys Ala Asn Ile Gln Asn Pro Asp Pro Ala Val Tyr
        130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275

<210> SEQ ID NO 37
<211> LENGTH: 313
<212> TYPE: PRT
<213> ORGANISM: Homo sapiens

<400> SEQUENCE: 37

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Arg Gly Thr Val Thr Ser Ser Leu Met Asn Thr Glu Ala Phe Phe Gly
        115                 120                 125

Gln Gly Thr Arg Leu Thr Val Val Glu Asp Leu Asn Lys Val Phe Pro
    130                 135                 140

Pro Glu Val Ala Val Phe Glu Pro Ser Glu Ala Glu Ile Ser His Thr
145                 150                 155                 160

Gln Lys Ala Thr Leu Val Cys Leu Ala Thr Gly Phe Phe Pro Asp His
                165                 170                 175

Val Glu Leu Ser Trp Trp Val Asn Gly Lys Glu Val His Ser Gly Val

| | 180 | | | 185 | | | 190 | | | |
|---|---|---|---|---|---|---|---|---|---|---|

Ser Thr Asp Pro Gln Pro Leu Lys Glu Gln Pro Ala Leu Asn Asp Ser
        195                    200                  205

Arg Tyr Cys Leu Ser Ser Arg Leu Arg Val Ser Ala Thr Phe Trp Gln
210                    215                  220

Asn Pro Arg Asn His Phe Arg Cys Gln Val Gln Phe Tyr Gly Leu Ser
225                230                  235                  240

Glu Asn Asp Glu Trp Thr Gln Asp Arg Ala Lys Pro Val Thr Gln Ile
                245                  250                  255

Val Ser Ala Glu Ala Trp Gly Arg Ala Asp Cys Gly Phe Thr Ser Val
        260                    265                  270

Ser Tyr Gln Gln Gly Val Leu Ser Ala Thr Ile Leu Tyr Glu Ile Leu
    275                    280                  285

Leu Gly Lys Ala Thr Leu Tyr Ala Val Leu Val Ser Ala Leu Val Leu
290                    295                  300

Met Ala Met Val Lys Arg Lys Asp Phe
305                    310

<210> SEQ ID NO 38
<211> LENGTH: 268
<212> TYPE: PRT
<213> ORGANISM: Homo sapiens

<400> SEQUENCE: 38

Met Trp Gly Ala Phe Leu Leu Tyr Val Ser Met Lys Met Gly Gly Thr
1                    5                    10                  15

Ala Gly Gln Ser Leu Glu Gln Pro Ser Glu Val Thr Ala Val Glu Gly
                20                  25                  30

Ala Ile Val Gln Ile Asn Cys Thr Tyr Gln Thr Ser Gly Phe Tyr Gly
        35                    40                  45

Leu Ser Trp Tyr Gln Gln His Asp Gly Gly Ala Pro Thr Phe Leu Ser
    50                    55                  60

Tyr Asn Ala Leu Asp Gly Leu Glu Glu Thr Gly Arg Phe Ser Ser Phe
65                    70                  75                  80

Leu Ser Arg Ser Asp Ser Tyr Gly Tyr Leu Leu Leu Gln Glu Leu Gln
                85                  90                  95

Met Lys Asp Ser Ala Ser Tyr Phe Cys Ala Val Arg Asp Lys Gln Gly
        100                    105                  110

Gly Lys Leu Ile Phe Gly Gln Gly Thr Glu Leu Ser Val Lys Pro Asn
        115                    120                  125

Ile Gln Asn Pro Asp Pro Ala Val Tyr Gln Leu Arg Asp Ser Lys Ser
130                    135                  140

Ser Asp Lys Ser Val Cys Leu Phe Thr Asp Phe Asp Ser Gln Thr Asn
145                    150                  155                  160

Val Ser Gln Ser Lys Asp Ser Asp Val Tyr Ile Thr Asp Lys Thr Val
                165                  170                  175

Leu Asp Met Arg Ser Met Asp Phe Lys Ser Asn Ser Ala Val Ala Trp
            180                    185                  190

Ser Asn Lys Ser Asp Phe Ala Cys Ala Asn Ala Phe Asn Asn Ser Ile
        195                    200                  205

Ile Pro Glu Asp Thr Phe Phe Pro Ser Pro Glu Ser Ser Cys Asp Val
        210                    215                  220

Lys Leu Val Glu Lys Ser Phe Glu Thr Asp Thr Asn Leu Asn Phe Gln
225                    230                  235                  240

```
Asn Leu Ser Val Ile Gly Phe Arg Ile Leu Leu Lys Val Ala Gly
            245                 250                 255

Phe Asn Leu Leu Met Thr Leu Arg Leu Trp Ser Ser
            260                 265

<210> SEQ ID NO 39
<211> LENGTH: 311
<212> TYPE: PRT
<213> ORGANISM: Homo sapiens

<400> SEQUENCE: 39

Met Gly Ser Arg Leu Leu Cys Cys Ala Val Leu Cys Leu Leu Gly Ala
1               5                   10                  15

Val Pro Ile Asp Thr Glu Val Thr Gln Thr Pro Lys His Leu Val Met
                20                  25                  30

Gly Met Thr Asn Lys Lys Ser Leu Lys Cys Glu Gln His Met Gly His
            35                  40                  45

Arg Ala Met Tyr Trp Tyr Lys Gln Lys Ala Lys Lys Pro Pro Glu Leu
        50                  55                  60

Met Phe Val Tyr Ser Tyr Glu Lys Leu Ser Ile Asn Glu Ser Val Pro
65                  70                  75                  80

Ser Arg Phe Ser Pro Glu Cys Pro Asn Ser Ser Leu Leu Asn Leu His
                85                  90                  95

Leu His Ala Leu Gln Pro Glu Asp Ser Ala Leu Tyr Leu Cys Ala Ser
            100                 105                 110

Met Gly Lys Arg Gly Gly Asn Glu Gln Phe Phe Gly Pro Gly Thr Arg
        115                 120                 125

Leu Thr Val Leu Glu Asp Leu Lys Asn Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
290                 295                 300

Lys Arg Lys Asp Ser Arg Gly
305                 310

<210> SEQ ID NO 40
<211> LENGTH: 274
<212> TYPE: PRT
<213> ORGANISM: Homo sapiens
```

-continued

<400> SEQUENCE: 40

```
Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
            20                  25                  30

Val Arg Glu Gly Asp Ser Ser Val Ile Asn Cys Thr Tyr Thr Asp Ser
        35                  40                  45

Ser Ser Thr Tyr Leu Tyr Trp Tyr Lys Gln Glu Pro Gly Ala Gly Leu
    50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Arg Gly Gln Asp Ser Asn Tyr Gln Leu Ile Trp Gly Ala Gly Thr Lys
        115                 120                 125

Leu Ile Ile Lys Pro Asp Ile Gln Asn Pro Asp Pro Ala Val Tyr Gln
130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser
```

<210> SEQ ID NO 41
<211> LENGTH: 315
<212> TYPE: PRT
<213> ORGANISM: Homo sapiens

<400> SEQUENCE: 41

```
Met Gly Thr Arg Leu Leu Phe Trp Val Leu Leu Cys Leu Leu Gly Ala
1               5                   10                  15

Gly Pro Val Asp Ala Gly Val Thr Gln Ser Pro Thr His Leu Ile Lys
            20                  25                  30

Thr Arg Gly Gln His Val Thr Leu Arg Cys Ser Pro Ile Ser Gly His
        35                  40                  45

Lys Ser Val Ser Trp Tyr Gln Gln Val Leu Gly Gln Gly Pro Gln Phe
    50                  55                  60

Ile Phe Gln Tyr Tyr Glu Lys Glu Glu Arg Gly Arg Gly Asn Phe Pro
65                  70                  75                  80
```

```
Asp Arg Phe Ser Ala Arg Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Gly Trp Thr Gly Arg Ser Phe Gly Gly Gly Ala Gln Tyr Phe Gly
            115                 120                 125

Pro Gly Thr Arg Leu Leu Val Leu Glu Asp Leu Lys Asn Val Phe Pro
            130                 135                 140

Pro Glu Val Ala Val Phe Glu Pro Ser Glu Ala Glu Ile Ser His Thr
145                 150                 155                 160

Gln Lys Ala Thr Leu Val Cys Leu Ala Thr Gly Phe Tyr Pro Asp His
                165                 170                 175

Val Glu Leu Ser Trp Trp Val Asn Gly Lys Glu Val His Ser Gly Val
            180                 185                 190

Ser Thr Asp Pro Gln Pro Leu Lys Glu Gln Pro Ala Leu Asn Asp Ser
            195                 200                 205

Arg Tyr Cys Leu Ser Ser Arg Leu Arg Val Ser Ala Thr Phe Trp Gln
            210                 215                 220

Asn Pro Arg Asn His Phe Arg Cys Gln Val Gln Phe Tyr Gly Leu Ser
225                 230                 235                 240

Glu Asn Asp Glu Trp Thr Gln Asp Arg Ala Lys Pro Val Thr Gln Ile
                245                 250                 255

Val Ser Ala Glu Ala Trp Gly Arg Ala Asp Cys Gly Phe Thr Ser Glu
            260                 265                 270

Ser Tyr Gln Gln Gly Val Leu Ser Ala Thr Ile Leu Tyr Glu Ile Leu
            275                 280                 285

Leu Gly Lys Ala Thr Leu Tyr Ala Val Leu Val Ser Ala Leu Val Leu
            290                 295                 300

Met Ala Met Val Lys Arg Lys Asp Ser Arg Gly
305                 310                 315

<210> SEQ ID NO 42
<211> LENGTH: 278
<212> TYPE: PRT
<213> ORGANISM: Homo sapiens

<400> SEQUENCE: 42

Met Ile Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
            35                  40                  45

Arg Gly Ser Gln Ser Phe Phe Trp Tyr Arg Gln Tyr Ser Gly Lys Ser
        50                  55                  60

Pro Glu Leu Ile Met Ser Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Pro Tyr Tyr Trp Ser Ser Gly Ser Asn Tyr Lys Leu Thr Phe Gly
            115                 120                 125

Lys Gly Thr Leu Leu Thr Val Asn Pro Asn Ile Gln Asn Pro Asp Pro
            130                 135                 140
```

```
Ala Val Tyr Gln Leu Arg Asp Ser Lys Ser Ser Asp Lys Ser Val Cys
145                 150                 155                 160

Leu Phe Thr Asp Phe Asp Ser Gln Thr Asn Val Ser Gln Ser Lys Asp
                165                 170                 175

Ser Asp Val Tyr Ile Thr Asp Lys Thr Val Leu Asp Met Arg Ser Met
            180                 185                 190

Asp Phe Lys Ser Asn Ser Ala Val Ala Trp Ser Asn Lys Ser Asp Phe
                195                 200                 205

Ala Cys Ala Asn Ala Phe Asn Asn Ser Ile Ile Pro Glu Asp Thr Phe
        210                 215                 220

Phe Pro Ser Pro Glu Ser Ser Cys Asp Val Lys Leu Val Glu Lys Ser
225                 230                 235                 240

Phe Glu Thr Asp Thr Asn Leu Asn Phe Gln Asn Leu Ser Val Ile Gly
                245                 250                 255

Phe Arg Ile Leu Leu Leu Lys Val Ala Gly Phe Asn Leu Leu Met Thr
            260                 265                 270

Leu Arg Leu Trp Ser Ser
            275

<210> SEQ ID NO 43
<211> LENGTH: 311
<212> TYPE: PRT
<213> ORGANISM: Homo sapiens

<400> SEQUENCE: 43

Met Gly Ser Arg Leu Leu Cys Cys Ala Val Leu Cys Leu Leu Gly Ala
1               5                   10                  15

Val Pro Ile Asp Thr Glu Val Thr Gln Thr Pro Lys His Leu Val Met
                20                  25                  30

Gly Met Thr Asn Lys Lys Ser Leu Lys Cys Glu Gln His Met Gly His
            35                  40                  45

Arg Ala Met Tyr Trp Tyr Lys Gln Lys Ala Lys Lys Pro Pro Glu Leu
        50                  55                  60

Met Phe Val Tyr Ser Tyr Glu Lys Leu Ser Ile Asn Glu Ser Val Pro
65                  70                  75                  80

Ser Arg Phe Ser Pro Glu Cys Pro Asn Ser Ser Leu Leu Asn Leu His
                85                  90                  95

Leu His Ala Leu Gln Pro Glu Asp Ser Ala Leu Tyr Leu Cys Ala Ser
            100                 105                 110

Ser Gln Ser Gly Leu Glu Glu Thr Gln Tyr Phe Gly Pro Gly Thr Arg
        115                 120                 125

Leu Leu Val Leu Glu Asp Leu Lys Asn Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
            165                 170                 175

Trp Trp Val Asn Gly Lys Glu Val His Ser Gly Val Ser Thr Asp Pro
        180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
        210                 215                 220

His Phe Arg Cys Gln Val Gln Phe Tyr Gly Leu Ser Glu Asn Asp Glu
```

```
            225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
                260                 265                 270

Gly Val Leu Ser Ala Thr Ile Leu Tyr Glu Ile Leu Gly Lys Ala
                275                 280                 285

Thr Leu Tyr Ala Val Leu Val Ser Ala Leu Val Leu Met Ala Met Val
                290                 295                 300

Lys Arg Lys Asp Ser Arg Gly
305                 310

<210> SEQ ID NO 44
<211> LENGTH: 267
<212> TYPE: PRT
<213> ORGANISM: Homo sapiens

<400> SEQUENCE: 44

Met Lys Arg Ile Leu Gly Ala Leu Leu Gly Leu Leu Ser Ala Gln Val
1               5                   10                  15

Cys Cys Val Arg Gly Ile Gln Val Glu Gln Ser Pro Pro Asp Leu Ile
                20                  25                  30

Leu Gln Glu Gly Ala Asn Ser Thr Leu Arg Cys Asn Phe Ser Asp Ser
            35                  40                  45

Val Asn Asn Leu Gln Trp Phe His Gln Asn Pro Trp Gly Gln Leu Ile
50                  55                  60

Asn Leu Phe Tyr Ile Pro Ser Gly Thr Lys Gln Asn Gly Arg Leu Ser
65                  70                  75                  80

Ala Thr Thr Val Ala Thr Glu Arg Tyr Ser Leu Leu Tyr Ile Ser Ser
                85                  90                  95

Ser Gln Thr Thr Asp Ser Gly Val Tyr Phe Cys Ala Val Asn Asp Tyr
            100                 105                 110

Lys Leu Ser Phe Gly Ala Gly Thr Thr Val Thr Val Arg Ala Asn Ile
        115                 120                 125

Gln Lys Pro Asp Pro Ala Val Tyr Gln Leu Arg Asp Ser Lys Ser Ser
    130                 135                 140

Asp Lys Ser Val Cys Leu Phe Thr Asp Phe Asp Ser Gln Thr Asn Val
145                 150                 155                 160

Ser Gln Ser Lys Asp Ser Asp Val Tyr Ile Thr Asp Lys Thr Val Leu
                165                 170                 175

Asp Met Arg Ser Met Asp Phe Lys Ser Asn Ser Ala Val Ala Trp Ser
            180                 185                 190

Asn Lys Ser Asp Phe Ala Cys Ala Asn Ala Phe Asn Asn Ser Ile Ile
        195                 200                 205

Pro Glu Asp Thr Phe Phe Pro Ser Pro Glu Ser Ser Cys Asp Val Lys
    210                 215                 220

Leu Val Glu Lys Ser Phe Glu Thr Asp Thr Asn Leu Asn Phe Gln Asn
225                 230                 235                 240

Leu Ser Val Ile Gly Phe Arg Ile Leu Leu Leu Lys Val Ala Gly Phe
                245                 250                 255

Asn Leu Leu Met Thr Leu Arg Leu Trp Ser Ser
            260                 265

<210> SEQ ID NO 45
<211> LENGTH: 310
```

```
<212> TYPE: PRT
<213> ORGANISM: Homo sapiens

<400> SEQUENCE: 45

Met Gly Thr Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Pro Gly Val Ser Gly Thr Thr Glu Ala Phe Phe Gly Gln Gly Thr
        115                 120                 125

Arg Leu Thr Val Val Glu Asp Leu Asn Lys Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Phe
305                 310

<210> SEQ ID NO 46
<211> LENGTH: 273
<212> TYPE: PRT
<213> ORGANISM: Homo sapiens

<400> SEQUENCE: 46

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30
```

-continued

```
Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
 50                  55                  60

Gly Pro Glu Leu Leu Met Tyr Thr Tyr Ser Ser Gly Asn Lys Glu Asp
 65                  70                  75                  80

Gly Arg Phe Thr Ala Gln Val Asp Lys Ser Ser Lys Tyr Ile Ser Leu
             85                  90                  95

Phe Ile Arg Asp Ser Gln Pro Ser Asp Ser Ala Thr Tyr Leu Cys Ala
            100                 105                 110

Met Ser Lys Gly Ala Gln Lys Leu Val Phe Gly Gln Gly Thr Arg Leu
            115                 120                 125

Thr Ile Asn Pro Asn Ile Gln Asn Pro Asp Pro Ala Val Tyr Gln Leu
        130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 47
<211> LENGTH: 313
<212> TYPE: PRT
<213> ORGANISM: Homo sapiens

<400> SEQUENCE: 47

Met Gly Thr Arg Leu Leu Cys Trp Ala Ala Leu Cys Leu Leu Gly Ala
1               5                  10                  15

Glu Leu Thr Glu Ala Gly Val Ala Gln Ser Pro Arg Tyr Lys Ile Ile
            20                  25                  30

Glu Lys Arg Gln Ser Val Ala Phe Trp Cys Asn Pro Ile Ser Gly His
        35                  40                  45

Ala Thr Leu Tyr Trp Tyr Gln Gln Ile Leu Gly Gln Gly Pro Lys Leu
    50                  55                  60

Leu Ile Gln Phe Gln Asn Asn Gly Val Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Lys Leu Glu Asp Ser Ala Val Tyr Leu Cys Ala
            100                 105                 110

Ser Ser Leu Gly Asp Ser Asn Thr Gly Glu Leu Phe Phe Gly Glu Gly
        115                 120                 125
```

```
Ser Arg Leu Thr Val Leu Glu Asp Leu Lys Asn Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Glu Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
290                 295                 300

Met Val Lys Arg Lys Asp Ser Arg Gly
305                 310

<210> SEQ ID NO 48
<211> LENGTH: 268
<212> TYPE: PRT
<213> ORGANISM: Homo sapiens

<400> SEQUENCE: 48

Met Val Leu Lys Phe Ser Val Ser Ile Leu Trp Ile Gln Leu Ala Trp
1               5                   10                  15

Val Ser Thr Gln Leu Leu Glu Gln Ser Pro Gln Phe Leu Ser Ile Gln
                20                  25                  30

Glu Gly Glu Asn Leu Thr Val Tyr Cys Asn Ser Ser Ser Val Phe Ser
            35                  40                  45

Ser Leu Gln Trp Tyr Arg Gln Glu Pro Gly Glu Gly Pro Val Leu Leu
        50                  55                  60

Val Thr Val Val Thr Gly Gly Glu Val Lys Lys Leu Lys Arg Leu Thr
65                  70                  75                  80

Phe Gln Phe Gly Asp Ala Arg Lys Asp Ser Ser Leu His Ile Thr Ala
                85                  90                  95

Ala Gln Pro Gly Asp Thr Gly Leu Tyr Leu Cys Ala Gly Ala Gln Gly
                100                 105                 110

Gln Lys Leu Leu Phe Ala Arg Gly Thr Met Leu Lys Val Asp Leu Asn
        115                 120                 125

Ile Gln Asn Pro Asp Pro Ala Val Tyr Gln Leu Arg Asp Ser Lys Ser
    130                 135                 140

Ser Asp Lys Ser Val Cys Leu Phe Thr Asp Phe Asp Ser Gln Thr Asn
145                 150                 155                 160

Val Ser Gln Ser Lys Asp Ser Asp Val Tyr Ile Thr Asp Lys Thr Val
                165                 170                 175

Leu Asp Met Arg Ser Met Asp Phe Lys Ser Asn Ser Ala Val Ala Trp
            180                 185                 190
```

```
Ser Asn Lys Ser Asp Phe Ala Cys Ala Asn Ala Phe Asn Asn Ser Ile
            195                 200                 205

Ile Pro Glu Asp Thr Phe Phe Pro Ser Pro Glu Ser Ser Cys Asp Val
        210                 215                 220

Lys Leu Val Glu Lys Ser Phe Glu Thr Asp Thr Asn Leu Asn Phe Gln
225                 230                 235                 240

Asn Leu Ser Val Ile Gly Phe Arg Ile Leu Leu Lys Val Ala Gly
            245                 250                 255

Phe Asn Leu Leu Met Thr Leu Arg Leu Trp Ser Ser
            260                 265

<210> SEQ ID NO 49
<211> LENGTH: 314
<212> TYPE: PRT
<213> ORGANISM: Homo sapiens

<400> SEQUENCE: 49

Met Gly Thr Arg Leu Leu Cys Trp Met Ala Leu Cys Leu Leu Gly Ala
1               5                   10                  15

Asp His Ala Asp Thr Gly Val Ser Gln Asn Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser His Leu Ala Gly Gly Asn Thr Gly Glu Leu Phe Phe Gly Glu
        115                 120                 125

Gly Ser Arg Leu Thr Val Leu Glu Asp Leu Lys Asn Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
```

```
                290                 295                 300
Ala Met Val Lys Arg Lys Asp Ser Arg Gly
305                 310
```

<210> SEQ ID NO 50
<211> LENGTH: 276
<212> TYPE: PRT
<213> ORGANISM: Homo sapiens

<400> SEQUENCE: 50

```
Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
            20                  25                  30

Val Val Glu Lys Glu Asp Val Thr Leu Asp Cys Val Tyr Glu Thr Arg
        35                  40                  45

Asp Thr Thr Tyr Tyr Leu Phe Trp Tyr Lys Gln Pro Pro Ser Gly Glu
    50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
            100                 105                 110

Ala Leu Ile Glu Ala Ala Ala Gly Asn Lys Leu Thr Phe Gly Gly Gly
        115                 120                 125

Thr Arg Val Leu Val Lys Pro Asn Ile Gln Asn Pro Asp Pro Ala Val
130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
        275
```

<210> SEQ ID NO 51
<211> LENGTH: 313
<212> TYPE: PRT
<213> ORGANISM: Homo sapiens

<400> SEQUENCE: 51

```
Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
```

```
                20                  25                  30
Glu Met Gly Gln Glu Val Thr Leu Arg Cys Lys Pro Ile Ser Gly His
            35                  40                  45
Asp Tyr Leu Phe Trp Tyr Arg Gln Thr Met Met Arg Gly Leu Glu Leu
        50                  55                  60
Leu Ile Tyr Phe Asn Asn Val Pro Ile Asp Ser Gly Met Pro
65                  70                  75                  80
Glu Asp Arg Phe Ser Ala Lys Met Pro Asn Ala Ser Phe Ser Thr Leu
                85                  90                  95
Lys Ile Gln Pro Ser Glu Pro Arg Asp Ser Ala Val Tyr Phe Cys Ala
            100                 105                 110
Gly Ser Leu Arg Leu Ala Gly Ala Glu Gln Tyr Phe Gly Pro Gly
            115                 120                 125
Thr Arg Leu Thr Val Thr Glu Asp Leu Lys Asn Val Phe Pro Pro Glu
            130                 135                 140
Val Ala Val Phe Glu Pro Ser Glu Ala Glu Ile Ser His Thr Gln Lys
145                 150                 155                 160
Ala Thr Leu Val Cys Leu Ala Thr Gly Phe Tyr Pro Asp His Val Glu
                165                 170                 175
Leu Ser Trp Trp Val Asn Gly Lys Glu Val His Ser Gly Val Ser Thr
                180                 185                 190
Asp Pro Gln Pro Leu Lys Glu Gln Pro Ala Leu Asn Asp Ser Arg Tyr
            195                 200                 205
Cys Leu Ser Ser Arg Leu Arg Val Ser Ala Thr Phe Trp Gln Asn Pro
        210                 215                 220
Arg Asn His Phe Arg Cys Gln Val Gln Phe Tyr Gly Leu Ser Glu Asn
225                 230                 235                 240
Asp Glu Trp Thr Gln Asp Arg Ala Lys Pro Val Thr Gln Ile Val Ser
                245                 250                 255
Ala Glu Ala Trp Gly Arg Ala Asp Cys Gly Phe Thr Ser Glu Ser Tyr
            260                 265                 270
Gln Gln Gly Val Leu Ser Ala Thr Ile Leu Tyr Glu Ile Leu Leu Gly
            275                 280                 285
Lys Ala Thr Leu Tyr Ala Val Leu Val Ser Ala Leu Val Leu Met Ala
        290                 295                 300
Met Val Lys Arg Lys Asp Ser Arg Gly
305                 310

<210> SEQ ID NO 52
<211> LENGTH: 276
<212> TYPE: PRT
<213> ORGANISM: Homo sapiens

<400> SEQUENCE: 52

Met Ser Leu Ser Ser Leu Leu Lys Val Val Thr Ala Ser Leu Trp Leu
1               5                   10                  15
Gly Pro Gly Ile Ala Gln Lys Ile Thr Gln Thr Gln Pro Gly Met Phe
            20                  25                  30
Val Gln Glu Lys Glu Ala Val Thr Leu Asp Cys Thr Tyr Asp Thr Ser
            35                  40                  45
Asp Pro Ser Tyr Gly Leu Phe Trp Tyr Lys Gln Pro Ser Ser Gly Glu
        50                  55                  60
Met Ile Phe Leu Ile Tyr Gln Gly Ser Tyr Asp Gln Gln Asn Ala Thr
65                  70                  75                  80
```

```
Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Thr Ala Ser Asn Phe Gly Asn Glu Lys Leu Thr Phe Gly Thr Gly
            115                 120                 125

Thr Arg Leu Thr Ile Ile Pro Asn Ile Gln Asn Pro Asp Pro Ala Val
        130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
            165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
            195                 200                 205

Ala Asn Ala Phe Asn Asn Ser Ile Ile Pro Glu Asp Thr Phe Phe Pro
            210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
            245                 250                 255

Ile Leu Leu Leu Lys Val Ala Gly Phe Asn Leu Leu Met Thr Leu Arg
            260                 265                 270

Leu Trp Ser Ser
        275

<210> SEQ ID NO 53
<211> LENGTH: 306
<212> TYPE: PRT
<213> ORGANISM: Homo sapiens

<400> SEQUENCE: 53

Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
            20                  25                  30

Ser Leu Thr Ile Gln Cys Gln Val Asp Ser Gln Val Thr Met Met Phe
        35                  40                  45

Trp Tyr Arg Gln Gln Pro Gly Gln Ser Leu Thr Leu Ile Ala Thr Ala
    50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
            85                  90                  95

Asn Met Ser Pro Glu Asp Ser Ser Ile Tyr Leu Cys Ser Val Asp Arg
            100                 105                 110

Asp Arg Glu Asp Gly Tyr Thr Phe Gly Ser Gly Thr Arg Leu Thr Val
            115                 120                 125

Val Glu Asp Leu Asn Lys Val Phe Pro Pro Glu Val Ala Val Phe Glu
            130                 135                 140

Pro Ser Glu Ala Glu Ile Ser His Thr Gln Lys Ala Thr Leu Val Cys
145                 150                 155                 160

Leu Ala Thr Gly Phe Phe Pro Asp His Val Glu Leu Ser Trp Trp Val
            165                 170                 175
```

Asn Gly Lys Glu Val His Ser Gly Val Ser Thr Asp Pro Gln Pro Leu
            180                 185                 190

Lys Glu Gln Pro Ala Leu Asn Asp Ser Arg Tyr Cys Leu Ser Ser Arg
        195                 200                 205

Leu Arg Val Ser Ala Thr Phe Trp Gln Asn Pro Arg Asn His Phe Arg
    210                 215                 220

Cys Gln Val Gln Phe Tyr Gly Leu Ser Glu Asn Asp Glu Trp Thr Gln
225                 230                 235                 240

Asp Arg Ala Lys Pro Val Thr Gln Ile Val Ser Ala Glu Ala Trp Gly
                245                 250                 255

Arg Ala Asp Cys Gly Phe Thr Ser Val Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Ala Leu Val Leu Met Ala Met Val Lys Arg Lys
    290                 295                 300

Asp Phe
305

<210> SEQ ID NO 54
<211> LENGTH: 276
<212> TYPE: PRT
<213> ORGANISM: Homo sapiens

<400> SEQUENCE: 54

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Tyr Ser Arg Thr Ser Gly Thr Tyr Lys Tyr Ile Phe Gly Thr Gly
        115                 120                 125

Thr Arg Leu Lys Val Leu Ala Asn Ile Gln Asn Pro Asp Pro Ala Val
    130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu

```
                225                 230                 235                 240

Thr Asp Thr Asn Leu Asn Phe Gln Asn Leu Ser Val Ile Gly Phe Arg
                        245                 250                 255

Ile Leu Leu Leu Lys Val Ala Gly Phe Asn Leu Leu Met Thr Leu Arg
                        260                 265                 270

Leu Trp Ser Ser
                275

<210> SEQ ID NO 55
<211> LENGTH: 313
<212> TYPE: PRT
<213> ORGANISM: Homo sapiens

<400> SEQUENCE: 55

Met Ser Asn Gln Val Leu Cys Cys Ala Val Leu Cys Leu Leu Gly Ala
        1               5                   10                  15

Val Pro Met Glu Thr Gly Val Thr Gln Thr Pro Arg His Leu Val Met
                        20                  25                  30

Gly Met Thr Asn Lys Lys Ser Leu Lys Cys Glu Gln His Leu Gly His
                        35                  40                  45

Asn Ala Met Tyr Trp Tyr Lys Gln Ser Ala Lys Lys Pro Leu Glu Leu
        50                      55                  60

Met Phe Val Tyr Asn Phe Lys Glu Gln Thr Glu Asn Asn Ser Val Pro
        65                      70                  75                  80

Ser Arg Phe Ser Pro Glu Cys Pro Asn Ser Ser His Leu Phe Leu His
                        85                  90                  95

Leu His Thr Leu Gln Pro Glu Asp Ser Ala Leu Tyr Leu Cys Ala Ser
                        100                 105                 110

Ser Gln Glu Ile Ser Gly Ser Ser Tyr Glu Gln Tyr Phe Gly Pro Gly
                        115                 120                 125

Thr Arg Leu Thr Val Thr Glu Asp Leu Lys Asn Val Phe Pro Pro Glu
                        130                 135                 140

Val Ala Val Phe Glu Pro Ser Glu Ala Glu Ile Ser His Thr Gln Lys
        145                 150                 155                 160

Ala Thr Leu Val Cys Leu Ala Thr Gly Phe Tyr Pro Asp His Val Glu
                        165                 170                 175

Leu Ser Trp Trp Val Asn Gly Lys Glu Val His Ser Gly Val Ser Thr
                        180                 185                 190

Asp Pro Gln Pro Leu Lys Glu Gln Pro Ala Leu Asn Asp Ser Arg Tyr
                        195                 200                 205

Cys Leu Ser Ser Arg Leu Arg Val Ser Ala Thr Phe Trp Gln Asn Pro
                        210                 215                 220

Arg Asn His Phe Arg Cys Gln Val Gln Phe Tyr Gly Leu Ser Glu Asn
        225                 230                 235                 240

Asp Glu Trp Thr Gln Asp Arg Ala Lys Pro Val Thr Gln Ile Val Ser
                        245                 250                 255

Ala Glu Ala Trp Gly Arg Ala Asp Cys Gly Phe Thr Ser Glu Ser Tyr
                        260                 265                 270

Gln Gln Gly Val Leu Ser Ala Thr Ile Leu Tyr Glu Ile Leu Leu Gly
                        275                 280                 285

Lys Ala Thr Leu Tyr Ala Val Leu Val Ser Ala Leu Val Leu Met Ala
                        290                 295                 300

Met Val Lys Arg Lys Asp Ser Arg Gly
        305                 310
```

```
<210> SEQ ID NO 56
<211> LENGTH: 275
<212> TYPE: PRT
<213> ORGANISM: Homo sapiens

<400> SEQUENCE: 56

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Ser Ala Val Ser Phe Gly Asn Val Leu His Cys Gly Ser Gly Thr
        115                 120                 125

Gln Val Ile Val Leu Pro His Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275

<210> SEQ ID NO 57
<211> LENGTH: 307
<212> TYPE: PRT
<213> ORGANISM: Homo sapiens

<400> SEQUENCE: 57

Met Gly Thr Arg Leu Leu Cys Trp Val Leu Leu Cys Leu Leu Gly Ala
1               5                   10                  15

Gly Ser Val Glu Thr Gly Val Thr Gln Ser Pro Thr His Leu Ile Lys
            20                  25                  30

Thr Arg Gly Gln Gln Val Thr Leu Arg Cys Ser Ser Gln Ser Gly His
        35                  40                  45
```

```
Asn Thr Val Ser Trp Tyr Gln Gln Ala Leu Gly Gln Gly Pro Gln Phe
    50                  55                  60

Ile Phe Gln Tyr Tyr Arg Glu Glu Asn Gly Arg Gly Asn Phe Pro
65                  70                  75                  80

Pro Arg Phe Ser Gly Leu Gln Phe Pro Asn Tyr Ser Ser Glu Leu Asn
                85                  90                  95

Val Asn Ala Leu Glu Leu Asp Asp Ser Ala Leu Tyr Leu Cys Ala Ser
            100                 105                 110

Ser Phe Gly Glu Asn Thr Ile Tyr Phe Gly Gly Ser Trp Leu Thr
        115                 120                 125

Val Val Glu Asp Leu Asn Lys Val Phe Pro Glu Val Ala Val Phe
130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
290                 295                 300

Lys Asp Phe
305

<210> SEQ ID NO 58
<211> LENGTH: 279
<212> TYPE: PRT
<213> ORGANISM: Homo sapiens

<400> SEQUENCE: 58

Met Thr Arg Val Ser Leu Leu Trp Ala Val Val Ser Thr Cys Leu
1               5                   10                  15

Glu Ser Gly Met Ala Gln Thr Val Thr Gln Ser Gln Pro Glu Met Ser
                20                  25                  30

Val Gln Glu Ala Glu Thr Val Thr Leu Ser Cys Thr Tyr Asp Thr Ser
            35                  40                  45

Glu Asn Asn Tyr Tyr Leu Phe Trp Tyr Lys Gln Pro Pro Ser Arg Gln
        50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Thr Ala Met Tyr Phe Cys
            100                 105                 110
```

-continued

```
Ala Phe Met Lys His Pro Ser Gly Gly Ala Asp Gly Leu Thr Phe
            115                 120                 125

Gly Lys Gly Thr His Leu Ile Ile Gln Pro Tyr Ile Gln Asn Pro Asp
130                 135                 140

Pro Ala Val Tyr Gln Leu Arg Asp Ser Lys Ser Ser Asp Lys Ser Val
145                 150                 155                 160

Cys Leu Phe Thr Asp Phe Asp Ser Gln Thr Asn Val Ser Gln Ser Lys
                165                 170                 175

Asp Ser Asp Val Tyr Ile Thr Asp Lys Thr Val Leu Asp Met Arg Ser
            180                 185                 190

Met Asp Phe Lys Ser Asn Ser Ala Val Ala Trp Ser Asn Lys Ser Asp
            195                 200                 205

Phe Ala Cys Ala Asn Ala Phe Asn Asn Ser Ile Ile Pro Glu Asp Thr
210                 215                 220

Phe Phe Pro Ser Pro Glu Ser Ser Cys Asp Val Lys Leu Val Glu Lys
225                 230                 235                 240

Ser Phe Glu Thr Asp Thr Asn Leu Asn Phe Gln Asn Leu Ser Val Ile
                245                 250                 255

Gly Phe Arg Ile Leu Leu Leu Lys Val Ala Gly Phe Asn Leu Leu Met
            260                 265                 270

Thr Leu Arg Leu Trp Ser Ser
            275

<210> SEQ ID NO 59
<211> LENGTH: 312
<212> TYPE: PRT
<213> ORGANISM: Homo sapiens

<400> SEQUENCE: 59

Met Gly Thr Arg Leu Leu Cys Cys Val Val Phe Cys Leu Leu Gln Ala
1               5                   10                  15

Gly Pro Leu Asp Thr Ala Val Ser Gln Thr Pro Lys Tyr Leu Val Thr
                20                  25                  30

Gln Met Gly Asn Asp Lys Ser Ile Lys Cys Glu Gln Asn Leu Gly His
            35                  40                  45

Asp Thr Met Tyr Trp Tyr Lys Gln Asp Ser Lys Lys Phe Leu Lys Ile
50                  55                  60

Met Phe Ser Tyr Asn Asn Lys Glu Leu Ile Ile Asn Glu Thr Val Pro
65                  70                  75                  80

Asn Arg Phe Ser Pro Lys Ser Pro Asp Lys Ala His Leu Asn Leu His
                85                  90                  95

Ile Asn Ser Leu Glu Leu Gly Asp Ser Ala Val Tyr Phe Cys Ala Ser
            100                 105                 110

Ser His Glu Arg Gly Gly Ala Tyr Glu Gln Tyr Phe Gly Pro Gly Thr
        115                 120                 125

Arg Leu Thr Val Thr Glu Asp Leu Lys Asn Val Phe Pro Pro Glu Val
130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
```

```
                195                 200                 205
Leu Ser Ser Arg Leu Arg Val Ser Ala Thr Phe Trp Gln Asn Pro Arg
210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
                260                 265                 270

Gln Gly Val Leu Ser Ala Thr Ile Leu Tyr Glu Ile Leu Leu Gly Lys
            275                 280                 285

Ala Thr Leu Tyr Ala Val Leu Val Ser Ala Leu Val Leu Met Ala Met
        290                 295                 300

Val Lys Arg Lys Asp Ser Arg Gly
305                 310

<210> SEQ ID NO 60
<211> LENGTH: 272
<212> TYPE: PRT
<213> ORGANISM: Homo sapiens

<400> SEQUENCE: 60

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
                20                  25                  30

Ile Gln Glu Gly Glu Asn Ala Thr Met Asn Cys Ser Tyr Lys Thr Ser
            35                  40                  45

Ile Asn Asn Leu Gln Trp Tyr Arg Gln Asn Ser Gly Arg Gly Leu Val
        50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
                85                  90                  95

Thr Ala Ser Arg Ala Ala Asp Thr Ala Ser Tyr Phe Cys Ala Gly Tyr
            100                 105                 110

Asn Thr Asn Ala Gly Lys Ser Thr Phe Gly Asp Gly Thr Thr Leu Thr
        115                 120                 125

Val Lys Pro Asn Ile Gln Asn Pro Asp Pro Ala Val Tyr Gln Leu Arg
130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255
```

```
Lys Val Ala Gly Phe Asn Leu Leu Met Thr Leu Arg Leu Trp Ser Ser
            260                 265                 270
```

<210> SEQ ID NO 61
<211> LENGTH: 312
<212> TYPE: PRT
<213> ORGANISM: Homo sapiens

<400> SEQUENCE: 61

```
Met Ser Leu Gly Leu Leu Cys Cys Ala Ala Phe Pro Leu Leu Trp Ala
1               5                   10                  15

Gly Pro Val Asn Ala Gly Val Thr Gln Thr Pro Lys Phe Arg Ile Leu
            20                  25                  30

Lys Ile Gly Gln Ser Met Thr Leu Gln Cys Ala Gln Asp Met Asn His
        35                  40                  45

Asn Tyr Met Tyr Trp Tyr Arg Gln Asp Pro Gly Met Gly Leu Lys Leu
    50                  55                  60

Ile Tyr Tyr Ser Val Gly Ala Gly Ile Thr Asp Lys Gly Glu Val Pro
65                  70                  75                  80

Asn Gly Tyr Asn Val Ser Arg Ser Thr Thr Glu Asp Phe Pro Leu Arg
                85                  90                  95

Leu Glu Leu Ala Ala Pro Ser Gln Thr Ser Val Tyr Phe Cys Ala Ser
            100                 105                 110

Ser Phe Gly Gln Val Trp Ala Asp Thr Gln Tyr Phe Gly Pro Gly Thr
        115                 120                 125

Arg Leu Thr Val Leu Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310
```

<210> SEQ ID NO 62
<211> LENGTH: 274
<212> TYPE: PRT
<213> ORGANISM: Homo sapiens

<400> SEQUENCE: 62

```
Met Glu Lys Met Leu Glu Cys Ala Phe Ile Val Leu Trp Leu Gln Leu
1               5                   10                  15

Gly Trp Leu Ser Gly Glu Asp Gln Val Thr Gln Ser Pro Glu Ala Leu
            20                  25                  30

Arg Leu Gln Glu Gly Glu Ser Ser Leu Asn Cys Ser Tyr Thr Val
        35                  40                  45

Ser Gly Leu Arg Gly Leu Phe Trp Tyr Arg Gln His Pro Gly Lys Gly
50                  55                  60

Pro Glu Phe Leu Phe Thr Leu Tyr Ser Ala Gly Glu Glu Lys Glu Lys
65                  70                  75                  80

Glu Arg Leu Lys Ala Thr Leu Thr Lys Lys Glu Ser Phe Leu His Ile
                85                  90                  95

Thr Ala Pro Lys Pro Glu Asp Ser Ala Thr Tyr Leu Cys Ala Val Gln
            100                 105                 110

Ala Ser Asn Ser Gly Asn Thr Pro Leu Val Phe Gly Lys Gly Thr Arg
            115                 120                 125

Leu Ser Val Ile Ala Asn Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 63
<211> LENGTH: 313
<212> TYPE: PRT
<213> ORGANISM: Homo sapiens

<400> SEQUENCE: 63

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95
```

-continued

```
Val Thr Ser Ala Gln Lys Asn Pro Thr Ala Phe Tyr Leu Cys Ala Ser
            100                 105                 110

Ser Ala Pro His Gln Arg Gly Thr Asn Glu Gln Phe Gly Pro Gly
        115                 120                 125

Thr Arg Leu Thr Val Leu Glu Asp Leu Lys Asn Val Phe Pro Pro Glu
130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Ser Thr
                180                 185                 190

Asp Pro Gln Pro Leu Lys Glu Gln Pro Ala Leu Asn Asp Ser Arg Tyr
            195                 200                 205

Cys Leu Ser Ser Arg Leu Arg Val Ser Ala Thr Phe Trp Gln Asn Pro
210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Glu Ser Tyr
                260                 265                 270

Gln Gln Gly Val Leu Ser Ala Thr Ile Leu Tyr Glu Ile Leu Leu Gly
            275                 280                 285

Lys Ala Thr Leu Tyr Ala Val Leu Val Ser Ala Leu Val Leu Met Ala
290                 295                 300

Met Val Lys Arg Lys Asp Ser Arg Gly
305                 310

<210> SEQ ID NO 64
<211> LENGTH: 279
<212> TYPE: PRT
<213> ORGANISM: Homo sapiens

<400> SEQUENCE: 64

Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Ser Pro Asn Thr Gly Asn Gln Phe Tyr Phe
        115                 120                 125

Gly Thr Gly Thr Ser Leu Thr Val Ile Pro Asn Ile Gln Asn Pro Asp
130                 135                 140

Pro Ala Val Tyr Gln Leu Arg Asp Ser Lys Ser Ser Asp Lys Ser Val
145                 150                 155                 160
```

```
Cys Leu Phe Thr Asp Phe Asp Ser Gln Thr Asn Val Ser Gln Ser Lys
                165                 170                 175

Asp Ser Asp Val Tyr Ile Thr Asp Lys Thr Val Leu Asp Met Arg Ser
            180                 185                 190

Met Asp Phe Lys Ser Asn Ser Ala Val Ala Trp Ser Asn Lys Ser Asp
        195                 200                 205

Phe Ala Cys Ala Asn Ala Phe Asn Asn Ser Ile Ile Pro Glu Asp Thr
    210                 215                 220

Phe Phe Pro Ser Pro Glu Ser Ser Cys Asp Val Lys Leu Val Glu Lys
225                 230                 235                 240

Ser Phe Glu Thr Asp Thr Asn Leu Asn Phe Gln Asn Leu Ser Val Ile
                245                 250                 255

Gly Phe Arg Ile Leu Leu Leu Lys Val Ala Gly Phe Asn Leu Leu Met
            260                 265                 270

Thr Leu Arg Leu Trp Ser Ser
        275

<210> SEQ ID NO 65
<211> LENGTH: 312
<212> TYPE: PRT
<213> ORGANISM: Homo sapiens

<400> SEQUENCE: 65

Met Gly Thr Arg Leu Leu Phe Trp Val Ala Phe Cys Leu Leu Gly Ala
1               5                   10                  15

Asp His Thr Gly Ala Gly Val Ser Gln Ser Pro Ser Asn Lys Val Thr
            20                  25                  30

Glu Lys Gly Lys Asp Val Glu Leu Arg Cys Asp Pro Ile Ser Gly His
        35                  40                  45

Thr Ala Leu Tyr Trp Tyr Arg Gln Ser Leu Gly Gln Gly Leu Glu Phe
    50                  55                  60

Leu Ile Tyr Phe Gln Gly Asn Ser Ala Pro Asp Lys Ser Gly Leu Pro
65                  70                  75                  80

Ser Asp Arg Phe Ser Ala Glu Arg Thr Gly Gly Ser Val Ser Thr Leu
                85                  90                  95

Thr Ile Gln Arg Thr Gln Gln Glu Asp Ser Ala Val Tyr Leu Cys Ala
            100                 105                 110

Ser Ser Leu Thr Gly Gly Pro Tyr Glu Gln Tyr Phe Gly Pro Gly Thr
        115                 120                 125

Arg Leu Thr Val Thr Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
```

245                 250                 255
Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310

<210> SEQ ID NO 66
<211> LENGTH: 274
<212> TYPE: PRT
<213> ORGANISM: Homo sapiens

<400> SEQUENCE: 66

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Arg Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Leu
            100                 105                 110

Tyr Ser Gly Gly Gly Ala Asp Gly Leu Thr Phe Gly Lys Gly Thr His
        115                 120                 125

Leu Ile Ile Gln Pro Tyr Ile Gln Lys Pro Asp Pro Ala Val Tyr Gln
130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 67
<211> LENGTH: 310
<212> TYPE: PRT

<213> ORGANISM: Homo sapiens

<400> SEQUENCE: 67

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Ile Gly Gly Val Asn Thr Glu Ala Phe Phe Gly Gln Gly Thr
        115                 120                 125

Arg Leu Thr Val Val Glu Asp Leu Asn Lys Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Phe
305                 310

<210> SEQ ID NO 68
<211> LENGTH: 281
<212> TYPE: PRT
<213> ORGANISM: Homo sapiens

<400> SEQUENCE: 68

Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn

```
            35                  40                  45
Cys Asp Tyr Thr Asn Ser Met Phe Asp Tyr Phe Leu Trp Tyr Lys Lys
 50                  55                  60

Tyr Pro Ala Glu Gly Pro Thr Phe Leu Ile Ser Ile Ser Ser Ile Lys
 65                  70                  75                  80

Asp Lys Asn Glu Asp Gly Arg Phe Thr Val Phe Leu Asn Lys Ser Ala
                 85                  90                  95

Lys His Leu Ser Leu His Ile Val Pro Ser Gln Pro Gly Asp Ser Ala
                100                 105                 110

Val Tyr Phe Cys Ala Ala Arg Ser Tyr Gly Gly Ser Gln Gly Asn Leu
            115                 120                 125

Ile Phe Gly Lys Gly Thr Lys Leu Ser Val Lys Pro Asn Ile Gln Lys
130                 135                 140

Pro Asp Pro Ala Val Tyr Gln Leu Arg Asp Ser Lys Ser Ser Asp Lys
145                 150                 155                 160

Ser Val Cys Leu Phe Thr Asp Phe Asp Ser Gln Thr Asn Val Ser Gln
                165                 170                 175

Ser Lys Asp Ser Asp Val Tyr Ile Thr Asp Lys Thr Val Leu Asp Met
                180                 185                 190

Arg Ser Met Asp Phe Lys Ser Asn Ser Ala Val Ala Trp Ser Asn Lys
            195                 200                 205

Ser Asp Phe Ala Cys Ala Asn Ala Phe Asn Asn Ser Ile Ile Pro Glu
210                 215                 220

Asp Thr Phe Phe Pro Ser Pro Glu Ser Ser Cys Asp Val Lys Leu Val
225                 230                 235                 240

Glu Lys Ser Phe Glu Thr Asp Thr Asn Leu Asn Phe Gln Asn Leu Ser
                245                 250                 255

Val Ile Gly Phe Arg Ile Leu Leu Leu Lys Val Ala Gly Phe Asn Leu
            260                 265                 270

Leu Met Thr Leu Arg Leu Trp Ser Ser
            275                 280

<210> SEQ ID NO 69
<211> LENGTH: 312
<212> TYPE: PRT
<213> ORGANISM: Homo sapiens

<400> SEQUENCE: 69

Met Ala Ser Leu Leu Phe Phe Cys Gly Ala Phe His Leu Leu Gly Thr
  1               5                  10                  15

Gly Ser Met Asp Ala Asp Val Thr Gln Thr Pro Arg Asn Arg Ile Thr
                 20                  25                  30

Lys Thr Gly Lys Arg Ile Met Leu Glu Cys Ser Gln Thr Lys Gly His
             35                  40                  45

Asp Arg Met Tyr Trp Tyr Arg Gln Asp Pro Gly Leu Gly Leu Arg Leu
 50                  55                  60

Ile Tyr Tyr Ser Phe Asp Val Lys Asp Ile Asn Lys Gly Glu Ile Ser
 65                  70                  75                  80

Asp Gly Tyr Ser Val Ser Arg Gln Ala Gln Ala Lys Phe Ser Leu Ser
                 85                  90                  95

Leu Glu Ser Ala Ile Pro Asn Gln Thr Ala Leu Tyr Phe Cys Ala Thr
                100                 105                 110

Ser Asp Thr Gly Thr Ser Arg Asn Glu Gln Phe Phe Gly Pro Gly Thr
            115                 120                 125
```

```
Arg Leu Thr Val Leu Glu Asp Leu Lys Asn Val Phe Pro Pro Glu Val
130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
290                 295                 300

Val Lys Arg Lys Asp Ser Arg Gly
305                 310

<210> SEQ ID NO 70
<211> LENGTH: 272
<212> TYPE: PRT
<213> ORGANISM: Homo sapiens

<400> SEQUENCE: 70

Met Lys Lys Leu Leu Ala Met Ile Leu Trp Leu Gln Leu Asp Arg Leu
1               5                   10                  15

Ser Gly Glu Leu Lys Val Glu Gln Asn Pro Leu Phe Leu Ser Met Gln
            20                  25                  30

Glu Gly Lys Asn Tyr Thr Ile Tyr Cys Asn Tyr Ser Thr Thr Ser Asp
        35                  40                  45

Arg Leu Tyr Trp Tyr Arg Gln Asp Pro Gly Lys Ser Leu Glu Ser Leu
    50                  55                  60

Phe Val Leu Leu Ser Asn Gly Ala Val Lys Gln Glu Gly Arg Leu Met
65                  70                  75                  80

Ala Ser Leu Asp Thr Lys Ala Arg Leu Ser Thr Leu His Ile Thr Ala
                85                  90                  95

Ala Val His Asp Leu Ser Ala Thr Tyr Phe Cys Ala Val Gly Phe Arg
            100                 105                 110

Gly Ser Thr Leu Gly Arg Leu Tyr Phe Gly Arg Gly Thr Gln Leu Thr
        115                 120                 125

Val Trp Pro Asp Ile Gln Lys Pro Asp Pro Ala Val Tyr Gln Leu Arg
130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190
```

```
Ala Val Ala Trp Ser Asn Lys Ser Asp Phe Ala Cys Ala Asn Ala Phe
            195                 200                 205

Asn Asn Ser Ile Ile Pro Glu Asp Thr Phe Pro Ser Pro Glu Ser
210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
                260                 265                 270

<210> SEQ ID NO 71
<211> LENGTH: 309
<212> TYPE: PRT
<213> ORGANISM: Homo sapiens

<400> SEQUENCE: 71

Met Gly Thr Arg Leu Leu Cys Trp Val Leu Cys Leu Leu Gly Ala
1               5                   10                  15

Gly Pro Val Asp Ala Gly Val Thr Gln Ser Pro Thr His Leu Ile Lys
                20                  25                  30

Thr Arg Gly Gln His Val Thr Leu Arg Cys Ser Pro Ile Ser Gly His
            35                  40                  45

Lys Ser Val Ser Trp Tyr Gln Gln Val Leu Gly Gln Gly Pro Gln Phe
50                  55                  60

Ile Phe Gln Tyr Tyr Glu Lys Glu Glu Arg Gly Arg Gly Asn Phe Pro
65                  70                  75                  80

Asp Arg Phe Ser Ala Arg Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
                100                 105                 110

Ser Trp Gly Gln Gly Asn Glu Lys Leu Phe Phe Gly Ser Gly Thr Gln
            115                 120                 125

Leu Ser Val Leu Glu Asp Leu Asn Lys Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
                180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
                260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
```

Lys Arg Lys Asp Phe
305

<210> SEQ ID NO 72
<211> LENGTH: 270
<212> TYPE: PRT
<213> ORGANISM: Homo sapiens

<400> SEQUENCE: 72

Met Leu Leu Ile Thr Ser Met Leu Val Leu Trp Met Gln Leu Ser Gln
1               5                   10                  15

Val Asn Gly Gln Gln Val Met Gln Ile Pro Gln Tyr Gln His Val Gln
            20                  25                  30

Glu Gly Glu Asp Phe Thr Thr Tyr Cys Asn Ser Ser Thr Thr Leu Ser
        35                  40                  45

Asn Ile Gln Trp Tyr Lys Gln Arg Pro Gly Gly His Pro Val Phe Leu
    50                  55                  60

Ile Gln Leu Val Lys Ser Gly Glu Val Lys Lys Gln Lys Arg Leu Thr
65                  70                  75                  80

Phe Gln Phe Gly Glu Ala Lys Lys Asn Ser Ser Leu His Ile Thr Ala
                85                  90                  95

Thr Gln Thr Thr Asp Val Gly Thr Tyr Phe Cys Ala Gly Ser Thr Gly
            100                 105                 110

Gly Gly Asn Lys Leu Thr Phe Gly Thr Gly Thr Gln Leu Lys Val Glu
        115                 120                 125

Leu Asn Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 73
<211> LENGTH: 309
<212> TYPE: PRT
<213> ORGANISM: Homo sapiens

<400> SEQUENCE: 73

Met Asp Ile Trp Leu Val Cys Trp Val Val Leu Gly Phe Leu Gly Thr
1               5                   10                  15

Asp His Thr Gly Ala Gly Val Ser Gln Ser Pro Arg Tyr Lys Val Ala
            20                  25                  30

Lys Arg Gly Gln Asp Val Ala Leu Arg Cys Asp Pro Ile Ser Gly His

```
                35                  40                  45
Val Ser Leu Phe Trp Tyr Gln Gln Ala Leu Gly Gln Gly Pro Glu Phe
 50                  55                  60

Leu Thr Tyr Phe Gln Asn Glu Ala Gln Leu Asp Lys Ser Gly Leu Pro
 65                  70                  75                  80

Ser Asp Arg Phe Phe Ala Glu Arg Pro Glu Gly Ser Val Ser Thr Leu
                 85                  90                  95

Lys Ile Gln Arg Thr Gln Gln Glu Asp Ser Ala Val Tyr Leu Cys Ala
                100                 105                 110

Ser Ser Asp Phe Tyr Glu Gln Tyr Phe Gly Pro Gly Thr Arg Leu Thr
                115                 120                 125

Val Thr Glu Asp Leu Lys Asn Val Phe Pro Pro Glu Val Ala Val Phe
130                 135                 140

Glu Pro Ser Glu Ala Glu Ile Ser His Thr Gln Lys Ala Thr Leu Val
145                 150                 155                 160

Cys Leu Ala Thr Gly Phe Tyr Pro Asp His Val Glu Leu Ser Trp Trp
                165                 170                 175

Val Asn Gly Lys Glu Val His Ser Gly Val Ser Thr Asp Pro Gln Pro
                180                 185                 190

Leu Lys Glu Gln Pro Ala Leu Asn Asp Ser Arg Tyr Cys Leu Ser Ser
                195                 200                 205

Arg Leu Arg Val Ser Ala Thr Phe Trp Gln Asn Pro Arg Asn His Phe
210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Glu Ser Tyr Gln Gln Gly Val
                260                 265                 270

Leu Ser Ala Thr Ile Leu Tyr Glu Ile Leu Leu Gly Lys Ala Thr Leu
                275                 280                 285

Tyr Ala Val Leu Val Ser Ala Leu Val Leu Met Ala Met Val Lys Arg
                290                 295                 300

Lys Asp Ser Arg Gly
305

<210> SEQ ID NO 74
<211> LENGTH: 272
<212> TYPE: PRT
<213> ORGANISM: Homo sapiens

<400> SEQUENCE: 74

Met Ala Gly Ile Arg Ala Leu Phe Met Tyr Leu Trp Leu Gln Leu Asp
  1               5                  10                  15

Trp Val Ser Arg Gly Glu Ser Val Gly Leu His Leu Pro Thr Leu Ser
                 20                  25                  30

Val Gln Glu Gly Asp Asn Ser Ile Ile Asn Cys Ala Tyr Ser Asn Ser
                 35                  40                  45

Ala Ser Asp Tyr Phe Ile Trp Tyr Lys Gln Glu Ser Gly Lys Gly Pro
 50                  55                  60

Gln Phe Ile Ile Asp Ile Arg Ser Asn Met Asp Lys Arg Gln Gly Gln
 65                  70                  75                  80

Arg Val Thr Val Leu Leu Asn Lys Thr Val Lys His Leu Ser Leu Gln
                 85                  90                  95
```

```
Ile Ala Ala Thr Gln Pro Gly Asp Ser Ala Val Tyr Phe Cys Ala Glu
                100                 105                 110

Thr Arg Gln Gly Gly Lys Leu Ile Phe Gly Gln Gly Thr Glu Leu Ser
                115                 120                 125

Val Lys Pro Asn Ile Gln Asn Pro Asp Pro Ala Val Tyr Gln Leu Arg
        130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
        180                 185                 190

Ala Val Ala Trp Ser Asn Lys Ser Asp Phe Ala Cys Ala Asn Ala Phe
            195                 200                 205

Asn Asn Ser Ile Ile Pro Glu Asp Thr Phe Phe Pro Ser Pro Glu Ser
        210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 75
<211> LENGTH: 309
<212> TYPE: PRT
<213> ORGANISM: Homo sapiens

<400> SEQUENCE: 75

Met Leu Leu Leu Leu Leu Leu Gly Pro Gly Ser Gly Leu Gly Ala
1               5                   10                  15

Val Val Ser Gln His Pro Ser Trp Val Ile Cys Lys Ser Gly Thr Ser
                20                  25                  30

Val Lys Ile Glu Cys Arg Ser Leu Asp Phe Gln Ala Thr Thr Met Phe
            35                  40                  45

Trp Tyr Arg Gln Phe Pro Lys Gln Ser Leu Met Leu Met Ala Thr Ser
50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Pro Pro
                100                 105                 110

Gly Val Thr Val Arg Ala Tyr Gly Tyr Thr Phe Gly Ser Gly Thr Arg
            115                 120                 125

Leu Thr Val Val Glu Asp Leu Asn Lys Val Phe Pro Pro Glu Val Ala
        130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205
```

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
            245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe
305

<210> SEQ ID NO 76
<211> LENGTH: 277
<212> TYPE: PRT
<213> ORGANISM: Homo sapiens

<400> SEQUENCE: 76

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
                20                  25                  30

Val Gln Glu Ala Glu Thr Val Thr Leu Ser Cys Thr Tyr Asp Thr Ser
            35                  40                  45

Glu Ser Asp Tyr Tyr Leu Phe Trp Tyr Lys Gln Pro Pro Ser Arg Gln
        50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Tyr Arg Asn Tyr Gly Gly Ser Gln Gly Asn Leu Ile Phe Gly Lys
        115                 120                 125

Gly Thr Lys Leu Ser Val Lys Pro Asn Ile Gln Asn Pro Asp Pro Ala
130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu

-continued

```
            260                 265                 270
Arg Leu Trp Ser Ser
        275

<210> SEQ ID NO 77
<211> LENGTH: 307
<212> TYPE: PRT
<213> ORGANISM: Homo sapiens

<400> SEQUENCE: 77

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Asn Arg Leu Asn Thr Glu Ala Phe Phe Gly Gln Gly Thr Arg Leu Thr
        115                 120                 125

Val Val Glu Asp Leu Asn Lys Val Phe Pro Pro Glu Val Ala Val Phe
    130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Phe
305

<210> SEQ ID NO 78
<211> LENGTH: 275
<212> TYPE: PRT
<213> ORGANISM: Homo sapiens
```

<400> SEQUENCE: 78

Met Thr Arg Val Ser Leu Leu Trp Ala Val Val Ser Thr Cys Leu
1               5                   10                  15

Glu Ser Gly Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Asn Asn Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Thr Ala Met Tyr Phe Cys
            100                 105                 110

Ala Phe Met Lys Asn Thr Gly Asn Gln Phe Tyr Phe Gly Thr Gly Thr
        115                 120                 125

Ser Leu Thr Val Ile Pro Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275

<210> SEQ ID NO 79
<211> LENGTH: 313
<212> TYPE: PRT
<213> ORGANISM: Homo sapiens

<400> SEQUENCE: 79

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
            85                  90                  95

Val Thr Ser Ala Gln Lys Asn Pro Thr Ala Phe Tyr Leu Cys Ala Ser
            100                 105                 110

Arg Arg Leu Asp Gly Leu Gly Ile Gly Glu Leu Phe Phe Gly Glu Gly
            115                 120                 125

Ser Arg Leu Thr Val Leu Glu Asp Leu Lys Asn Val Phe Pro Pro Glu
        130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
            245                 250                 255

Ala Glu Ala Trp Gly Arg Ala Asp Cys Gly Phe Thr Ser Glu Ser Tyr
            260                 265                 270

Gln Gln Gly Val Leu Ser Ala Thr Ile Leu Tyr Glu Ile Leu Leu Gly
            275                 280                 285

Lys Ala Thr Leu Tyr Ala Val Leu Val Ser Ala Leu Val Leu Met Ala
        290                 295                 300

Met Val Lys Arg Lys Asp Ser Arg Gly
305                 310

<210> SEQ ID NO 80
<211> LENGTH: 273
<212> TYPE: PRT
<213> ORGANISM: Homo sapiens

<400> SEQUENCE: 80

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Arg Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Leu
            100                 105                 110

Ser Gly Gly Ser Asn Tyr Lys Leu Thr Phe Gly Lys Gly Thr Leu Leu
        115                 120                 125

Thr Val Asn Pro Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
            165                 170                 175

Thr Asp Lys Thr Val Leu Asp Met Arg Ser Met Asp Phe Lys Ser Asn
        180                 185                 190

Ser Ala Val Ala Trp Ser Asn Lys Ser Asp Phe Ala Cys Ala Asn Ala
            195                 200                 205

Phe Asn Asn Ser Ile Ile Pro Glu Asp Thr Phe Phe Pro Ser Pro Glu
210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
            245                 250                 255

Leu Lys Val Ala Gly Phe Asn Leu Leu Met Thr Leu Arg Leu Trp Ser
            260                 265                 270

Ser

<210> SEQ ID NO 81
<211> LENGTH: 309
<212> TYPE: PRT
<213> ORGANISM: Homo sapiens

<400> SEQUENCE: 81

Met Val Ser Arg Leu Leu Ser Leu Val Ser Leu Cys Leu Leu Gly Ala
1               5                   10                  15

Lys His Ile Glu Ala Gly Val Thr Gln Phe Pro Ser His Ser Val Ile
            20                  25                  30

Glu Lys Gly Gln Thr Val Thr Leu Arg Cys Asp Pro Ile Ser Gly His
        35                  40                  45

Asp Asn Leu Tyr Trp Tyr Arg Arg Val Met Gly Lys Glu Ile Lys Phe
50                  55                  60

Leu Leu His Phe Val Lys Glu Ser Lys Gln Asp Glu Ser Gly Met Pro
65                  70                  75                  80

Asn Asn Arg Phe Leu Ala Glu Arg Thr Gly Gly Thr Tyr Ser Thr Leu
            85                  90                  95

Lys Val Gln Pro Ala Glu Leu Glu Asp Ser Gly Val Tyr Phe Cys Ala
        100                 105                 110

Ser Ser Gln Gln Glu Asn Thr Glu Ala Phe Phe Gly Gln Gly Thr Arg
    115                 120                 125

Leu Thr Val Val Glu Asp Leu Asn Lys Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
            165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

```
Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
290                 295                 300

Lys Arg Lys Asp Phe
305

<210> SEQ ID NO 82
<211> LENGTH: 275
<212> TYPE: PRT
<213> ORGANISM: Homo sapiens

<400> SEQUENCE: 82

Met Ala Met Leu Leu Glu Leu Ile Pro Leu Gly Ile His Phe Val
1               5                   10                  15

Leu Arg Thr Ala Arg Ala Gln Ser Val Thr Gln Pro Asp Ile His Ile
            20                  25                  30

Thr Val Ser Glu Gly Ala Ser Leu Glu Leu Arg Cys Asn Tyr Ser Tyr
        35                  40                  45

Gly Ala Thr Pro Tyr Leu Phe Trp Tyr Val Gln Ser Pro Gly Gln Gly
    50                  55                  60

Leu Gln Leu Leu Leu Lys Tyr Phe Ser Gly Asp Thr Leu Val Gln Gly
65                  70                  75                  80

Ile Lys Gly Phe Glu Ala Glu Phe Lys Arg Ser Gln Ser Ser Phe Asn
                85                  90                  95

Leu Arg Lys Pro Ser Val His Trp Ser Asp Ala Ala Glu Tyr Phe Cys
            100                 105                 110

Ala Val Gly Ala Gln Gly Ala Gln Lys Leu Val Phe Gly Gln Gly Thr
        115                 120                 125

Arg Leu Thr Ile Asn Pro Asn Ile Gln Asn Pro Asp Pro Ala Val Tyr
130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275
```

<210> SEQ ID NO 83
<211> LENGTH: 312
<212> TYPE: PRT
<213> ORGANISM: Homo sapiens

<400> SEQUENCE: 83

Met Ser Leu Gly Leu Leu Cys Cys Val Ala Phe Ser Leu Leu Trp Ala
1               5                   10                  15

Ser Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Asn Ser Met Tyr Trp Tyr Arg Gln Asp Pro Gly Met Gly Leu Arg Leu
    50                  55                  60

Ile Tyr Tyr Ser Ala Ser Glu Gly Thr Thr Asp Lys Gly Glu Val Pro
65                  70                  75                  80

Asn Gly Tyr Asn Val Ser Arg Leu Asn Lys Arg Glu Phe Ser Leu Arg
                85                  90                  95

Leu Glu Ser Ala Ala Pro Ser Gln Thr Ser Val Tyr Phe Cys Ala Ser
            100                 105                 110

Ser Glu Ala Gly Gly Ser Ser Phe Glu Gln Tyr Phe Gly Pro Gly Thr
        115                 120                 125

Arg Leu Thr Val Thr Glu Asp Leu Lys Asn Val Phe Pro Pro Glu Val
130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310

<210> SEQ ID NO 84
<211> LENGTH: 269
<212> TYPE: PRT
<213> ORGANISM: Homo sapiens

<400> SEQUENCE: 84

Met Asn Tyr Ser Pro Gly Leu Val Ser Leu Ile Leu Leu Leu Leu Gly
1               5                   10                  15

Arg Thr Arg Gly Asn Ser Val Thr Gln Met Glu Gly Pro Val Thr Leu

```
                   20                  25                  30
Ser Glu Glu Ala Phe Leu Thr Ile Asn Cys Thr Tyr Thr Ala Thr Gly
            35                  40                  45

Tyr Pro Ser Leu Phe Trp Tyr Val Gln Tyr Pro Gly Glu Gly Leu Gln
        50                  55                  60

Leu Leu Leu Lys Ala Thr Lys Ala Asp Asp Lys Gly Ser Asn Lys Gly
65                  70                  75                  80

Phe Glu Ala Thr Tyr Arg Lys Glu Thr Thr Ser Phe His Leu Glu Lys
                85                  90                  95

Gly Ser Val Gln Val Ser Asp Ser Ala Val Tyr Phe Cys Ala Leu Gly
            100                 105                 110

Arg Gly Lys Leu Ile Phe Gly Gln Gly Thr Glu Leu Ser Val Lys Pro
        115                 120                 125

Asn Ile Gln Asn Pro Asp Pro Ala Val Tyr Gln Leu Arg Asp Ser Lys
        130                 135                 140

Ser Ser Asp Lys Ser Val Cys Leu Phe Thr Asp Phe Asp Ser Gln Thr
145                 150                 155                 160

Asn Val Ser Gln Ser Lys Asp Ser Asp Val Tyr Ile Thr Asp Lys Thr
                165                 170                 175

Val Leu Asp Met Arg Ser Met Asp Phe Lys Ser Asn Ser Ala Val Ala
            180                 185                 190

Trp Ser Asn Lys Ser Asp Phe Ala Cys Ala Asn Ala Phe Asn Asn Ser
        195                 200                 205

Ile Ile Pro Glu Asp Thr Phe Phe Pro Ser Pro Glu Ser Ser Cys Asp
        210                 215                 220

Val Lys Leu Val Glu Lys Ser Phe Glu Thr Asp Thr Asn Leu Asn Phe
225                 230                 235                 240

Gln Asn Leu Ser Val Ile Gly Phe Arg Ile Leu Leu Leu Lys Val Ala
                245                 250                 255

Gly Phe Asn Leu Leu Met Thr Leu Arg Leu Trp Ser Ser
            260                 265

<210> SEQ ID NO 85
<211> LENGTH: 305
<212> TYPE: PRT
<213> ORGANISM: Homo sapiens

<400> SEQUENCE: 85

Met Leu Leu Leu Leu Leu Leu Gly Pro Gly Ser Gly Leu Gly Ala
1               5                   10                  15

Val Val Ser Gln His Pro Ser Trp Val Ile Cys Lys Ser Gly Thr Ser
            20                  25                  30

Val Lys Ile Glu Cys Arg Ser Leu Asp Phe Gln Ala Thr Thr Met Phe
        35                  40                  45

Trp Tyr Arg Gln Phe Pro Lys Gln Ser Leu Met Leu Met Ala Thr Ser
        50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Val Asp
            100                 105                 110

Ser Asp Leu Glu Ala Phe Phe Gly Gln Gly Thr Arg Leu Thr Val Val
        115                 120                 125
```

```
Glu Asp Leu Asn Lys Val Phe Pro Pro Val Ala Val Phe Glu Pro
130                 135                 140

Ser Glu Ala Glu Ile Ser His Thr Gln Lys Ala Thr Leu Val Cys Leu
145                 150                 155                 160

Ala Thr Gly Phe Phe Pro Asp His Val Glu Leu Ser Trp Trp Val Asn
                165                 170                 175

Gly Lys Glu Val His Ser Gly Val Ser Thr Asp Pro Gln Pro Leu Lys
                180                 185                 190

Glu Gln Pro Ala Leu Asn Asp Ser Arg Tyr Cys Leu Ser Ser Arg Leu
                195                 200                 205

Arg Val Ser Ala Thr Phe Trp Gln Asn Pro Arg Asn His Phe Arg Cys
210                 215                 220

Gln Val Gln Phe Tyr Gly Leu Ser Glu Asn Asp Glu Trp Thr Gln Asp
225                 230                 235                 240

Arg Ala Lys Pro Val Thr Gln Ile Val Ser Ala Glu Ala Trp Gly Arg
                245                 250                 255

Ala Asp Cys Gly Phe Thr Ser Val Ser Tyr Gln Gln Gly Val Leu Ser
                260                 265                 270

Ala Thr Ile Leu Tyr Glu Ile Leu Leu Gly Lys Ala Thr Leu Tyr Ala
                275                 280                 285

Val Leu Val Ser Ala Leu Val Leu Met Ala Met Val Lys Arg Lys Asp
290                 295                 300

Phe
305

<210> SEQ ID NO 86
<211> LENGTH: 277
<212> TYPE: PRT
<213> ORGANISM: Homo sapiens

<400> SEQUENCE: 86

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
                20                  25                  30

Val Gln Glu Ala Glu Thr Val Thr Leu Ser Cys Thr Tyr Asp Thr Ser
                35                  40                  45

Glu Ser Asp Tyr Tyr Leu Phe Trp Tyr Lys Gln Pro Pro Ser Arg Gln
50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
                100                 105                 110

Ala Tyr Arg Ser Ala Val Tyr Asn Thr Asp Lys Leu Ile Phe Gly Thr
                115                 120                 125

Gly Thr Arg Leu Gln Val Phe Pro Asn Ile Gln Asn Pro Asp Pro Ala
130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
                180                 185                 190
```

```
Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
                260                 265                 270

Arg Leu Trp Ser Ser
            275

<210> SEQ ID NO 87
<211> LENGTH: 310
<212> TYPE: PRT
<213> ORGANISM: Homo sapiens

<400> SEQUENCE: 87

Met Gly Ser Arg Leu Leu Cys Trp Val Leu Leu Cys Leu Leu Gly Ala
1               5                   10                  15

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
        35                  40                  45

Arg Ser Val Ser Trp Tyr Gln Gln Thr Pro Gly Gln Gly Leu Gln Phe
    50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95

Val Ser Thr Leu Glu Leu Gly Asp Ser Ala Leu Tyr Leu Cys Ala Ser
            100                 105                 110

Ser Phe Ser Ser Tyr Asn Glu Gln Phe Phe Gly Pro Gly Thr Arg Leu
        115                 120                 125

Thr Val Leu Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
```

```
                275                 280                 285
Leu Tyr Ala Val Leu Val Ser Ala Leu Val Leu Met Ala Met Val Lys
        290                 295                 300

Arg Lys Asp Ser Arg Gly
305                 310

<210> SEQ ID NO 88
<211> LENGTH: 274
<212> TYPE: PRT
<213> ORGANISM: Homo sapiens

<400> SEQUENCE: 88

Met Leu Leu Leu Leu Ile Pro Val Leu Gly Met Ile Phe Ala Leu Arg
1               5                   10                  15

Asp Ala Arg Ala Gln Ser Val Ser Gln His Asn His His Val Ile Leu
            20                  25                  30

Ser Glu Ala Ala Ser Leu Glu Leu Gly Cys Asn Tyr Ser Tyr Gly Gly
        35                  40                  45

Thr Val Asn Leu Phe Trp Tyr Val Gln Tyr Pro Gly Gln His Leu Gln
    50                  55                  60

Leu Leu Leu Lys Tyr Phe Ser Gly Asp Pro Leu Val Lys Gly Ile Lys
65                  70                  75                  80

Gly Phe Glu Ala Glu Phe Ile Lys Ser Lys Phe Ser Phe Asn Leu Arg
                85                  90                  95

Lys Pro Ser Val Gln Trp Ser Asp Thr Ala Glu Tyr Phe Cys Ala Val
            100                 105                 110

Asn Ala Arg Asp Asn Ala Gly Lys Ser Thr Phe Gly Asp Gly Thr Thr
        115                 120                 125

Leu Thr Val Lys Pro Asn Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 89
<211> LENGTH: 311
<212> TYPE: PRT
<213> ORGANISM: Homo sapiens

<400> SEQUENCE: 89

Met Gly Ser Arg Leu Leu Cys Trp Val Leu Leu Cys Leu Leu Gly Ala
1               5                   10                  15
```

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
        35                  40                  45

Arg Ser Val Ser Trp Tyr Gln Gln Thr Pro Gly Gln Gly Leu Gln Phe
50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95

Val Ser Thr Leu Glu Leu Gly Asp Ser Ala Leu Tyr Leu Cys Ala Ser
            100                 105                 110

Arg Gly Glu Pro Ser Ser Tyr Glu Gln Tyr Phe Gly Pro Gly Thr Arg
        115                 120                 125

Leu Thr Val Thr Glu Asp Leu Lys Asn Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
290                 295                 300

Lys Arg Lys Asp Ser Arg Gly
305                 310

<210> SEQ ID NO 90
<211> LENGTH: 266
<212> TYPE: PRT
<213> ORGANISM: Homo sapiens

<400> SEQUENCE: 90

Met Lys Lys Leu Leu Ala Met Ile Leu Trp Leu Gln Leu Asp Arg Leu
1               5                   10                  15

Ser Gly Glu Leu Lys Val Glu Gln Asn Pro Leu Phe Leu Ser Met Gln
            20                  25                  30

Glu Gly Lys Asn Tyr Thr Ile Tyr Cys Asn Tyr Ser Thr Thr Ser Asp
        35                  40                  45

Arg Leu Tyr Trp Tyr Arg Gln Asp Pro Gly Lys Ser Leu Glu Ser Leu
50                  55                  60

Phe Val Leu Leu Ser Asn Gly Ala Val Lys Gln Glu Gly Arg Leu Met

```
                65                  70                  75                  80
Ala Ser Leu Asp Thr Lys Ala Arg Leu Ser Thr Leu His Ile Thr Ala
                    85                  90                  95

Ala Val His Asp Leu Ser Ala Thr Tyr Phe Cys Ala Val Asp Asn Glu
                100                 105                 110

Phe Tyr Phe Gly Thr Gly Thr Ser Leu Thr Val Ile Pro Asn Ile Gln
                115                 120                 125

Asn Pro Asp Pro Ala Val Tyr Gln Leu Arg Asp Ser Lys Ser Ser Asp
            130                 135                 140

Lys Ser Val Cys Leu Phe Thr Asp Phe Asp Ser Gln Thr Asn Val Ser
145                 150                 155                 160

Gln Ser Lys Asp Ser Asp Val Tyr Ile Thr Asp Lys Thr Val Leu Asp
                165                 170                 175

Met Arg Ser Met Asp Phe Lys Ser Asn Ser Ala Val Ala Trp Ser Asn
                180                 185                 190

Lys Ser Asp Phe Ala Cys Ala Asn Ala Phe Asn Asn Ser Ile Ile Pro
            195                 200                 205

Glu Asp Thr Phe Phe Pro Ser Pro Glu Ser Ser Cys Asp Val Lys Leu
        210                 215                 220

Val Glu Lys Ser Phe Glu Thr Asp Thr Asn Leu Asn Phe Gln Asn Leu
225                 230                 235                 240

Ser Val Ile Gly Phe Arg Ile Leu Leu Leu Lys Val Ala Gly Phe Asn
                245                 250                 255

Leu Leu Met Thr Leu Arg Leu Trp Ser Ser
            260                 265

<210> SEQ ID NO 91
<211> LENGTH: 312
<212> TYPE: PRT
<213> ORGANISM: Homo sapiens

<400> SEQUENCE: 91

Met Gly Thr Arg Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
                20                  25                  30

Lys Arg Gly Gln Asn Val Thr Phe Arg Cys Asp Pro Ile Ser Glu His
            35                  40                  45

Asn Arg Leu Tyr Trp Tyr Arg Gln Thr Leu Gly Gln Gly Pro Glu Phe
        50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
                100                 105                 110

Ser Ser Leu Leu Gly Ala Gly Asn Ile Gln Tyr Phe Gly Ala Gly Thr
            115                 120                 125

Arg Leu Ser Val Leu Glu Asp Leu Lys Asn Val Phe Pro Pro Glu Val
        130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175
```

-continued

Ser Trp Trp Val Asn Gly Lys Glu Val His Ser Gly Val Ser Thr Asp
              180                 185                 190

Pro Gln Pro Leu Lys Glu Gln Pro Ala Leu Asn Asp Ser Arg Tyr Cys
          195                 200                 205

Leu Ser Ser Arg Leu Arg Val Ser Ala Thr Phe Trp Gln Asn Pro Arg
      210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                  245                 250                 255

Glu Ala Trp Gly Arg Ala Asp Cys Gly Phe Thr Ser Glu Ser Tyr Gln
              260                 265                 270

Gln Gly Val Leu Ser Ala Thr Ile Leu Tyr Glu Ile Leu Leu Gly Lys
          275                 280                 285

Ala Thr Leu Tyr Ala Val Leu Val Ser Ala Leu Val Leu Met Ala Met
      290                 295                 300

Val Lys Arg Lys Asp Ser Arg Gly
305                 310

<210> SEQ ID NO 92
<211> LENGTH: 273
<212> TYPE: PRT
<213> ORGANISM: Homo sapiens

<400> SEQUENCE: 92

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
              20                  25                  30

Leu Ser Val Pro Glu Gly Ala Ile Val Ser Leu Asn Cys Thr Tyr Ser
          35                  40                  45

Asn Ser Ala Phe Gln Tyr Phe Met Trp Tyr Arg Gln Tyr Ser Arg Lys
      50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                  85                  90                  95

Phe Ile Arg Asp Ser Gln Pro Ser Asp Ser Ala Thr Tyr Leu Cys Ala
              100                 105                 110

Leu Tyr Thr Gly Gly Phe Lys Thr Ile Phe Gly Ala Gly Thr Arg Leu
          115                 120                 125

Phe Val Lys Ala Asn Ile Gln Asn Pro Asp Pro Ala Val Tyr Gln Leu
      130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                  165                 170                 175

Thr Asp Lys Thr Val Leu Asp Met Arg Ser Met Asp Phe Lys Ser Asn
              180                 185                 190

Ser Ala Val Ala Trp Ser Asn Lys Ser Asp Phe Ala Cys Ala Asn Ala
          195                 200                 205

Phe Asn Asn Ser Ile Ile Pro Glu Asp Thr Phe Phe Pro Ser Pro Glu
      210                 215                 220

Ser Ser Cys Asp Val Lys Leu Val Glu Lys Ser Phe Glu Thr Asp Thr
225                 230                 235                 240

```
Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 93
<211> LENGTH: 309
<212> TYPE: PRT
<213> ORGANISM: Homo sapiens

<400> SEQUENCE: 93

Met Gly Ser Arg Leu Leu Cys Trp Val Leu Leu Cys Leu Leu Gly Ala
1               5                   10                  15

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
        35                  40                  45

Arg Ser Val Ser Trp Tyr Gln Gln Thr Pro Gly Gln Gly Leu Gln Phe
    50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95

Val Ser Thr Leu Glu Leu Gly Asp Ser Ala Leu Tyr Leu Cys Ala Ser
            100                 105                 110

Ser Phe Met Gly Thr Glu Gln Tyr Phe Gly Pro Gly Thr Arg Leu Thr
        115                 120                 125

Val Thr Glu Asp Leu Lys Asn Val Phe Pro Pro Glu Val Ala Val Phe
    130                 135                 140

Glu Pro Ser Glu Ala Glu Ile Ser His Thr Gln Lys Ala Thr Leu Val
145                 150                 155                 160

Cys Leu Ala Thr Gly Phe Tyr Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Glu Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Ser Arg Gly
305

<210> SEQ ID NO 94
```

```
<211> LENGTH: 276
<212> TYPE: PRT
<213> ORGANISM: Homo sapiens

<400> SEQUENCE: 94

Met Leu Leu Glu Leu Ile Pro Leu Leu Gly Ile His Phe Val Leu Arg
1               5                   10                  15

Thr Ala Arg Ala Gln Ser Val Thr Gln Pro Asp Ile His Ile Thr Val
            20                  25                  30

Ser Glu Gly Ala Ser Leu Glu Leu Arg Cys Asn Tyr Ser Tyr Gly Ala
        35                  40                  45

Thr Pro Tyr Leu Phe Trp Tyr Val Gln Ser Pro Gly Gln Gly Leu Gln
    50                  55                  60

Leu Leu Leu Lys Tyr Phe Ser Gly Asp Thr Leu Val Gln Gly Ile Lys
65                  70                  75                  80

Gly Phe Glu Ala Glu Phe Lys Arg Ser Gln Ser Ser Phe Asn Leu Arg
                85                  90                  95

Lys Pro Ser Val His Trp Ser Asp Ala Ala Glu Tyr Phe Cys Ala Val
            100                 105                 110

Gly Ala Phe Thr Arg Gly Gly Ser Glu Lys Leu Val Phe Gly Lys Gly
        115                 120                 125

Met Lys Leu Thr Val Asn Pro Tyr Ile Gln Asn Pro Asp Pro Ala Val
    130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Met Thr Leu Arg
            260                 265                 270

Leu Trp Ser Ser
        275

<210> SEQ ID NO 95
<211> LENGTH: 310
<212> TYPE: PRT
<213> ORGANISM: Homo sapiens

<400> SEQUENCE: 95

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60
```

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
            85                  90                  95

Val Thr Ser Ala Gln Lys Asn Pro Thr Ala Phe Tyr Leu Cys Ala Thr
            100                 105                 110

Gly Ser Tyr Val Gly Tyr Glu Gln Tyr Phe Gly Pro Gly Thr Arg Leu
            115                 120                 125

Thr Val Thr Glu Asp Leu Lys Asn Val Phe Pro Pro Glu Val Ala Val
130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
            165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
            195                 200                 205

Ser Arg Leu Arg Val Ser Ala Thr Phe Trp Gln Asn Pro Arg Asn His
210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
            245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
290                 295                 300

Arg Lys Asp Ser Arg Gly
305                 310

<210> SEQ ID NO 96
<211> LENGTH: 279
<212> TYPE: PRT
<213> ORGANISM: Homo sapiens

<400> SEQUENCE: 96

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
            35                  40                  45

Asp Pro Ser Tyr Gly Leu Phe Trp Tyr Lys Gln Pro Ser Ser Gly Glu
        50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
            85                  90                  95

Leu Val Ile Ser Ala Ser Gln Leu Gly Asp Ser Ala Met Tyr Phe Cys
            100                 105                 110

Ala Met Arg Glu Gly Leu Ala Lys Thr Ser Tyr Asp Lys Val Ile Phe

```
            115                 120                 125
Gly Pro Gly Thr Ser Leu Ser Val Ile Pro Asn Ile Gln Asn Pro Asp
    130                 135                 140

Pro Ala Val Tyr Gln Leu Arg Asp Ser Lys Ser Ser Asp Lys Ser Val
145                 150                 155                 160

Cys Leu Phe Thr Asp Phe Asp Ser Gln Thr Asn Val Ser Gln Ser Lys
                165                 170                 175

Asp Ser Asp Val Tyr Ile Thr Asp Lys Thr Val Leu Asp Met Arg Ser
            180                 185                 190

Met Asp Phe Lys Ser Asn Ser Ala Val Ala Trp Ser Asn Lys Ser Asp
        195                 200                 205

Phe Ala Cys Ala Asn Ala Phe Asn Asn Ser Ile Ile Pro Glu Asp Thr
    210                 215                 220

Phe Phe Pro Ser Pro Glu Ser Ser Cys Asp Val Lys Leu Val Glu Lys
225                 230                 235                 240

Ser Phe Glu Thr Asp Thr Asn Leu Asn Phe Gln Asn Leu Ser Val Ile
                245                 250                 255

Gly Phe Arg Ile Leu Leu Leu Lys Val Ala Gly Phe Asn Leu Leu Met
            260                 265                 270

Thr Leu Arg Leu Trp Ser Ser
        275

<210> SEQ ID NO 97
<211> LENGTH: 310
<212> TYPE: PRT
<213> ORGANISM: Homo sapiens

<400> SEQUENCE: 97

Met Leu Leu Leu Leu Leu Leu Gly Pro Gly Ser Gly Leu Gly Ala
1               5                   10                  15

Val Val Ser Gln His Pro Ser Trp Val Ile Cys Lys Ser Gly Thr Ser
            20                  25                  30

Val Lys Ile Glu Cys Arg Ser Leu Asp Phe Gln Ala Thr Thr Met Phe
        35                  40                  45

Trp Tyr Arg Gln Phe Pro Lys Gln Ser Leu Met Leu Met Ala Thr Ser
    50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Pro Gly
            100                 105                 110

Thr Gly His Ser Ala Gly Glu Leu Phe Phe Gly Glu Gly Ser Arg Leu
        115                 120                 125

Thr Val Leu Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205
```

```
Ser Arg Leu Arg Val Ser Ala Thr Phe Trp Gln Asn Pro Arg Asn His
    210                 215                 220
Phe Arg Cys Gln Val Gln Phe Tyr Gly Leu Ser Glu Asn Asp Glu Trp
225                 230                 235                 240
Thr Gln Asp Arg Ala Lys Pro Val Thr Gln Ile Val Ser Ala Glu Ala
                245                 250                 255
Trp Gly Arg Ala Asp Cys Gly Phe Thr Ser Glu Ser Tyr Gln Gln Gly
                260                 265                 270
Val Leu Ser Ala Thr Ile Leu Tyr Glu Ile Leu Leu Gly Lys Ala Thr
            275                 280                 285
Leu Tyr Ala Val Leu Val Ser Ala Leu Val Leu Met Ala Met Val Lys
    290                 295                 300
Arg Lys Asp Ser Arg Gly
305             310

<210> SEQ ID NO 98
<211> LENGTH: 273
<212> TYPE: PRT
<213> ORGANISM: Homo sapiens

<400> SEQUENCE: 98

Met Leu Leu Leu Val Pro Ala Phe Gln Val Ile Phe Thr Leu Gly
1               5                   10                  15

Gly Thr Arg Ala Gln Ser Val Thr Gln Leu Asp Ser Gln Val Pro Val
                20                  25                  30

Phe Glu Glu Ala Pro Val Glu Leu Arg Cys Asn Tyr Ser Ser Ser Val
                35                  40                  45

Ser Val Tyr Leu Phe Trp Tyr Val Gln Tyr Pro Asn Gln Gly Leu Gln
    50                  55                  60

Leu Leu Leu Lys Tyr Leu Ser Gly Ser Thr Leu Val Lys Gly Ile Asn
65                  70                  75                  80

Gly Phe Glu Ala Glu Phe Asn Lys Ser Gln Thr Ser Phe His Leu Arg
                85                  90                  95

Lys Pro Ser Val His Ile Ser Asp Thr Ala Glu Tyr Phe Cys Ala Val
                100                 105                 110

Gly Pro Asn Asn Phe Asn Lys Phe Tyr Phe Gly Ser Gly Thr Lys Leu
            115                 120                 125

Asn Val Lys Pro Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
                180                 185                 190

Ser Ala Val Ala Trp Ser Asn Lys Ser Asp Phe Ala Cys Ala Asn Ala
            195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270
```

Ser

<210> SEQ ID NO 99
<211> LENGTH: 311
<212> TYPE: PRT
<213> ORGANISM: Homo sapiens

<400> SEQUENCE: 99

```
Met Asp Ile Trp Leu Val Cys Trp Ala Ile Phe Ser Leu Leu Lys Ala
1               5                   10                  15
Gly Leu Thr Glu Pro Glu Val Thr Gln Thr Pro Ser His Gln Val Thr
            20                  25                  30
Gln Met Gly Gln Glu Val Ile Leu Arg Cys Val Pro Ile Ser Asn His
        35                  40                  45
Leu Tyr Phe Tyr Trp Tyr Arg Gln Ile Leu Gly Gln Lys Val Glu Phe
    50                  55                  60
Leu Val Ser Phe Tyr Asn Asn Glu Ile Ser Glu Lys Ser Glu Ile Phe
65                  70                  75                  80
Asp Asp Gln Phe Ser Val Glu Arg Pro Asp Gly Ser Asn Phe Thr Leu
                85                  90                  95
Lys Ile Arg Ser Thr Lys Leu Glu Asp Ser Ala Met Tyr Phe Cys Ala
            100                 105                 110
Ser Ser Pro Val Gly Gly Tyr Asn Ser Pro Leu His Phe Gly Asn Gly
        115                 120                 125
Thr Arg Leu Thr Val Thr Glu Asp Leu Asn Lys Val Phe Pro Pro Glu
    130                 135                 140
Val Ala Val Phe Glu Pro Ser Glu Ala Glu Ile Ser His Thr Gln Lys
145                 150                 155                 160
Ala Thr Leu Val Cys Leu Ala Thr Gly Phe Phe Pro Asp His Val Glu
                165                 170                 175
Leu Ser Trp Trp Val Asn Gly Lys Glu Val His Ser Gly Val Ser Thr
            180                 185                 190
Asp Pro Gln Pro Leu Lys Glu Gln Pro Ala Leu Asn Asp Ser Arg Tyr
        195                 200                 205
Cys Leu Ser Ser Arg Leu Arg Val Ser Ala Thr Phe Trp Gln Asn Pro
    210                 215                 220
Arg Asn His Phe Arg Cys Gln Val Gln Phe Tyr Gly Leu Ser Glu Asn
225                 230                 235                 240
Asp Glu Trp Thr Gln Asp Arg Ala Lys Pro Val Thr Gln Ile Val Ser
                245                 250                 255
Ala Glu Ala Trp Gly Arg Ala Asp Cys Gly Phe Thr Ser Val Ser Tyr
            260                 265                 270
Gln Gln Gly Val Leu Ser Ala Thr Ile Leu Tyr Glu Ile Leu Leu Gly
        275                 280                 285
Lys Ala Thr Leu Tyr Ala Val Leu Val Ser Ala Leu Val Leu Met Ala
    290                 295                 300
Met Val Lys Arg Lys Asp Phe
305                 310
```

<210> SEQ ID NO 100
<211> LENGTH: 276
<212> TYPE: PRT
<213> ORGANISM: Homo sapiens

<400> SEQUENCE: 100

```
Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Tyr Arg Ser Tyr Asn Ala Gly Asn Met Leu Thr Phe Gly Gly Gly
        115                 120                 125

Thr Arg Leu Met Val Lys Pro His Ile Gln Asn Pro Asp Pro Ala Val
130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
        275

<210> SEQ ID NO 101
<211> LENGTH: 312
<212> TYPE: PRT
<213> ORGANISM: Homo sapiens

<400> SEQUENCE: 101

Met Gly Ser Arg Leu Leu Cys Leu Val Leu Leu Cys Leu Leu Gly Ala
1               5                   10                  15

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
        35                  40                  45

Arg Ser Val Ser Trp Tyr Gln Gln Thr Pro Gly Gln Gly Leu Gln Phe
    50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95
```

Val Ser Thr Leu Glu Leu Gly Asp Ser Ala Leu Tyr Leu Cys Ala Ser
            100                 105                 110

Ser Asp Thr Ser Gly Gly Gly Glu Gln Phe Phe Gly Pro Gly Thr
        115                 120                 125

Arg Leu Thr Val Leu Glu Asp Leu Lys Asn Val Phe Pro Pro Glu Val
130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310

<210> SEQ ID NO 102
<211> LENGTH: 274
<212> TYPE: PRT
<213> ORGANISM: Homo sapiens

<400> SEQUENCE: 102

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
                20                  25                  30

Val Gln Glu Ala Glu Thr Val Thr Leu Ser Cys Thr Tyr Asp Thr Ser
            35                  40                  45

Glu Ser Asp Tyr Tyr Leu Phe Trp Tyr Lys Gln Pro Pro Ser Arg Gln
        50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Tyr Arg Ser Ala Gly Leu Leu Thr Phe Gly Gly Gly Thr Arg
        115                 120                 125

Leu Met Val Lys Pro His Ile Gln Asn Pro Asp Pro Ala Val Tyr Gln
    130                 135                 140

Leu Arg Asp Ser Lys Ser Ser Asp Lys Ser Val Cys Leu Phe Thr Asp

```
                145                 150                 155                 160
Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
                180                 185                 190

Asn Ser Ala Val Ala Trp Ser Asn Lys Ser Asp Phe Ala Cys Ala Asn
                195                 200                 205

Ala Phe Asn Asn Ser Ile Ile Pro Glu Asp Thr Phe Phe Pro Ser Pro
                210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
                260                 265                 270

Ser Ser

<210> SEQ ID NO 103
<211> LENGTH: 316
<212> TYPE: PRT
<213> ORGANISM: Homo sapiens

<400> SEQUENCE: 103

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
                20                  25                  30

Lys Glu Gly Gln Asn Val Thr Leu Ser Cys Glu Gln Asn Leu Asn His
            35                  40                  45

Asp Ala Met Tyr Trp Tyr Arg Gln Asp Pro Gly Gln Gly Leu Arg Leu
        50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
                100                 105                 110

Ser Lys Ala Pro Gly Gln Gly Asn Thr Gln Gly Trp Glu Gln Tyr Phe
            115                 120                 125

Gly Pro Gly Thr Arg Leu Thr Val Thr Glu Asp Leu Lys Asn Val Phe
        130                 135                 140

Pro Pro Glu Val Ala Val Phe Glu Pro Ser Glu Ala Glu Ile Ser His
145                 150                 155                 160

Thr Gln Lys Ala Thr Leu Val Cys Leu Ala Thr Gly Phe Tyr Pro Asp
                165                 170                 175

His Val Glu Leu Ser Trp Trp Val Asn Gly Lys Glu Val His Ser Gly
                180                 185                 190

Val Ser Thr Asp Pro Gln Pro Leu Lys Glu Gln Pro Ala Leu Asn Asp
            195                 200                 205

Ser Arg Tyr Cys Leu Ser Ser Arg Leu Arg Val Ser Ala Thr Phe Trp
        210                 215                 220

Gln Asn Pro Arg Asn His Phe Arg Cys Gln Val Gln Phe Tyr Gly Leu
225                 230                 235                 240

Ser Glu Asn Asp Glu Trp Thr Gln Asp Arg Ala Lys Pro Val Thr Gln
```

```
                       245                 250                 255
Ile Val Ser Ala Glu Ala Trp Gly Arg Ala Asp Cys Gly Phe Thr Ser
            260                 265                 270

Glu Ser Tyr Gln Gln Gly Val Leu Ser Ala Thr Ile Leu Tyr Glu Ile
            275                 280                 285

Leu Leu Gly Lys Ala Thr Leu Tyr Ala Val Leu Val Ser Ala Leu Val
            290                 295                 300

Leu Met Ala Met Val Lys Arg Lys Asp Ser Arg Gly
305                 310                 315

<210> SEQ ID NO 104
<211> LENGTH: 271
<212> TYPE: PRT
<213> ORGANISM: Homo sapiens

<400> SEQUENCE: 104

Met Lys Lys Leu Leu Ala Met Ile Leu Trp Leu Gln Leu Asp Arg Leu
1               5                   10                  15

Ser Gly Glu Leu Lys Val Glu Gln Asn Pro Leu Phe Leu Ser Met Gln
            20                  25                  30

Glu Gly Lys Asn Tyr Thr Ile Tyr Cys Asn Tyr Ser Thr Thr Ser Asp
        35                  40                  45

Arg Leu Tyr Trp Tyr Arg Gln Asp Pro Gly Lys Ser Leu Glu Ser Leu
    50                  55                  60

Phe Val Leu Leu Ser Asn Gly Ala Val Lys Gln Glu Gly Arg Leu Met
65                  70                  75                  80

Ala Ser Leu Asp Thr Lys Ala Arg Leu Ser Thr Leu His Ile Thr Ala
                85                  90                  95

Ala Val His Asp Leu Ser Ala Thr Tyr Phe Cys Ala Val Asp Met Trp
            100                 105                 110

Asn Asn Asn Ala Arg Leu Met Phe Gly Asp Gly Thr Gln Leu Val Val
        115                 120                 125

Lys Pro Asn Ile Gln Asn Pro Asp Pro Ala Val Tyr Gln Leu Arg Asp
    130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 105
<211> LENGTH: 312
<212> TYPE: PRT
<213> ORGANISM: Homo sapiens
```

<400> SEQUENCE: 105

| Met | Gly | Ser | Arg | Leu | Leu | Cys | Trp | Val | Leu | Leu | Cys | Leu | Leu | Gly | Ala |
|---|---|---|---|---|---|---|---|---|---|---|---|---|---|---|---|
| 1 | | | | 5 | | | | | 10 | | | | | 15 | |

| Gly | Pro | Val | Lys | Ala | Gly | Val | Thr | Gln | Thr | Pro | Arg | Tyr | Leu | Ile | Lys |
|---|---|---|---|---|---|---|---|---|---|---|---|---|---|---|---|
| | | | 20 | | | | | 25 | | | | | 30 | | |

| Thr | Arg | Gly | Gln | Gln | Val | Thr | Leu | Ser | Cys | Ser | Pro | Ile | Ser | Gly | His |
|---|---|---|---|---|---|---|---|---|---|---|---|---|---|---|---|
| | | 35 | | | | | 40 | | | | | 45 | | | |

| Arg | Ser | Val | Ser | Trp | Tyr | Gln | Gln | Thr | Pro | Gly | Gln | Gly | Leu | Gln | Phe |
|---|---|---|---|---|---|---|---|---|---|---|---|---|---|---|---|
| 50 | | | | | 55 | | | | | 60 | | | | | |

| Leu | Phe | Glu | Tyr | Phe | Ser | Glu | Thr | Gln | Arg | Asn | Lys | Gly | Asn | Phe | Pro |
|---|---|---|---|---|---|---|---|---|---|---|---|---|---|---|---|
| 65 | | | | | 70 | | | | | 75 | | | | | 80 |

| Gly | Arg | Phe | Ser | Gly | Arg | Gln | Phe | Ser | Asn | Ser | Arg | Ser | Glu | Met | Asn |
|---|---|---|---|---|---|---|---|---|---|---|---|---|---|---|---|
| | | | | 85 | | | | | 90 | | | | | 95 | |

| Val | Ser | Thr | Leu | Glu | Leu | Gly | Asp | Ser | Ala | Leu | Tyr | Leu | Cys | Ala | Ser |
|---|---|---|---|---|---|---|---|---|---|---|---|---|---|---|---|
| | | | 100 | | | | | 105 | | | | | 110 | | |

| Ser | Leu | Ala | Gln | Ser | Gly | Ala | Asn | Val | Leu | Thr | Phe | Gly | Ala | Gly | Ser |
|---|---|---|---|---|---|---|---|---|---|---|---|---|---|---|---|
| | | | 115 | | | | | 120 | | | | | 125 | | |

| Arg | Leu | Thr | Val | Leu | Glu | Asp | Leu | Lys | Asn | Val | Phe | Pro | Pro | Glu | Val |
|---|---|---|---|---|---|---|---|---|---|---|---|---|---|---|---|
| | 130 | | | | | 135 | | | | | 140 | | | | |

| Ala | Val | Phe | Glu | Pro | Ser | Glu | Ala | Glu | Ile | Ser | His | Thr | Gln | Lys | Ala |
|---|---|---|---|---|---|---|---|---|---|---|---|---|---|---|---|
| 145 | | | | | 150 | | | | | 155 | | | | | 160 |

| Thr | Leu | Val | Cys | Leu | Ala | Thr | Gly | Phe | Tyr | Pro | Asp | His | Val | Glu | Leu |
|---|---|---|---|---|---|---|---|---|---|---|---|---|---|---|---|
| | | | | 165 | | | | | 170 | | | | | 175 | |

| Ser | Trp | Trp | Val | Asn | Gly | Lys | Glu | Val | His | Ser | Gly | Val | Ser | Thr | Asp |
|---|---|---|---|---|---|---|---|---|---|---|---|---|---|---|---|
| | | | 180 | | | | | 185 | | | | | 190 | | |

| Pro | Gln | Pro | Leu | Lys | Glu | Gln | Pro | Ala | Leu | Asn | Asp | Ser | Arg | Tyr | Cys |
|---|---|---|---|---|---|---|---|---|---|---|---|---|---|---|---|
| | | 195 | | | | | 200 | | | | | 205 | | | |

| Leu | Ser | Ser | Arg | Leu | Arg | Val | Ser | Ala | Thr | Phe | Trp | Gln | Asn | Pro | Arg |
|---|---|---|---|---|---|---|---|---|---|---|---|---|---|---|---|
| | 210 | | | | | 215 | | | | | 220 | | | | |

| Asn | His | Phe | Arg | Cys | Gln | Val | Gln | Phe | Tyr | Gly | Leu | Ser | Glu | Asn | Asp |
|---|---|---|---|---|---|---|---|---|---|---|---|---|---|---|---|
| 225 | | | | | 230 | | | | | 235 | | | | | 240 |

| Glu | Trp | Thr | Gln | Asp | Arg | Ala | Lys | Pro | Val | Thr | Gln | Ile | Val | Ser | Ala |
|---|---|---|---|---|---|---|---|---|---|---|---|---|---|---|---|
| | | | | 245 | | | | | 250 | | | | | 255 | |

| Glu | Ala | Trp | Gly | Arg | Ala | Asp | Cys | Gly | Phe | Thr | Ser | Glu | Ser | Tyr | Gln |
|---|---|---|---|---|---|---|---|---|---|---|---|---|---|---|---|
| | | | 260 | | | | | 265 | | | | | 270 | | |

| Gln | Gly | Val | Leu | Ser | Ala | Thr | Ile | Leu | Tyr | Glu | Ile | Leu | Leu | Gly | Lys |
|---|---|---|---|---|---|---|---|---|---|---|---|---|---|---|---|
| | | | 275 | | | | | 280 | | | | | 285 | | |

| Ala | Thr | Leu | Tyr | Ala | Val | Leu | Val | Ser | Ala | Leu | Val | Leu | Met | Ala | Met |
|---|---|---|---|---|---|---|---|---|---|---|---|---|---|---|---|
| | 290 | | | | | 295 | | | | | 300 | | | | |

| Val | Lys | Arg | Lys | Asp | Ser | Arg | Gly |
|---|---|---|---|---|---|---|---|
| 305 | | | | 310 | | | |

<210> SEQ ID NO 106
<211> LENGTH: 272
<212> TYPE: PRT
<213> ORGANISM: Homo sapiens

<400> SEQUENCE: 106

| Met | Glu | Lys | Met | Leu | Glu | Cys | Ala | Phe | Ile | Val | Leu | Trp | Leu | Gln | Leu |
|---|---|---|---|---|---|---|---|---|---|---|---|---|---|---|---|
| 1 | | | | 5 | | | | | 10 | | | | | 15 | |

| Gly | Trp | Leu | Ser | Gly | Glu | Asp | Gln | Val | Thr | Gln | Ser | Pro | Glu | Ala | Leu |
|---|---|---|---|---|---|---|---|---|---|---|---|---|---|---|---|
| | | | 20 | | | | | 25 | | | | | 30 | | |

| Arg | Leu | Gln | Glu | Gly | Glu | Ser | Ser | Leu | Asn | Cys | Ser | Tyr | Thr | Val |
|---|---|---|---|---|---|---|---|---|---|---|---|---|---|---|
| | | | 35 | | | | | 40 | | | | | 45 | |

```
Ser Gly Leu Arg Gly Leu Phe Trp Tyr Arg Gln Asp Pro Gly Lys Gly
    50                  55                  60

Pro Glu Phe Leu Phe Thr Leu Tyr Ser Ala Gly Glu Glu Lys Glu Lys
 65                  70                  75                  80

Glu Arg Leu Lys Ala Thr Leu Thr Lys Lys Glu Ser Phe Leu His Ile
                 85                  90                  95

Thr Ala Pro Lys Pro Glu Asp Ser Ala Thr Tyr Leu Cys Ala Val Leu
                100                 105                 110

Gly Gly Ser Asn Tyr Lys Leu Thr Phe Gly Lys Gly Thr Leu Leu Thr
            115                 120                 125

Val Asn Pro Asn Ile Gln Asn Pro Asp Pro Ala Val Tyr Gln Leu Arg
130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
                180                 185                 190

Ala Val Ala Trp Ser Asn Lys Ser Asp Phe Ala Cys Ala Asn Ala Phe
            195                 200                 205

Asn Asn Ser Ile Ile Pro Glu Asp Thr Phe Phe Pro Ser Pro Glu Ser
210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 107
<211> LENGTH: 309
<212> TYPE: PRT
<213> ORGANISM: Homo sapiens

<400> SEQUENCE: 107

Met Ser Leu Gly Leu Leu Cys Cys Val Ala Phe Ser Leu Leu Trp Ala
 1               5                  10                  15

Ser Pro Val Asn Ala Gly Val Thr Gln Thr Pro Lys Phe Gln Val Leu
                 20                  25                  30

Lys Thr Gly Gln Ser Met Thr Leu Gln Cys Ala Gln Asp Met Asn His
             35                  40                  45

Asn Ser Met Tyr Trp Tyr Arg Gln Asp Pro Gly Met Gly Leu Arg Leu
 50                  55                  60

Ile Tyr Tyr Ser Ala Ser Glu Gly Thr Thr Asp Lys Gly Glu Val Pro
 65                  70                  75                  80

Asn Gly Tyr Asn Val Ser Arg Leu Asn Lys Arg Glu Phe Ser Leu Arg
                 85                  90                  95

Leu Glu Ser Ala Ala Pro Ser Gln Thr Ser Val Tyr Phe Cys Ala Ile
                100                 105                 110

Ser Arg Asp Ser Tyr Glu Gln Tyr Phe Gly Pro Gly Thr Arg Leu Thr
            115                 120                 125

Val Thr Glu Asp Leu Lys Asn Val Phe Pro Pro Glu Val Ala Val Phe
130                 135                 140

Glu Pro Ser Glu Ala Glu Ile Ser His Thr Gln Lys Ala Thr Leu Val
145                 150                 155                 160
```

```
Cys Leu Ala Thr Gly Phe Tyr Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Glu Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Ser Arg Gly
305

<210> SEQ ID NO 108
<211> LENGTH: 23
<212> TYPE: PRT
<213> ORGANISM: Cytomegalovirus

<400> SEQUENCE: 108

Pro Leu Lys Met Leu Asn Ile Pro Ser Ile Asn Val His His Tyr Pro
1               5                   10                  15

Ser Ala Ala Glu Arg Lys His
            20

<210> SEQ ID NO 109
<211> LENGTH: 9
<212> TYPE: PRT
<213> ORGANISM: Cytomegalovirus

<400> SEQUENCE: 109

Asn Leu Val Pro Met Val Ala Thr Val
1               5

<210> SEQ ID NO 110
<211> LENGTH: 23
<212> TYPE: PRT
<213> ORGANISM: Cytomegalovirus

<400> SEQUENCE: 110

Val Glu Leu Arg Gln Tyr Asp Pro Val Ala Ala Leu Phe Phe Phe Asp
1               5                   10                  15

Ile Asp Leu Leu Leu Gln Arg
            20

<210> SEQ ID NO 111
<211> LENGTH: 9
<212> TYPE: PRT
<213> ORGANISM: Homo sapiens

<400> SEQUENCE: 111

Leu Ala Met Pro Phe Ala Thr Pro Met
```

```
1               5

<210> SEQ ID NO 112
<211> LENGTH: 15
<212> TYPE: PRT
<213> ORGANISM: Homo sapiens

<400> SEQUENCE: 112

Ala Met Pro Phe Ala Thr Pro Met Glu Ala Glu Leu Ala Arg Arg
1               5                   10                  15

<210> SEQ ID NO 113
<211> LENGTH: 15
<212> TYPE: PRT
<213> ORGANISM: Homo sapiens

<400> SEQUENCE: 113

Ala Thr Pro Met Glu Ala Glu Leu Ala Arg Arg Ser Leu Ala Gln
1               5                   10                  15

<210> SEQ ID NO 114
<211> LENGTH: 15
<212> TYPE: PRT
<213> ORGANISM: Homo sapiens

<400> SEQUENCE: 114

Ser Arg Leu Leu Glu Phe Tyr Leu Ala Met Pro Phe Ala Thr Pro
1               5                   10                  15

<210> SEQ ID NO 115
<211> LENGTH: 23
<212> TYPE: PRT
<213> ORGANISM: Homo sapiens

<400> SEQUENCE: 115

Pro Val Pro Gly Val Leu Leu Lys Glu Phe Thr Val Ser Gly Asn Ile
1               5                   10                  15

Leu Thr Ile Arg Leu Thr Ala
            20

<210> SEQ ID NO 116
<211> LENGTH: 19
<212> TYPE: PRT
<213> ORGANISM: Homo sapiens

<400> SEQUENCE: 116

Ser Gly Asn Ile Leu Thr Ile Arg Leu Thr Ala Ala Asp His Arg Gln
1               5                   10                  15

Leu Gln Leu

<210> SEQ ID NO 117
<211> LENGTH: 16
<212> TYPE: PRT
<213> ORGANISM: Homo sapiens

<400> SEQUENCE: 117

Cys Phe Leu Pro Val Phe Leu Ala Gln Pro Pro Ser Gly Gln Arg Arg
1               5                   10                  15

<210> SEQ ID NO 118
<211> LENGTH: 15
<212> TYPE: PRT
<213> ORGANISM: Homo sapiens
```

<400> SEQUENCE: 118

Arg Asn Ile Pro Arg Trp Thr His Leu Leu Arg Leu Leu Arg Leu
1               5                   10                  15

<210> SEQ ID NO 119
<211> LENGTH: 9
<212> TYPE: PRT
<213> ORGANISM: Homo sapiens

<400> SEQUENCE: 119

Tyr Pro Ser Asp Phe Ala Val Glu Ile
1               5

<210> SEQ ID NO 120
<211> LENGTH: 19
<212> TYPE: PRT
<213> ORGANISM: Homo sapiens

<400> SEQUENCE: 120

Ser Pro Ile Ser Glu Ser Val Leu Ala Arg Leu Ser Lys Phe Glu Val
1               5                   10                  15

Glu Asp Ala

<210> SEQ ID NO 121
<211> LENGTH: 15
<212> TYPE: PRT
<213> ORGANISM: Homo sapiens

<400> SEQUENCE: 121

Ile Lys Lys Ile Val His Ser Ile Val Ser Ser Phe Ala Phe Gly
1               5                   10                  15

<210> SEQ ID NO 122
<211> LENGTH: 19
<212> TYPE: PRT
<213> ORGANISM: Homo sapiens

<400> SEQUENCE: 122

Ile Leu Ala Asp Leu Ile Phe Thr Asp Ser Lys Leu Tyr Ile Pro Leu
1               5                   10                  15

Glu Tyr Arg

<210> SEQ ID NO 123
<211> LENGTH: 19
<212> TYPE: PRT
<213> ORGANISM: Homo sapiens

<400> SEQUENCE: 123

Asp Ser Lys Leu Tyr Ile Pro Leu Glu Tyr Arg Ser Ile Ser Leu Ala
1               5                   10                  15

Ile Ala Leu

<210> SEQ ID NO 124
<211> LENGTH: 15
<212> TYPE: PRT
<213> ORGANISM: Homo sapiens

<400> SEQUENCE: 124

Val Leu Leu Arg Val Phe Val Glu Arg Arg Gln Gln Tyr Phe Ser
1               5                   10                  15

<210> SEQ ID NO 125

```
<211> LENGTH: 15
<212> TYPE: PRT
<213> ORGANISM: Homo sapiens

<400> SEQUENCE: 125

Asp Val Val Tyr Ile Phe Phe Asp Ile Lys Leu Leu Arg Asn Ile
1               5                   10                  15

<210> SEQ ID NO 126
<211> LENGTH: 15
<212> TYPE: PRT
<213> ORGANISM: Homo sapiens

<400> SEQUENCE: 126

Ile Phe Phe Asp Ile Lys Leu Leu Arg Asn Ile Pro Arg Trp Thr
1               5                   10                  15

<210> SEQ ID NO 127
<211> LENGTH: 19
<212> TYPE: PRT
<213> ORGANISM: Homo sapiens

<400> SEQUENCE: 127

Ile Phe Phe Asp Ile Lys Leu Leu Arg Asn Ile Pro Arg Trp Thr His
1               5                   10                  15

Leu Leu Arg

<210> SEQ ID NO 128
<211> LENGTH: 15
<212> TYPE: PRT
<213> ORGANISM: Homo sapiens

<400> SEQUENCE: 128

Ile Lys Leu Leu Arg Asn Ile Pro Arg Trp Thr His Leu Leu Arg
1               5                   10                  15

<210> SEQ ID NO 129
<211> LENGTH: 15
<212> TYPE: PRT
<213> ORGANISM: Homo sapiens

<400> SEQUENCE: 129

Lys Leu Ile Arg Arg Val Ser Glu Asn Lys Arg Arg Tyr Thr
1               5                   10                  15

<210> SEQ ID NO 130
<211> LENGTH: 15
<212> TYPE: PRT
<213> ORGANISM: Homo sapiens

<400> SEQUENCE: 130

Arg Arg Val Ser Glu Asn Lys Arg Arg Tyr Thr Arg Asp Gly Phe
1               5                   10                  15

<210> SEQ ID NO 131
<211> LENGTH: 15
<212> TYPE: PRT
<213> ORGANISM: Homo sapiens

<400> SEQUENCE: 131

Arg Phe Leu Asp Lys Lys His Arg Asn His Tyr Arg Val Tyr Asn
1               5                   10                  15

<210> SEQ ID NO 132
```

```
<211> LENGTH: 15
<212> TYPE: PRT
<213> ORGANISM: Homo sapiens

<400> SEQUENCE: 132

Asn His Tyr Arg Val Tyr Asn Leu Cys Ser Glu Arg Ala Tyr Asp
1               5                   10                  15

<210> SEQ ID NO 133
<211> LENGTH: 19
<212> TYPE: PRT
<213> ORGANISM: Homo sapiens

<400> SEQUENCE: 133

Tyr Val Ala Tyr Phe Ala Gln Val Lys His Leu Tyr Asn Trp Asn Leu
1               5                   10                  15

Pro Pro Arg

<210> SEQ ID NO 134
<211> LENGTH: 19
<212> TYPE: PRT
<213> ORGANISM: Homo sapiens

<400> SEQUENCE: 134

Asn Trp Asn Leu Pro Pro Arg Arg Ile Leu Phe Ile Lys His Phe Ile
1               5                   10                  15

Ile Tyr Ser

<210> SEQ ID NO 135
<211> LENGTH: 15
<212> TYPE: PRT
<213> ORGANISM: Homo sapiens

<400> SEQUENCE: 135

Pro Pro Arg Arg Ile Leu Phe Ile Lys His Phe Ile Ile Tyr Ser
1               5                   10                  15

<210> SEQ ID NO 136
<211> LENGTH: 15
<212> TYPE: PRT
<213> ORGANISM: Homo sapiens

<400> SEQUENCE: 136

Ile Leu Phe Ile Lys His Phe Ile Ile Tyr Ser Ile Pro Arg Tyr
1               5                   10                  15

<210> SEQ ID NO 137
<211> LENGTH: 19
<212> TYPE: PRT
<213> ORGANISM: Homo sapiens

<400> SEQUENCE: 137

Lys His Phe Ile Ile Tyr Ser Ile Pro Arg Tyr Val Arg Asp Leu Lys
1               5                   10                  15

Ile Gln Ile

<210> SEQ ID NO 138
<211> LENGTH: 15
<212> TYPE: PRT
<213> ORGANISM: Homo sapiens

<400> SEQUENCE: 138

Val Leu Asp Asn Ile Thr Thr Asp Lys Ile Leu Ile Asp Val Phe
```

<210> SEQ ID NO 139
<211> LENGTH: 19
<212> TYPE: PRT
<213> ORGANISM: Homo sapiens

<400> SEQUENCE: 139

Trp Leu His Thr Ser Phe Ile Glu Asn Asn Arg Leu Tyr Leu Pro Lys
1               5                   10                  15

Asn Glu Leu

<210> SEQ ID NO 140
<211> LENGTH: 275
<212> TYPE: PRT
<213> ORGANISM: Homo sapiens

<400> SEQUENCE: 140

Met Leu Leu Leu Leu Val Pro Val Leu Glu Val Ile Phe Thr Leu Gly
1               5                   10                  15

Gly Thr Arg Ala Gln Ser Val Thr Gln Leu Gly Ser His Val Ser Val
                20                  25                  30

Ser Glu Gly Ala Leu Val Leu Leu Arg Cys Asn Tyr Ser Ser Ser Val
            35                  40                  45

Pro Pro Tyr Leu Phe Trp Tyr Val Gln Tyr Pro Asn Gln Gly Leu Gln
        50                  55                  60

Leu Leu Leu Lys Tyr Thr Thr Gly Ala Thr Leu Val Lys Gly Ile Asn
65                  70                  75                  80

Gly Phe Glu Ala Glu Phe Lys Lys Ser Glu Thr Ser Phe His Leu Thr
                85                  90                  95

Lys Pro Ser Ala His Met Ser Asp Ala Ala Glu Tyr Phe Cys Ala Val
            100                 105                 110

Ser Arg Ala Asn Phe Gly Asn Glu Lys Leu Thr Phe Gly Thr Gly Thr
        115                 120                 125

Arg Leu Thr Ile Ile Pro Asn Ile Gln Asn Pro Asp Pro Ala Val Tyr
130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275

<210> SEQ ID NO 141

```
<211> LENGTH: 309
<212> TYPE: PRT
<213> ORGANISM: Homo sapiens

<400> SEQUENCE: 141

Met Ser Asn Gln Val Leu Cys Cys Ala Val Leu Cys Leu Leu Gly Ala
1               5                   10                  15

Val Pro Ile Asp Thr Glu Val Thr Gln Thr Pro Lys His Leu Val Met
            20                  25                  30

Gly Met Thr Asn Lys Lys Ser Leu Lys Cys Glu Gln His Met Gly His
        35                  40                  45

Arg Ala Met Tyr Trp Tyr Lys Gln Lys Ala Lys Lys Pro Pro Glu Leu
    50                  55                  60

Met Phe Val Tyr Ser Tyr Glu Lys Leu Ser Ile Asn Glu Ser Val Pro
65                  70                  75                  80

Ser Arg Phe Ser Pro Glu Cys Pro Asn Ser Ser Leu Leu Asn Leu His
                85                  90                  95

Leu His Ala Leu Gln Pro Glu Asp Ser Ala Leu Tyr Leu Cys Ala Ser
            100                 105                 110

Ser Gln Asp Pro Arg Gly Gly Pro Gln His Phe Gly Asp Gly Thr Arg
        115                 120                 125

Leu Ser Ile Leu Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe
305

<210> SEQ ID NO 142
<211> LENGTH: 274
<212> TYPE: PRT
<213> ORGANISM: Homo sapiens

<400> SEQUENCE: 142

Met Leu Leu Leu Leu Val Pro Ala Phe Gln Val Ile Phe Thr Leu Gly
1               5                   10                  15

Gly Thr Arg Ala Gln Ser Val Thr Gln Leu Asp Ser Gln Val Pro Val
            20                  25                  30
```

Phe Glu Glu Ala Pro Val Glu Leu Arg Cys Asn Tyr Ser Ser Val
           35                  40                  45

Ser Val Tyr Leu Phe Trp Tyr Val Gln Tyr Pro Asn Gln Gly Leu Gln
 50                      55                  60

Leu Leu Leu Lys Tyr Leu Ser Gly Ser Thr Leu Val Lys Gly Ile Asn
65                   70                  75                  80

Gly Phe Glu Ala Glu Phe Asn Lys Ser Gln Thr Ser Phe His Leu Arg
             85                  90                  95

Lys Pro Ser Val His Ile Ser Asp Thr Ala Glu Tyr Phe Cys Ala Val
            100                 105                 110

Ser Lys Ser Gly Gly Tyr Gln Lys Val Thr Phe Gly Thr Gly Thr Lys
            115                 120                 125

Leu Gln Val Ile Pro Asn Ile Gln Asn Pro Asp Pro Ala Val Tyr Gln
        130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
            195                 200                 205

Ala Phe Asn Asn Ser Ile Ile Pro Glu Asp Thr Phe Phe Pro Ser Pro
        210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 143
<211> LENGTH: 312
<212> TYPE: PRT
<213> ORGANISM: Homo sapiens

<400> SEQUENCE: 143

Met Leu Leu Leu Leu Leu Leu Gly Pro Gly Ser Gly Leu Gly Ala
1               5                   10                  15

Val Val Ser Gln His Pro Ser Trp Val Ile Cys Lys Ser Gly Thr Ser
                20                  25                  30

Val Lys Ile Glu Cys Arg Ser Leu Asp Phe Gln Ala Thr Thr Met Phe
            35                  40                  45

Trp Tyr Arg Gln Phe Pro Lys Gln Ser Leu Met Leu Met Ala Thr Ser
 50                      55                  60

Asn Glu Gly Ser Lys Ala Thr Tyr Glu Gln Gly Val Glu Lys Asp Lys
65                   70                  75                  80

Phe Leu Ile Asn His Ala Ser Leu Thr Leu Ser Thr Leu Thr Val Thr
             85                  90                  95

Ser Ala His Pro Glu Asp Ser Ser Phe Tyr Ile Cys Ser Ala Ala Pro
            100                 105                 110

Gly Leu Ala Gly Gly Gln Gly Gly Ser Gln Tyr Phe Gly Pro Gly Thr
            115                 120                 125

```
Arg Leu Leu Val Leu Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
                180                 185                 190

Pro Gln Pro Leu Lys Glu Gln Pro Ala Leu Asn Asp Ser Arg Tyr Cys
            195                 200                 205

Leu Ser Ser Arg Leu Arg Val Ser Ala Thr Phe Trp Gln Asn Pro Arg
210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310

<210> SEQ ID NO 144
<211> LENGTH: 275
<212> TYPE: PRT
<213> ORGANISM: Homo sapiens

<400> SEQUENCE: 144

Met Asn Tyr Ser Pro Gly Leu Val Ser Leu Ile Leu Leu Leu Leu Gly
1               5                   10                  15

Arg Thr Arg Gly Asp Ser Val Thr Gln Met Glu Gly Pro Val Thr Leu
            20                  25                  30

Ser Glu Glu Ala Phe Leu Thr Ile Asn Cys Thr Tyr Thr Ala Thr Gly
        35                  40                  45

Tyr Pro Ser Leu Phe Trp Tyr Val Gln Tyr Pro Gly Glu Gly Leu Gln
    50                  55                  60

Leu Leu Leu Lys Ala Thr Lys Ala Asp Asp Lys Gly Ser Asn Lys Gly
65                  70                  75                  80

Phe Glu Ala Thr Tyr Arg Lys Glu Thr Thr Ser Phe His Leu Glu Lys
                85                  90                  95

Gly Ser Val Gln Val Ser Asp Ser Ala Val Tyr Phe Cys Ala Arg Ala
            100                 105                 110

Val Asn Tyr Gly Gly Ser Gln Gly Asn Leu Ile Phe Gly Lys Gly Thr
        115                 120                 125

Lys Leu Ser Val Lys Pro Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
```

```
            180                 185                 190
Ser Asn Ser Ala Val Ala Trp Ser Asn Lys Ser Asp Phe Ala Cys Ala
            195                 200                 205

Asn Ala Phe Asn Asn Ser Ile Ile Pro Glu Asp Thr Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275

<210> SEQ ID NO 145
<211> LENGTH: 309
<212> TYPE: PRT
<213> ORGANISM: Homo sapiens

<400> SEQUENCE: 145

Met Gly Thr Arg Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu Gly His Glu Gln Tyr Phe Gly Pro Gly Thr Arg Leu Thr
        115                 120                 125

Val Thr Glu Asp Leu Lys Asn Val Phe Pro Pro Glu Val Ala Val Phe
130                 135                 140

Glu Pro Ser Glu Ala Glu Ile Ser His Thr Gln Lys Ala Thr Leu Val
145                 150                 155                 160

Cys Leu Ala Thr Gly Phe Tyr Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Glu Ser Tyr Gln Gln Gly Val
            260                 265                 270
```

Leu Ser Ala Thr Ile Leu Tyr Glu Ile Leu Leu Gly Lys Ala Thr Leu
                275                 280                 285

Tyr Ala Val Leu Val Ser Ala Leu Val Leu Met Ala Met Val Lys Arg
290                 295                 300

Lys Asp Ser Arg Gly
305

<210> SEQ ID NO 146
<211> LENGTH: 276
<212> TYPE: PRT
<213> ORGANISM: Homo sapiens

<400> SEQUENCE: 146

Met Leu Leu Leu Leu Ile Pro Val Leu Gly Met Ile Phe Ala Leu Arg
1               5                   10                  15

Asp Ala Arg Ala Gln Ser Val Ser Gln His Asn His His Val Ile Leu
            20                  25                  30

Ser Glu Ala Ala Ser Leu Glu Leu Gly Cys Asn Tyr Ser Tyr Gly Gly
        35                  40                  45

Thr Val Asn Leu Phe Trp Tyr Val Gln Tyr Pro Gly Gln His Leu Gln
    50                  55                  60

Leu Leu Leu Lys Tyr Phe Ser Gly Asp Pro Leu Val Lys Gly Ile Lys
65                  70                  75                  80

Gly Phe Glu Ala Glu Phe Ile Lys Ser Lys Phe Ser Phe Asn Leu Arg
                85                  90                  95

Lys Pro Ser Val Gln Trp Ser Asp Thr Ala Glu Tyr Phe Cys Ala Val
            100                 105                 110

Asn Arg Arg Thr Gly Asn Gln Gly Gly Lys Leu Ile Phe Gly Gln Gly
        115                 120                 125

Thr Glu Leu Ser Val Lys Pro Asn Ile Gln Asn Pro Asp Pro Ala Val
    130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
        275

<210> SEQ ID NO 147
<211> LENGTH: 312
<212> TYPE: PRT
<213> ORGANISM: Homo sapiens

<400> SEQUENCE: 147

```
Met Gly Thr Arg Leu Leu Cys Trp Ala Ala Leu Cys Leu Leu Gly Ala
1               5                   10                  15

Glu Leu Thr Glu Ala Gly Val Ala Gln Ser Pro Arg Tyr Lys Ile Ile
            20                  25                  30

Glu Lys Arg Gln Ser Val Ala Phe Trp Cys Asn Pro Ile Ser Gly His
        35                  40                  45

Ala Thr Leu Tyr Trp Tyr Gln Gln Ile Leu Gly Gln Gly Pro Lys Leu
50                  55                  60

Leu Ile Gln Phe Gln Asn Asn Gly Val Val Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Lys Leu Glu Asp Ser Ala Val Tyr Leu Cys Ala
            100                 105                 110

Ser Ser Leu Gly Pro Tyr Ile Asp Gly Ala Gly Cys Thr Phe Gly Ser
        115                 120                 125

Gly Thr Arg Leu Thr Val Val Glu Asp Leu Asn Lys Val Phe Pro Pro
130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Phe Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Val Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
290                 295                 300

Ala Met Val Lys Arg Lys Asp Phe
305                 310

<210> SEQ ID NO 148
<211> LENGTH: 272
<212> TYPE: PRT
<213> ORGANISM: Homo sapiens

<400> SEQUENCE: 148

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
50                  55                  60
```

Ser Leu Leu Leu Ile Gln Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Pro
            100                 105                 110

Thr Asp Ser Trp Gly Lys Leu Gln Phe Gly Ala Gly Thr Gln Val Val
            115                 120                 125

Val Thr Pro Asp Ile Gln Asn Pro Asp Pro Ala Val Tyr Gln Leu Arg
130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
            195                 200                 205

Asn Asn Ser Ile Ile Pro Glu Asp Thr Phe Phe Pro Ser Pro Glu Ser
210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 149
<211> LENGTH: 317
<212> TYPE: PRT
<213> ORGANISM: Homo sapiens

<400> SEQUENCE: 149

Met Gly Thr Arg Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Ser Lys Leu Thr Gly Ile Pro Glu Gly Thr Asp Thr Gln Tyr
            115                 120                 125

Phe Gly Pro Gly Thr Arg Leu Thr Val Leu Glu Asp Leu Lys Asn Val
130                 135                 140

Phe Pro Pro Glu Val Ala Val Phe Glu Pro Ser Glu Ala Glu Ile Ser
145                 150                 155                 160

His Thr Gln Lys Ala Thr Leu Val Cys Leu Ala Thr Gly Phe Tyr Pro

```
                165                 170                 175
Asp His Val Glu Leu Ser Trp Trp Val Asn Gly Lys Glu Val His Ser
                180                 185                 190

Gly Val Ser Thr Asp Pro Gln Pro Leu Lys Glu Gln Pro Ala Leu Asn
                195                 200                 205

Asp Ser Arg Tyr Cys Leu Ser Ser Arg Leu Arg Val Ser Ala Thr Phe
            210                 215                 220

Trp Gln Asn Pro Arg Asn His Phe Arg Cys Gln Val Gln Phe Tyr Gly
225                 230                 235                 240

Leu Ser Glu Asn Asp Glu Trp Thr Gln Asp Arg Ala Lys Pro Val Thr
                245                 250                 255

Gln Ile Val Ser Ala Glu Ala Trp Gly Arg Ala Asp Cys Gly Phe Thr
                260                 265                 270

Ser Glu Ser Tyr Gln Gln Gly Val Leu Ser Ala Thr Ile Leu Tyr Glu
                275                 280                 285

Ile Leu Leu Gly Lys Ala Thr Leu Tyr Ala Val Leu Val Ser Ala Leu
                290                 295                 300

Val Leu Met Ala Met Val Lys Arg Lys Asp Ser Arg Gly
305                 310                 315

<210> SEQ ID NO 150
<211> LENGTH: 273
<212> TYPE: PRT
<213> ORGANISM: Homo sapiens

<400> SEQUENCE: 150

Met Leu Leu Leu Leu Val Pro Val Leu Glu Val Ile Phe Thr Leu Gly
1               5                   10                  15

Gly Thr Arg Ala Gln Ser Val Thr Gln Leu Gly Ser His Val Ser Val
                20                  25                  30

Ser Glu Gly Ala Leu Val Leu Leu Arg Cys Asn Tyr Ser Ser Ser Val
                35                  40                  45

Pro Pro Tyr Leu Phe Trp Tyr Val Gln Tyr Pro Asn Gln Gly Leu Gln
            50                  55                  60

Leu Leu Leu Lys Tyr Thr Thr Gly Ala Thr Leu Val Lys Gly Ile Asn
65                  70                  75                  80

Gly Phe Glu Ala Glu Phe Lys Lys Ser Glu Thr Ser Phe His Leu Thr
                85                  90                  95

Lys Pro Ser Ala His Met Ser Asp Ala Ala Glu Tyr Phe Cys Ala Val
                100                 105                 110

Lys Lys Gly Gly Gly Asn Lys Leu Thr Phe Gly Thr Gly Thr Gln Leu
                115                 120                 125

Lys Val Glu Leu Asn Ile Gln Asn Pro Asp Pro Ala Val Tyr Gln Leu
            130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
                180                 185                 190

Ser Ala Val Ala Trp Ser Asn Lys Ser Asp Phe Ala Cys Ala Asn Ala
            195                 200                 205

Phe Asn Asn Ser Ile Ile Pro Glu Asp Thr Phe Phe Pro Ser Pro Glu
            210                 215                 220
```

```
Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
            245                 250                 255

Leu Lys Val Ala Gly Phe Asn Leu Leu Met Thr Leu Arg Leu Trp Ser
        260                 265                 270

Ser

<210> SEQ ID NO 151
<211> LENGTH: 307
<212> TYPE: PRT
<213> ORGANISM: Homo sapiens

<400> SEQUENCE: 151

Met Leu Leu Leu Leu Leu Leu Gly Pro Gly Ser Gly Leu Gly Ala
1               5                   10                  15

Val Val Ser Gln His Pro Ser Trp Val Ile Cys Lys Ser Gly Thr Ser
            20                  25                  30

Val Lys Ile Glu Cys Arg Ser Leu Asp Phe Gln Ala Thr Thr Met Phe
        35                  40                  45

Trp Tyr Arg Gln Phe Pro Lys Gln Ser Leu Met Leu Met Ala Thr Ser
    50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Thr Gly
            100                 105                 110

Pro Ser Glu His Gln Pro Gln His Phe Gly Asp Gly Thr Arg Leu Ser
        115                 120                 125

Ile Leu Glu Asp Leu Asn Lys Val Phe Pro Pro Glu Val Ala Val Phe
    130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Phe
305
```

<210> SEQ ID NO 152
<211> LENGTH: 269
<212> TYPE: PRT
<213> ORGANISM: Mus musculus

<400> SEQUENCE: 152

Met Asn Ser Phe Pro Gly Phe Val Ala Val Ile Leu Leu Ile Leu Gly
1               5                   10                  15

Arg Thr His Gly Asp Ser Val Thr Gln Thr Glu Gly Gln Val Thr Val
            20                  25                  30

Ser Glu Ser Lys Ser Leu Ile Ile Asn Cys Thr Tyr Ser Ala Thr Ser
        35                  40                  45

Ile Gly Tyr Pro Asn Leu Phe Trp Tyr Val Arg Tyr Pro Gly Glu Gly
    50                  55                  60

Leu Gln Leu Leu Leu Lys Val Ile Thr Ala Gly Gln Lys Gly Ser Ser
65                  70                  75                  80

Arg Gly Phe Glu Ala Thr Tyr Asn Lys Glu Ala Thr Ser Phe His Leu
                85                  90                  95

Gln Lys Ala Ser Val Gln Glu Ser Asp Ser Ala Val Tyr Tyr Cys Ala
            100                 105                 110

Leu Ser Asp Ser Asn Tyr Gln Leu Ile Trp Gly Ser Gly Thr Lys Leu
        115                 120                 125

Ile Ile Lys Pro Asp Ile Gln Asn Pro Glu Pro Ala Val Tyr Gln Leu
    130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Thr Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
        195                 200                 205

Phe Lys Glu Thr Asn Ala Thr Tyr Pro Ser Ser Asp Val Pro Cys Asp
    210                 215                 220

Ala Thr Leu Thr Glu Lys Ser Phe Glu Thr Asp Met Asn Leu Asn Phe
225                 230                 235                 240

Gln Asn Leu Ser Val Met Gly Leu Arg Ile Leu Leu Leu Lys Val Ala
                245                 250                 255

Gly Phe Asn Leu Leu Met Thr Leu Arg Leu Trp Ser Ser
            260                 265

<210> SEQ ID NO 153
<211> LENGTH: 305
<212> TYPE: PRT
<213> ORGANISM: Mus musculus

<400> SEQUENCE: 153

Met Gly Ser Ile Phe Leu Ser Cys Leu Ala Val Cys Leu Leu Val Ala
1               5                   10                  15

Gly Pro Val Asp Pro Lys Ile Ile Gln Lys Pro Lys Tyr Leu Val Ala
            20                  25                  30

Val Thr Gly Ser Glu Lys Ile Leu Ile Cys Glu Gln Tyr Leu Gly His
        35                  40                  45

Asn Ala Met Tyr Trp Tyr Arg Gln Ser Ala Lys Lys Pro Leu Glu Phe
    50                  55                  60

```
Met Phe Ser Tyr Ser Tyr Gln Lys Leu Met Asp Asn Gln Thr Ala Ser
 65                  70                  75                  80

Ser Arg Phe Gln Pro Gln Ser Ser Lys Lys Asn His Leu Asp Leu Gln
                 85                  90                  95

Ile Thr Ala Leu Lys Pro Asp Asp Ser Ala Thr Tyr Phe Cys Ala Ser
            100                 105                 110

Ser Pro Asp Asn Ser Gly Asn Thr Leu Tyr Phe Gly Glu Gly Ser Arg
        115                 120                 125

Leu Ile Val Val Glu Asp Leu Arg Asn Val Thr Pro Pro Lys Val Ser
130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Ser Thr Asp Pro
                180                 185                 190

Gln Ala Tyr Lys Glu Ser Asn Tyr Ser Tyr Cys Leu Ser Ser Arg Leu
                195                 200                 205

Arg Val Ser Ala Thr Phe Trp His Asn Pro Arg Asn His Phe Arg Cys
210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
                260                 265                 270

Ala Thr Ile Leu Tyr Glu Ile Leu Leu Gly Lys Ala Thr Leu Tyr Ala
                275                 280                 285

Val Leu Val Ser Thr Leu Val Val Met Ala Met Val Lys Arg Lys Asn
290                 295                 300

Ser
305

<210> SEQ ID NO 154
<211> LENGTH: 267
<212> TYPE: PRT
<213> ORGANISM: Mus musculus

<400> SEQUENCE: 154

Met Leu Leu Val Phe Ile Ser Phe Leu Gly Ile His Phe Phe Leu Asp
1                   5                   10                  15

Val Gln Thr Gln Thr Val Ser Gln Ser Asp Ala His Val Thr Val Phe
                20                  25                  30

Glu Gly Asp Ser Val Glu Leu Arg Cys Asn Tyr Ser Tyr Gly Gly Ser
            35                  40                  45

Ile Tyr Leu Ser Trp Tyr Ile Gln His His Gly Arg Gly Leu Gln Phe
        50                  55                  60

Leu Leu Lys Tyr Tyr Ser Gly Asn Pro Val Val Gln Gly Val Asn Gly
 65                 70                  75                  80

Phe Lys Ala Glu Phe Ser Lys Ser Asp Ser Ser Phe His Leu Arg Lys
                85                  90                  95

Ala Ser Val His Trp Ser Asp Ser Ala Val Tyr Phe Cys Ala Val Ser
            100                 105                 110

Ala Gly Gly Tyr Lys Val Val Phe Gly Ser Gly Thr Arg Leu Leu Val
        115                 120                 125
```

-continued

```
Ser Pro Asp Ile Gln Asn Pro Glu Pro Ala Val Tyr Gln Leu Lys Asp
            130                 135                 140

Pro Arg Ser Gln Asp Ser Thr Leu Cys Leu Phe Thr Asp Phe Asp Ser
145                 150                 155                 160

Gln Ile Asn Val Pro Lys Thr Met Glu Ser Gly Thr Phe Ile Thr Asp
                165                 170                 175

Lys Thr Val Leu Asp Met Lys Ala Met Asp Ser Lys Ser Asn Gly Ala
            180                 185                 190

Ile Ala Trp Ser Asn Gln Thr Ser Phe Thr Cys Gln Asp Ile Phe Lys
        195                 200                 205

Glu Thr Asn Ala Thr Tyr Pro Ser Ser Asp Val Pro Cys Asp Ala Thr
210                 215                 220

Leu Thr Glu Lys Ser Phe Glu Thr Asp Met Asn Leu Asn Phe Gln Asn
225                 230                 235                 240

Leu Ser Val Met Gly Leu Arg Ile Leu Leu Lys Val Ala Gly Phe
                245                 250                 255

Asn Leu Leu Met Thr Leu Arg Leu Trp Ser Ser
            260                 265
```

<210> SEQ ID NO 155
<211> LENGTH: 302
<212> TYPE: PRT
<213> ORGANISM: Mus musculus

<400> SEQUENCE: 155

```
Met Ser Cys Arg Leu Leu Leu Tyr Val Ser Leu Cys Leu Val Glu Thr
1               5                   10                  15

Ala Leu Met Asn Thr Lys Ile Thr Gln Ser Pro Arg Tyr Leu Ile Leu
            20                  25                  30

Gly Arg Ala Asn Lys Ser Leu Glu Cys Glu Gln His Leu Gly His Asn
        35                  40                  45

Ala Met Tyr Trp Tyr Lys Gln Ser Ala Glu Lys Pro Pro Glu Leu Met
    50                  55                  60

Phe Leu Tyr Asn Leu Lys Gln Leu Ile Arg Asn Glu Thr Val Pro Ser
65                  70                  75                  80

Arg Phe Ile Pro Glu Cys Pro Asp Ser Ser Lys Leu Leu Leu His Ile
                85                  90                  95

Ser Ala Val Asp Pro Glu Asp Ser Ala Val Tyr Phe Cys Ala Ser Ser
            100                 105                 110

Pro Gly Gly Ala Glu Gln Phe Phe Gly Pro Gly Thr Arg Leu Thr Val
        115                 120                 125

Leu Glu Asp Leu Arg Asn Val Thr Pro Pro Lys Val Ser Leu Phe Glu
130                 135                 140

Pro Ser Lys Ala Glu Ile Ala Asn Lys Gln Lys Ala Thr Leu Val Cys
145                 150                 155                 160

Leu Ala Arg Gly Phe Phe Pro Asp His Val Glu Leu Ser Trp Trp Val
                165                 170                 175

Asn Gly Lys Glu Val His Ser Gly Val Ser Thr Asp Pro Gln Ala Tyr
            180                 185                 190

Lys Glu Ser Asn Tyr Ser Tyr Cys Leu Ser Ser Arg Leu Arg Val Ser
        195                 200                 205

Ala Thr Phe Trp His Asn Pro Arg Asn His Phe Arg Cys Gln Val Gln
    210                 215                 220

Phe His Gly Leu Ser Glu Glu Asp Lys Trp Pro Glu Gly Ser Pro Lys
```

```
            225                 230                 235                 240

Pro Val Thr Gln Asn Ile Ser Ala Glu Ala Trp Gly Arg Ala Asp Cys
                245                 250                 255

Gly Ile Thr Ser Ala Ser Tyr His Gln Gly Val Leu Ser Ala Thr Ile
                260                 265                 270

Leu Tyr Glu Ile Leu Leu Gly Lys Ala Thr Leu Tyr Ala Val Leu Val
                275                 280                 285

Ser Gly Leu Val Leu Met Ala Met Val Lys Lys Lys Asn Ser
                290                 295                 300

<210> SEQ ID NO 156
<211> LENGTH: 268
<212> TYPE: PRT
<213> ORGANISM: Mus musculus

<400> SEQUENCE: 156

Met Glu Arg Asn Leu Gly Ala Val Leu Gly Ile Leu Trp Val Gln Ile
1               5                   10                  15

Cys Trp Val Arg Gly Asp Gln Val Glu Gln Ser Pro Ser Ala Leu Ser
                20                  25                  30

Leu His Glu Gly Thr Gly Ser Ala Leu Arg Cys Asn Phe Thr Thr Thr
            35                  40                  45

Met Arg Ala Val Gln Trp Phe Gln Gln Asn Ser Arg Gly Ser Leu Ile
        50                  55                  60

Asn Leu Phe Tyr Leu Ala Ser Gly Thr Lys Glu Asn Gly Arg Leu Lys
65                  70                  75                  80

Ser Thr Phe Asn Ser Lys Glu Ser Tyr Ser Thr Leu His Ile Arg Asp
                85                  90                  95

Ala Gln Leu Glu Asp Ser Gly Thr Tyr Phe Cys Ala Ala Pro Phe Val
            100                 105                 110

Thr Gly Ser Gly Gly Lys Leu Thr Leu Gly Ala Gly Thr Arg Leu Gln
        115                 120                 125

Val Asn Leu Asp Ile Gln Asn Pro Glu Pro Ala Val Tyr Gln Leu Lys
    130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
    210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255

Phe Asn Leu Leu Met Thr Leu Arg Leu Trp Ser Ser
            260                 265

<210> SEQ ID NO 157
<211> LENGTH: 305
<212> TYPE: PRT
<213> ORGANISM: Mus musculus
```

<400> SEQUENCE: 157

Met Gly Ser Ile Phe Leu Ser Cys Leu Ala Val Cys Leu Leu Val Ala
1               5                   10                  15

Gly Pro Val Asp Pro Lys Ile Ile Gln Lys Pro Lys Tyr Leu Val Ala
                20                  25                  30

Val Thr Gly Ser Glu Lys Ile Leu Ile Cys Glu Gln Tyr Leu Gly His
            35                  40                  45

Asn Ala Met Tyr Trp Tyr Arg Gln Ser Ala Lys Lys Pro Leu Glu Phe
        50                  55                  60

Met Phe Ser Tyr Ser Tyr Gln Lys Leu Met Asp Asn Gln Thr Ala Ser
65                  70                  75                  80

Ser Arg Phe Gln Pro Gln Ser Ser Lys Lys Asn His Leu Asp Leu Gln
                85                  90                  95

Ile Thr Ala Leu Lys Pro Asp Asp Ser Ala Thr Tyr Phe Cys Ala Ser
            100                 105                 110

Ser Gln Asp Gly Trp Gly Tyr Glu Gln Tyr Phe Gly Pro Gly Thr Arg
        115                 120                 125

Leu Thr Val Leu Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr His Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Gly Leu Val Leu Met Ala Met Val Lys Lys Lys Asn
    290                 295                 300

Ser
305

<210> SEQ ID NO 158
<211> LENGTH: 268
<212> TYPE: PRT
<213> ORGANISM: Mus musculus

<400> SEQUENCE: 158

Met Asn Ser Ser Pro Gly Phe Val Ala Val Ile Leu Leu Ile Leu Gly
1               5                   10                  15

Arg Thr His Gly Asp Ser Val Thr Gln Thr Glu Gly Pro Val Thr Val
                20                  25                  30

Ser Glu Ser Glu Ser Leu Ile Ile Asn Cys Thr Tyr Ser Ala Thr Ser
            35                  40                  45

```
Ile Ala Tyr Pro Asn Leu Phe Trp Tyr Val Arg Tyr Pro Gly Glu Gly
        50                  55                  60

Leu Gln Leu Leu Leu Lys Val Ile Thr Ala Gly Gln Lys Gly Ser Ser
 65                  70                  75                  80

Arg Gly Phe Glu Ala Thr Tyr Asn Lys Glu Thr Thr Ser Phe His Leu
                 85                  90                  95

Gln Lys Ala Ser Val Gln Glu Ser Asp Ser Ala Val Tyr Tyr Cys Ala
            100                 105                 110

Leu Gly Leu Gly Tyr Lys Leu Thr Phe Gly Thr Gly Thr Ser Leu Leu
            115                 120                 125

Val Asp Pro Asn Ile Gln Asn Pro Glu Pro Ala Val Tyr Gln Leu Lys
130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
            195                 200                 205

Lys Glu Thr Asn Ala Thr Tyr Pro Ser Ser Asp Val Pro Cys Asp Ala
210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255

Phe Asn Leu Leu Met Thr Leu Arg Leu Trp Ser Ser
            260                 265

<210> SEQ ID NO 159
<211> LENGTH: 305
<212> TYPE: PRT
<213> ORGANISM: Mus musculus

<400> SEQUENCE: 159

Met Gly Ser Ile Phe Leu Ser Cys Leu Ala Val Cys Leu Leu Val Ala
 1               5                  10                  15

Gly Pro Val Asp Pro Lys Ile Ile Gln Lys Pro Lys Tyr Leu Val Ala
             20                  25                  30

Val Thr Gly Ser Glu Lys Ile Leu Ile Cys Glu Gln Tyr Leu Gly His
             35                  40                  45

Asn Ala Met Tyr Trp Tyr Arg Gln Ser Ala Lys Lys Pro Leu Glu Phe
         50                  55                  60

Met Phe Ser Tyr Ser Tyr Gln Lys Leu Met Asp Asn Gln Thr Ala Ser
 65                  70                  75                  80

Ser Arg Phe Gln Pro Gln Ser Ser Lys Lys Asn His Leu Asp Leu Gln
                 85                  90                  95

Ile Thr Ala Leu Lys Pro Asp Asp Ser Ala Thr Tyr Phe Cys Ala Ser
            100                 105                 110

Ser Gly Asp Asn Ser Gly Asn Thr Leu Tyr Phe Gly Glu Gly Ser Arg
            115                 120                 125

Leu Ile Val Val Glu Asp Leu Arg Asn Val Thr Pro Pro Lys Val Ser
130                 135                 140

Leu Phe Glu Pro Ser Lys Ala Glu Ile Ala Asn Lys Gln Lys Ala Thr
145                 150                 155                 160
```

```
Leu Val Cys Leu Ala Arg Gly Phe Phe Pro Asp His Val Glu Leu Ser
            165                 170                 175

Trp Trp Val Asn Gly Lys Glu Val His Ser Gly Val Ser Thr Asp Pro
        180                 185                 190

Gln Ala Tyr Lys Glu Ser Asn Tyr Ser Tyr Cys Leu Ser Ser Arg Leu
    195                 200                 205

Arg Val Ser Ala Thr Phe Trp His Asn Pro Arg Asn His Phe Arg Cys
210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser
305

<210> SEQ ID NO 160
<211> LENGTH: 266
<212> TYPE: PRT
<213> ORGANISM: Mus musculus

<400> SEQUENCE: 160

Met Glu Arg Asn Leu Gly Ala Val Leu Gly Ile Leu Trp Val Gln Ile
1               5                   10                  15

Cys Trp Val Arg Gly Asp Gln Val Glu Gln Ser Pro Ser Ala Leu Ser
            20                  25                  30

Leu His Glu Gly Thr Gly Ser Ala Leu Arg Cys Asn Phe Thr Thr Thr
        35                  40                  45

Met Arg Ala Val Gln Trp Phe Gln Gln Asn Ser Arg Gly Ser Leu Ile
    50                  55                  60

Asn Leu Phe Tyr Leu Ala Ser Gly Thr Lys Glu Asn Gly Arg Leu Lys
65                  70                  75                  80

Ser Thr Phe Asn Ser Lys Glu Ser Tyr Ser Thr Leu His Ile Arg Asp
                85                  90                  95

Ala Gln Leu Glu Asp Ser Gly Thr Tyr Phe Cys Ala Ala Val Asn Thr
            100                 105                 110

Asn Thr Gly Lys Leu Thr Phe Gly Asp Gly Thr Val Leu Thr Val Lys
        115                 120                 125

Pro Asn Ile Gln Asn Pro Glu Pro Ala Val Tyr Gln Leu Lys Asp Pro
    130                 135                 140

Arg Ser Gln Asp Ser Thr Leu Cys Leu Phe Thr Asp Phe Asp Ser Gln
145                 150                 155                 160

Ile Asn Val Pro Lys Thr Met Glu Ser Gly Thr Phe Ile Thr Asp Lys
                165                 170                 175

Thr Val Leu Asp Met Lys Ala Met Asp Ser Lys Ser Asn Gly Ala Ile
            180                 185                 190

Ala Trp Ser Asn Gln Thr Ser Phe Thr Cys Gln Asp Ile Phe Lys Glu
        195                 200                 205

Thr Asn Ala Thr Tyr Pro Ser Ser Asp Val Pro Cys Asp Ala Thr Leu
```

```
                  210                 215                 220
Thr Glu Lys Ser Phe Glu Thr Asp Met Asn Leu Asn Phe Gln Asn Leu
225                 230                 235                 240

Ser Val Met Gly Leu Arg Ile Leu Leu Leu Lys Val Ala Gly Phe Asn
                245                 250                 255

Leu Leu Met Thr Leu Arg Leu Trp Ser Ser
                260                 265

<210> SEQ ID NO 161
<211> LENGTH: 302
<212> TYPE: PRT
<213> ORGANISM: Mus musculus

<400> SEQUENCE: 161

Met Trp Thr Phe Leu Leu Leu Trp Ser Gln Gly Ser Val Phe Ser
1               5                  10                  15

Val Leu Leu Tyr Gln Lys Pro Asn Arg Asp Ile Cys Gln Ser Gly Thr
                20                  25                  30

Ser Leu Lys Ile Gln Cys Val Ala Asp Ser Gln Val Val Ser Met Phe
            35                  40                  45

Trp Tyr Gln Gln Phe Gln Glu Gln Ser Leu Met Leu Met Ala Thr Ala
    50                  55                  60

Asn Glu Gly Ser Glu Ala Thr Tyr Glu Ser Gly Phe Thr Lys Asp Lys
65                  70                  75                  80

Phe Pro Ile Ser Arg Pro Asn Leu Thr Phe Ser Thr Leu Thr Val Asn
                85                  90                  95

Asn Ala Arg Pro Gly Asp Ser Ser Ile Tyr Phe Cys Ser Ser Arg Thr
            100                 105                 110

Pro Asn Thr Gly Gln Leu Tyr Phe Gly Glu Gly Ser Lys Leu Thr Val
        115                 120                 125

Leu Glu Asp Leu Arg Asn Val Thr Pro Pro Lys Val Ser Leu Phe Glu
130                 135                 140

Pro Ser Lys Ala Glu Ile Ala Asn Lys Gln Lys Ala Thr Leu Val Cys
145                 150                 155                 160

Leu Ala Arg Gly Phe Phe Pro Asp His Val Glu Leu Ser Trp Trp Val
                165                 170                 175

Asn Gly Lys Glu Val His Ser Gly Val Ser Thr Asp Pro Gln Ala Tyr
            180                 185                 190

Lys Glu Ser Asn Tyr Ser Tyr Cys Leu Ser Ser Arg Leu Arg Val Ser
        195                 200                 205

Ala Thr Phe Trp His Asn Pro Arg Asn His Phe Arg Cys Gln Val Gln
    210                 215                 220

Phe His Gly Leu Ser Glu Glu Asp Lys Trp Pro Glu Gly Ser Pro Lys
225                 230                 235                 240

Pro Val Thr Gln Asn Ile Ser Ala Glu Ala Trp Gly Arg Ala Asp Cys
                245                 250                 255

Gly Ile Thr Ser Ala Ser Tyr His Gln Gly Val Leu Ser Ala Thr Ile
            260                 265                 270

Leu Tyr Glu Ile Leu Leu Gly Lys Ala Thr Leu Tyr Ala Val Leu Val
        275                 280                 285

Ser Gly Leu Val Leu Met Ala Met Val Lys Lys Asn Ser
    290                 295                 300

<210> SEQ ID NO 162
<211> LENGTH: 267
```

```
<212> TYPE: PRT
<213> ORGANISM: Mus musculus

<400> SEQUENCE: 162

Met Leu Leu Val Leu Ile Ser Phe Leu Gly Ile His Phe Leu Asp
1               5                   10                  15

Val Gln Thr Gln Thr Val Ser Gln Ser Asp Ala His Val Thr Val Phe
            20                  25                  30

Glu Gly Asp Ser Val Glu Leu Arg Cys Asn Tyr Ser Tyr Gly Gly Ser
                35                  40                  45

Ile Tyr Leu Ser Trp Tyr Ile Gln His His Gly His Gly Leu Gln Phe
            50                  55                  60

Leu Leu Lys Tyr Tyr Ser Gly Asn Pro Val Val Gln Gly Val Asn Gly
65                  70                  75                  80

Phe Glu Ala Glu Phe Ser Lys Ser Asp Ser Phe His Leu Arg Lys
                85                  90                  95

Ala Ser Val His Trp Ser Asp Ser Ala Val Tyr Phe Cys Ala Val Ser
                100                 105                 110

Ser Gly Gly Tyr Lys Val Val Phe Gly Ser Gly Thr Arg Leu Leu Val
            115                 120                 125

Ser Pro Asp Ile Gln Asn Pro Glu Pro Ala Val Tyr Gln Leu Lys Asp
            130                 135                 140

Pro Arg Ser Gln Asp Ser Thr Leu Cys Leu Phe Thr Asp Phe Asp Ser
145                 150                 155                 160

Gln Ile Asn Val Pro Lys Thr Met Glu Ser Gly Thr Phe Ile Thr Asp
                165                 170                 175

Lys Thr Val Leu Asp Met Lys Ala Met Asp Ser Lys Ser Asn Gly Ala
            180                 185                 190

Ile Ala Trp Ser Asn Gln Thr Ser Phe Thr Cys Gln Asp Ile Phe Lys
            195                 200                 205

Glu Thr Asn Ala Thr Tyr Pro Ser Ser Asp Val Pro Cys Asp Ala Thr
        210                 215                 220

Leu Thr Glu Lys Ser Phe Glu Thr Asp Met Asn Leu Asn Phe Gln Asn
225                 230                 235                 240

Leu Ser Val Met Gly Leu Arg Ile Leu Leu Leu Lys Val Ala Gly Phe
                245                 250                 255

Asn Leu Leu Met Thr Leu Arg Leu Trp Ser Ser
            260                 265

<210> SEQ ID NO 163
<211> LENGTH: 302
<212> TYPE: PRT
<213> ORGANISM: Mus musculus

<400> SEQUENCE: 163

Met Ser Cys Arg Leu Leu Leu Tyr Val Ser Leu Cys Leu Val Glu Thr
1               5                   10                  15

Ala Leu Met Asn Thr Lys Ile Thr Gln Ser Pro Arg Tyr Leu Ile Leu
            20                  25                  30

Gly Arg Ala Asn Lys Ser Leu Glu Cys Glu Gln His Leu Gly His Asn
                35                  40                  45

Ala Met Tyr Trp Tyr Lys Gln Ser Ala Glu Lys Pro Pro Glu Leu Met
        50                  55                  60

Phe Leu Tyr Asn Leu Lys Gln Leu Ile Arg Asn Glu Thr Val Pro Ser
65                  70                  75                  80
```

Arg Phe Ile Pro Glu Cys Pro Asp Ser Ser Lys Leu Leu His Ile
                85                  90                  95

Ser Ala Val Asp Pro Glu Asp Ser Ala Val Tyr Phe Cys Ala Ser Ser
            100                 105                 110

Gln Gly Gly Thr Glu Val Phe Phe Gly Lys Gly Thr Arg Leu Thr Val
            115                 120                 125

Val Glu Asp Leu Arg Asn Val Thr Pro Pro Lys Val Ser Leu Phe Glu
130                 135                 140

Pro Ser Lys Ala Glu Ile Ala Asn Lys Gln Lys Ala Thr Leu Val Cys
145                 150                 155                 160

Leu Ala Arg Gly Phe Phe Pro Asp His Val Glu Leu Ser Trp Trp Val
                165                 170                 175

Asn Gly Lys Glu Val His Ser Gly Val Ser Thr Asp Pro Gln Ala Tyr
            180                 185                 190

Lys Glu Ser Asn Tyr Ser Tyr Cys Leu Ser Ser Arg Leu Arg Val Ser
        195                 200                 205

Ala Thr Phe Trp His Asn Pro Arg Asn His Phe Arg Cys Gln Val Gln
    210                 215                 220

Phe His Gly Leu Ser Glu Glu Asp Lys Trp Pro Glu Gly Ser Pro Lys
225                 230                 235                 240

Pro Val Thr Gln Asn Ile Ser Ala Glu Ala Trp Gly Arg Ala Asp Cys
                245                 250                 255

Gly Ile Thr Ser Ala Ser Tyr Gln Gln Gly Val Leu Ser Ala Thr Ile
            260                 265                 270

Leu Tyr Glu Ile Leu Leu Gly Lys Ala Thr Leu Tyr Ala Val Leu Val
        275                 280                 285

Ser Thr Leu Val Val Met Ala Met Val Lys Arg Lys Asn Ser
    290                 295                 300

<210> SEQ ID NO 164
<211> LENGTH: 273
<212> TYPE: PRT
<213> ORGANISM: Mus musculus

<400> SEQUENCE: 164

Met Asp Lys Ile Leu Thr Ala Thr Phe Leu Leu Leu Gly Leu His Leu
1               5                   10                  15

Ala Gly Val Asn Gly Gln Gln Gln Glu Lys Arg Asp Gln Gln Gln Val
            20                  25                  30

Arg Gln Ser Pro Gln Ser Leu Thr Val Trp Glu Gly Glu Thr Ala Ile
        35                  40                  45

Leu Asn Cys Ser Tyr Glu Asp Ser Thr Phe Asn Tyr Phe Pro Trp Tyr
50                  55                  60

Gln Gln Phe Pro Gly Glu Gly Pro Ala Leu Leu Ile Ser Ile Arg Ser
65                  70                  75                  80

Val Ser Asp Lys Lys Glu Asp Gly Arg Phe Thr Ile Phe Phe Asn Lys
                85                  90                  95

Arg Glu Lys Lys Leu Ser Leu His Ile Thr Asp Ser Gln Pro Gly Asp
            100                 105                 110

Ser Ala Thr Tyr Phe Cys Ala Pro Asn Asn Arg Ile Phe Phe Gly Asp
            115                 120                 125

Gly Thr Gln Leu Val Val Lys Pro Asn Ile Gln Asn Pro Glu Pro Ala
        130                 135                 140

Val Tyr Gln Leu Lys Asp Pro Arg Ser Gln Asp Ser Thr Leu Cys Leu
145                 150                 155                 160

```
Phe Thr Asp Phe Asp Ser Gln Ile Asn Val Pro Lys Thr Met Glu Ser
                165                 170                 175

Gly Thr Phe Ile Thr Asp Lys Thr Val Leu Asp Met Lys Ala Met Asp
            180                 185                 190

Ser Lys Ser Asn Gly Ala Ile Ala Trp Ser Asn Gln Thr Ser Phe Thr
        195                 200                 205

Cys Gln Asp Ile Phe Lys Glu Thr Asn Ala Thr Tyr Pro Ser Ser Asp
    210                 215                 220

Val Pro Cys Asp Ala Thr Leu Thr Glu Lys Ser Phe Glu Thr Asp Met
225                 230                 235                 240

Asn Leu Asn Phe Gln Asn Leu Ser Val Met Gly Leu Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 165
<211> LENGTH: 303
<212> TYPE: PRT
<213> ORGANISM: Mus musculus

<400> SEQUENCE: 165

Met Gly Ser Arg Leu Phe Phe Val Leu Ser Ser Leu Leu Cys Ser Lys
1               5                   10                  15

His Met Glu Ala Ala Val Thr Gln Ser Pro Arg Asn Lys Val Ala Val
                20                  25                  30

Thr Gly Gly Lys Val Thr Leu Ser Cys Asn Gln Thr Asn Asn His Asn
            35                  40                  45

Asn Met Tyr Trp Tyr Arg Gln Asp Thr Gly His Gly Leu Arg Leu Ile
        50                  55                  60

His Tyr Ser Tyr Gly Ala Gly Ser Thr Glu Lys Gly Asp Ile Pro Asp
65                  70                  75                  80

Gly Tyr Lys Ala Ser Arg Pro Ser Gln Glu Asn Phe Ser Leu Ile Leu
                85                  90                  95

Glu Leu Ala Thr Pro Ser Gln Thr Ser Val Tyr Phe Cys Ala Ser Leu
                100                 105                 110

Gly Tyr Asn Tyr Ala Glu Gln Phe Phe Gly Pro Gly Thr Arg Leu Thr
            115                 120                 125

Val Leu Glu Asp Leu Arg Asn Val Thr Pro Pro Lys Val Ser Leu Phe
130                 135                 140

Glu Pro Ser Lys Ala Glu Ile Ala Asn Lys Gln Lys Ala Thr Leu Val
145                 150                 155                 160

Cys Leu Ala Arg Gly Phe Phe Pro Asp His Val Glu Leu Ser Trp Trp
                165                 170                 175

Val Asn Gly Lys Glu Val His Ser Gly Val Ser Thr Asp Pro Gln Ala
            180                 185                 190

Tyr Lys Glu Ser Asn Tyr Ser Tyr Cys Leu Ser Ser Arg Leu Arg Val
        195                 200                 205

Ser Ala Thr Phe Trp His Asn Pro Arg Asn His Phe Arg Cys Gln Val
    210                 215                 220

Gln Phe His Gly Leu Ser Glu Glu Asp Lys Trp Pro Glu Gly Ser Pro
225                 230                 235                 240

Lys Pro Val Thr Gln Asn Ile Ser Ala Glu Ala Trp Gly Arg Ala Asp
                245                 250                 255
```

Cys Gly Ile Thr Ser Ala Ser Tyr His Gln Gly Val Leu Ser Ala Thr
         260                 265                 270

Ile Leu Tyr Glu Ile Leu Leu Gly Lys Ala Thr Leu Tyr Ala Val Leu
         275                 280                 285

Val Ser Gly Leu Val Leu Met Ala Met Val Lys Lys Lys Asn Ser
         290                 295                 300

<210> SEQ ID NO 166
<211> LENGTH: 269
<212> TYPE: PRT
<213> ORGANISM: Mus musculus

<400> SEQUENCE: 166

Met Asn Asn Ser Pro Ala Leu Val Thr Val Met Leu Phe Ile Leu Gly
1               5                   10                  15

Arg Thr His Gly Asp Ser Val Ile Gln Met Gln Gly Gln Val Thr Leu
            20                  25                  30

Ser Glu Asn Asp Phe Leu Phe Ile Asn Cys Thr Tyr Ser Thr Thr Gly
        35                  40                  45

Tyr Pro Thr Leu Phe Trp Tyr Val Gln Tyr Ser Gly Glu Gly Pro Gln
    50                  55                  60

Leu Leu Leu Gln Val Thr Thr Ala Asn Asn Lys Gly Ser Ser Arg Gly
65                  70                  75                  80

Phe Glu Ala Thr Tyr Asp Lys Gly Thr Thr Ser Phe His Leu Gln Lys
                85                  90                  95

Thr Ser Val Gln Glu Ile Asp Ser Ala Val Tyr Tyr Cys Ala Met Ser
            100                 105                 110

Asp Ala Ser Gly Ser Trp Gln Leu Ile Phe Gly Ser Gly Thr Gln Leu
        115                 120                 125

Thr Val Met Pro Asp Ile Gln Asn Pro Glu Pro Ala Val Tyr Gln Leu
130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Thr Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
        195                 200                 205

Phe Lys Glu Thr Asn Ala Thr Tyr Pro Ser Ser Asp Val Pro Cys Asp
    210                 215                 220

Ala Thr Leu Thr Glu Lys Ser Phe Glu Thr Asp Met Asn Leu Asn Phe
225                 230                 235                 240

Gln Asn Leu Ser Val Met Gly Leu Arg Ile Leu Leu Leu Lys Val Ala
                245                 250                 255

Gly Phe Asn Leu Leu Met Thr Leu Arg Leu Trp Ser Ser
            260                 265

<210> SEQ ID NO 167
<211> LENGTH: 306
<212> TYPE: PRT
<213> ORGANISM: Mus musculus

<400> SEQUENCE: 167

Met Gly Ser Arg Leu Phe Phe Val Val Leu Ile Leu Leu Cys Ala Lys
1               5                   10                  15

His Met Glu Ala Ala Val Thr Gln Ser Pro Arg Ser Lys Val Ala Val
            20                  25                  30

Thr Gly Gly Lys Val Thr Leu Ser Cys His Gln Thr Asn Asn His Asp
        35                  40                  45

Tyr Met Tyr Trp Tyr Arg Gln Asp Thr Gly His Gly Leu Arg Leu Ile
    50                  55                  60

His Tyr Ser Tyr Val Ala Asp Ser Thr Glu Lys Gly Asp Ile Pro Asp
65                  70                  75                  80

Gly Tyr Lys Ala Ser Arg Pro Ser Gln Glu Asn Phe Ser Leu Ile Leu
                85                  90                  95

Glu Leu Ala Ser Leu Ser Gln Thr Ala Val Tyr Phe Cys Ala Ser Ser
            100                 105                 110

Pro Asp Arg Pro Ser Tyr Asn Ser Pro Leu Tyr Phe Ala Ala Gly Thr
        115                 120                 125

Arg Leu Thr Val Thr Glu Asp Leu Arg Asn Val Thr Pro Pro Lys Val
130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Thr Leu Val Val Met Ala Met Val Lys Arg Lys
    290                 295                 300

Asn Ser
305

<210> SEQ ID NO 168
<211> LENGTH: 272
<212> TYPE: PRT
<213> ORGANISM: Mus musculus

<400> SEQUENCE: 168

Met Arg Pro Gly Thr Cys Ser Val Leu Val Leu Leu Leu Met Leu Arg
1               5                   10                  15

Arg Ser Asn Gly Asp Gly Asp Ser Val Thr Gln Lys Glu Gly Leu Val
            20                  25                  30

Thr Leu Thr Glu Gly Leu Pro Val Met Leu Asn Cys Thr Tyr Gln Thr
        35                  40                  45

Ile Tyr Ser Asn Ala Phe Leu Phe Trp Tyr Val His Tyr Leu Asn Glu
    50                  55                  60

Ser Pro Arg Leu Leu Leu Lys Ser Ser Thr Asp Asn Lys Arg Thr Glu

```
                65                  70                  75                  80
His Gln Gly Phe His Ala Thr Leu His Lys Ser Ser Ser Phe His
                    85                  90                  95

Leu Gln Lys Ser Ser Ala Gln Leu Ser Asp Ser Ala Leu Tyr Tyr Cys
                100                 105                 110

Ala Leu Asn Asn Val Gly Asp Asn Ser Lys Leu Ile Trp Gly Leu Gly
            115                 120                 125

Thr Ser Leu Val Val Asn Pro Asn Ile Gln Asn Pro Glu Pro Ala Val
130                 135                 140

Tyr Gln Leu Lys Asp Pro Arg Ser Gln Asp Ser Thr Leu Cys Leu Phe
145                 150                 155                 160

Thr Asp Phe Asp Ser Gln Ile Asn Val Pro Lys Thr Met Glu Ser Gly
                165                 170                 175

Thr Phe Ile Thr Asp Lys Thr Val Leu Asp Met Lys Ala Met Asp Ser
                180                 185                 190

Lys Ser Asn Gly Ala Ile Ala Trp Ser Asn Gln Thr Ser Phe Thr Cys
            195                 200                 205

Gln Asp Ile Phe Lys Glu Thr Asn Ala Thr Tyr Pro Ser Ser Asp Val
    210                 215                 220

Pro Cys Asp Ala Thr Leu Thr Glu Lys Ser Phe Glu Thr Asp Met Asn
225                 230                 235                 240

Leu Asn Phe Gln Asn Leu Ser Val Met Gly Leu Arg Ile Leu Leu Leu
                245                 250                 255

Lys Val Ala Gly Phe Asn Leu Leu Met Thr Leu Arg Leu Trp Ser Ser
                260                 265                 270

<210> SEQ ID NO 169
<211> LENGTH: 305
<212> TYPE: PRT
<213> ORGANISM: Mus musculus

<400> SEQUENCE: 169

Met Ser Cys Arg Leu Leu Leu Tyr Val Ser Leu Cys Leu Val Glu Thr
1               5                   10                  15

Ala Leu Met Asn Thr Lys Ile Thr Gln Ser Pro Arg Tyr Leu Ile Leu
                20                  25                  30

Gly Arg Ala Asn Lys Ser Leu Glu Cys Glu Gln His Leu Gly His Asn
            35                  40                  45

Ala Met Tyr Trp Tyr Lys Gln Ser Ala Glu Lys Pro Pro Glu Leu Met
    50                  55                  60

Phe Leu Tyr Asn Leu Lys Gln Leu Ile Arg Asn Glu Thr Val Pro Ser
65                  70                  75                  80

Arg Phe Ile Pro Glu Cys Pro Asp Ser Ser Lys Leu Leu Leu His Ile
                85                  90                  95

Ser Ala Val Asp Pro Glu Asp Ser Ala Val Tyr Phe Cys Ala Ser Ser
                100                 105                 110

Gln Tyr Gly Gly Ala Asn Thr Glu Val Phe Phe Gly Lys Gly Thr Arg
            115                 120                 125

Leu Thr Val Val Glu Asp Leu Arg Asn Val Thr Pro Pro Lys Val Ser
130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175
```

```
Trp Trp Val Asn Gly Lys Glu Val His Ser Gly Val Ser Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser
305

<210> SEQ ID NO 170
<211> LENGTH: 265
<212> TYPE: PRT
<213> ORGANISM: Mus musculus

<400> SEQUENCE: 170

Met Lys Arg Leu Leu Cys Ser Leu Leu Gly Leu Leu Cys Thr Gln Val
1               5                   10                  15

Cys Trp Val Lys Gly Gln Gln Val Gln Gln Ser Pro Ala Ser Leu Val
            20                  25                  30

Leu Gln Glu Gly Glu Asn Ala Glu Leu Gln Cys Asn Phe Ser Ser Thr
        35                  40                  45

Ala Thr Arg Leu Gln Trp Phe Tyr Gln His Pro Gly Gly Arg Leu Val
    50                  55                  60

Ser Leu Phe Tyr Asn Pro Ser Gly Thr Lys His Thr Gly Arg Leu Thr
65                  70                  75                  80

Ser Thr Thr Val Thr Asn Glu Arg Arg Ser Ser Leu His Ile Ser Ser
                85                  90                  95

Ser Gln Thr Thr Asp Ser Gly Thr Tyr Phe Cys Ala Ala Ala Ser Asn
            100                 105                 110

Thr Asn Lys Val Val Phe Gly Thr Gly Thr Arg Leu Gln Val Leu Pro
        115                 120                 125

Asn Ile Gln Asn Pro Glu Pro Ala Val Tyr Gln Leu Lys Asp Pro Arg
    130                 135                 140

Ser Gln Asp Ser Thr Leu Cys Leu Phe Thr Asp Phe Asp Ser Gln Ile
145                 150                 155                 160

Asn Val Pro Lys Thr Met Glu Ser Gly Thr Phe Ile Thr Asp Lys Thr
                165                 170                 175

Val Leu Asp Met Lys Ala Met Asp Ser Lys Ser Asn Gly Ala Ile Ala
            180                 185                 190

Trp Ser Asn Gln Thr Ser Phe Thr Cys Gln Asp Ile Phe Lys Glu Thr
        195                 200                 205

Asn Ala Thr Tyr Pro Ser Ser Asp Val Pro Cys Asp Ala Thr Leu Thr
    210                 215                 220

Glu Lys Ser Phe Glu Thr Asp Met Asn Leu Asn Phe Gln Asn Leu Ser
225                 230                 235                 240
```

-continued

Val Met Gly Leu Arg Ile Leu Leu Lys Val Ala Gly Phe Asn Leu
            245                 250                 255

Leu Met Thr Leu Arg Leu Trp Ser Ser
            260                 265

<210> SEQ ID NO 171
<211> LENGTH: 302
<212> TYPE: PRT
<213> ORGANISM: Mus musculus

<400> SEQUENCE: 171

Met Leu Leu Leu Leu Leu Gly Pro Gly Cys Gly Leu Gly Ala
1               5                   10                  15

Leu Val Tyr Gln Tyr Pro Arg Arg Thr Ile Cys Lys Ser Gly Thr Ser
            20                  25                  30

Met Arg Met Glu Cys Gln Ala Val Gly Phe Gln Ala Thr Ser Val Ala
        35                  40                  45

Trp Tyr Arg Gln Ser Pro Gln Lys Thr Phe Glu Leu Ile Ala Leu Ser
    50                  55                  60

Thr Val Asn Ser Ala Ile Lys Tyr Glu Gln Asn Phe Thr Gln Glu Lys
65                  70                  75                  80

Phe Pro Ile Ser His Pro Asn Leu Ser Phe Ser Ser Met Thr Val Leu
                85                  90                  95

Asn Ala Tyr Leu Glu Asp Arg Gly Leu Tyr Leu Cys Gly Val Asp Arg
            100                 105                 110

Ala Asn Tyr Ala Glu Gln Phe Phe Gly Pro Gly Thr Arg Leu Thr Val
        115                 120                 125

Leu Glu Asp Leu Arg Asn Val Thr Pro Pro Lys Val Ser Leu Phe Glu
    130                 135                 140

Pro Ser Lys Ala Glu Ile Ala Asn Lys Gln Lys Ala Thr Leu Val Cys
145                 150                 155                 160

Leu Ala Arg Gly Phe Phe Pro Asp His Val Glu Leu Ser Trp Trp Val
                165                 170                 175

Asn Gly Lys Glu Val His Ser Gly Val Ser Thr Asp Pro Gln Ala Tyr
            180                 185                 190

Lys Glu Ser Asn Tyr Ser Tyr Cys Leu Ser Ser Arg Leu Arg Val Ser
        195                 200                 205

Ala Thr Phe Trp His Asn Pro Arg Asn His Phe Arg Cys Gln Val Gln
    210                 215                 220

Phe His Gly Leu Ser Glu Glu Asp Lys Trp Pro Glu Gly Ser Pro Lys
225                 230                 235                 240

Pro Val Thr Gln Asn Ile Ser Ala Glu Ala Trp Gly Arg Ala Asp Cys
                245                 250                 255

Gly Ile Thr Ser Ala Ser Tyr His Gln Gly Val Leu Ser Ala Thr Ile
            260                 265                 270

Leu Tyr Glu Ile Leu Leu Gly Lys Ala Thr Leu Tyr Ala Val Leu Val
        275                 280                 285

Ser Gly Leu Val Leu Met Ala Met Val Lys Lys Lys Asn Ser
    290                 295                 300

<210> SEQ ID NO 172
<211> LENGTH: 9
<212> TYPE: PRT
<213> ORGANISM: Homo sapiens

<400> SEQUENCE: 172

```
Val Leu Cys Ser Ile Asp Trp Phe Met
1               5
```

<210> SEQ ID NO 173
<211> LENGTH: 12
<212> TYPE: PRT
<213> ORGANISM: Homo sapiens

<400> SEQUENCE: 173

```
Cys Ser Ile Asp Trp Phe Met Val Thr Val His Pro
1               5                   10
```

<210> SEQ ID NO 174
<211> LENGTH: 212
<212> TYPE: PRT
<213> ORGANISM: Homo sapiens

<400> SEQUENCE: 174

```
Met Lys Val Phe Lys Phe Ile Gly Leu Met Ile Leu Leu Thr Ser Ala
1               5                   10                  15

Phe Ser Ala Gly Ser Gly Gln Ser Pro Met Thr Val Leu Cys Ser Ile
            20                  25                  30

Asp Trp Phe Met Val Thr Val His Pro Phe Met Leu Asn Asn Asp Val
        35                  40                  45

Cys Val His Phe His Glu Leu His Leu Gly Leu Gly Cys Pro Pro Asn
    50                  55                  60

His Val Gln Pro His Ala Tyr Gln Phe Thr Tyr Arg Val Thr Glu Cys
65                  70                  75                  80

Gly Ile Arg Ala Lys Ala Val Ser Gln Asp Met Val Ile Tyr Ser Thr
                85                  90                  95

Glu Ile His Tyr Ser Ser Lys Gly Thr Pro Ser Lys Phe Val Ile Pro
            100                 105                 110

Val Ser Cys Ala Ala Pro Gln Lys Ser Pro Trp Leu Thr Lys Pro Cys
        115                 120                 125

Ser Met Arg Val Ala Ser Lys Ser Arg Ala Thr Ala Gln Lys Asp Glu
    130                 135                 140

Lys Cys Tyr Glu Val Phe Ser Leu Ser Gln Ser Ser Gln Arg Pro Asn
145                 150                 155                 160

Cys Asp Cys Pro Pro Cys Val Phe Ser Glu Glu His Thr Gln Val
                165                 170                 175

Pro Cys His Gln Ala Gly Ala Gln Glu Ala Gln Pro Leu Gln Pro Ser
            180                 185                 190

His Phe Leu Asp Ile Ser Glu Asp Trp Ser Leu His Thr Asp Asp Met
        195                 200                 205

Ile Gly Ser Met
    210
```

<210> SEQ ID NO 175
<211> LENGTH: 15
<212> TYPE: PRT
<213> ORGANISM: Homo sapiens

<400> SEQUENCE: 175

```
Val Leu Leu Lys Glu Phe Thr Val Ser Gly Asn Ile Leu Thr Ile
1               5                   10                  15
```

<210> SEQ ID NO 176
<211> LENGTH: 275

```
<212> TYPE: PRT
<213> ORGANISM: Homo sapiens

<400> SEQUENCE: 176

Met Leu Leu Leu Leu Val Pro Val Leu Glu Val Ile Phe Thr Leu Gly
1               5                   10                  15

Gly Thr Arg Ala Gln Ser Val Thr Gln Leu Gly Ser His Val Ser Val
            20                  25                  30

Ser Glu Gly Ala Leu Val Leu Leu Arg Cys Asn Tyr Ser Ser Ser Val
        35                  40                  45

Pro Pro Tyr Leu Phe Trp Tyr Val Gln Tyr Pro Asn Gln Gly Leu Gln
    50                  55                  60

Leu Leu Leu Lys Tyr Thr Thr Gly Ala Thr Leu Val Lys Gly Ile Asn
65                  70                  75                  80

Gly Phe Glu Ala Glu Phe Lys Lys Ser Glu Thr Ser Phe His Leu Thr
                85                  90                  95

Lys Pro Ser Ala His Met Ser Asp Ala Ala Glu Tyr Phe Cys Ala Val
            100                 105                 110

Ser Lys Gly Ser Ser Asn Thr Gly Lys Leu Ile Phe Gly Gln Gly Thr
        115                 120                 125

Thr Leu Gln Val Lys Pro Asp Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275

<210> SEQ ID NO 177
<211> LENGTH: 311
<212> TYPE: PRT
<213> ORGANISM: Homo sapiens

<400> SEQUENCE: 177

Met Gly Thr Arg Leu Leu Cys Cys Val Val Phe Cys Leu Leu Gln Ala
1               5                   10                  15

Gly Pro Leu Asp Thr Ala Val Ser Gln Thr Pro Lys Tyr Leu Val Thr
            20                  25                  30

Gln Met Gly Asn Asp Lys Ser Ile Lys Cys Glu Gln Asn Leu Gly His
        35                  40                  45

Asp Thr Met Tyr Trp Tyr Lys Gln Asp Ser Lys Lys Phe Leu Lys Ile
    50                  55                  60
```

```
Met Phe Ser Tyr Asn Asn Lys Glu Leu Ile Ile Asn Glu Thr Val Pro
 65                  70                  75                  80

Asn Arg Phe Ser Pro Lys Ser Pro Asp Lys Ala His Leu Asn Leu His
                 85                  90                  95

Ile Asn Ser Leu Glu Leu Gly Asp Ser Ala Val Tyr Phe Cys Ala Ser
            100                 105                 110

Ser Gln Asp Pro Gly Gly Ala Gly Asn Thr Ile Tyr Phe Gly Glu Gly
        115                 120                 125

Ser Trp Leu Thr Val Val Glu Asp Leu Asn Lys Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Val Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
    290                 295                 300

Met Val Lys Arg Lys Asp Phe
305                 310

<210> SEQ ID NO 178
<211> LENGTH: 9
<212> TYPE: PRT
<213> ORGANISM: Homo sapiens

<400> SEQUENCE: 178

Val Leu Leu Asp Val Thr Leu Ile Leu
1               5

<210> SEQ ID NO 179
<211> LENGTH: 9
<212> TYPE: PRT
<213> ORGANISM: Homo sapiens

<400> SEQUENCE: 179

Ala Ile Ile Val Ile Leu Leu Leu Val
1               5

<210> SEQ ID NO 180
<211> LENGTH: 9
<212> TYPE: PRT
<213> ORGANISM: Homo sapiens

<400> SEQUENCE: 180

Pro Arg Trp Thr His Leu Leu Arg Leu
```

<210> SEQ ID NO 181
<211> LENGTH: 15
<212> TYPE: PRT
<213> ORGANISM: Homo sapiens

<400> SEQUENCE: 181

Ser Pro Ile Ser Glu Ser Val Leu Ala Arg Leu Ser Lys Phe Glu
1               5                   10                  15

<210> SEQ ID NO 182
<211> LENGTH: 15
<212> TYPE: PRT
<213> ORGANISM: Homo sapiens

<400> SEQUENCE: 182

Tyr Asp Ser Lys Ile Lys Lys Ile Val His Ser Ile Val Ser Ser
1               5                   10                  15

<210> SEQ ID NO 183
<211> LENGTH: 15
<212> TYPE: PRT
<213> ORGANISM: Homo sapiens

<400> SEQUENCE: 183

Tyr Ile Pro Leu Glu Tyr Arg Ser Ile Ser Leu Ala Ile Ala Leu
1               5                   10                  15

<210> SEQ ID NO 184
<211> LENGTH: 15
<212> TYPE: PRT
<213> ORGANISM: Homo sapiens

<400> SEQUENCE: 184

Val Phe Val Glu Arg Arg Gln Gln Tyr Phe Ser Asp Leu Phe Asn
1               5                   10                  15

<210> SEQ ID NO 185
<211> LENGTH: 15
<212> TYPE: PRT
<213> ORGANISM: Homo sapiens

<400> SEQUENCE: 185

Arg Arg Gln Gln Tyr Phe Ser Asp Leu Phe Asn Ile Leu Asp Thr
1               5                   10                  15

<210> SEQ ID NO 186
<211> LENGTH: 15
<212> TYPE: PRT
<213> ORGANISM: Homo sapiens

<400> SEQUENCE: 186

Leu Phe Asn Ile Leu Asp Thr Ala Ile Ile Val Ile Leu Leu Leu
1               5                   10                  15

<210> SEQ ID NO 187
<211> LENGTH: 15
<212> TYPE: PRT
<213> ORGANISM: Homo sapiens

<400> SEQUENCE: 187

Arg Ile Ile Ala Met Ser Phe Pro Ser Ser Gly Arg Gln Ser Phe
1               5                   10                  15

```
<210> SEQ ID NO 188
<211> LENGTH: 276
<212> TYPE: PRT
<213> ORGANISM: Homo sapiens

<400> SEQUENCE: 188

Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
            20                  25                  30

Val Val Glu Lys Glu Asp Val Thr Leu Asp Cys Val Tyr Glu Thr Arg
        35                  40                  45

Asp Thr Thr Tyr Tyr Leu Phe Trp Tyr Lys Gln Pro Pro Ser Gly Glu
    50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
            100                 105                 110

Ala Leu Ile Glu Ala Ala Gly Asn Lys Leu Thr Phe Gly Gly Gly
        115                 120                 125

Thr Arg Val Leu Val Lys Pro Asn Ile Gln Asn Pro Asp Pro Ala Val
    130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
    275

<210> SEQ ID NO 189
<211> LENGTH: 306
<212> TYPE: PRT
<213> ORGANISM: Homo sapiens

<400> SEQUENCE: 189

Met Ser Leu Gly Leu Leu Cys Cys Gly Val Phe Ser Leu Leu Trp Ala
1               5                   10                  15

Gly Pro Val Asn Ala Gly Val Thr Gln Thr Pro Lys Phe Arg Val Leu
            20                  25                  30

Lys Thr Gly Gln Ser Met Thr Leu Leu Cys Ala Gln Asp Met Asn His
        35                  40                  45
```

```
Glu Tyr Met Tyr Trp Tyr Arg Gln Asp Pro Gly Met Gly Leu Arg Leu
 50                  55                  60

Ile His Tyr Ser Val Gly Glu Gly Thr Thr Ala Lys Gly Glu Val Pro
 65                  70                  75                  80

Asp Gly Tyr Asn Val Ser Arg Leu Lys Lys Gln Asn Phe Leu Leu Gly
                 85                  90                  95

Leu Glu Ser Ala Ala Pro Ser Gln Thr Ser Val Tyr Phe Cys Ala Ser
                100                 105                 110

Ser Asp Gly Tyr Gly Tyr Thr Phe Gly Ser Gly Thr Arg Leu Thr Val
                115                 120                 125

Val Glu Asp Leu Asn Lys Val Phe Pro Pro Glu Val Ala Val Phe Glu
130                 135                 140

Pro Ser Glu Ala Glu Ile Ser His Thr Gln Lys Ala Thr Leu Val Cys
145                 150                 155                 160

Leu Ala Thr Gly Phe Phe Pro Asp His Val Glu Leu Ser Trp Trp Val
                165                 170                 175

Asn Gly Lys Glu Val His Ser Gly Val Ser Thr Asp Pro Gln Pro Leu
                180                 185                 190

Lys Glu Gln Pro Ala Leu Asn Asp Ser Arg Tyr Cys Leu Ser Ser Arg
                195                 200                 205

Leu Arg Val Ser Ala Thr Phe Trp Gln Asn Pro Arg Asn His Phe Arg
210                 215                 220

Cys Gln Val Gln Phe Tyr Gly Leu Ser Glu Asn Asp Glu Trp Thr Gln
225                 230                 235                 240

Asp Arg Ala Lys Pro Val Thr Gln Ile Val Ser Ala Glu Ala Trp Gly
                245                 250                 255

Arg Ala Asp Cys Gly Phe Thr Ser Val Ser Tyr Gln Gln Gly Val Leu
                260                 265                 270

Ser Ala Thr Ile Leu Tyr Glu Ile Leu Leu Gly Lys Ala Thr Leu Tyr
                275                 280                 285

Ala Val Leu Val Ser Ala Leu Val Leu Met Ala Met Val Lys Arg Lys
                290                 295                 300

Asp Phe
305

<210> SEQ ID NO 190
<211> LENGTH: 281
<212> TYPE: PRT
<213> ORGANISM: Homo sapiens

<400> SEQUENCE: 190

Met Asp Lys Ile Leu Gly Ala Ser Phe Leu Val Leu Trp Leu Gln Leu
1                   5                  10                  15

Cys Trp Val Ser Gly Gln Gln Lys Glu Lys Ser Asp Gln Gln Gln Val
                 20                  25                  30

Lys Gln Ser Pro Gln Ser Leu Ile Val Gln Lys Gly Gly Ile Ser Ile
                 35                  40                  45

Ile Asn Cys Ala Tyr Glu Asn Thr Ala Phe Asp Tyr Phe Pro Trp Tyr
 50                  55                  60

Gln Gln Phe Pro Gly Lys Gly Pro Ala Leu Leu Ile Ala Ile Arg Pro
 65                  70                  75                  80

Asp Val Ser Glu Lys Lys Glu Gly Arg Phe Thr Ile Ser Phe Asn Lys
                 85                  90                  95

Ser Ala Lys Gln Phe Ser Leu His Ile Met Asp Ser Gln Pro Gly Asp
                100                 105                 110
```

```
Ser Ala Thr Tyr Phe Cys Ala Ala Ser Phe Tyr Thr Gly Asn Gln Phe
            115                 120                 125

Tyr Phe Gly Thr Gly Thr Ser Leu Thr Val Ile Pro Asn Ile Gln Asn
        130                 135                 140

Pro Asp Pro Ala Val Tyr Gln Leu Arg Asp Ser Lys Ser Ser Asp Lys
145                 150                 155                 160

Ser Val Cys Leu Phe Thr Asp Phe Asp Ser Gln Thr Asn Val Ser Gln
                165                 170                 175

Ser Lys Asp Ser Asp Val Tyr Ile Thr Asp Lys Thr Val Leu Asp Met
            180                 185                 190

Arg Ser Met Asp Phe Lys Ser Asn Ser Ala Val Ala Trp Ser Asn Lys
        195                 200                 205

Ser Asp Phe Ala Cys Ala Asn Ala Phe Asn Asn Ser Ile Ile Pro Glu
210                 215                 220

Asp Thr Phe Phe Pro Ser Pro Glu Ser Ser Cys Asp Val Lys Leu Val
225                 230                 235                 240

Glu Lys Ser Phe Glu Thr Asp Thr Asn Leu Asn Phe Gln Asn Leu Ser
                245                 250                 255

Val Ile Gly Phe Arg Ile Leu Leu Leu Lys Val Ala Gly Phe Asn Leu
            260                 265                 270

Leu Met Thr Leu Arg Leu Trp Ser Ser
        275                 280

<210> SEQ ID NO 191
<211> LENGTH: 311
<212> TYPE: PRT
<213> ORGANISM: Homo sapiens

<400> SEQUENCE: 191

Met Gly Thr Arg Leu Leu Cys Cys Val Val Phe Cys Leu Leu Gln Ala
1               5                   10                  15

Gly Pro Leu Asp Thr Ala Val Ser Gln Thr Pro Lys Tyr Leu Val Thr
            20                  25                  30

Gln Met Gly Asn Asp Lys Ser Ile Lys Cys Glu Gln Asn Leu Gly His
        35                  40                  45

Asp Thr Met Tyr Trp Tyr Lys Gln Asp Ser Lys Lys Phe Leu Lys Ile
    50                  55                  60

Met Phe Ser Tyr Asn Asn Lys Glu Leu Ile Ile Asn Glu Thr Val Pro
65                  70                  75                  80

Asn Arg Phe Ser Pro Lys Ser Pro Asp Lys Ala His Leu Asn Leu His
                85                  90                  95

Ile Asn Ser Leu Glu Leu Gly Asp Ser Ala Val Tyr Phe Cys Ala Ser
            100                 105                 110

Ser Gln Glu Ala Leu Gly Gly Gly Tyr Gly Tyr Thr Phe Gly Ser Gly
        115                 120                 125

Thr Arg Leu Thr Val Val Glu Asp Leu Asn Lys Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
```

195                 200                 205
Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Val Ser Tyr
            260                 265                 270

Gln Gln Gly Val Leu Ser Ala Thr Ile Leu Tyr Glu Ile Leu Leu Gly
                275                 280                 285

Lys Ala Thr Leu Tyr Ala Val Leu Val Ser Ala Leu Val Leu Met Ala
    290                 295                 300

Met Val Lys Arg Lys Asp Phe
305                 310

<210> SEQ ID NO 192
<211> LENGTH: 270
<212> TYPE: PRT
<213> ORGANISM: Homo sapiens

<400> SEQUENCE: 192

Met Leu Leu Val Leu Ile Pro Leu Leu Gly Ile His Phe Val Leu Arg
1               5                   10                  15

Thr Ala Arg Ala Gln Ser Val Thr Gln Pro Asp Ile His Ile Thr Val
            20                  25                  30

Ser Glu Gly Ala Ser Leu Glu Leu Arg Cys Asn Tyr Ser Tyr Gly Ala
        35                  40                  45

Thr Pro Tyr Leu Phe Trp Tyr Val Gln Ser Pro Gly Gln Gly Leu Gln
    50                  55                  60

Leu Leu Leu Lys Tyr Phe Ser Gly Asp Thr Leu Val Gln Gly Ile Lys
65                  70                  75                  80

Gly Phe Glu Ala Glu Phe Lys Arg Ser Gln Ser Ser Phe Asn Leu Arg
                85                  90                  95

Lys Pro Ser Val His Trp Ser Asp Ala Ala Glu Tyr Phe Cys Ala Val
            100                 105                 110

Gly Ala Tyr Asp Met Arg Phe Gly Ala Gly Thr Arg Leu Thr Val Lys
        115                 120                 125

Pro Asn Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

```
Ala Gly Phe Asn Leu Leu Met Thr Leu Arg Leu Trp Ser Ser
            260                 265                 270
```

<210> SEQ ID NO 193
<211> LENGTH: 307
<212> TYPE: PRT
<213> ORGANISM: Homo sapiens

<400> SEQUENCE: 193

```
Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Asn Arg Leu Asn Thr Glu Ala Phe Phe Gly Gln Gly Thr Arg Leu Thr
        115                 120                 125

Val Val Glu Asp Leu Asn Lys Val Phe Pro Pro Glu Val Ala Val Phe
    130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Phe
305
```

<210> SEQ ID NO 194
<211> LENGTH: 261
<212> TYPE: PRT
<213> ORGANISM: Homo sapiens

<400> SEQUENCE: 194

```
Met His Ser Leu Leu Gly Leu Leu Leu Trp Leu Gln Leu Thr Arg Val
1               5                   10                  15

Asn Ser Gln Leu Ala Glu Glu Asn Ser Trp Ala Leu Ser Val His Glu
            20                  25                  30

Gly Glu Ser Val Thr Val Asn Cys Ser Tyr Lys Thr Ser Ile Thr Ala
            35                  40                  45

Leu Gln Trp Tyr Arg Gln Lys Ser Gly Lys Gly Pro Ala Gln Leu Ile
    50                  55                  60

Leu Ile Arg Ser Asn Glu Arg Glu Lys Arg Asn Gly Arg Leu Arg Ala
65                  70                  75                  80

Thr Leu Asp Thr Ser Ser Gln Ser Ser Ser Leu Ser Ile Thr Ala Thr
                85                  90                  95

Arg Cys Glu Asp Thr Ala Val Tyr Phe Cys Ala Thr Asp Asn Val Leu
                100                 105                 110

Tyr Phe Gly Ser Gly Thr Lys Leu Thr Val Glu Pro Asn Ile Gln Asn
            115                 120                 125

Pro Glu Pro Ala Val Tyr Gln Leu Lys Asp Pro Arg Ser Gln Asp Ser
    130                 135                 140

Thr Leu Cys Leu Phe Thr Asp Phe Asp Ser Gln Ile Asn Val Pro Lys
145                 150                 155                 160

Thr Met Glu Ser Gly Thr Phe Ile Thr Asp Lys Thr Val Leu Asp Met
                165                 170                 175

Lys Ala Met Asp Ser Lys Ser Asn Gly Ala Ile Ala Trp Ser Asn Gln
                180                 185                 190

Thr Ser Phe Thr Cys Gln Asp Ile Phe Lys Glu Thr Asn Ala Thr Tyr
    195                 200                 205

Pro Ser Ser Asp Val Pro Cys Asp Ala Thr Leu Thr Glu Lys Ser Phe
    210                 215                 220

Glu Thr Asp Met Asn Leu Asn Phe Gln Asn Leu Ser Val Met Gly Leu
225                 230                 235                 240

Arg Ile Leu Leu Leu Lys Val Ala Gly Phe Asn Leu Leu Met Thr Leu
                245                 250                 255

Arg Leu Trp Ser Ser
                260

<210> SEQ ID NO 195
<211> LENGTH: 302
<212> TYPE: PRT
<213> ORGANISM: Homo sapiens

<400> SEQUENCE: 195

Met Leu Tyr Ser Leu Leu Ala Phe Leu Leu Gly Met Phe Leu Gly Val
1               5                   10                  15

Ser Ala Gln Thr Ile His Gln Trp Pro Val Ala Glu Ile Lys Ala Val
            20                  25                  30

Gly Ser Pro Leu Ser Leu Gly Cys Thr Ile Lys Gly Lys Ser Ser Pro
            35                  40                  45

Asn Leu Tyr Trp Tyr Trp Gln Ala Thr Gly Gly Thr Leu Gln Gln Leu
    50                  55                  60

Phe Tyr Ser Ile Thr Val Gly Gln Val Glu Ser Val Val Gln Leu Asn
65                  70                  75                  80

Leu Ser Ala Ser Arg Pro Lys Asp Asp Gln Phe Ile Leu Ser Thr Glu
                85                  90                  95

Lys Leu Leu Leu Ser His Ser Gly Phe Tyr Leu Cys Ala Trp Lys Leu
                100                 105                 110
```

```
Gly Asn Tyr Ala Glu Gln Phe Phe Gly Pro Gly Thr Arg Leu Thr Val
        115                 120                 125

Leu Glu Asp Leu Arg Asn Val Thr Pro Pro Lys Val Ser Leu Phe Glu
        130                 135                 140

Pro Ser Lys Ala Glu Ile Ala Asn Lys Gln Lys Ala Thr Leu Val Cys
145                 150                 155                 160

Leu Ala Arg Gly Phe Phe Pro Asp His Val Glu Leu Ser Trp Trp Val
                165                 170                 175

Asn Gly Lys Glu Val His Ser Gly Val Ser Thr Asp Pro Gln Ala Tyr
        180                 185                 190

Lys Glu Ser Asn Tyr Ser Tyr Cys Leu Ser Ser Arg Leu Arg Val Ser
        195                 200                 205

Ala Thr Phe Trp His Asn Pro Arg Asn His Phe Arg Cys Gln Val Gln
        210                 215                 220

Phe His Gly Leu Ser Glu Glu Asp Lys Trp Pro Glu Gly Ser Pro Lys
225                 230                 235                 240

Pro Val Thr Gln Asn Ile Ser Ala Glu Ala Trp Gly Arg Ala Asp Cys
                245                 250                 255

Gly Ile Thr Ser Ala Ser Tyr His Gln Gly Val Leu Ser Ala Thr Ile
                260                 265                 270

Leu Tyr Glu Ile Leu Leu Gly Lys Ala Thr Leu Tyr Ala Val Leu Val
        275                 280                 285

Ser Gly Leu Val Leu Met Ala Met Val Lys Lys Lys Asn Ser
        290                 295                 300

<210> SEQ ID NO 196
<211> LENGTH: 19
<212> TYPE: PRT
<213> ORGANISM: Homo sapiens

<400> SEQUENCE: 196

Pro Met Thr Val Leu Cys Ser Ile Asp Trp Phe Met Val Thr Val His
1               5                   10                  15

Pro Phe Met
```